(12) United States Patent
Visco et al.

(10) Patent No.: US 10,601,071 B2
(45) Date of Patent: Mar. 24, 2020

(54) METHODS OF MAKING AND INSPECTING A WEB OF VITREOUS LITHIUM SULFIDE SEPARATOR SHEET AND LITHIUM ELECTRODE ASSEMBLIES

(71) Applicant: PolyPlus Battery Company, Berkeley, CA (US)

(72) Inventors: Steven J. Visco, Berkeley, CA (US); Yevgeniy S. Nimon, Danville, CA (US); Lutgard C. De Jonghe, Lafayette, CA (US); Bruce D. Katz, Moraga, CA (US); Vitaliy Nimon, San Francisco, CA (US)

(73) Assignee: POLYPLUS BATTERY COMPANY, Berkeley, CA (US)

( * ) Notice: Subject to any disclaimer, the term of this patent is extended or adjusted under 35 U.S.C. 154(b) by 98 days.

(21) Appl. No.: 15/380,989

(22) Filed: Dec. 15, 2016

(65) Prior Publication Data

US 2017/0229731 A1 Aug. 10, 2017

Related U.S. Application Data

(60) Provisional application No. 62/271,180, filed on Dec. 22, 2015, provisional application No. 62/342,155, (Continued)

(51) Int. Cl.
*H01M 10/05* (2010.01)
*H01M 10/0562* (2010.01)
(Continued)

(52) U.S. Cl.
CPC ........ *H01M 10/0562* (2013.01); *G01N 21/31* (2013.01); *G01N 21/896* (2013.01);
(Continued)

(58) Field of Classification Search
CPC .. H01M 10/0562; G01N 21/31; G01N 21/896
See application file for complete search history.

(56) References Cited

U.S. PATENT DOCUMENTS 4,042,482 A 8/1977 Shannon et al.
4,208,474 A 6/1980 Jacobson et al.
(Continued)

FOREIGN PATENT DOCUMENTS

CN 101494299 A 7/2009
EP 0774654 B1 1/2000
(Continued)

OTHER PUBLICATIONS

WO patent application No. PCT/US2016/067338, International Search Report and Written Opinion dated May 19, 2017.
(Continued)

*Primary Examiner* — Ula C Ruddock
*Assistant Examiner* — Frank A Chernow
(74) *Attorney, Agent, or Firm* — Weaver Austin Villenueve & Sampson LLP

(57) ABSTRACT

A lithium ion-conductive solid electrolyte including a free-standing inorganic vitreous sheet of sulfide-based lithium ion conducting glass is capable of high performance in a lithium metal battery by providing a high degree of lithium ion conductivity while being highly resistant to the initiation and/or propagation of lithium dendrites. Such an electrolyte is also itself manufacturable, and readily adaptable for battery cell and cell component manufacture, in a cost-effective, scalable manner. An automated machine based system, apparatus and methods assessing and inspecting the quality of such vitreous solid electrolyte sheets, electrode sub-assemblies and lithium electrode assemblies can be based on spectrophotometry and can be performed inline with fabricating the sheet or web (e.g., inline with drawing (Continued)

of the vitreous Li ion conducting glass) and/or with the manufacturing of associated electrode sub-assemblies and lithium electrode assemblies and battery cells.

8 Claims, 50 Drawing Sheets

Related U.S. Application Data filed on May 26, 2016, provisional application No. 62/344,349, filed on Jun. 1, 2016.

(51) Int. Cl.
    *G01N 21/896*     (2006.01)
    *H01M 2/16*     (2006.01)
    *H01M 4/134*     (2010.01)
    *H01M 4/04*     (2006.01)
    *G01N 21/31*     (2006.01)
    *H01M 4/1395*     (2010.01)
    *H01M 2/14*     (2006.01)
    *H01M 10/0525*     (2010.01)
    *H01M 10/0566*     (2010.01)

(52) U.S. Cl.
    CPC ......... *H01M 2/145* (2013.01); *H01M 2/1646* (2013.01); *H01M 2/1673* (2013.01); *H01M 4/0407* (2013.01); *H01M 4/134* (2013.01); *H01M 4/1395* (2013.01); *H01M 10/0525* (2013.01); *G01N 2021/8967* (2013.01); *H01M 10/0566* (2013.01); *H01M 2300/0068* (2013.01)

(56) References Cited

U.S. PATENT DOCUMENTS

| | | |
|---|---|---|
| 4,331,750 A | 5/1982 | Malugani et al. |
| 4,444,857 A | 4/1984 | Duchange et al. |
| 4,465,745 A | 8/1984 | Akridge |
| 4,465,746 A | 8/1984 | Akridge |
| 4,477,545 A | 10/1984 | Akridge et al. |
| 4,478,920 A | 10/1984 | Gabano et al. |
| 4,513,070 A | 4/1985 | Carette et al. |
| 4,585,714 A | 4/1986 | Akridge et al. |
| 4,599,284 A | 7/1986 | Adridge |
| 4,985,317 A | 1/1991 | Adachi et al. |
| 5,314,765 A | 5/1994 | Bates |
| 5,338,625 A | 8/1994 | Bates et al. |
| 5,455,126 A | 10/1995 | Bates et al. |
| 5,512,147 A | 4/1996 | Bates et al. |
| 5,567,210 A | 10/1996 | Bates et al. |
| 5,569,520 A | 10/1996 | Bates |
| 5,597,660 A | 1/1997 | Bates et al. |
| 5,612,152 A | 3/1997 | Bates |
| 5,648,187 A | 7/1997 | Skotheim |
| 5,702,995 A | 12/1997 | Fu |
| 5,958,281 A | 9/1999 | Takada et al. |
| 5,961,672 A | 10/1999 | Skotheim et al. |
| 6,030,909 A | 2/2000 | Fu |
| 6,214,061 B1 | 4/2001 | Visco et al. |
| 6,315,881 B1 | 11/2001 | Fu |
| 6,402,795 B1 | 6/2002 | Chu et al. |
| 6,432,584 B1 | 8/2002 | Visco et al. |
| 6,485,622 B1 | 11/2002 | Fu |
| 6,723,140 B2 | 4/2004 | Chu et al. |
| 6,733,924 B1 | 5/2004 | Skotheim et al. |
| 6,797,428 B1 | 9/2004 | Skotheim et al. |
| 7,211,532 B2 | 5/2007 | Fu |
| 7,247,408 B2 | 7/2007 | Skotheim |
| 7,273,682 B2 | 9/2007 | Park et al. |
| 7,282,295 B2 | 10/2007 | Visco et al. |
| 7,282,296 B2 | 10/2007 | Visco et al. |
| 7,282,302 B2 | 10/2007 | Visco et al. |
| 7,390,591 B2 | 6/2008 | Visco et al. |
| 7,645,543 B2 | 1/2010 | Visco et al. |
| 7,666,233 B2 | 2/2010 | Visco et al. |
| 7,824,806 B2 | 11/2010 | Visco et al. |
| 7,829,212 B2 | 11/2010 | Visco et al. |
| 7,838,144 B2 | 11/2010 | Visco et al. |
| 7,858,223 B2 | 12/2010 | Visco et al. |
| 8,048,570 B2 | 11/2011 | Visco et al. |
| 8,048,571 B2 | 11/2011 | Visco et al. |
| 8,114,171 B2 | 2/2012 | Visco et al. |
| 8,129,052 B2 | 3/2012 | Visco et al. |
| 8,182,943 B2 | 5/2012 | Visco et al. |
| 8,202,649 B2 | 6/2012 | Visco et al. |
| 8,293,398 B2 | 10/2012 | Visco et al. |
| 8,323,820 B2 | 12/2012 | Visco et al. |
| 8,334,075 B2 | 12/2012 | Visco et al. |
| 8,389,147 B2 | 3/2013 | Visco et al. |
| 8,445,136 B2 | 5/2013 | Visco et al. |
| 8,455,131 B2 | 6/2013 | Visco et al. |
| 8,501,339 B2 | 8/2013 | Visco et al. |
| 8,652,686 B2 | 2/2014 | Visco et al. |
| 8,658,304 B2 | 2/2014 | Visco et al. |
| 8,673,477 B2 | 3/2014 | Visco et al. |
| 8,691,444 B2 | 4/2014 | Visco et al. |
| 8,778,522 B2 | 7/2014 | Visco et al. |
| 8,778,543 B2 | 7/2014 | Shinohara et al. |
| 8,828,573 B2 | 9/2014 | Visco et al. |
| 8,828,574 B2 | 9/2014 | Visco et al. |
| 8,828,575 B2 | 9/2014 | Visco et al. |
| 8,828,580 B2 | 9/2014 | Visco et al. |
| 9,123,941 B2 | 9/2015 | Visco et al. |
| 9,130,198 B2 | 9/2015 | Visco et al. |
| 9,136,568 B2 | 9/2015 | Visco et al. |
| 9,287,573 B2 | 3/2016 | Visco et al. |
| 9,362,538 B2 | 6/2016 | Visco et al. |
| 9,660,265 B2 | 5/2017 | Visco et al. |
| 10,147,968 B2 | 12/2018 | Visco et al. |
| 10,164,289 B2 | 12/2018 | Visco et al. |
| 2002/0012846 A1 | 1/2002 | Skotheim et al. |
| 2002/0036131 A1 | 3/2002 | Kugai et al. |
| 2007/0037058 A1 | 2/2007 | Visco et al. |
| 2007/0087269 A1 | 4/2007 | Inda |
| 2007/0231704 A1 | 10/2007 | Inda |
| 2007/0248888 A1 | 10/2007 | Seino et al. |
| 2007/0295385 A1 | 12/2007 | Sheats et al. |
| 2008/0057386 A1 | 3/2008 | Visco et al. |
| 2008/0057399 A1 | 3/2008 | Visco et al. |
| 2009/0142669 A1 | 6/2009 | Shinohara et al. |
| 2009/0159839 A1 | 6/2009 | Seino et al. |
| 2010/0040952 A1 | 2/2010 | Kimura et al. |
| 2010/0075209 A1 | 3/2010 | Kimura et al. |
| 2010/0190063 A1 | 7/2010 | Fukumoto et al. |
| 2011/0065007 A1 | 3/2011 | Kamya et al. |
| 2011/0076570 A1 | 3/2011 | Hama et al. |
| 2011/0108642 A1 | 5/2011 | Hama et al. |
| 2011/0117726 A1 | 5/2011 | Pinnington et al. |
| 2012/0034529 A1 | 2/2012 | Tatsumisago et al. |
| 2012/0094188 A1 | 4/2012 | Visco et al. |
| 2012/0177997 A1 | 7/2012 | Nakamoto et al. |
| 2012/0189918 A1 | 7/2012 | Tatsumisago et al. |
| 2013/0164631 A1 | 6/2013 | Ohtomo et al. |
| 2013/0164632 A1 | 6/2013 | Kato et al. |
| 2013/0288134 A1 | 10/2013 | Hama et al. |
| 2014/0072875 A1 | 3/2014 | Uchiyama |
| 2014/0093785 A1 | 4/2014 | Sugiura et al. |
| 2014/0141341 A1 | 5/2014 | Ohtomo et al. |
| 2014/0151371 A1 | 6/2014 | Chang et al. |
| 2014/0162108 A1 | 6/2014 | Visco et al. |
| 2014/0170465 A1 | 6/2014 | Visco et al. |
| 2014/0322584 A1 | 10/2014 | Visco et al. |
| 2015/0214555 A1 | 7/2015 | Visco et al. |
| 2015/0340720 A1 | 11/2015 | Visco et al. |
| 2015/0349371 A1* | 12/2015 | Neudecker ............ H01M 10/02 429/152 |
| 2016/0028053 A1 | 1/2016 | Visco et al. |
| 2016/0028063 A1 | 1/2016 | Visco et al. |
| 2016/0156065 A1 | 6/2016 | Visco et al. |
| 2016/0190640 A1 | 6/2016 | Visco et al. |
| 2016/0197326 A1 | 7/2016 | Visco et al. |

(56) References Cited

U.S. PATENT DOCUMENTS

| | | |
|---|---|---|
| 2016/0351878 A1 | 12/2016 | Visco et al. |
| 2016/0351879 A1 | 12/2016 | Visco et al. |
| 2017/0331156 A1 | 11/2017 | Visco et al. |
| 2017/0365853 A1 | 12/2017 | Visco et al. |
| 2018/0131040 A1 | 5/2018 | Visco et al. |
| 2019/0013546 A1 | 1/2019 | Visco et al. |
| 2019/0148768 A1 | 5/2019 | Visco et al. |
| 2019/0173128 A1 | 6/2019 | Visco et al. |
| 2019/0181496 A1 | 6/2019 | Visco et al. |
| 2019/0229370 A1 | 7/2019 | Visco et al. |
| 2020/0014063 A1 | 1/2020 | Visco et al. |

FOREIGN PATENT DOCUMENTS

| | | | |
|---|---|---|---|
| JP | 2004-063419 | A | 2/2004 |
| JP | 2008-103229 | A | 5/2008 |
| JP | 2008-300300 | A | 12/2008 |
| JP | 2009-158476 | A | 7/2009 |
| JP | 2010-108881 | | 5/2010 |
| JP | 2012-043654 | | 3/2012 |
| JP | 2012-043654 | A | 3/2012 |
| JP | 2012-089424 | | 5/2012 |
| JP | 2012-096793 | A | 5/2012 |
| JP | 2012-096973 | A | 5/2012 |
| JP | 2013-117398 | A | 1/2013 |
| JP | 2013-118398 | A | 6/2013 |
| JP | 2013-232335 | | 11/2013 |
| JP | 2014-035989 | A | 2/2014 |
| JP | 2014-096311 | | 5/2014 |
| JP | 2014-221714 | | 11/2014 |
| WO | 2016/089889 | A1 | 6/2016 |
| WO | 2016/089897 | A1 | 6/2016 |
| WO | 2017/112550 | A1 | 6/2017 |
| WO | 2017/197039 | A1 | 11/2017 |
| WO | 2019/010047 | A1 | 1/2019 |

OTHER PUBLICATIONS

WO patent application No. PCT/US2015/063231, International Search Report and Written Opinion dated Mar. 11, 2016.
WO patent application No. PCT/US2015/063234, International Search Report and Written Opinion dated Apr. 1, 2016.
Akridge, James R. et al., "Solid state batteries using vitreous solid electrolytes," Solid State Ionics 18 & 19 (1986) 1082-1087.
Bartholomew, Roger F. et al., "Electrical properties of new glasses based on the $Li_2S$—$SiS_2$ system," Journal of Non-Crystalline Solids 256&257 (1999) 242-247.
Bates, J.B. et al., "Thin-film rechargeable lithium batteries," 1995, Journal of Power Sources.
Bates, J.B. et al., "Electrical properties of amorphous lithium electrolyte thin films," 1992, Solid State Ionics.
Burckhardt, W. et al., "Fast $Li^+$ ion transport in iodine-thioborate glasses," Mat. Res. Bull., vol. 19, pp. 1083-1089, 1984.
Cao, Can et al., "Recent advances in inorganic solid electrolytes for lithium batteries," Frontiers in Energy Research, Jun. 2014, vol. 2, Article 25, pp. 1-10.
Fu, Jie, "Fast Li+ Ion Conduction in $Li_2O$—$Al_2O_3$—$TiO_2$—$SiO_2$—$P_2O_5$ Glass-Ceramics," Journal of the American Ceramics Society, vol. 80, No. 7, Jul. 1997, pp. 1-5.
Fu, Jie, "Superionic conductivity of glass-ceramics in the system $Li_2O$—$Al_2O_3TiO_{3\text{-}P_2O_5}$", Solid State Ionics 96 (1997), pp. 195-200.
Fu, Jie, "Fast Li+ ion conducting glass-ceramics in the system $Li_2O$—$Al_2O_3$—$GeO_2$—$P_2O_5$" Solid State Ionics 104 (1997), pp. 191-194.
Hayashi, Akitoshi et al., "Characterization of $Li_2S$—$P_2S_5$ glass-ceramics as a solid electrolyte for lithium secondary batteries," Solid State Ionics 175 (2004) 683-686.
Hayashi, Akitoshi et al., "Formation of superionic crystals from mechanically milled $Li_2S$—$P_2S_5$ glasses," Electrochemistry Communications 5 (2003) 111-114, Nov. 26, 2002.
Hayashi, Akitoshi et al., "Preparation and ionic conductivity of $Li_7P_3S_{11-z}$ glass-ceramic electrolytes," Journal of Non-Crystalline Solids 356 (2010) 2670-2673.
Hayashi, Akitoshi et al., "Preparation of $Li_2S$—$P_2S_5$ amorphous solid electrolytes by mechanical milling," J. Am. Ceram. Soc., 84 [2] 477-79 (2001).
Hayashi, Akitoshi et al., "Mechanochemical synthesis of amorphous solid electrolytes using $SiS_2$ and various lithium compounds," Solid State Ionics 175 (2004) 637-640, Dec. 9, 2003.
Jones, Steven D. et al., "A thin-film solid-state microbattery," Journal of Power Sources, 43-44 (1993) 505-513.
Kennedy, John H. et al., "Improved stability for the $SiS_2$—$P_2S_5$—$Li_2S$ -LiI glass system," Solid State Ionics 28-30 (1998) 726-728.
Kennedy, J.H., "Ionically conductive glasses based on $SiS_2$," Materials Chemistry and Physics, 23 (1989) 29-50.
Kennedy, John H. et al., "Ionically conductive sulfide-based lithium glasses," Journal of Non-Crystalline Solids 123 (1990) 328-338.
Kennedy, John H. et al., "Preparation and conductivity measurements of $SiS_2$—$Li_2S$ glasses doped with LiBr and LiCl," Solid State Ionics 18 & 19 (1986) 368-371.
Kitaura, Hirokazu et al., "Fabrication of electrode-electrolyte interfaces in all-solid-state rechargeable lithium batteries by using a supercooled liquid state of the glassy electrolytes," J. Mater. Chem., 2011, 21, 118.
Kondo, S. et al., "New lithium ion conductors based on $Li_2S$—$SiS_2$ system," Solid State Ionics 53-56 (1992) 1183-1186.
Malugani, J.P. et al., "Preparation and electrical properties of the 0,37 $Li_2S$—0,18$P_2S_5$-0,45 LiI glass," Solid State Ionics 1 (1980) 519-523.
Mercier, René et al., "Superionic conduction in $Li_2S$—$P_2S_5$-LiI— glasses," Solid State Ionics 5 (1981) 663-666.
Minami, Keiichi et al., "Electical and electrochemical properties of glass-ceramic electrolytes in the systems $Li_2S$—$P_2S_5$—$P_2S_3$ and $Li_2S$—$P_2S_5$—$P_2O_5$," Solid State Ionics 192 (2011) 122-125.
Minami, Keiichi et al., "Mechanochemical synthesis of $Li_2S$—$P_2S_5$ glass electrolytes with lithium salts," Solid State Ionics 181 (2010) 1505-1509.
Minami, Keiichi et al., "Preparation and characterization of lithium ion conducting $Li_2S$—$P_2S_5$—$GeS_2$ glasses and glass-ceramics," Journal of Non-Crystalline Solids 356 (2010) 2666-2669.
Minami, Tsutomu et al., "Preparation and characterization of lithium ion-conducting oxysulfide glasses," Solid State Ionics 136-137 (2000) 1015-1023.
Mizuno, Fuminori et al., "Lithium ion conducting solid electrolytes prepared from Li2S, elemental P and S," Solid State Ionics 177 (2006) 2753-2757.
Ohtomo, Takamasa et al., "All-solid-state lithium secondary batteries using the 75$Li_2S$•25$P_2S_5$glass and the 70$Li_2S$•30$P_2S_5$ glass-ceramic as solid electrolytes," Journal of Power Sources 233 (2013) 231-235.
Ohtomo, Takamasa et al., "Electrical and electrochemical properties of $Li_2S$—$P_2S_5$—$P_2$—$O_5$ 5 glass-ceramic electrolytes," Journal of Power Sources 146 (2005) 715-718.
Ohtomo, Takamasa et al., "Mechanochemical synthesis of lithium ion conducting glasses and glass-ceramics in the system $Li_2S$—P—S," Solid State Ionics 176 (2005) 2349-2353.
Pradel, Annie et al., "Electrical properties of lithium conductive silicon sulfide glasses prepared by twin roller quenching," Solid State Ionics 18 & 19 (1986) 351-355.
Rudolph, B. et al., "Cyclic voltammetry studies of the lithiumthioborate glass-indium interface," Electrochimica Acta, vol. 34, No. 11, pp. 1519-1521, 1989.
Sahami, Saeed et al., "Preparation and conductivity measurements of $SiS_2$—$Li_2S$—LiBr lithium ion conductive glasses," Journal of the Electrochemical Society,Apr. 1985, pp. 985-986.
Sakuda, Atsushi et al., "Sulfide solid electrolyte with favorable mechanical property for all-solid-state lithium battery," Scientific Reports 3:2261, Jul. 23, 2013.
Tatsumisago, Masahiro, "Glassy materials based on $Li_2S$ for all-solid-state lithium secondary batteries," Solid State Ionics 175 (2004) 13-18.

(56) References Cited

OTHER PUBLICATIONS

Tatsumisago, Masahiro et al., "Preparation and structure of lithium-ion-conducting mixed-anion glasses in the system $LiBO_2$—$LiBS_2$," *J. Am. Ceram. Soc.*, 71 [9] 766-69 (1988).

Tatsumisago, Masahiro et al., "Recent development of sulfide solid electrolytes and interfacial modification for all-solid-state rechargeable lithium batteries," *Journal of Asian Ceramic Societies* 1 (2013) 17-25.

Trevey, James et al., "Glass-ceramic $Li_2S$—$P_2S_5$ electrolytes prepared by a single step ball billing process and their appliction for all-solid-state lithium-ion batteries," Electrochemistry Communications 11 (2009) 1830-1833.

Visco, Steven J. et al., "Complex plane and $^7Li$ NMR studies of highly conductive sulfide-based lithium glasses," *Battery Testing*, vol. 132, No. 4, pp. 751-753.

Visco, Steven J. et al., "Complex plane and $^7Li$ NMR studies of arsenic sulfide-based lithium glasses," *J. Electrochem. Soc.: Solid-State Science and Technology*, Jul. 1985, pp. 1766-1770.

Yang, Min et al., "Membranes in lithium ion batteries," *Membranes* 2012, 2, 367-383.

Non-Final Office Action for U.S. Appl. No. 14/954,812, dated Aug. 1, 2018.

Non-Final Office Action for U.S. Appl. No. 14/954,816, dated Aug. 1, 2018.

Notice of Allowance for U.S. Appl. No. 14/954,816, dated Oct. 15, 2018.

Notice of Allowance for U.S. Appl. No. 14/954,812, dated Oct. 30, 2018.

Extended European Search Report, dated May 22, 2018, for European Patent Application No. 15864779.2.

WO patent application No. PCT/US2015/063234, International Preliminary Report on Patentability, dated Jun. 15, 2017.

WO patent application No. PCT/US2015/063231, International Preliminary Report on Patentability, dated Jun. 15, 2017.

WO patent application No. PCT/US2016/067338, International Preliminary Report on Patentability, dated Jul. 5, 2017.

WO patent application No. PCT/US2018/039862, Invitation to Pay Additional Fees and, where applicable, Protest Fee, dated Aug. 28, 2018.

WO patent application No. PCT/US2018/042476, Invitation to Pay Additional Fees and, where applicable, Protest Fee, dated Sep. 12, 2018.

WO patent application No. PCT/US2018/039862, International Search Report and Written Opinion dated Oct. 19, 2018.

WO patent application No. PCT/US2018/042476, International Search Report and Written Opinion dated Nov. 9, 2018.

Communication Pursuant to Rules 161(2) and 162 EPC, (request for extra claims fees), dated Aug. 4, 2018, for European Patent Application No. 15864779.2.

U.S. Appl. No. 16/012,588, filed Jun. 19, 2018, Visco et al.
U.S. Appl. No. 16/161,720, filed Oct. 16, 2018, Visco et al.
U.S. Appl. No. 16/174,058, filed Oct. 29, 2018, Visco et al.
U.S. Appl. No. 16/179,803, filed Nov. 2, 2018, Visco et al.

Restriction Requirement for U.S. Appl. No. 15/726,302, dated May 6, 2019.

Communication Pursuant to Rules 70(2) and 70a(2), dated Jun. 8, 2018, deadline for response to Extended European Search Report, for European Patent Application No. 15864779.2.

First Office Action, dated Feb. 3, 2019, for Chinese Patent Application No. 201580075233.0, with Chinese Search Report and English Translation.

Communication Pursuant to Article 94(3) EPC, First Office Action, dated May 13, 2019, for European Patent Application No. 15864779.2.

Notice of Reasons for Rejection, dated May 24, 2019, for Japanese Patent Application No. 2017-529785, with machine translation.

U.S. Appl. No. 16/341,874, filed Apr. 12, 2019, Visco et al.

Restriction Requirement for U.S. Appl. No. 15/726,302, dated Nov. 19, 2019.

Notice of Allowance for U.S. Appl. No. 16/012,588, dated Dec. 3, 2019.

U.S. Appl. No. 16/663,177, filed Oct. 24, 2019, Visco et al.
U.S. Appl. No. 16/721,787, filed Dec. 19, 2019, Visco et al.

Second Office Action, dated Nov. 15, 2019, for Chinese Patent Application No. 201580075233.0, with English Translation.

Notice of Reasons for Rejection, dated Jan. 14, 2020, for Japanese Patent Application No. 2017-529785, with machine translation.

\* cited by examiner

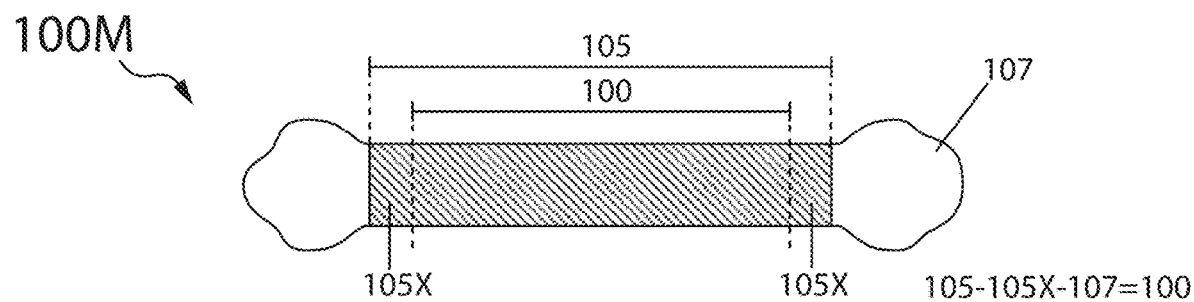
Figure 1E
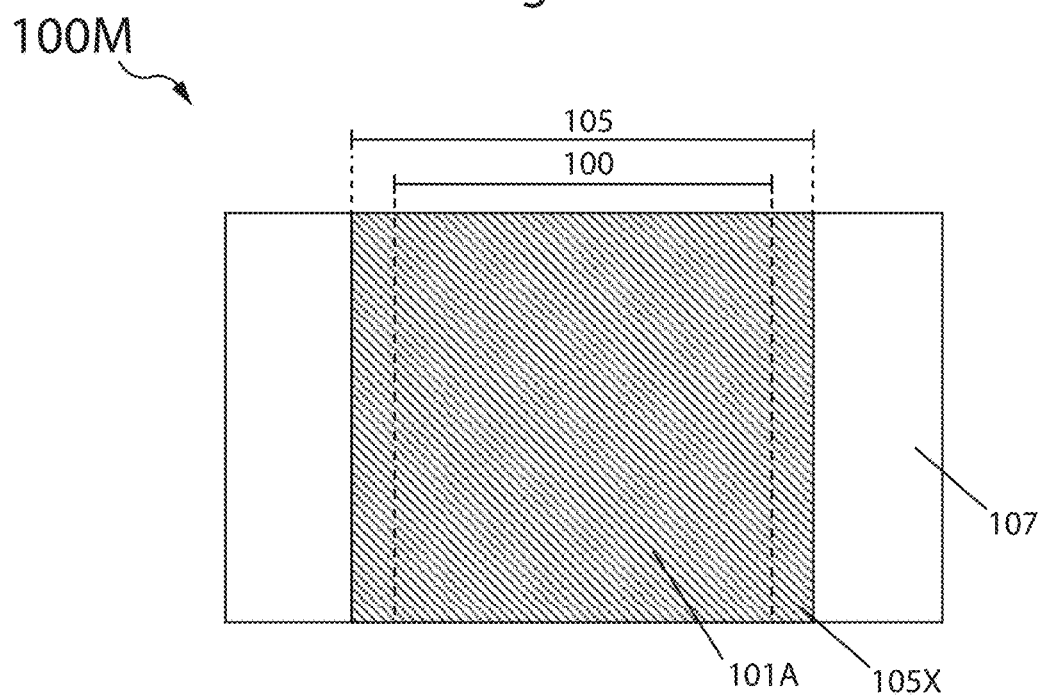
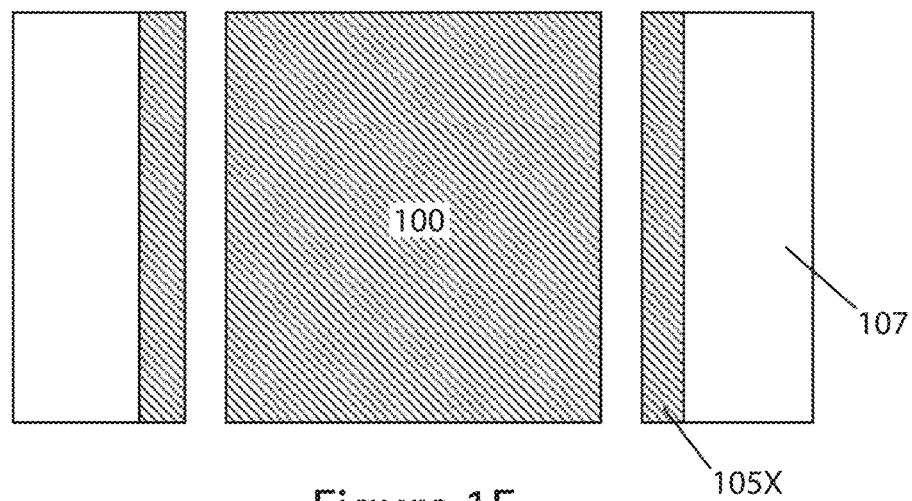
Figure 1F

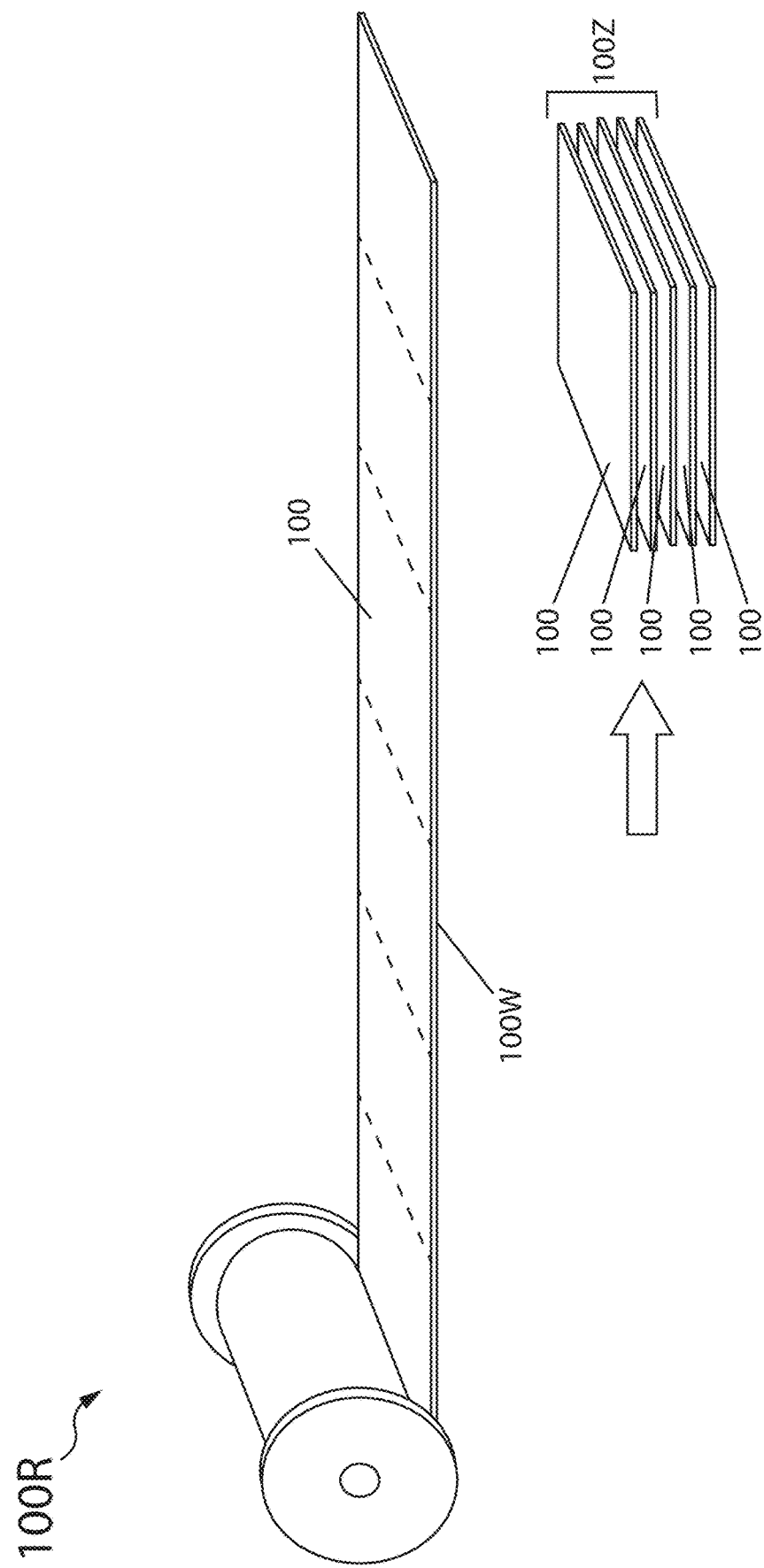

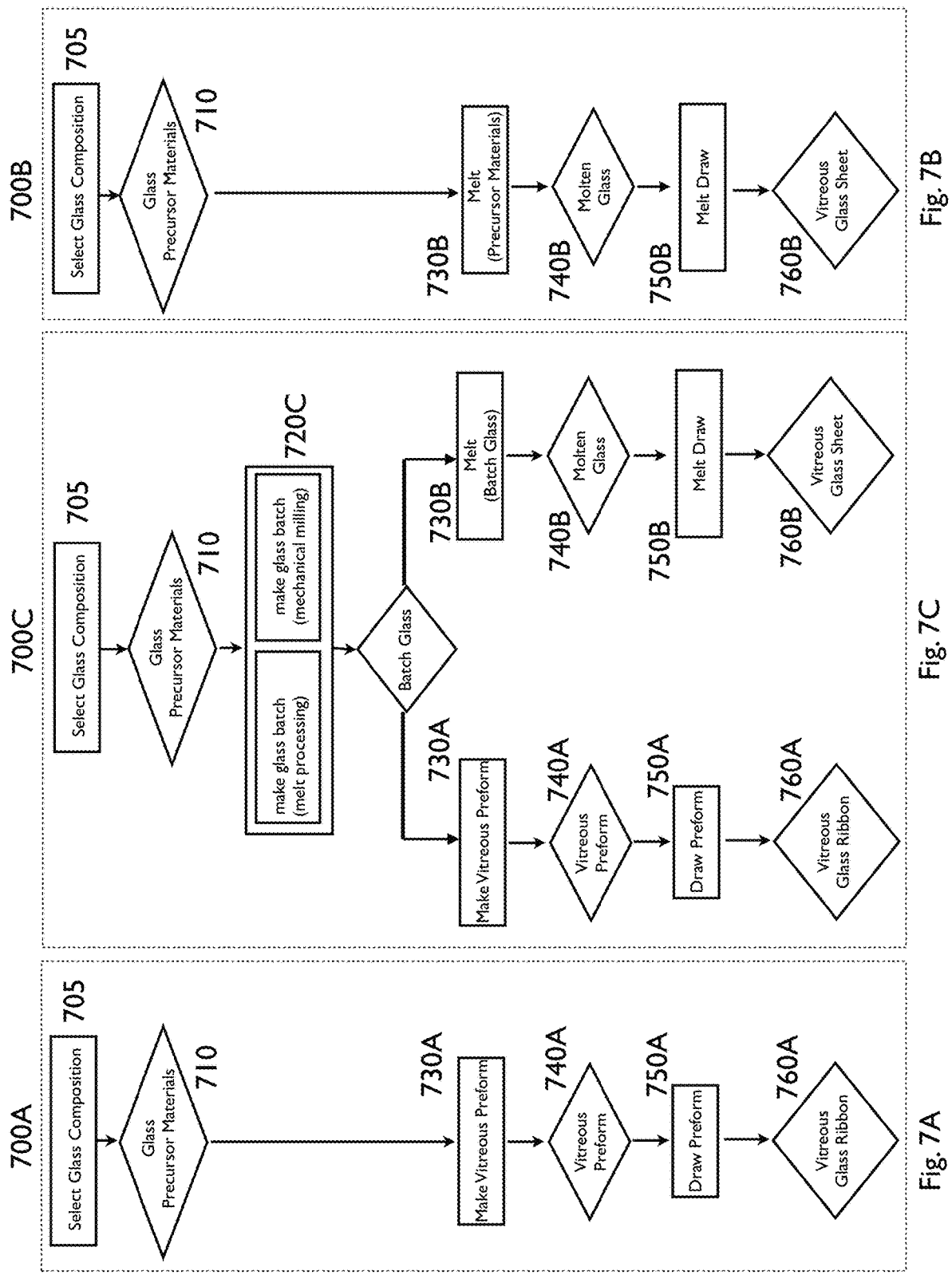

1100B
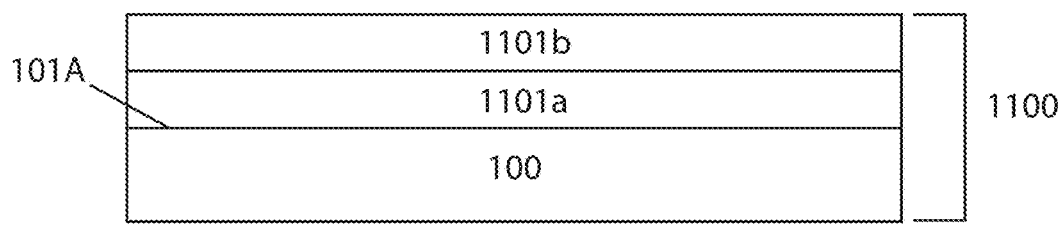
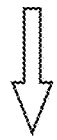 Electrochemical Plating of Lithium Metal
1300D
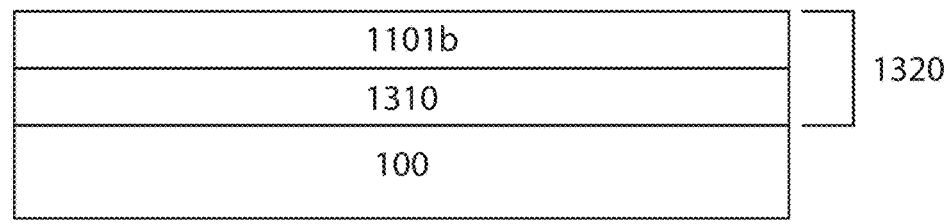
Figure 13D

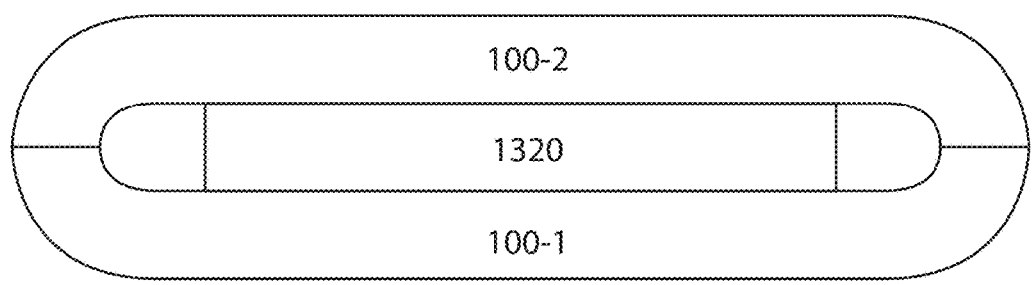
Figure 13H
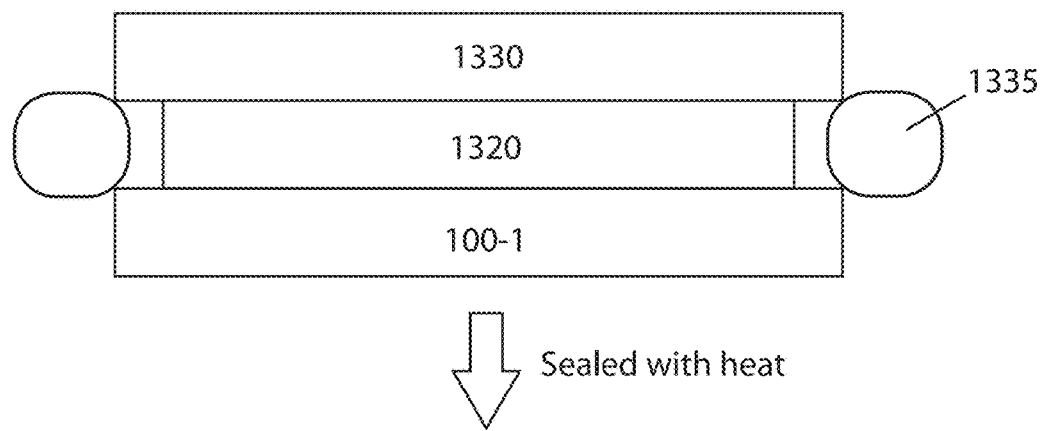
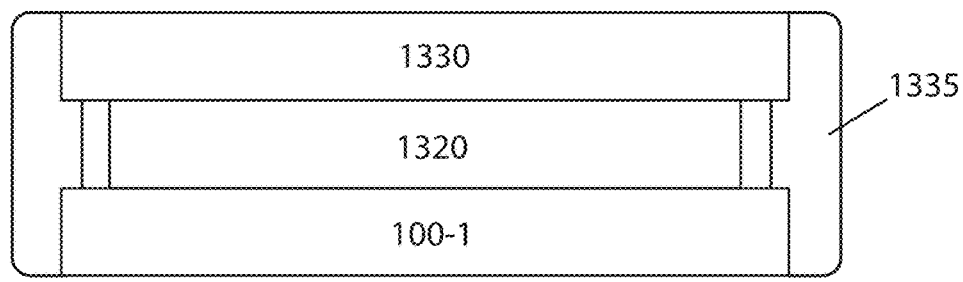
Figure 13I

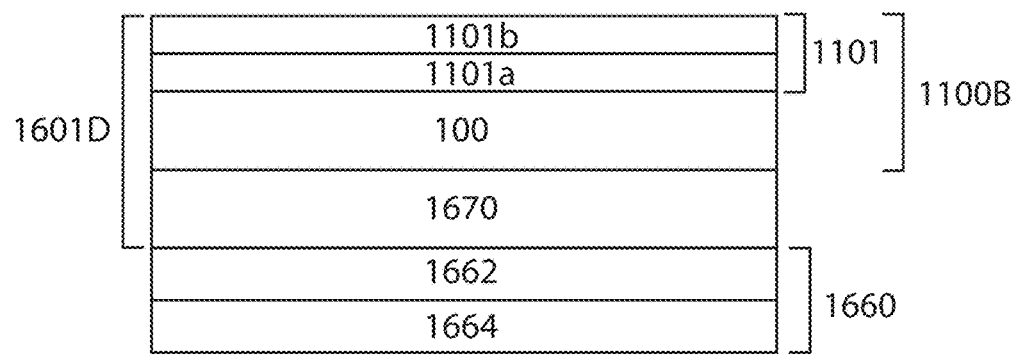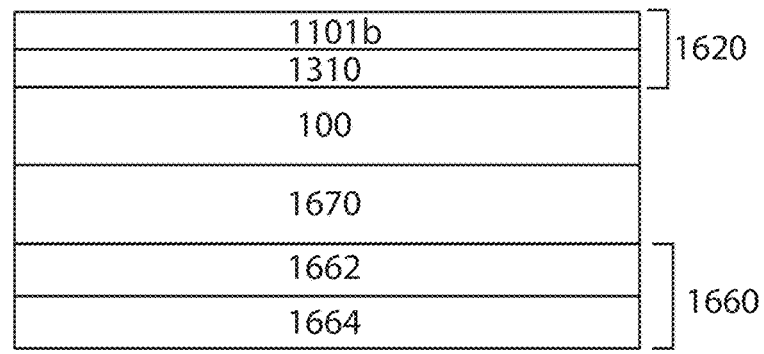
Figure 16D a. Initial configuration
(before alloy formation)

b. Final configuration
(Li alloy formation is completed)

Measurements of local resistance in glass electrolyte

Measurements of local resistance in glass electrolyte performed in cell having liquid electrolyte

METHODS OF MAKING AND INSPECTING A WEB OF VITREOUS LITHIUM SULFIDE SEPARATOR SHEET AND LITHIUM ELECTRODE ASSEMBLIES

CROSS-REFERENCE TO RELATED APPLICATIONS AND APPLICATIONS INCORPORATED BY REFERENCE

This application claims priority from U.S. Provisional Patent Application 62/271,180 filed Dec. 22, 2015, titled VITREOUS SOLID ELECTROLYTE SHEETS OF LI ION CONDUCTING SULFUR-BASED GLASS AND ASSOCIATED STRUCTURES, CELLS AND METHODS; U.S. Provisional Patent Application 62/342,155 filed May 26, 2016, titled METHODS OF MAKING AND INSPECTING A WEB OF VITREOUS LITHIUM SULFIDE SEPARATOR SHEET AND LITHIUM ELECTRODE ASSEMBLIES; and U.S. Provisional Patent Application 62/344,349 filed Jun. 1, 2016, titled METHODS OF MAKING AND INSPECTING A WEB OF VITREOUS LITHIUM SULFIDE SEPARATOR SHEET AND LITHIUM ELECTRODE ASSEMBLIES; the disclosures of which are incorporated by reference herein in their entirety.

This application also incorporates by reference in their entirety the following applications: U.S. Provisional Patent Application 62/086,641, filed Dec. 2, 2014, titled LITHIUM ION CONDUCTING GLASS LAYERS AND ASSOCIATED PROTECTED LITHIUM METAL ELECTRODES AND BATTERY CELLS; U.S. Provisional Patent Application 62/111,048, filed Feb. 2, 2015, titled LITHIUM ION CONDUCTING GLASS LAYERS AND ASSOCIATED PROTECTED LITHIUM METAL ELECTRODES AND BATTERY CELLS; U.S. Provisional Patent Application U.S. Provisional Application 62/126,319, filed Feb. 27, 2015, titled CHARACTERIZATION AND QUALITY CONTROL OF GLASS ELECTROLYTE LAYERS; U.S. Provisional Patent Application 62/146,809, filed Apr. 13, 2015, titled FREESTANDING LITHIUM ION CONDUCTING ARTICLES AND ASSOCIATED ELECTRODE ASSEMBLIES AND BATTERY CELLS; U.S. Provisional Patent Application 62/149,250, filed Apr. 17, 2015, titled FREESTANDING LITHIUM ION CONDUCTING ARTICLES AND ASSOCIATED ELECTRODE ASSEMBLIES AND BATTERY CELLS; U.S. Provisional Patent Application 62/165,791, filed May 22, 2015, titled LITHIUM ION CONDUCTING WALL STRUCTURES AND LITHIUM ELECTRODE ASSEMBLIES AND ASSOCIATED CONTINUOUS ROLLS AND LITHIUM BATTERY CELLS AND METHODS OF MAKING THEREOF; U.S. Provisional Patent Application 62/171,561, filed Jun. 5, 2015, titled STANDALONE INORGANIC SOLID ELECTROLYTE SHEETS, AND STANDALONE LITHIUM ION CONDUCTIVE SOLID ELECTROLYTE SEPARATORS, CONTINUOUS INORGANIC SEPARATOR ROLLS, LITHIUM ELECTRODE ASSEMBLIES, AND BATTERY CELLS THEREOF, AS WELL AS METHODS OF MAKING THEREOF; U.S. Provisional Patent Application 62/196,247, filed Jul. 23, 2015, titled STANDALONE INORGANIC SOLID ELECTROLYTE SHEETS, AND STANDALONE LITHIUM ION CONDUCTIVE SOLID ELECTROLYTE SEPARATORS, CONTINUOUS INORGANIC SEPARATOR ROLLS, LITHIUM ELECTRODE ASSEMBLIES, BATTERY CELLS THEREOF, AND METHODS OF MAKING; U.S. Provisional Patent Application 62/222,408, filed Sep. 23, 2015, titled VITREOUS SOLID ELECTROLYTE SHEETS OF Li ION CONDUCTING SULFUR BASED GLASS AND ASSOCIATED STRUCTURES, CELLS AND METHODS; U.S. patent application Ser. No. 14/954,812 filed Nov. 30, 2015, titled VITREOUS SOLID ELECTROLYTE SHEETS OF Li ION CONDUCTING SULFUR-BASED GLASS AND ASSOCIATED STRUCTURES, CELLS AND METHODS; U.S. patent application Ser. No. 14/954,816 filed Nov. 30, 2015, titled STANDALONE SULFIDE BASED LITHIUM ION-CONDUCTING GLASS SOLID ELECTROLYTE AND ASSOCIATED STRUCTURES, CELLS AND METHODS.

STATEMENT OF GOVERNMENT SUPPORT

This invention was made with Government support under Award No.: DE-AR0000349 awarded by the Advanced Research Projects Agency—Energy (ARPA-E), U.S. Department of Energy. The Government has certain rights in this invention.

FIELD OF THIS DISCLOSURE

This disclosure relates generally to the field of lithium electrochemical devices and lithium components thereof, and in particular to lithium battery cells, lithium electrode assemblies, and lithium ion conducting solid electrolyte components (e.g., separators and solid electrolyte sheets) for use in lithium battery cells, as well as methods for making said components, electrode assemblies and battery cells.

BACKGROUND OF THIS DISCLOSURE

There is a continuing need for high performance battery cells and their associated cell components, and particularly for high energy density secondary batteries.

SUMMARY

Provided herein is a standalone lithium ion-conductive solid electrolyte, methods of making and using the electrolyte, and battery cells and cell components incorporating the electrolyte. A standalone lithium ion-conductive solid electrolyte in accordance with this disclosure can include a freestanding inorganic vitreous sheet of sulfide-based lithium ion conducting glass capable of high performance in a lithium metal battery by providing a high degree of lithium ion conductivity while being highly resistant to the initiation and/or propagation of lithium dendrites. Such an electrolyte is also itself manufacturable, and readily adaptable for battery cell and cell component manufacture, in a cost-effective, scalable manner.

In one aspect, provided is a standalone Li ion conductive solid electrolyte separator for use in an electrode assembly or lithium battery cell, the separator comprising a freestanding substantially amorphous Li ion conductive thin walled solid electrolyte structure (i.e., a wall structure), typically in the form of a dense inorganic sheet, such as a ribbon (i.e., a relatively long narrow sheet), having substantially parallel lengthwise edges, battery serviceable size, and Li ion conductivity $\geq 10^{-5}$ S/cm, preferably $\geq 10^{-4}$ S/cm, and more preferably $\geq 10^{-3}$ S/cm.

In various embodiments the freestanding solid electrolyte wall structure is a continuous vitreous solid electrolyte sheet of Li ion conducting sulfur-based glass that is readily scalable to long continuous lengths (e.g., >25 cm, $\geq 50$ cm or $\geq 100$ cm), large areas (e.g., $\geq 100$ cm$^2$), and manufacturably alterable length (l) to width (w) area aspect ratios (l/w). For example, in various embodiments the continuous vitreous solid electrolyte sheet of sulfur-based glass is a self-supporting and substrate-less material layer having a uniform thickness ≤100 m, an area aspect ratio no less than 10 (e.g., (l/w) ≥20), and a width no less than 1 cm (e.g., about 2-10 cm wide). In various embodiments the substantially amorphous vitreous sheet is preferably essentially free of crystalline phases, and even more preferably the vitreous sheet is a homogeneous glass.

In various embodiments the vitreous solid electrolyte sheet is formed as a continuous web from which cut-to-size sheets are excised for incorporation into one or more battery cells and/or electrode assemblies as a solid electrolyte separator or component thereof. In particular embodiments the manufacturing process for making the vitreous web is integrated into a production process for fabricating lithium electrode assemblies of the present disclosure and battery cells.

The freestanding substantially amorphous inorganic solid electrolyte sheet provided herein is highly conductive of Li ions, and, in various embodiments, the solid electrolyte sheet is devoid of continuous interconnected microscopic pathways, which, if otherwise present, could allow for through penetration of lithium metal dendrites. As used herein, by highly conductive it is meant that the inorganic solid electrolyte sheet has a room temperature Li ion conductivity of at least $10^{-5}$ S/cm, preferably at least $10^{-4}$ S/cm, and more preferably at least $10^{-3}$ S/cm. Preferably, the inorganic Li ion-conductive sheet is substantially impenetrable to lithium metal dendrites, and thus, when employed as a solid electrolyte separator, the instant sheet, entirely inorganic, enables the realization of a safe lithium metal secondary battery cell.

In accordance with the disclosure, the freestanding inorganic solid electrolyte sheet comprises a continuous inorganic Li ion conducting amorphous solid material phase having an intrinsic room temperature Li ion conductivity ≥$10^{-5}$ S/cm, preferably ≥$10^{-4}$ S/cm, and more preferably ≥$10^{-3}$ S/cm. In various embodiments, the continuous inorganic Li ion conducting amorphous material phase is an inorganic glass, and in embodiments the inorganic glass may be characterized as having at least one glass network former and glass network modifier. In exemplary embodiments the inorganic glass is a Li ion conducting sulfur-based glass. In various embodiments the elemental constituents of the sulfur-based glass includes sulfur, lithium and one or more elemental constituents selected from the group consisting of boron, phosphorous, silicon, germanium, arsenic and oxygen.

In various embodiments, to create a dendrite resistant microstructure, the continuous Li ion conducting glass phase is not only amorphous, and thereby devoid of crystal grains and associated crystalline grain boundaries, it is also characterized as "vitreous" (i.e., a vitreous glass), which is a term used herein to describe a continuous glass phase, glass layer (e.g., a vitreous glass stratum) or glass article (e.g., a vitreous glass sheet) that is formed directly from the melt or derived from a continuous solidified melt, and thus, is not, and does not contain, an agglomeration of pressed or discrete glass-powder particles (e.g., sulfide glass-powder/ amorphous-powder particles); and therefore, the vitreous glass phase (or more simply vitreous phase) or vitreous glass sheet (or more simply vitreous sheet) is also entirely devoid of glass-powder/amorphous powder inter-particle boundaries, and preferably absent of microstructural features similar to those that result from compacting glass particles, such as an undue density of internal pores and surface voids.

In various embodiments the solid electrolyte sheet is a vitreous monolith wherein the continuous Li ion conducting vitreous glass phase (e.g., sulfur-based glass) is present in an uninterrupted fashion throughout the entirety of the solid electrolyte sheet, and therewith provides a continuous vitreous matrix devoid of crystalline grain boundaries and glass-powder inter-particle boundaries. In various embodiments, the solid electrolyte sheet is a vitreous monolith of a Li ion conducting sulfur-containing glass essentially free of crystalline regions. Preferably the vitreous glass sheet is homogeneous, and by this it is meant that the sheet is essentially free of secondary phases, including crystalline phases and secondary amorphous phases.

The vitreous solid electrolyte sheet of this disclosure is further advantaged by the quality of its bulk and surface, and, in particular, its lack of features. In various embodiments the vitreous sheet has liquid-like surfaces commensurate with preventing dendrite initiation. The vitreous glass sheet is not plagued by flaws normally associated with powder particle consolidation, such as an undue amount of void-like defects, including internal micropores and irregularly shaped surface microvoids, both of which are commonplace for die pressed and hot-pressed sulfide glass powder compacts.

In some embodiments, the sulfur-based glass is of a type $Li_2S$—$YS_n$; $Li_2S$—$YS_n$—$YO_n$, and combinations thereof, wherein Y is selected from the group consisting of Ge, Si, As, B, or P, and n=2, 3/2 or 5/2, and the glass is chemically and electrochemically compatible in contact with lithium metal. Suitable glass may comprise $Li_2S$ and/or $Li_2O$ as a glass modifier and one or more of a glass former selected from the group consisting of $P_2S_5$, $P_2O_5$, $SiS_2$, $SiO_2$, $B_2S_3$ and $B_2O_3$. In some embodiments, the glass may be devoid of phosphorous. In some embodiments the glass may be devoid of phosphorous and/or silicon. In other embodiments the glass includes silicon in an amount between 2 to 20 mole %, and phosphorous in an amount between 0.1 to 5 mole %, or between 0.1 to 2 mole %. In some embodiments the glass includes silicon in an amount between 0.1 to 5 mole %, or between 0.1 to 2 mole %.

In another aspect this disclosure is directed to methods of making highly conductive and freestanding vitreous solid electrolytes, (e.g., discrete Li ion conducting solid electrolyte glass sheets). In various embodiments the vitreous sheet is formed by continuous manufacturing processes, which are readily scalable to long continuous lengths, large areas and alterable length to width aspect ratios, including making a standalone continuous web of vitreous Li ion conducting sulfur-based glass.

In various embodiments the method of making the vitreous solid electrolyte glass sheet involves forming a vitreous Li ion conductive sulfur-based glass into a thin inorganic fluid sheet of unbroken continuity (e.g., a liquid glass stream), and, while ensuring that the lengthwise edges are unconstrained, causing or allowing the fluid sheet to flow, as a fluid stream, along its lengthwise dimension with substantially parallel lengthwise edges.

In various embodiments significant advantage is realized by solidifying the fluid glass stream in the absence of foreign solid contact. For instance, the vitreous sheet solidified such that its first and second principal side surfaces are untouched by a foreign solid surface, and thus are chemically and physically pristine in their virgin state as a solid—yielding benefit as it pertains to surface smoothness, flaws, and purity, and, in particular, minimizing surface contaminants as well as facilitating a high quality liquid-like surface in the absence of polishing.

In various embodiments the thickness of the solid electrolyte sheet in its virgin state as a solid is of a predetermined and uniform value, and by this expedient circumvents the need to cut or grind down the surfaces in order to achieve a desired thickness, and therefore the principal side surfaces may be kept untouched by an abrasive foreign solid surface during sheet manufacture and storage.

Accordingly, in various embodiments, the first and second principal side surfaces of the solid electrolyte sheet are not subjected to one or more of the following post-solidification processes: mechanical grinding, in-plane slicing (i.e., cutting parallel to the principal opposing surfaces), or polishing. The ability to achieve a thin and uniform thickness in the virgin state is highly beneficial as it eliminates costly processing steps and circumvents damage (e.g., surface flaws) that might otherwise arise by thinning (e.g., grinding). Various cutting/slicing methods are contemplated herein, including mechanical slicing with a scribe or other sharp tool or wire saw, as well as ultrasonic vibration machining, or laser cutting, such as with a $CO_2$ laser, green laser, or UV laser, including ablation and filament propagation techniques, and combinations thereof.

In various embodiments the method of making the freestanding vitreous sheet or web of Li ion conducting glass is by drawing. In various embodiments the drawing process is continuous. In various embodiments the drawing method is a melt draw, preform draw or a capillary draw.

In various embodiments the method of making the vitreous solid electrolyte sheet of Li ion conducting sulfur-based glass involves selecting a base glass composition of constituent elements (e.g., main constituent elements) and adjusting the mole percent of the constituent elements or the mole ratio of certain constituent elements of the glass, and/or incorporating additives (e.g., secondary constituent elements) into the base glass in an amount effective to impart particular properties desirable for processing and/or performance of the glass as a separator sheet component in a battery cell. These properties include one or more of the glass stability factor, liquidus viscosity, thermal expansion, Li ion conductivity and chemical as well as electrochemical compatible with lithium metal.

In another aspect provided is a long continuous vitreous sheet of Li ion conducting glass in the form of a vitreous web. Discrete freestanding solid electrolyte sheets may be cut-to-size from the web by slicing (e.g., laser cutting) along its widthwise and/or lengthwise dimension. In various embodiments the continuous web of vitreous Li ion conducting glass is sufficiently large in area (or length) to yield a plurality of cut-to-size solid electrolyte sheets, or the web may serve as a substrate for downstream processing of battery cell components, including electrode subassemblies and electrode assemblies of the present disclosure.

In various embodiments the vitreous Li ion conducting glass web has length greater than 50 cm and width between 1 cm to 10 cm, and typically greater than 100 cm long, such as hundreds of centimeters long (e.g., at least 100 cm, 200 cm, 300 cm, 400 cm, 500 cm, 600 cm, 700 cm, 800 cm, 900 cm, or at least 1 meter in length). Typically the web, or discrete vitreous solid electrolyte sheet, has substantially uniform and preferably uniform thickness less than 500 m, such as 10 µm to 500 µm thick, and typically 10 µm to 100 m, or more typically between 20 µm to 50 µm thick (e.g., about 20 m, about 25 m, about 30 m, about 35 m, about 40 m, about 45 m, or about 50 m).

Preferably, the vitreous web of solid electrolyte glass is flexible, and sufficiently robust when flexed to be configurable (without fracture) as a continuous coil of glass, typically wound about a spool, for storage, transportation and component manufacture. For instance, the continuous coil serving as a source/supply roll of vitreous sheet for roll-to-roll ($R_2R$) manufacturing of downstream battery cell components, including electrode subassemblies, electrode assemblies, and battery cells of the present disclosure. Preferably, the solid electrolyte web, as formed, has sufficient surface quality and thickness uniformity that it requires no post solidification grinding and/or polishing.

Various processing steps are contemplated herein for improving the quality and performance of the vitreous solid electrolyte web/sheet as well as for making downstream battery cell components, including: i) removing low quality peripheral edge portions by cutting/slicing (e.g., mechanically with a scribe or other sharp tool or wire saw, ultrasonic vibration machining, or with a laser, such as a $CO_2$ laser, green laser, or UV laser, including ablation and filament propagation techniques); ii) fire polishing the surfaces/edges; iii) incorporating edge-protector elements that interface with the sheet along its lengthwise edges; iv) and coating the first and/or second principal side surfaces of the sheet with a thin material layer, typically <1 µm thick (e.g., a tie-layer on the first principal side surface for enhancing the interface between the solid electrolyte sheet in direct contact with a lithium metal layer, or a physical vapor deposited dense Li ion conducting inorganic material layer on the first/second principal side surface for improving chemical compatibility with battery cell components).

In another aspect the disclosure provides an electrode subassembly, which is a substrate laminate composed of the vitreous solid electrolyte sheet coated on its first principal side with a material tie-layer and/or current collector layer that functions to facilitate an electrochemically effective solid-state interface with a lithium metal layer subsequently disposed/deposited on its surface during the formation of a standalone lithium metal electrode assembly of the present disclosure, or the formation of the lithium metal layer may be realized within the confines of a battery cell during initial charge. In various embodiments depositing the tie-layer layer and/or current collector layer directly onto a vitreous solid electrolyte web, including making use of sheet to roll and $R_2R$ manufacturing, forms a continuous web of electrode subassemblies.

In another aspect the disclosure provides a standalone electrode assembly comprising the instant solid electrolyte wall structure (e.g., a substantially impervious vitreous solid electrolyte sheet) and an electroactive material, typically as part of an electroactive component layer (e.g., a multi-layer) having first and second major opposing surfaces. For example, the electroactive component layer may be a bi-layer of an electroactive material layer (e.g., lithium metal) on a current collecting layer, or a tri-layer of a current collector layer sandwiched between a pair of lithium metal layers, or more generally electroactive material layers.

The standalone electrode assembly may be a negative or positive electrode assembly, depending on the nature of the electroactive material, and its intended use in a battery cell.

In various embodiments the standalone electrode assembly is termed "solid-state" in that it contains a solid-state laminate composed of the electroactive component layer encapsulated in direct contact on at least one major surface by the first principal side surface of the vitreous solid electrolyte sheet. The direct contact between the electroactive component layer and the vitreous solid electrolyte sheet forms a solid-state interface that is, and remains, devoid of liquid (including liquid electrolytes). In various embodiments the electroactive material is lithium metal, and the solid-state interface is made from a dense lithium metal layer in direct contact with the vitreous solid electrolyte sheet. In alternative embodiments, the solid-state electrode assembly has an electroactive component layer comprising a powder particle composite of electroactive particles (e.g., having a potential within about 1V of lithium metal, such as intercalatable carbons), and glass or glass-ceramic particles highly conductive of Li ions (e.g., sulfur-based glasses/glass ceramics). In various embodiments the particle composite electroactive component layer is dense, with total pore volume that is less than 10 vol % (i.e., the layer at least 90% dense), and preferably less than 5 vol % (i.e., the layer at least 95% dense), and even more preferably less than 2 vol % (i.e., the layer at least 98% dense).

In various embodiments the standalone electrode assembly may be termed "single-sided" or "double-sided" depending on whether one or both of the major opposing sides of the electrode assembly is electrochemically functional in that it allows electrical through migration of Li ions. A double-sided assembly is electrochemically operable on both of its sides, whereas a single-sided assembly is operable on just one side. When double sided, the electrode assembly includes a second solid electrolyte sheet of the present disclosure. For example, in double-sided solid-state lithium metal electrode assembly, the first principal side surfaces of the first and second solid electrolyte sheets form a solid-state interface with lithium metal of the electroactive component layer.

In various embodiments the standalone electrode assembly is sealed to prevent external constituents from contacting the electroactive material inside the assembly, and to prevent internal constituents (e.g., liquid electrolytes, when present) from seeping out.

In various embodiments the negative electrode assembly is a sealed solid-state lithium metal negative electrode assembly, typically double-sided.

In other embodiments, the sealed electrode assembly is not solid-state, and includes a liquid phase electrolyte at the interface between the solid electrolyte sheet and the electoactive material, to enhance electrochemical performance. For example, a double-sided positive electrode assembly comprising a liquid electrolyte that is sealed inside the assembly in direct contact with a Li ion intercalation compound as the electroactive material of the assembly (e.g., having a potential vs. lithium metal greater than 3V, and preferably greater than 4V).

In another aspect provided herein are lithium battery cells comprising the solid electrolyte separator of the present disclosure. In various embodiments the cells are of a wound or folded construction, and the solid electrolyte separator is sufficiently flexible to be wound as such without fracture.

In various embodiments, the battery cell has a hybrid cell construction comprising a sealed electrode assembly (e.g., a sealed solid-state lithium metal negative electrode assembly); an opposing electrode (e.g., a positive electrode), and a liquid electrolyte in direct touching contact with the positive electrode but unable to contact the lithium metal inside the sealed assembly.

In some embodiments, the battery cell is fully solid state, and thus devoid of a liquid phase electrolyte.

In other embodiments, the battery cell includes a common liquid electrolyte or common gel or polymer electrolyte in direct contact with the positive and negative electrode of the cell, with the solid electrolyte separator of the present disclosure providing a wall structure disposed between the electrodes to improve battery cell safety, especially as it pertains to mitigating/preventing thermal runaway. For example, the solid electrolyte separator disposed between intercalation electrodes in an otherwise conventional lithium ion battery cell.

In other aspects, the disclosure provides methods for making the aforesaid lithium battery cells. In various embodiments, the method involves $R_2R$ manufacturing, or sheet-to-roll, or roll-to-sheet processing.

In yet other aspects, the disclosure provides an automated machine based system and methods for assessing and inspecting the quality of the instant vitreous solid electrolyte sheets, electrode sub-assemblies and lithium electrode assemblies. In various embodiments the inspection is based on spectrophotometry and performed inline with fabricating the sheet or web (e.g., inline with drawing of the vitreous Li ion conducting glass).

Accordingly, in another aspect, the disclosure provides a manufacturing/fabrication system and apparatus for making a vitreous solid electrolyte sheet that includes a first section for making the vitreous solid electrolyte sheet and a second section that is an automated defect inspection system, which is inline with the sheet making section, and is based on spectrophotometry (e.g., light attenuation), the inspection system comprising one or more light sources and one or more sensors for detecting reflected and/or transmitted light.

In another aspect, the disclosure provides a manufacturing system for making an electrode sub-assembly or electrode assembly that includes a first section for making the vitreous solid electrolyte sheet, an optional second section (or station) for inspecting the vitreous sheet using spectrophotometry, a third section for applying one or more material layers on one or more surfaces of the vitreous solid electrolyte sheet (e.g., laminating a lithium metal layer onto the vitreous solid electrolyte sheet or onto a sub-electrode assembly of the vitreous sheet coated with, for example, a tie-layer such as a thin metal layer (e.g., In, Sn or Al); and a fourth automated section for inspecting the quality of the sub-electrode assembly and/or lithium electrode assembly using spectrophotometric methods such as light attenuation based on reflected or transmitted light, and/or using automated local electrical resistance measurements.

In various embodiments, the automated spectrophotometric inspection system includes one or more stations for inspecting the surface of the vitreous solid electrolyte sheet and interfaces between the vitreous solid electrolyte sheet and a material layer (e.g., a lithium alloy layer or lithium metal layer). In embodiments, the automated inspection system includes a source of light, sensors for detecting reflected/transmitted light, and a computer for collecting and storing data. In various embodiments, the first inspection station is configured to inspect the surfaces and/or interior of the vitreous solid electrolyte sheet for defects and flaws, the second inspection station is configured to inspect the interface between the solid electrolyte sheet and a reflective coating layer (e.g., a metal layer) that is devoid of lithium metal, and a third inspection station is configured to inspect the interface between the solid electrolyte sheet and a material layer comprising lithium metal (e.g., a lithium metal layer or a lithium alloy layer).

In another aspect, the disclosure provides a method of making a battery cell separator layer. The method involves providing at least two precursor ingredients for making a Li ion conducting sulfide glass in a reaction vessel, subjecting the precursor ingredients to a mechanical operation that mechanically induces a self-propagating reaction to form an amorphous solid powder, heating the amorphous solid powder to a temperature sufficient to melt the amorphous powder (e.g., at or above $T_{liq}$, when the powder is a glass), cooling the melt (e.g., below $T_g$, or to room temperature) to form a vitreous Li ion conducting sulfide glass sheet or preform, and optionally re-heating the vitreous sulfide glass preform above Tg for shaping the glass to a sheet (e.g., at or about the softening temperature).

These and other aspects are described further below with reference to the drawings.

BRIEF DESCRIPTION OF THE DRAWINGS

FIGS. 1E-F illustrate a freestanding Li ion conducting solid electrolyte sheet of this disclosure and a mother-sheet from which it is excised.

FIG. 3B illustrates a continuous roll of the instant Li ion conducting solid electrolyte sheet in the form of a web from which individual discrete solid electrolyte sheets are excised and stacked.

FIGS. 6A-B illustrate a fusion draw apparatus; FIG. 6C illustrate a slot draw apparatus; and FIG. 6D illustrate a preform draw apparatus; and FIG. 6E illustrate a float process.

FIGS. 7A-C illustrate flowcharts for methods of making a continuous solid electrolyte sheet of this disclosure.

FIGS. 13B-D illustrate methods of making a lithium electrode assembly in accordance with various embodiments of this disclosure.

FIGS. 13H-J illustrate cross sectional depictions of edge sealed lithium metal electrode assemblies, in accordance with various embodiments of this disclosure.

FIGS. 16A-E illustrate battery cells in accordance with various embodiments of this disclosure. In various embodiments the battery cell is a solid-state cell; a cell having a common liquid electrolyte; a hybrid cell having a sealed electrode assembly of this disclosure; a cell constructed with a lithium metal free laminate; and a hybrid cell having a positive electrode assembly of this disclosure.

DETAILED DESCRIPTION OF SPECIFIC EMBODIMENTS

Figure 1A:
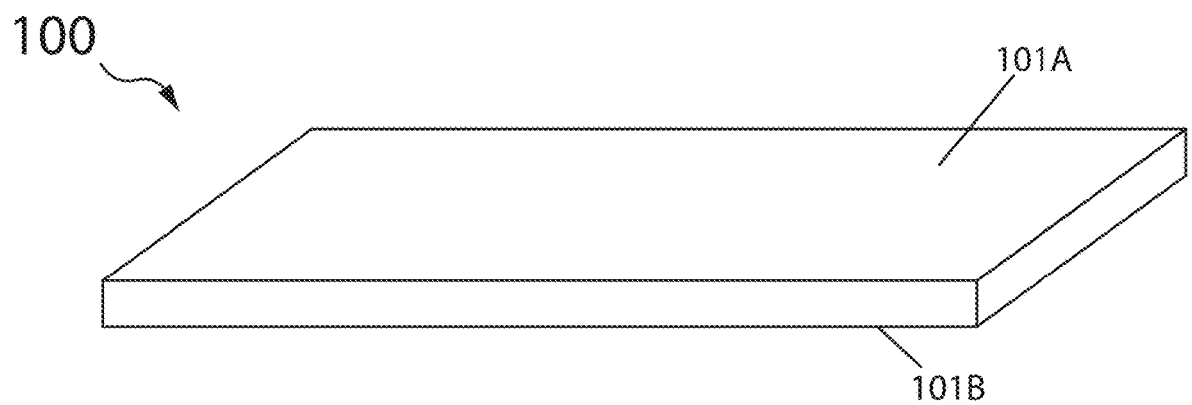
FIGS. 1A-D illustrate a freestanding Li ion conducting solid electrolyte sheet of this disclosure.

Reference will now be made in detail to specific embodiments of this disclosure. Examples of the specific embodiments are illustrated in the accompanying drawings. While this disclosure will be described in conjunction with these specific embodiments, it will be understood that it is not intended to limit this disclosure to such specific embodiments. On the contrary, it is intended to cover alternatives, modifications, and equivalents as may be included within the spirit and scope of this disclosure. In the following description, numerous specific details are set forth in order to provide a thorough understanding of this disclosure. This disclosure may be practiced without some or all of these specific details. In other instances, well known process operations have not been described in detail in order not to unnecessarily obscure this disclosure.

In one aspect, this disclosure is directed to a standalone Li ion conductive solid electrolyte for use in a lithium battery cell, the electrolyte comprising a dense freestanding inorganic and substantially amorphous Li ion conductive solid electrolyte wall structure typically in the form of a glass sheet, such as a ribbon (i.e., a relatively long narrow sheet), having substantially parallel lengthwise edges, battery serviceable size, and Li ion conductivity $\geq 10^{-5}$ S/cm, preferably $\geq 10^{-4}$ S/cm, and more preferably $\geq 10^{-3}$ S/cm.

The freestanding substantially amorphous solid electrolyte sheet of the present disclosure is highly conductive of Li ions, and, in various embodiments, the sheet is devoid of microscopic pathways, which, if otherwise present, would allow for through penetration of lithium metal dendrites. By highly conductive it is meant that the solid electrolyte sheet has room temperature (i.e., 25° C.) Li ion conductivity of at least $10^{-5}$ S/c m, preferably at least $10^{-4}$ S/cm, and more preferably at least $10^{-3}$ S/cm. In various embodiments, the Li ion conductive sheet is substantially impenetrable to lithium metal dendrites, and thus, when employed as a solid electrolyte separator component, the instant sheet, entirely inorganic, enables the realization of a safe lithium metal secondary battery cell.

By use of the term "substantially impenetrable," as it pertains to lithium metal dendrites, it is meant within the context of the instant wall structure (e.g., solid electrolyte sheet) configured in a lithium battery cell, and it means that over the service life of the battery cell, lithium metal dendrites are unable to penetrate across the sheet, and preferably cannot extend deeply or at all into the bulk of the solid electrolyte sheet (e.g., beyond 10% of the sheet thickness), and by this expedient the referenced battery cell is resistant to electrical shorting and fracture that might otherwise result from dendritic in-growth of lithium metal into pre-existing flaws or microstructural features on or nearby the sheet surface.

For example, when a substantially lithium dendrite impenetrable solid electrolyte sheet of the present disclosure is incorporated in a lithium metal battery cell as a separator layer adjacent to and in direct contact with a lithium metal electroactive layer, lithium metal deposits (e.g., lithium dendrites in the form of fibrils/filaments) are unable to penetrate deeply, if at all, into the bulk of the separator sheet during normal battery cell charging. Preferably, lithium metal deposits are unable to penetrate more than 10 µm into the bulk of the sheet; and preferably no more than 5 µm, more preferably no more than µm, and even more preferably lithium metal deposits are completely unable to penetrate the surface—the sheet, therefore, dendrite impenetrable.

In accordance with the disclosure, the continuous freestanding solid electrolyte sheet comprises a continuous inorganic Li ion conducting amorphous material phase having intrinsic room temperature Li ion conductivity $\geq 10^{-5}$ S/cm, preferably $\geq 10^{-4}$ S/cm, and more preferably $\geq 10^{-3}$ S/cm. In various embodiments, the continuous inorganic Li ion conducting amorphous material phase is an inorganic glass, and in embodiments the inorganic glass may be characterized as having at least one glass network former and at least one glass network modifier. To realize the requisite ionic conductivity in an inorganic amorphous phase, in various embodiments it is a Li ion conducting sulfur-based glass. In various embodiments the elemental constituents of the sulfur-based glass include sulfur, lithium and one or more elemental constituents selected from the group consisting of silicon, germanium, boron, phosphorous, arsenic and oxygen. In various embodiments the mole percent of one or more of these elemental constituents (i.e., the atomic percent), or the mole ratio of certain elemental constituents (i.e., the atomic ratio) is adjusted to enhance processing and/or interfacial stability in direct contact with lithium metal.

In various embodiments the freestanding solid electrolyte wall structure is a discrete substrate-less material layer in the form of a thin, long and relatively narrow sheet of sulfur-containing glass having substantially parallel lengthwise edges. For instance, in various embodiments the solid electrolyte sheet is a glass strip or ribbon of substantially uniform thickness $\leq 500$ µm; length dimension (l)$\geq 10$ cm; width dimension (w)$\geq 1$ cm; and area aspect ratio (l/w)$\geq 10$, and more typically $\geq 20$. Preferably the freestanding solid electrolyte sheet is sufficiently robust when flexed to be woundable for storage or for incorporation into a battery cell of wound or folded construction.

When using the term "substantially uniform thickness" it is meant that the thickness of the solid electrolyte sheet is sufficiently uniform for its intended purpose as a solid electrolyte sheet in a battery cell. When using the term "uniform thickness" (e.g., with respect to the thickness of the solid electrolyte sheet or a fluid stream of glass, it is meant that the thickness variation is at most 20% of the average thickness (t), and more preferably less. As specified below, the thickness variation (i.e., the difference between the maximum and minimum values of thickness) is a function of the average thickness. In embodiments, wherein the average thickness is 250 µm$\leq$t<500 µm, the thickness variation is preferably $\leq 2\%$, and more preferably $\leq 1\%$ of the average thickness; in embodiments wherein the average thickness is 100 µm$\leq$t<250 µm, the thickness variation is preferably $\leq 5\%$, and more preferably $\leq 2\%$; in embodiments wherein the average thickness is 50 µm$\leq$t<100 µm the thickness variation is preferably $\leq 10\%$, and more preferably $\leq 5\%$, and more preferably $\leq 2\%$; in embodiments wherein the average thickness is 10 µm$\leq$t<50 µm the thickness variation is preferably $\leq 20\%$, more preferably $\leq 10\%$, even more preferably $\leq 5\%$; and yet even more preferably $\leq 2\%$; and in embodiments wherein the average thickness is 5 µm$\leq$t<10 µm the thickness variation is preferably $\leq 20\%$, more preferably $\leq 10\%$, and even more preferably $\leq 5\%$ of the average thickness.

In various embodiments the freestanding solid electrolyte sheet is formed by a continuous manufacturing process that is readily scalable to achieve long continuous lengths (e.g., $\geq 50$ cm), large areas (e.g., $\geq 100$ cm$^2$), manufacturably adjustable area aspect ratios, and flexibility commensurate with winding. In various embodiments the sulfide glass sheet is formed as a continuous web, where from discrete sheets may be cut-to-size to yield solid electrolyte separators for incorporation into one or more battery cells and/or electrode assemblies. Preferably, the continuous web is sufficiently flexible to be stored as a coil; for example, wound about a spool to yield a standalone continuous supply roll of inorganic Li ion conducting sulfide glass ribbon, preferably essentially free of crystalline phases. In various embodiments the manufacturing process for making the Li ion conducting sulfide glass sheet or web is integrated into a production process for fabricating lithium electrode assemblies of the present disclosure and battery cells thereof.

Generally the continuous inorganic Li ion conducting sulfur-based glass phase constitutes a majority volume fraction of the solid electrolyte sheet, and thus is considered the primary material phase. In various embodiments the volume fraction of the continuous primary glass phase is at least 50%, or at least 60%, or at least 70%, or at least 80% of the overall solid volume of the sheet. In particular embodiments the volume fraction is at least 90% or at least 95% of the overall solid volume, and in preferred embodiments it constitutes about 100%, and thus, in such embodiments, the solid electrolyte sheet essentially consists of the Li ion conducting sulfur-based glass phase. When the volume fraction is less than 100%, the remaining solid volume is generally accounted for by secondary phase(s), which may be crystalline or amorphous. In various embodiments, the continuous Li ion conducting primary glass phase effectively serves as a glass matrix with any secondary phases (if present) typically embedded and isolated therein. In various embodiments the continuous Li ion conducting sulfur-based glass phase is the primary material phase of the sheet, as defined above, and it constitutes a majority area fraction of the first and/or second principal side surfaces (e.g., at least 50%, at least 60%, at least 70%, at least 80%, at least 90%, or at least 95%, and preferably 100% of the first and/or second principal side surface(s) is defined by the continuous Li ion conducting glass phase).

By use of the term "substantially amorphous" when referring to the instant solid electrolyte sheet or a surface thereof, it is meant to allow for the possibility that the sheet may contain some amount of crystalline phases. Typically the crystalline phases are incidental, generally non-conductive ($<10^{-8}$ S/cm), and isolated within the amorphous matrix of the primary Li ion conducting glass phase. However, it is contemplated that, when present, the crystalline phase may be somewhat conductive of Li ions ($>10^{-8}$ S/cm), and in some instances the conductivity of the crystalline phase may be greater than that of the primary glass phase. To be considered substantially amorphous, however, the volume fraction of crystalline phases in the solid electrolyte sheet should be less than 20 vol %, and more typically less than 10 vol %. Preferably the freestanding inorganic solid electrolyte sheet is completely amorphous, and as such is entirely devoid of detectable crystalline phases. In all circumstances, however, the crystalline phases, if present, do not, alone or in combination with each other, create continuous interconnected grain boundaries that extend across the thickness of the sheet, as this would create microscopic pathways for potential dendrite growth and through penetration. In alternative embodiments, it is contemplated that the solid electrolyte sheet is primarily amorphous, with a volume fraction of crystalline phases that is less than 50% (i.e., between 50 to 20%). In such embodiments, the crystalline phases are generally conductive of Li ions ($>10^{-8}$ S/cm and preferably $>10^{-7}$ S/cm), and more preferably highly conductive (e.g., $>10^{-5}$ S/cm), and in some embodiments it is contemplated that the crystalline phase is more conductive of Li ions than the continuous amorphous glass matrix in which it is embedded (e.g., $>10^{-4}$ S/cm or $>10^{-3}$ S/cm). As described in more detail below, in various embodiments, the substantially amorphous solid electrolyte sheet is essentially free of crystalline phases, and more preferably no crystalline phases are detectable.

In various embodiments the freestanding inorganic solid electrolyte sheet is amorphous as determined by X-ray diffraction (XRD), and thus does not produce a discrete diffraction pattern. In various embodiments, in addition to being amorphous by X-ray diffraction, the solid electrolyte sheet is preferably essentially free of crystalline phases, and even more preferably contains no detectable crystalline regions as determined by XRD, microscopy and/or optical methods. For the avoidance of doubt, by use of the term amorphous, it is meant that the constituent atoms are arranged in spatial patterns that exhibit no long-range order.

By use of the term "essentially free of crystalline phases," when referring to the solid electrolyte sheet, it is meant to allow for the possibility that it (the sheet) may contain a very small amount of crystalline phases, such as incidental and isolated random nanocrystals, that are undetectable by XRD, but if present, account for no more than 5% of the total sheet volume, and preferably no more than 2%, even more preferably no more than 1%; and yet even more preferably, when essentially free of crystalline phases, the sheet is completely devoid of crystalline phases (i.e., none are detectable). Likewise, when using the term "essentially free of secondary amorphous phases" it is meant to allow for the possibility that the sheet may contain a very small volume fraction of secondary amorphous phases, but no more than 5% of the total sheet volume, and preferably no more than 2%, and even more preferably no more than 1%; and yet even more preferably, when essentially free of secondary phases, the sheet is preferably devoid of secondary amorphous phases (i.e., none are detectable).

When referring to the instant wall structure (e.g., in the form of a solid electrolyte sheet) as "freestanding" or "freestandable" it is meant that the sheet is a self-supporting layer that displays a mechanical strength (e.g., tensile strength) sufficient to allow it (the sheet) to remain intact in the absence of a substrate (i.e., self-supporting), and thereby the freestanding solid electrolyte sheet is not dependent upon another self-supporting layer for its continuous intact existence (e.g., a positive or negative electrode layer or an inert carrier film). Accordingly, in various embodiments the instant freestanding solid electrolyte sheet is "substrateless."

By use of the term "standalone solid electrolyte separator" or "standalone solid electrolyte sheet" or "standalone solid electrolyte" it is meant that the separator or sheet or electrolyte is a discrete battery cell component, and thus is not, or has not yet been incorporated in a battery cell or an electrode assembly. When referring to the sheet or separator as a discrete battery cell component it is understood that the sheet or separator is absent of a positive or negative electrode, and furthermore devoid of electroactive material that would otherwise serve to provide ampere-hour capacity to a lithium battery cell. In various embodiments, at certain periods of time the standalone solid electrolyte sheet, freestanding and substrate-less, will have free principal opposing side surfaces that are directly exposed, or exposable, to the ambient environment in which it (the sheet) is stored or made; accordingly, during those periods, the sheet is not covered by a different material layer onto which the sheet is chemically bonded or physically adhered (permanently or temporarily). The term discrete is also sometimes used herein when referring to a cut-to-size solid electrolyte sheet that is excised from a mother-sheet of glass or from a long continuous web of Li ion conducting glass. By use of the term standalone when referring to an electrode assembly it is meant that the electrode assembly has not yet been combined with a second electrode of opposite polarity, and therefore the standalone electrode assembly has not yet been incorporated in a battery cell.

By "electroactive material" it is meant electroactive material that provides ampere-hour capacity to a lithium battery cell, and involves lithium in the electrochemical redox reaction (e.g., lithium intercalation materials and lithium metal).

By use of the term "wall structure" it is typically meant a thin sheet-like solid electrolyte, such as a continuous strip or ribbon having substantially parallel lengthwise edges. According to some embodiments, it is contemplated that the wall structure may take the form of a hollow prism-like receptacle, including rectangular and elliptical prisms. In alternative embodiments it is contemplated that the solid electrolyte wall structure may be flat with a circular or oval footprint.

When referring to a certain property/characteristic of the sheet as "battery serviceable," it is meant that the referenced characteristic is suitable to support the service of the sheet as a continuous Li ion conducting solid electrolyte separator component in a battery cell of defined type (e.g., liquid, gel, polymer or solid-state), form (e.g., wound, folded or stacked), dimension and/or having one or more predefined parameters, including, but not limited to, battery cell rated ampere-hour capacity (Ah), area ampere-hour capacity (mAh/cm$^2$), volumetric energy density (Wh/l), and current density (mA/cm$^2$).

By use of the term area specific resistance (ASR) it is meant the resistance of the solid electrolyte sheet as measured between opposing principal side surfaces, in contact with either blocking electrodes (e.g., gold coatings or platinum layers) or non-blocking electrodes (typically lithium metal). When measured against blocking electrodes, the ASR is generally at its lowest value because it is simply a measure of the ionic resistance, related to Li ion conductivity and thickness. In contrast, when measured against non-blocking Li metal electrodes, the ASR values are indicative of the interfacial resistance against Li metal as well as the ionic resistance of the sheet itself.

By use of the term "intrinsic," or "intrinsically conductive," when referring to the ionic conductivity of a material, it is meant the inherent conductivity of the material itself, in the absence of any other additional material agents, such as, for example, liquid solvents or organic molecules or organic material phases.

When referring to the instant solid electrolyte sheet as "inorganic" it is meant that the solid electrolyte sheet is entirely inorganic, and thereby devoid of organic material. The term "organic material" as used herein, means compounds containing carbon wherein the carbon is typically bonded to itself and to hydrogen, and often to other elements as well. Thus, the term "inorganic material" means any material that is not an organic material.

By use of the term "web" or "continuous web" when referring to the solid electrolyte sheet, it is meant an uninterrupted sheet of such continuous length that it may serve as a source for multiple discrete/individual solid electrolyte separator sheets, which are excised from the web (e.g., cut-to-size), for use in one or more battery cells or battery cell components. In various embodiments, the web of solid electrolyte sheet is stored, transported or used in downstream manufacture in the form of a roll, such as a supply roll or source roll. However, the disclosure is not limited as such and it is contemplated that discrete solid electrolyte sheets may be cut-to-size in-line with web fabrication, and by this expedient, by passing the rolling process. It is also contemplated that the continuous web may serve as a substrate for downstream cell component manufacture, such as by coating or laminating material layers to the web; for instance, in the forming of an electrode-subassembly web from which multiple subassemblies may be cut-to-size, or an electrode-assembly web for making cut-to-size multiples thereof.

When referring to the instant solid electrolyte sheet as "dense," it is meant that the density of the solid electrolyte sheet approaches that of the theoretical material from which it is formed, and is typically >90% of theoretical density, and more typically >95%, and preferably >98% (e.g., >99%).

Preferably, the dense solid electrolyte sheet is "substantially impervious" to liquids it comes into contact with during manufacture or operation of a device in which the sheet is incorporated. Accordingly, the substantially impervious sheet, typically dense, is devoid of through porosity such as pinholes, or, more generally, any pathway through which a liquid might seep across the sheet. Notably, the criterion of substantial imperviousness to liquids is insufficient to yield a sheet that is substantially impenetrable to lithium metal dendrites. For instance, polycrystalline material layers (e.g., polycrystalline ceramics) that are substantially impervious to fluids (e.g., gases and/or liquids) are nonetheless highly susceptible to lithium metal dendrite penetration via continuous grain boundary pathways. Accordingly, in various embodiments, the substantially amorphous solid electrolyte glass sheets of the present disclosure are both substantially impervious to liquids they come into direct contact with and substantially impenetrable to lithium metal dendrites. In various embodiments, especially wherein the vitreous sulfide based solid electrolyte sheet is intended for operation in a non-aqueous liquid electrolyte based battery cell, the vitreous sheet, in addition to having the property of substantial imperviousness (as described above), is preferably substantially or entirely insoluble in direct contact with the liquid electrolyte, and in particular in direct contact with dry organic solvent(s) used in the electrolyte, such as: i) exceptionally dry carbonates [e.g., one or more of cyclic carbonates such as propylene carbonate (PC), ethylene carbonate (EC), acyclic carbonates such as dimethyl carbonate (DMC), ethylmethyl carbonate (EMC) and diethyl carbonate (DEC)]; 2) exceptionally dry ethers [e.g., one or more of 2-Methyltetrahydrofuran (2-MeTHF), Tetrahydrofuran (THF), 4-Methyldioxolane (4-MeDIOX), Tetrahydropyran (THP) and 1,3-Dioxolane (DIOX)]; and 3) exceptionally dry glymes [e.g., one or more of 1,2-dimethoxyethane (DME/mono-glyme), di-glyme, tri-glyme, tetra-glyme and higher glymes]. By use of the term substantially insoluble it is meant, the amount of dissolved sulfur present in the liquid electrolyte or the organic solvent, as a result of dissolution from the vitreous glass sheet, preferably does not exceed 1000 ppm, and preferably is less than 500 ppm, and more preferably less than 100 ppm, even more preferably less than 50 ppm, or less than 20 ppm, or less than 10 ppm.

In contrast to polycrystalline ceramic layers or powder compacts, the substantially amorphous solid electrolyte sheet of the present disclosure is devoid of continuous microscopic pathways, such as contiguous (i.e., interconnected) crystalline grain boundaries or pressed powder interparticle boundaries, or such boundaries in combination with voids and/or cracks which alone or in combination create a continuous microscopic pathway, extending between the first and second principal side surfaces, and, which, if otherwise present, could provide a direct path for dendrite through penetration across the sheet. For example, the cavities and voids on the surface of a pressed powder compact are highly detrimental to dendrite impenetrability as they create highly localized hot spots for current focusing, which can lead to very high local current densities, followed by in-growth of Li metal and through penetration; for example, via crack propagation as material bridges between internal pores inside the powder compact collapse and/or the local current density at the hot spot reaches such a high value that solid Li metal penetrates across.

By "particle-to-particle boundaries" or "inter-particle boundaries" it is meant particle interfaces, including interfaces between regions of consolidated polycrystalline powder-particles, glass-ceramic powder-particles, and amorphous powder-particles (e.g., glass particles), and mixtures thereof; especially amorphous powder-particle to amorphous powder-particle boundaries and interfaces between compacted regions of pressed powder-particles that generally manifest in a pressed powder compact as discontinuities in the form of micro-cracks and voids (e.g., chain-like microvoids). By use of the term particle-to-particle boundary, particle boundary or inter-particle boundary it is referring to the boundary between consolidated powder-particles and compacted regions thereof, whereas crystalline grain boundaries are the interface between crystal grains of different crystalline orientation.

Accordingly, the solid electrolyte sheet of this disclosure is not a polycrystalline Li ion conducting ceramic membrane (e.g., a garnet-like or LTP/LGP membrane or derivatives thereof such as LATP membrane), nor is it a simple compact or hot pressed sinter of consolidated Li ion conducting sulfide glass powder-particles, for which obvious or residual inter-particle boundaries, or manifestations thereof, such as surface voids and internal pores, are generally unavoidable in manufacture, and the liquid-like surface lacks flaw manifestations of a pressed powder compact that are sufficient to initiate Li dendrite penetration. By use of the acronym LTP or LGP membrane it is meant a polycrystalline membrane based on Lithium Titanium Phosphate or Lithium Germanium Phosphate, and when a fraction of the titanium is replaced by Aluminum, the acronym LATP is commonly used. LTP or LGP polycrystalline ceramic membranes, and their compositional derivatives, may be fabricated by conventional solid-state sintering or by using a glass to ceramic approach. However, regardless of processing, LTP/LGP materials must be fully crystallized to be Li ion conductive, and thus only have battery utility as a polycrystalline membrane.

In a glass powder compact, the presence of microscopic inhomogeneities, such as microvoids and microcracks, are generally unavoidable. And while certain processes, such as heated die compaction, if performed over an extended period of time under high uniaxial pressure at or near the glass transition temperature, may provide some relief in the concentration and/or size of internal voids and cracks in a relatively thick pellet, hot compaction is a costly discontinuous batch processes, that is impractical as well as inadequate for eliminating surface flaws, and especially problematic for making thin pellets. During heated powder compaction, surface cavities are generated to account for void volume reduction at the particle interfaces, and if gaseous diffusion is limiting, other features including a scattering of internal pores (including micropores and nanopores) can appear distributed throughout the interior portion of the compact. For instance, thick hot pressed powder pellets, even if translucent or seemingly transparent, have a short finish due to the presence of pitted flaws on their surface, and internal pores will present as surface voids if the pellet is subsequently ground. Surface imprints and surface contamination will also diminish the surface quality, especially if pressing is performed near or at about $T_g$.

To create a dendrite resistant microstructure, the continuous Li ion conducting glass phase is not only amorphous, and thereby devoid of crystalline grains and associated grain boundaries, it is also "vitreous" (i.e., a vitreous glass), which is a term used herein to describe a glass phase, glass layer (e.g., a vitreous glass stratum), or glass article (e.g., a vitreous glass sheet) that is formed directly from the melt or derived from a continuous solidified melt, and thus, is not, and does not contain, compacted or discrete glass-powder particles (e.g., sulfur containing glass-powder particles), and therefore the vitreous glass phase (or more simply vitreous phase) or vitreous glass layer (or more simply vitreous layer) or vitreous glass article (or more simply vitreous article) is also entirely devoid of compacted glass-powder inter-particle boundaries, and thus not a glass powder compact or pressed pellet. Moreover, without intending to be limited by theory it is believed that the ability of the solid electrolyte sheet of the present disclosure to resist and preferably prevent dendritic through penetration in a lithium battery cell is based on its fabrication as a vitreous glass with liquid-like surfaces, by which it is meant a smooth amorphous surface, as resulting from the action of surface tension on a quiescent liquid.

In various embodiments, the freestanding solid electrolyte of the present disclosure is a vitreous monolithic glass sheet having liquid-like surfaces, wherein the continuous Li ion conducting amorphous material phase is a vitreous glass present in an uninterrupted fashion throughout the entirety of the solid electrolyte, and therewith effectively provides a continuous amorphous expanse of vitreous glass (i.e., a vitreous glass matrix) that is pervasive of the entire sheet.

When referring to the freestanding solid electrolyte sheet as a "vitreous monolith," or as a "vitreous monolithic sheet," it is meant by "monolith or monolithic" that the freestanding sheet is of substantially uniform glass composition. Accordingly, the vitreous monolithic sheet is not a laminate or multi-layer of two or more vitreous layers of different composition or microstructure, such as a physical or chemical vapor deposited layer (i.e., CVD or PVD) requiring a substrate for its formation and mere existence, and therefore not freestanding nor a monolith.

The vitreous solid electrolyte glass sheet of this disclosure addresses numerous shortcomings of pressed/hot-pressed sulfide glass powder compacts, polycrystalline ceramic membranes (e.g., garnets and LTP/LGP), and solid polymer electrolyte films (e.g., PEO-like).

For example, powder compaction is fraught with mechanical and electrochemical complications related to surface flaws, inter-particle boundaries and an undue density of void-like defects, which act as stress concentrators that limit strength, thwart flexibility and serve as Li dendrite initiators and facile pathways for dendritic shorting. And while simultaneous heating and pressing (i.e., hot pressing) at high pressures for extended times can be useful for improving inter-particle cohesion, it adds a costly additional step that complicates processing and does not adequately address surface flaws related to dendrite initiation, as expounded on in some detail herein below. Moreover, powder compaction, while suitable for making small pressed pellets, is a batch process that is not scalable, and cannot be used to make long flexible sheets of glass.

Mechanical failure of any glass (e.g., window glass) will occur when the stress and defect size reach a threshold combination. The reliability is therefore statistical, but nonetheless related to the largest sized flaws on the surface. In contrast, small shallow flaws are perceived as less important, since the underlying mechanical strength of the sheet is largely unaffected by their existence. When shallow flaws are small in number density, or even singular, their very existence is generally considered insignificant from a practical perspective.

At practical current densities however, a shallow flaw at an otherwise liquid-like surface can be prohibitive for realizing a dendrite resistant solid electrolyte glass sheet, if the flaw depth is beyond a threshold size for dendrite initiation. In a lithium metal battery cell, wherein a vitreous solid electrolyte sheet is in contact with a solid Li metal anode, a flaw extending beyond a threshold depth can create a highly localized hot spot for current focusing, which can lead to very high local current densities and dendritic penetration of Li metal into the sheet during cell charging, even for electrolytes with elastic moduli well above 20 GPa.

Considerations for determining the threshold flaw depth and the general functional relationship between the local and nominal current densities is described in more detail herein below. Preferably, the deepest flaw extension into the sheet is less than 1% of the sheet thickness, and preferably less than 0.1%, and generally no more than 5 µm. For example, the deepest flaw extension in a 100 µm thick sheet should be less than 1 µm, and more preferably less than 0.1 µm; and for a 50 µm thick sheet it should be less than 0.5 µm, and preferably less than 0.05 µm; and for a 40 µm thick sheet it should be less than 0.4 µm, and preferably less than 0.04 µm; and for a 40 µm thick sheet it should be less than 0.4 µm, and preferably less than 0.04 µm; and for a 40 µm thick sheet it should be less than 0.4 µm, and preferably less than 0.04 µm;

Considering the sensitivity of dendrite initiation to the presence of shallow flaws, processing methods which can yield pristine surfaces are desirable, and special care should be given to minimize contact damage during handling and downstream processing of cell components and cells.

In various embodiments, to achieve a liquid like surface of exceptional smoothness, or to ensure sufficient surface quality commensurate with a specified degree of flexibility or dendrite impenetrability, the instant solid electrolyte sheet may be subjected to a grind and/or polish. Preferably, the need to polish or grind is circumvented by fabricating a vitreous glass sheet having naturally formed high quality liquid-like surfaces with a pre-determined uniform thickness in its virgin state as a solid.

By use of the term "virgin state as a solid" or more simply "virgin state" or even more simply "virgin" when referring to the instant solid electrolyte sheet or its first and second principal side surfaces or the thickness of the sheet, it is meant to refer to the state of the solid electrolyte sheet, state of its surfaces, and its thickness immediately upon the sheet's formation as a solid (i.e., immediately upon solidification). More specifically the virgin state refers to the state of the solid electrolyte sheet immediately upon reaching a temperature below the lowest glass transition temperature ($T_g$) of the sheet, which may be determined by differential scanning calorimetry or differential thermal analysis. When referring to the solid electrolyte sheet or a principal side surface in its virgin state as a solid, it (the sheet or surface) is sometimes more simply referred to as the virgin solid electrolyte sheet or virgin principal side surface. And when referring to a particular property of the virgin solid electrolyte sheet, such as its thickness or surface roughness, the term virgin thickness or virgin surface roughness may be used to refer to the thickness or roughness of the sheet/surface in its virgin state as a solid.

In various embodiments the first and second principal side surfaces of the sheet are untouched by an abrasive foreign surface, and, the desired thickness and thickness uniformity is achieved in its virgin state as a solid. In various embodiments, the first and second principal side surfaces of the virgin solid electrolyte sheet are untouched by a foreign solid surface, and thus said surfaces are chemically and physically pristine (i.e., untouched) in their virgin state—yielding significant advantage as it pertains to surface smoothness, flaws, and contaminants. The pristine surfaces, formed naturally in vacuum or an inert fluid medium (e.g., an inert gaseous environment such as Argon or Helium), are not susceptible to surface imprints or other solid contact imperfections that may accompany solidification in direct contact with a foreign solid body surface. By use of the term "pristine" when referring to surfaces of the solid electrolyte sheet, it is meant that the referenced surfaces, in their virgin state, are untouched by a foreign solid surface.

In various embodiments, the as-solidified solid electrolyte sheet may be referred to herein as a mother-sheet having a high quality center portion, with uniform thickness and preferably smooth liquid-like surfaces, and lower quality peripheral edge portions, which generally extend along its lengthwise dimension, and are removed via a post solidification process of cutting, preferably with a laser beam (i.e., by laser cutting).

In order to achieve the high intrinsic Li ion conductivity as stipulated above for the inorganic amorphous material phase (i.e., $\geq 10^{-5}$ S/cm, preferably $\geq 10^{-4}$ S/cm, and more preferably $\geq 10^{-3}$ S/cm), sulfur-based Li ion conducting glasses are, for this purpose, particularly satisfactory—as the high polarizability of sulfur tends to enhance Li ion mobility by weakening interactions with sulfur-glass forming skeletal ions.

By use of the term "sulfur-based" or "sulfide" when referring to the inorganic Li ion conducting amorphous material phase, and in particular when referring to the inorganic sulfide or sulfur-based glasses, it is meant that the glass composition or glass system contains sulfur and mobile lithium as elemental constituents, and at least one more elemental constituent (e.g., phosphorous, silicon, boron, arsenic and germanium). The terms sulfur-based glass, sulfur-containing glass, and sulfide-glass are used interchangeably herein.

In various embodiments the sulfur-based glass is composed of main elemental constituents, as they are termed, except as additives or secondary elemental constituents are indicated. In various embodiments the main elemental constituents (including sulfur and lithium) have a mole percentage (i.e., atomic percentage) in the glass that is greater than 5% (e.g., at least 10%), and the secondary elemental constituents are present in the glass at a mole percentage of no more than 5%. In various embodiments the main elemental constituents are sulfur, lithium, and one or more selected from the group consisting of phosphorous, silicon, boron, aluminum, oxygen, and germanium (e.g., phosphorous, boron and silicon). In various embodiments the secondary elemental constituents are one or more of phosphorous, silicon, boron, arsenic, aluminum, indium, germanium, selenium, lanthanum, gallium and oxygen.

For the avoidance of doubt, the term "sulfide-glass" or sulfur-based glass is not meant to exclude oxygen or selenium as a constituent element of the glass, and in embodiments oxygen may be one of the main constituent elements. When containing oxygen and sulfur, the sulfide glass is sometimes referred to herein as an oxy-sulfide glass to specify, in the positive, that it contains both sulfur and oxygen. In various embodiments secondary constituent elements (e.g., silicon, oxygen, aluminum and phosphorous) may be incorporated in the glass composition for improving glass stability, increasing viscosity at the liquidus temperature and/or chemical/electrochemical compatibility with Li metal, even at the sacrifice of lower Li ion conductivity. By secondary constituent element it is meant an element present in the glass to an amount that is less than or equal to 5 mole %.

Highly conductive sulfide based Li ion conducting glasses are described in the following documents, all of which are incorporated by reference herein for their disclosure in connection with aspects of this disclosure: in Mercier R, Malugani J P, Fahys B, Robert G (1981) Solid State Ion 5:663; Pradel A, Ribes M (1986) Solid State Ion 18-19:351; Tatsumisago M, Hirai K, Minami T, Takada K, Kondo S (1993) J Ceram Soc Jpn 101:1315; Kanno R, Murayama M (2001) J Electrochem Soc 148:742; Murayama M, Sonoyama N, Yamada A, Kanno R (2004) Solid State Ion 170:173; Hayashi A, Hama S, Minami T, Tatsumisago M (2003) Electrochem Commun 5:111; Mizuno F, Hayashi A, Tadanaga K, Tatsumisago M (2005) Adv Mater 17:918; Mizuno F, Hayashi A, Tadanaga K, Tatsumisago M (2006) Solid State Ion 177:2721; H. Wada, et al., "Preparation and Ionic Conductivity of New $B_2S_3$—$Li_2$ S-LiI Glasses", Materials Research Bulletin, February 1983, vol. 18, No. 2, pp. 189-193; Fuminori Mizuno, et al., "All Solid-state Lithium Secondary Batteries Using High Lithium Ion Conducting $Li_2$ S—$P_2S_5$ Glass-Ceramics", Chemistry Letters 2002, No. 12, The Chemical Society of Japan, Dec. 5, 2002, pp. 1244-1245 (with 2 cover pages); Fuminori Mizuno, et al., "New, highly Ion-Conductive Crystals Precipitated from $Li_2S$—$P_2S_5$ Glasses", Advanced Materials 2005, vol. 17, No. 7, Apr. 4, 2005, pp. 918-921; Tatsumisago Masahiro., "Glassy Materials Based on $Li_2$ S for All-Solid-State Lithium Secondary Batteries" (2004) Solid State Ionics 175: 13-18; T. Ohtomo, F. Mizuno, A. Hayashi, K. Tadanaga, and M. Tatsumisago, "Mechanochemical Synthesis of Lithium Ion Conducting Glasses and Glass-Ceramics in the System $Li_2S$—P—S" (2005) Solid State Ionics 176: 2349-2353; US Patent Pub. No.: 20070160911; and U.S. Pat. No. 8,012,631.

Li ion conducting sulfide glasses are advantageous in several respects. Firstly, their Li ion conductivity is high, and secondly they are soft relative to other inorganic materials, so when fabricated by mechanical milling, the powder particles may be pressure formed to a compact. As a bulk glass, however, Li ion conducting sulfides have been previously perceived as prohibitively difficult to process into any sort of battery serviceable cell component, and work in that area focused on characterizing compositions and examining conductivity in pellets made by pulverizing the glass to a powder and pressing. Indeed, the perception that Li ion conducting sulfide glasses are highly prone to crystallization on cooling and highly susceptible to devitrification on heating is understandable. Li ion conducting sulfide glasses are considerably more fragile than oxide glasses, and the high ionic conductivity is predicated on having large amounts of bond breaking Li ions, which further destabilizes the glass. Perhaps this perception, combined with: i) their sensitivity to moisture and oxygen at high temperature; and ii) the advent of relatively simple and direct low temperature mechanical milling approaches to making Li ion conducting sulfide glass powders, has effectively led the industry to move exclusively in the direction of mechanically milling powders, followed by pressing powder compacts to fabricate components. Moreover, the mechanical milling approach seemingly has all the advantages of a low temperature process without any disadvantage. Previously unrecognized, however, is that cold shaped or hot pressed sulfide based solid electrolyte powder constructs are ultimately flawed both electrochemically and mechanically. Moreover, pressing dense powder compacts is not a scalable process, and it is certainly not conducive to making long continuous sheets of glass, or a web.

It has been unexpectedly discovered that battery serviceable freestanding vitreous sheets of sulfide based solid electrolyte glass, entirely devoid of powder inter-particle boundaries and residual imperfections thereof (such as surface voids and internal pores) can be formed in a different way. Li ion conducting sulfide glasses have been found to possess kinetic stability beyond that expected based on literature reports, thermodynamic properties, and rheological characteristics, and it is postulated that causing, or allowing, the sulfide glass to flow may enhance stability, and thereby improve glass formability as well as stability against crystallization, and, in particular, facilitate drawing the glass from a fluid or liquid state (e.g., drawing the sulfide glass from a preform or pulling on it as a molten sheet). In this way, a battery serviceable freestanding vitreous sheet of sulfide based Li ion conductive solid electrolyte glass, preferably substantially impenetrable to Li dendrites, and entirely devoid of powder inter-particle boundaries and residual imperfections derived from pressing a powder compact, may be formed.

In another aspect, this disclosure is directed to methods of making a thin dense wall structure of an inorganic Li ion conducting amorphous material phase, and, in particular embodiments, the wall structure is a thin vitreous sheet of sulfide-based Li ion conducting glass, and in various embodiments formed as a continuous web having substantially parallel lengthwise edges, and sufficient flexibility to be wound into a continuous roll without fracture.

In various embodiments the methods of this disclosure involve forming a Li ion conductive sulfide based glass material into a thin inorganic fluid sheet of unbroken continuity, and causing or allowing the fluid sheet to flow along its lengthwise dimension prior to solidifying (i.e., the flowing fluid sheet a fluid stream of glass). In various embodiments, the fluid stream of unbroken continuity retains substantially parallel lengthwise edges as it flows, and the stream has at least high quality center portion that is thin and preferably of substantially uniform thickness ≤500 µm.

By use of the term "fluid sheet" when referring to methods of making of the instant solid electrolyte sheets it refers to the sheet, or a section thereof, at a temperature that is greater than the glass transition temperature ($T_g$) of the material from which the sheet is made, and typically significantly higher than $T_g$. By use of the term "fluid stream" it is meant the fluid sheet flowing, and typically caused to flow by gravity and/or an external force, such as motorized pulling rods or rollers. In some embodiments, the fluid stream of unbroken continuity is formed from a liquid melt of a sulfur-containing glass, at or above the liquidus temperature ($T_{liq}$). In other embodiments the fluid stream of unbroken continuity is formed by heating a solid preform of sulfur-containing glass to a temperature at which it deforms under its own weight (e.g., above the softening temperature of the glass preform).

Recognizing the benefit of perfecting the sulfide glass into a vitreous monolith as opposed to a powder construct, methods and modified sulfur-based glass compositions that are less prone to crystallization and/or have higher melt viscosities but still retain a requisite level of Li ion conductivity (>$10^{-5}$ S/cm) have been developed. In particular, methods for increasing the glass stability factor and/or Hruby parameter, including increasing the amount of oxygen in the glass, increasing the oxygen to sulfur mole ratio, increasing the amount of oxide network former in the glass, increasing the ratio of oxide network former to sulfide network former, incorporating silicon for network forming, decreasing the amount of bond breaking lithium ions, tuning the composition of the base sulfide glass to have more than 4 elemental constituents (e.g., 5 main elemental constituents: S, Li, B, P, and O) or more than 5 elemental constituents (e.g., 6 main elemental constituents: S, Li, Si, B, P, and O) and combinations thereof are described. In addition, additives to the base glass are also contemplated for use herein as devitrifying agents and crystallization inhibitors.

Moreover, while apparently counterintuitive to decrease the Li ion conductivity of a glass that is specifically intended for use in a battery cell as a Li ion conductor, in various embodiments this is the approach contemplated herein for making and improving properties of the vitreous solid electrolyte sheets of this disclosure. Accordingly, in various embodiments the composition of the glass is adjusted to enhance thermal properties at the sacrifice of reduced conductivity.

A number of terms are used in the description for discussing the thermal properties of the glass. $\{T_x-T_g\}$ is the difference between the onset of crystallization ($T_x$) and the glass transition temperature ($T_g$), and is also referred to herein as the glass stability factor; $\{T_n-T_x\}$ is the difference between the temperature at which the glass is drawn ($T_n$) and the onset of crystallization. The liquidus temperature is ($T_{liq}$), and the viscosity of the glass at $T_{liq}$, is the liquidus viscosity. The melting temperature of the glass is ($T_m$). The strain temperature is the temperature at which the viscosity of the glass is approximately $10^{14.6}$ poise, and stresses may be relieved in hours. The annealing temperature is the temperature at which the viscosity is approximately $10^{13.4}$ poise, and stresses in a glass may be relieved in less than 1 hour or minutes. And finally, the softening temperature is defined as the temperature at which the glass has viscosity of $\sim 10^{7.6}$ poise. The glass is usually suitable for drawing at or above this temperature.

Several techniques exist for the measurement of these characteristic temperatures. Differential scanning calorimetry (DSC) and differential thermal analysis (DTA) are the most common. Generally, a large separation between $T_x$ and $T_g$ (i.e., a large glass stability factor) is desirable for drawing glass.

Another method of determining or estimating glass stability is through the Hruby parameter ($H_r$ parameter), as given by the following equation:

$$Hr = \frac{Tx - Tg}{Tm - Tc}$$

A high value of $H_r$ Suggests high glass stability, and the larger, the more stable the glass against crystallization. For example, a glass having $H_r<1$, is generally highly prone to crystallization and considered unstable.

In another aspect, the vitreous solid electrolyte sheet of Li ion conducting sulfide glass is manufactured in the form of a standalone vitreous web of glass. In various embodiments multiple discrete solid electrolyte sheets or ribbons are cut to size from the vitreous Li ion conducting glass web. In various embodiments the vitreous web is sufficiently thin, long and robust when flexed that it can be wound without fracture. In various embodiments, the web is wound about a spool to yield a continuous supply roll, or source roll, for storage, transportation, and/or R2R manufacture of downstream cell components and battery cells. When referring to the rolled web (e.g., rolled about a spool), the term coil is sometimes used herein interchangeably with the term roll.

In other aspects the disclosure provides battery cell components composed of the solid electrolyte sheets of this disclosure, including electrode sub-assemblies and electrode assemblies (e.g., positive and negative electrode assemblies), including sealed fully solid-state Li metal electrode assemblies, encapsulated electrode assemblies, and electrode assemblies having an unconstrained backplane architecture.

In yet other aspects the disclosure provides web laminates wherein the vitreous Li ion conducting glass web serves as a substrate for the formation of an electrode sub-assembly web and an electrode assembly web.

And in other aspects there are provided herein lithium battery cells comprising the solid electrolyte sheets and cell components of this disclosure, including lithium ion cells, lithium metal battery cells, hybrid lithium battery cells, solid-state lithium battery cells, and cells having a common liquid electrolyte.

Figure 1B:
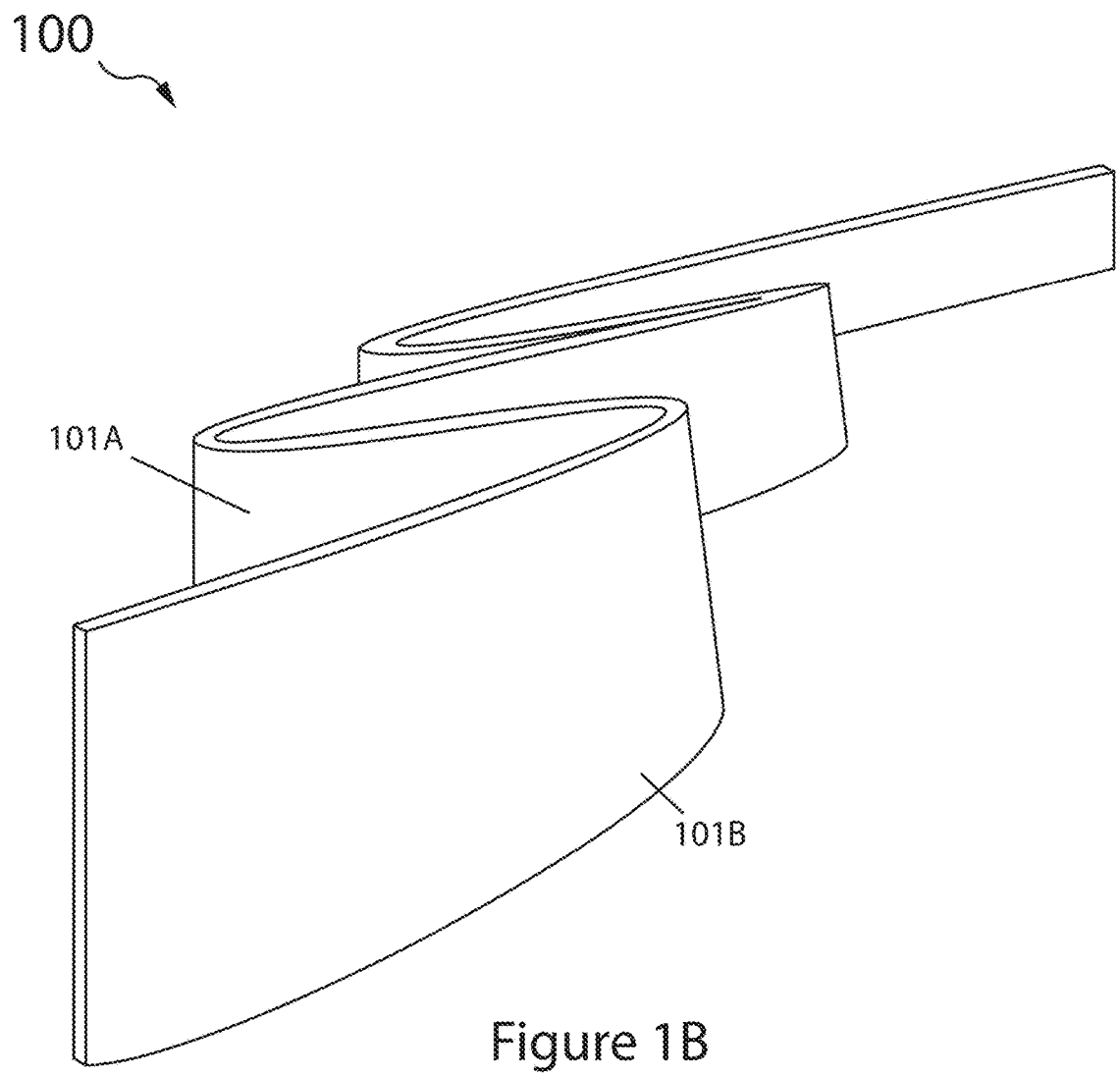
Figure 1C:
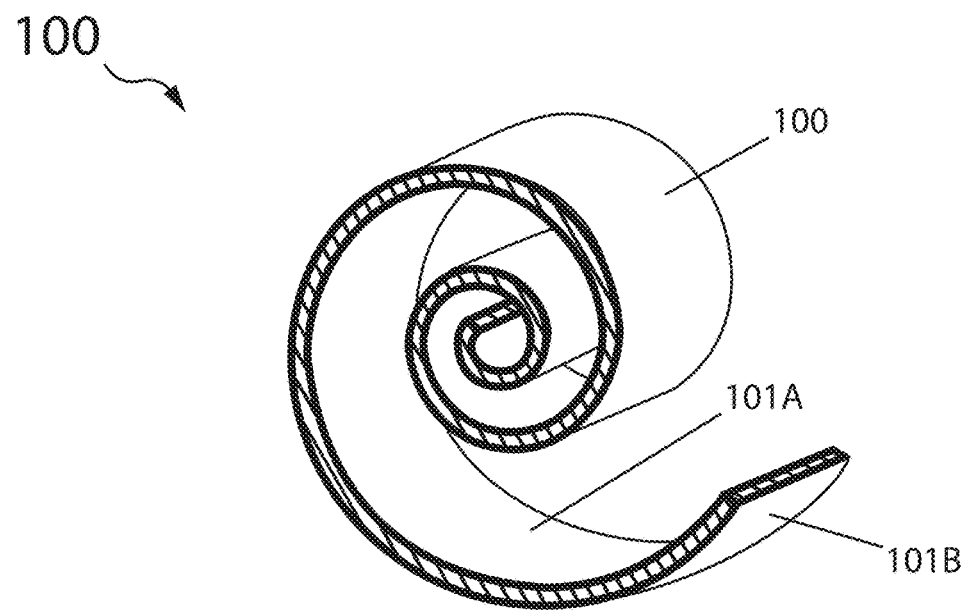
Figure 1D:
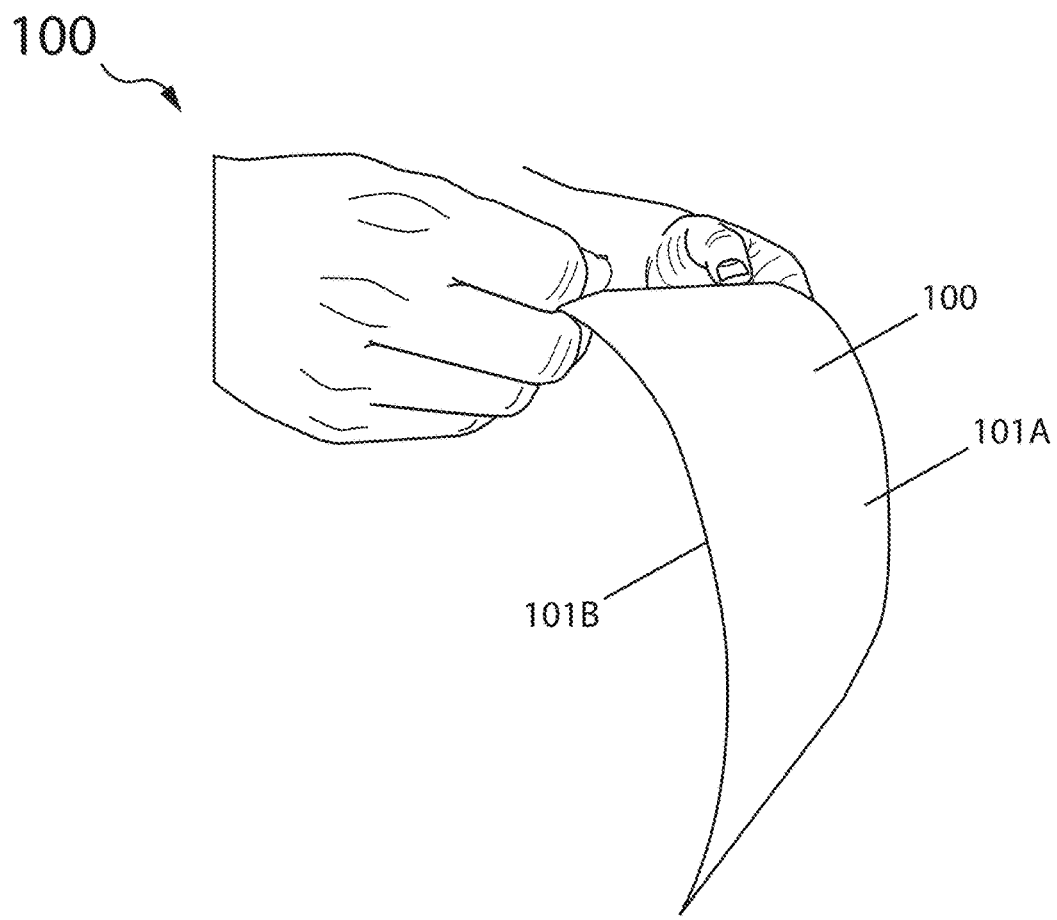
Figure 2A:
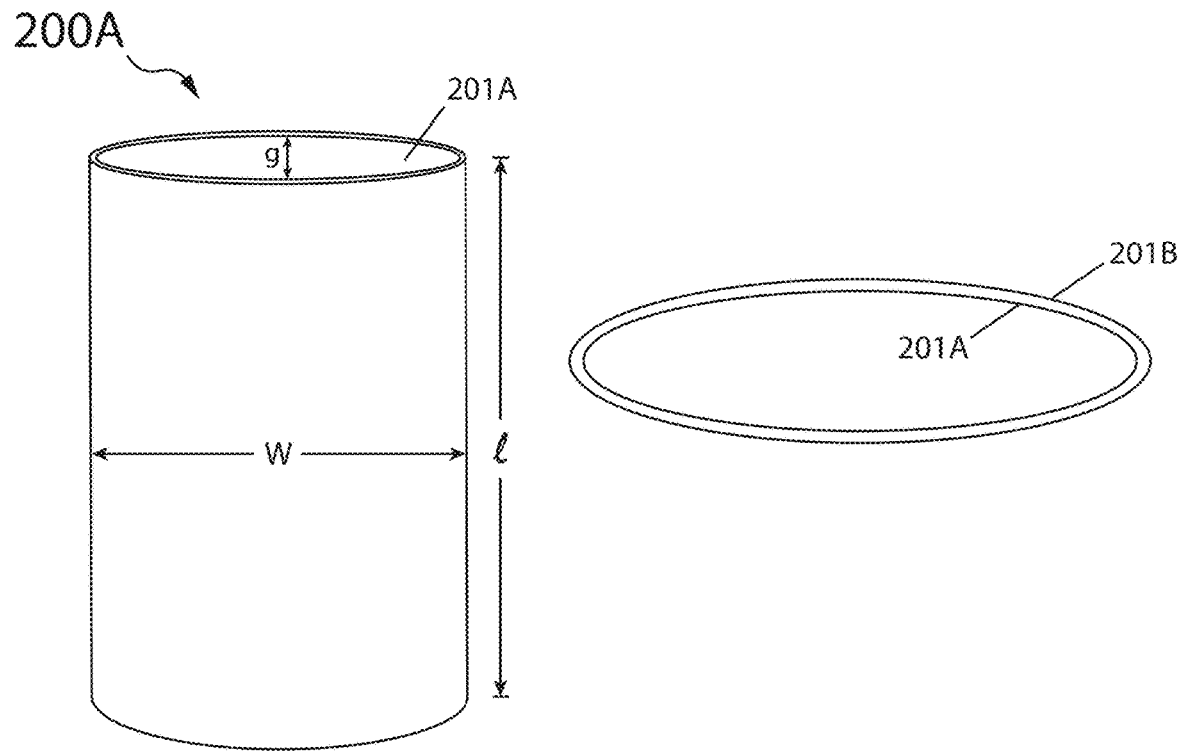
FIGS. 2A-B illustrate freestanding Li ion conducting solid electrolyte wall structures in accordance with various embodiments of the instant disclosure.
Figure 2B:
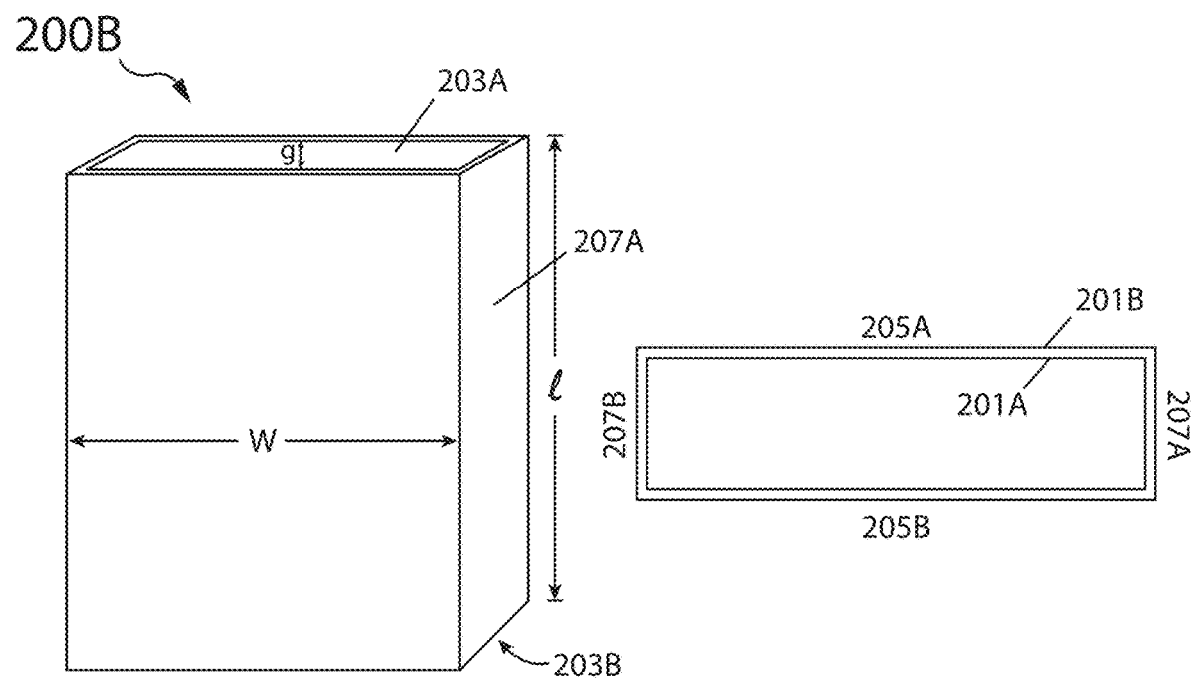

With reference to FIGS. 1A-D and FIGS. 2A-B there are illustrated Li ion conductive thin solid electrolyte wall structures 100 and 200A-B in accordance with various embodiments of this disclosure (i.e., solid electrolyte wall structures), as described above and herein below. Effectively, the solid electrolyte wall structure, as it is referred to herein, is a dense freestanding and substantially amorphous inorganic layer that is highly conductive of Li ions and composed of a continuous inorganic and amorphous material phase having intrinsic room temperature Li ion conductivity $\geq 10^{-5}$ S/cm, preferably $\geq 10^{-4}$ S/cm, and more preferably $\geq 10^{-3}$ S/cm. In various embodiments, the wall structure is in the form of a long sheet or ribbon 100 (see FIGS. 1A-D). However, in other embodiments the solid electrolyte layer is articulated to yield a wall structure in the form of a hollow prism-like receptacle, as shown in FIGS. 2A-B.

Notably, the continuous nature of the amorphous material phase is uninterrupted and thus gives rise to a bulk microstructure that is devoid of interconnected void-like pathways (e.g., grain boundaries or particle boundaries), which, if otherwise present, would allow facile penetration of lithium metal dendrites across the thickness of the layer (i.e., the wall). Preferably, the wall structure bears a liquid-like surface that renders it substantially impenetrable to lithium metal dendrites, and thus, when incorporated as a Li ion-conducting component in a solid electrolyte separator (or as the separator itself), the wall structure, entirely inorganic, is enabling for the realization of a reliable and safe lithium metal secondary battery.

With reference to FIGS. 1A-D, solid electrolyte wall structure 100 is a freestanding substantially amorphous and inorganic Li ion conducting solid electrolyte sheet (e.g., a long relatively narrow ribbon) having first and second opposing principal sides (101A and 101B respectively) and associated principal side surfaces, substantially parallel lengthwise edges, length dimension (l), width dimension (w), average thickness dimension (t), and an area aspect ratio defined as (l/w). Solid electrolyte sheet 100 is highly conductive of Li ions, and has Li ion conductivity, as measured between its first and second principal side surfaces, of at least $10^{-5}$ S/cm, preferably at least $10^{-4}$ S/cm, and more preferably at least $10^{-3}$ S/cm.

In various embodiments sheet 100 is thin with substantially uniform thickness (t), as measured between its first and second principal sides. By thin it is meant no thicker than about 500 μm, preferably no thicker than 250 μm, more preferably no thicker than 100 µm, and even more preferably no thicker than 50 µm. In various embodiments the vitreous solid electrolyte glass sheet has substantially uniform thickness and preferably uniform thickness in the range of 5≤t≤500 µm. In particular embodiments it has substantially uniform thickness and preferably a uniform thickness in the range of: 5≤t<10 µm; 10≤t<30 µm; 50≤t<50 µm; 50≤t<100 µm; 100≤t<250 µm; and 250≤t≤500 µm. Thicker solid electrolyte sheets, greater than 500 µm, are also contemplated for some applications, and may be of particular utility for grid storage backup, which does not necessarily require flexibility or high power density (Wh/l). For example, thick sheets having a uniform thickness in the range of 500 µm<t≤2 mm are contemplated for this purpose. Preferably, the specified thickness and thickness uniformity of the solid electrolyte sheet is achieved in its virgin state as a solid, and by this expedient benefit is gained in terms of cost, scaling and surface quality.

In various embodiments sheet 100 is large and readily scalable in size. In various embodiments solid electrolyte sheet 100 is greater than 10 cm², greater than 25 cm², greater than 50 cm², greater than 100 cm², or greater than 1000 cm². In various embodiments, freestanding solid electrolyte sheet 100 is long with substantially parallel lengthwise edges and a length dimension ≥10 cm, ≥20 cm, ≥30 cm, ≥50 cm, and ≥100 cm. In various embodiments, the width dimension of the long sheet is between 1 to 5 cm (e.g., about 1 cm, about 2 cm, about 3 cm, about 4 cm, or about 5 cm wide) or between 5 to 10 cm (e.g., about 5 cm, or about 6 cm, or about 7 cm, or about 8 cm or about 9 cm, or about 10 cm wide). In various embodiments the solid electrolyte sheet is in the shape of a thin ribbon of substantially uniform thickness and preferably uniform thickness as described above; and, for instance, the ribbon having length (l)≥10 cm, width (w) between 1 to 10 cm, and area aspect ratio (l/w)≥5, (l/w)≥10, (l/w)≥20. For example, the solid electrolyte sheet may have an area aspect ratio in the range of 5 to 20. The sheet may be cut into discrete pieces of suitable size for use, such as a separator, in a battery cell or as a battery cell component.

Sheet 100 Should have low area specific resistance (ASR), as measured between its first and second principal side surfaces. In accordance with the disclosure, the area specific resistance is sufficiently low to be battery serviceable, and substantially uniform across the entirety of the sheet. Preferably the sheet has area specific resistance <200 Ω-cm², more preferably <100 Ω-cm², even more preferably <50 Ω-cm²; and yet even more preferably <10 Ω-cm². When measured at various local points, the ASR preferably varies by less than 20% from the average value, more preferably the variance is less than 10%, and even more preferably less than 5%. For instance, if the ASR is about 100 Ω-cm², the area resistance at localized positions along the sheet is preferably between 80 to 120 Ω-cm², and more preferably between 90 to 110 Ω-cm², and yet even more preferably between 95 to 105 Ω-cm². To achieve such low ASR, the solid electrolyte sheets of this disclosure are highly conductive of Li ions, with conductivity of at least $10^{-5}$ S/cm, preferably ≥$10^{-4}$ S/cm and even more preferably ≥$10^{-3}$ S/cm.

With particular reference to FIGS. 1B-C, freestanding and substantially amorphous inorganic solid electrolyte sheet 100 is flexible, and preferably sufficiently robust when flexed that it can be rolled on a drum or spool for storage and/or transportation, and therefore suitable for roll processing, including roll-to-roll (R₂R) manufacturing (i.e., it is R₂R suitable), or for winding or folding into a battery cell.

Flexibility of sheet 100 is dependent upon its Young's modulus, thickness, and surface quality; and, in particular, the quantity and size of spurious edge cracks which may be present on its first or second principal side surfaces 101A/101B. The flexibility of sheet 100 may be characterized by its bending-radius (r), when the sheet is caused to bend without breaking. The bending-radius is defined as the minimum radius of the arc at the bending position where the sheet reaches maximum deflection before kinking or damaging or breaking. In various embodiments sheet 100 is sufficiently flexible to enable R₂R processing and preferably allow its use as a separator in a battery cell of wound or folded construction. For example, sheet 100 having a bending-radius ≤100 cm, preferably ≤50 cm, more preferably ≤10 cm, even more preferably ≤5 cm, yet even more preferably ≤2.5 cm. Or to enable its use in a wound/folded battery cell, the sheet having a bending-radius ≤2.5 cm, preferably ≤1 cm, more preferably ≤0.5 cm, even more preferably ≤0.25 cm, and yet even more preferably ≤0.1 cm.

Flaw location is also important, as the edges generally contain larger flaws. In various embodiments, if the solid electrolyte sheet is cut, it may be important to edge finish (e.g., by fire polishing). To be flexible enough to achieve a suitable bending-radius for roll manufacturing or battery cell winding, care should be taken in handling the solid electrolyte sheet to ensure that edge flaws are kept to a minimum. The threshold edge flaw size allowable depends on the thickness of the sheet (t), Young's modulus (E), fracture toughness ($K_{Ic}$) and the desired bending-radius (r), which, for the threshold crack size, may be ascertained from $4r^2(K_{Ic})^2/(\pi E^2 d^2)$. In various embodiments, the Young's modulus (E) of sheet 100 is less than 90 GPa, and edge cracks >10 µm should be avoided. Preferably solid electrolyte sheet 100 is devoid of any edge crack >10 µm, and preferably >5 µm, more preferably devoid of edge cracks >3 µm or >2 µm, and even more preferably devoid of edge cracks >1 um.

In accordance with the present disclosure, the instant solid electrolyte sheets are battery serviceable, and in various embodiments suitable for use as a continuous solid electrolyte separator in a variety of lithium battery cells, including cells of wound or stacked construction and moderate to high capacity (1 Ah-100 Ah).

In various embodiments freestanding sheet 100 is of battery serviceable size, shape, flexibility and thickness to serve as a continuous solid electrolyte separator in a battery cell defined by one or more of: i) a wound, folded or stacked construction; ii) a square, circular, rectangular or cylindrical footprint; iii) a rated cell capacity in the range of 250 mAh-500 mAh; 500 mAh-1 Ah, 1 Ah-5 Ah, 5 Ah-10 Ah, 10 Ah-20 Ah, 20 Ah-50 Ah, and 50 Ah-100 Ah; and iv) an area electrode capacity between 0.5 mAh/cm²-10 mAh/cm². By continuous solid electrolyte separator it is meant that the sheet provides a continuous separator between positive and negative electroactive layers of a cell in which it (sheet 100) is disposed.

In a particular embodiment, sheet 100 is battery serviceable as a continuous solid electrolyte separator in a lithium battery cell of wound or folded construction, and thus solid electrolyte sheet 100 has substantially parallel lengthwise edges and sufficient flexibility to be wound, typically around a mandrel, or folded, with a bending-radius ≤2.5 cm, preferably ≤1 cm, more preferably ≤0.25 cm, and yet even more preferably ≤0.1 cm.

In another particular embodiment solid electrolyte sheet 100 is battery serviceable as a continuous solid electrolyte separator in a lithium battery cell having a rated capacity in the range of 250 mAh-500 mAh and an area electrode capacity between 0.5-5 mAh/cm$^2$, and thus the continuous area of sheet 100 is in the range of 25 cm$^2$-1000 cm$^2$, and more typically in the range of about 125 cm$^2$-1000 cm$^2$ or about 250 cm$^2$-1000 cm$^2$. For example, sheet 100 having a width in the range of 0.5 cm-10 cm (e.g., about 1 cm-5 cm) and a length in the range of 20 cm-100 cm (e.g., about 50 cm to 100 cm).

In another particular embodiment continuous solid electrolyte sheet 100 is battery serviceable as a continuous separator layer in a lithium battery cell having a rated capacity in the range of 500 mAh-1 Ah and an area electrode capacity between 1-5 mAh/cm$^2$, and thus the continuous area of sheet 100 is in the range of 100 cm$^2$-1000 cm$^2$. For example, sheet 100 having a width in the range of 1 cm-10 cm (e.g., about 2 cm-5 cm) and a length in the range of 50 cm-500 cm.

In yet another particular embodiment sheet 100 is battery serviceable as a continuous separator layer in a lithium battery cell having a rated capacity in the range of 1 Ah-5 Ah and an area electrode capacity between 1-5 mAh/cm$^2$, and thus the continuous area of sheet 100 is in the range of 200 cm$^2$-5000 cm$^2$. For example, sheet 100 having a width in the range of 1 cm-10 cm (e.g., about 5 cm-10 cm) and a length in the range of 100 cm-1000 cm.

In still yet another particular embodiment sheet 100 is battery serviceable as a continuous separator layer in a lithium battery cell having a rated capacity in the range of 5 Ah-10 Ah and an area electrode capacity between 1-5 mAh/cm$^2$, and thus the continuous area of sheet 100 is in the range of 1000 cm$^2$-10000 cm$^2$. For example, sheet, 100 having a width in the range of 5 cm-10 cm and a length in the range of 100 cm-2000 cm.

In various embodiments, sheet 100 is battery serviceable for use as a continuous solid electrolyte separator in a lithium battery cell of defined rectangular footprint, including the cell having a width in the range of about 0.5 cm to 10 cm, and a rated cell capacity (Ah) and area electrode capacity (mAh/cm$^2$) as stipulated above for the various particular embodiments. For instance, sheet 100 having length dimension ≥10 cm, ≥20 cm, ≥30 cm, ≥50 cm, and in some embodiments ≥100 cm. For example, a width dimension between about 1 cm to 5 cm, and a length dimension between 10 cm to 50 cm (e.g., the width about 5 cm and the length about 20 cm-50 cm) or a width dimension of 5 cm to 10 cm and a length dimension of 50 cm to 100 cm.

The afore described battery serviceable characteristics (e.g., length, area, aspect ratio, uniform thickness, and flexibility) are not trivial for a vitreous sulfide-based solid electrolyte glass sheet, and such sheets should be held in stark contrast to that of Li ion conducting sulfide glass flakes made by rapid twin roller quenching, mechanically milled or pulverized glass powders, and unwieldy melt/quenched blobs which are generally irregularly shaped pieces of glass having virtually no dimensional or geometric shape tolerances, and therefore of inapplicable size, shape and thickness to be battery serviceable. In contradistinction, the thin vitreous solid electrolyte sheets of this disclosure are manufacturably reproducible, scalable and of battery serviceable size, shape, and uniform thickness.

Continuing with reference to FIGS. 1A-D, solid electrolyte sheet 100 is freestanding and not surrounded or supported by an external substrate or structure that serves as a support structure, such as a supporting material layer, dense or porous. Accordingly, freestanding solid electrolyte sheet 100 is a self-supporting layer that is not only devoid of a supporting electrode structure (e.g., a positive electrode layer), it is also devoid of inert supporting material layers, such as porous or dense carrier or release layers. Accordingly, in various embodiments the instant freestanding sulfide based solid electrolyte sheet is substrate-less, and by this it is meant to include the absence of an interior substrate within the bulk of sheet 100 (i.e., an internal supporting structure), as well as the absence of an exterior substrate covering principal side surfaces 101A or 101B. Moreover, solid electrolyte sheet 100 is completely inorganic, and therefore does not contain any organic polymeric binder material, or the like.

In various embodiments, solid electrolyte sheet 100 is cut-to-size from the high quality center portion of a mother-sheet. For instance, with reference to FIGS. 1E-F, there is illustrated a mother-sheet of vitreous Li ion conducting sulfur-containing glass made, for instance, by melt drawing or preform drawing. Mother-sheet 100M may be characterized as having a high quality center portion 105 and lower quality edge portions 107 which are removed by slicing (e.g., via laser cutting). To ensure utmost quality, peripheral portions of the high quality center region 105x are generally removed during the lengthwise cutting procedure.

Preferably, the high quality center portion 105 accounts for at least 20% of the mother-sheet's footprint/area (e.g., at least 30%, at least 40%, at least 50%, at least 60%, at least 70%, at least 80%, or at least 90%). Preferably the mother-sheet is of sufficient quality that it requires minimal or no edge removal in order to yield a solid electrolyte sheet with uniform thickness and/or smooth surfaces.

Preferably the high quality center portion of mother-sheet 100M has sufficient surface quality to circumvent the need to perform a post-solidification polishing step. For instance, in various embodiments, the major opposing surfaces of the high quality center portion of mother-sheet 100M has an average surface roughness $R_a$<1.0 m, preferably <0.5 µm, more preferably $R_a$<0.2 µm, even more preferably $R_a$<0.1 µm, yet even more preferably $R_a$≤0.05 µm, or $R_a$≤0.05 µm, or $R_a$≤0.01 µm. In addition to high surface quality, the high quality center portion is preferably of thickness and thickness uniformity to circumvent the need to grind down its surfaces, or more generally remove material from the surfaces in order to achieve a desired thickness and/or thickness uniformity. In various embodiments, the surfaces of the high quality center portion of mother-sheet 109 are chemically and physically pristine in their virgin state, and thus untouched by a foreign solid surface upon solidifying.

In accordance with the foregoing, in various embodiments, the cut-to-size virgin solid electrolyte sheet, or the high quality center portion of the as-solidified mother sheet, or the entire mother sheet itself, possesses one or more of the following characteristics: i) a thin uniform thickness ≤500 µm (e.g., ≤100 µm); ii) pristine liquid-like first and second principal side surfaces; iii) substantial flatness; iv) average surface roughness $R_a$<1 µm; v) sufficient surface quality and thinness to enable flexibility commensurate with winding the solid electrolyte sheet to a radius of curvature ≤10 cm without fracturing; pristine first and second principal side surfaces having optical quality.

Figure 1G:
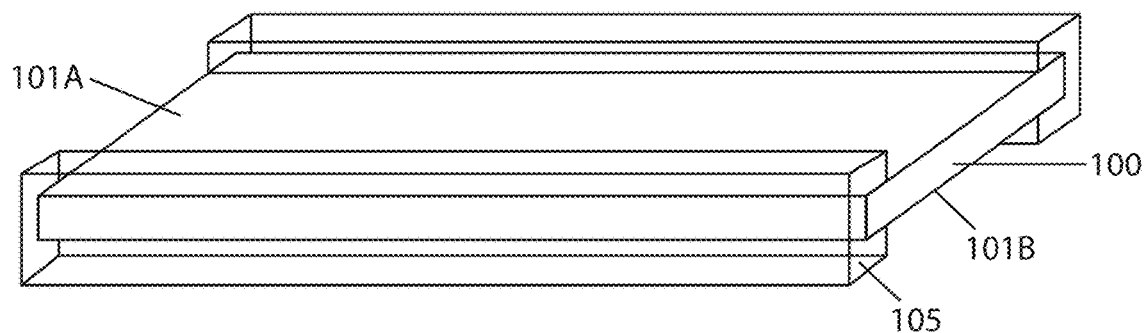
FIG. 1G illustrates a freestanding Li ion conducting solid electrolyte sheet of this disclosure having a discrete edge-protector element.

With reference to FIG. 1G there is illustrated an edge protected electrolyte sheet 101G composed of sheet 100 fitted with electrically insulating edge-protector element(s) 105, which, in addition to safeguarding against physical damage to an edge, provide ancillary benefit as it pertains to mechanical strength and wind-ability, including embodiments wherein the edge-protector elements are engineered as a spacer to prevent contact between adjacent surfaces when it (the sheet) is wound as a continuous roll of solid electrolyte sheet (e.g., as a supply or source roll). In various embodiments the edge-protector elements may be a polymer film, such as a tape adhered to and covering the edges, or a rigid square-like polymeric bracket snug fit to the edges; the edge-protector element(s) may be removable or permanent.

Figure 1H:
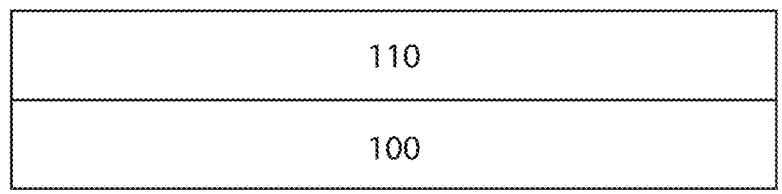
FIG. 1H illustrates an electrode subassembly of this disclosure.

Notwithstanding the freestanding nature of solid electrolyte sheet 100, this disclosure contemplates that freestanding and substrate-less sheet 100 may have on one or both of its principal side surfaces a material layer, such as a coating or thin film, that serves, in part or in whole, to protect one or both principal surfaces, but it (the protective material coating/film) is not relied upon to support the sheet. Indeed, quite the opposite, the sheet in such instances is generally relied upon to serve as a substrate support for the surface protecting material layer. For instance, as illustrated in FIG. 1H and described in more detail herein below, in various embodiments freestanding solid electrolyte sheet 100 may be subjected to a coating process whereby the first and/or second material side surface 101A and/or 101B is coated with one or more thin material layers 110 to form what is termed herein an electrode sub-assembly 101H, which is effectively sheet 100 coated by material layer 110. In various embodiments layer 110 is a tie-layer that protects surface 101A while also providing a reactive/bonding layer for making intimate contact with Li metal on contact, or layer 110 may be a current collector coating, or layer 110 may be a multi-layer of a tie-layer and a current collecting layer. Generally, material layer(s) 110 of electrode sub-assembly 101H are not Li ion conducting layers (i.e., $\sigma^{Li} < 10^{-9}$ S/cm). However, the disclosure does contemplate otherwise, and in such instances, the Li ion-conducting layer is coated directly onto the first and/or second principal side surface (101A and/or 101B), optionally followed by a tie-layer and/or current collector coating. Accordingly, in various embodiments, the instant freestanding solid electrolyte sheet serves as a substrate for making a battery cell or an electrode assembly, and thereby, when used as such, sheet 100 is sometimes referred to herein as a substrate-sheet. For instance, the first or second principal side surface may be coated with a thin Li ion conducting glass film for improved chemical compatibility in contact with Li metal or battery cell components (e.g., a sulfide glass of different composition or a very thin lithium oxide, lithium phosphate or lithium oxynitride glass film). Indeed, the freestanding nature of the vitreous solid electrolyte sheet combined with its smooth liquid-like surfaces, provides significant advantage for creating and utilizing dense exceptionally thin surface films (e.g., <1 µm thick, or <0.5 µm thick, or <0.1 µm thick), and so enabling of glassy inorganic materials with intrinsic Li ion conductivity less than $10^{-6}$ S/cm.

Continuing with reference to FIGS. 1A-D, standalone solid electrolyte sheet 100 is clearly devoid of an exterior substrate, as its principal side surfaces are directly exposed or directly exposable to the adjacent ambient gaseous environment. For instance, in various embodiments substrate-less sheet 100 (flexible or otherwise) may be handle-able by gloved hand or apparatus, and remain intact when placed in a suspended state (e.g., when dangled by holding the sheet along an edge). Standalone and freestanding sheet 100 is not a PVD or CVD layer that requires a substrate for its formation and existence. In fact, in various embodiments substrate-less sheet 100 may be fabricated in the absence of a substrate or even in the absence of a contacting surface (such as a mold surface). In such embodiments, solid electrolyte sheet 100 is formed with both first and second principal side surfaces fully exposed to the ambient gaseous environment (inert). And by this expedient, the sheet so formed, is absent imperfections, imprints, chemical reaction products, and contaminants that would otherwise appear on or nearby its surface if the sheet were solidified in direct contact with a foreign solid body surface.

In various embodiments sheet 100 is fabricated to ensure that it is substantially impervious to liquids that it may contact during operation of a device in which it is incorporated, such as a liquid electrolyte in a battery cell of the instant disclosure. In such embodiments sheet 100 Should be free (i.e., devoid) of through porosity including pinholes or defects which would otherwise allow a liquid electrolyte to seep through the sheet from the first to the second principal side, or vice versa. In other embodiments liquid impermeability is not a requisite property of the solid electrolyte sheet, albeit perhaps a desirable one; for instance, sheet 100 incorporated in a fully solid-state battery cell as a solid electrolyte separator.

With reference to FIGS. 1A-D, in various embodiments at least first principal side surface 101A is chemically compatible in direct contact with lithium metal, and in some embodiments both first and second principal side surfaces 101A/101B are chemically compatible in direct contact with lithium metal. However, the disclosure is not limited as such, and in some embodiments the first and/or second principal side surfaces may be chemically incompatible in direct contact with lithium metal. For instance, solid electrolyte sheet 100 may be employed as a solid electrolyte separator disposed between a pair of porous separator layers or gel layers impregnated with a liquid electrolyte, or solid electrolyte sheet 100 may be coated (on one or both principal side surfaces) with a glassy Li ion conducting film to form a solid-state protective membrane architecture as described in more detail herein below.

In alternative embodiments, as illustrated in FIGS. 2A-B, the freestanding substantially amorphous and inorganic Li ion conducting solid electrolyte layer, as described above, provides a wall structure in the form of a hollow prismatic receptacle 200A-B, having interior and exterior surfaces 201A and 201B, length dimension (l), width dimension (w) and layer/wall thickness dimension (t). When a prismatic receptacle, the two parallel end portions (203A/203B) are typically open (as shown), but the disclosure is not limited as such, and it is contemplated that the wall structure may have a closed end defined by the solid electrolyte layer in contiguity with the receptacle portion. Moreover, hollow prism 200A-B may be further characterized as having major and minor opposing lateral wall portions, specifically major opposing wall portions 205a and 205b, and minor opposing wall portions 207a and 207b. In a particular embodiment wall structure 200A is a hollow prism in the form of an open-ended elliptical cylinder. In another embodiment the wall structure is a hollow rectangular prism 200B, optionally having exterior and/or interior corners substantially rounded as shown in FIG. 2B. Moreover, the interior volume (V) is defined by the interior gap (g), width dimension (w) and length dimension (l), and when elliptical, the interior gap is defined as the distance across the semi-minor axis of the elliptically shaped end portion.

Figure 3A:
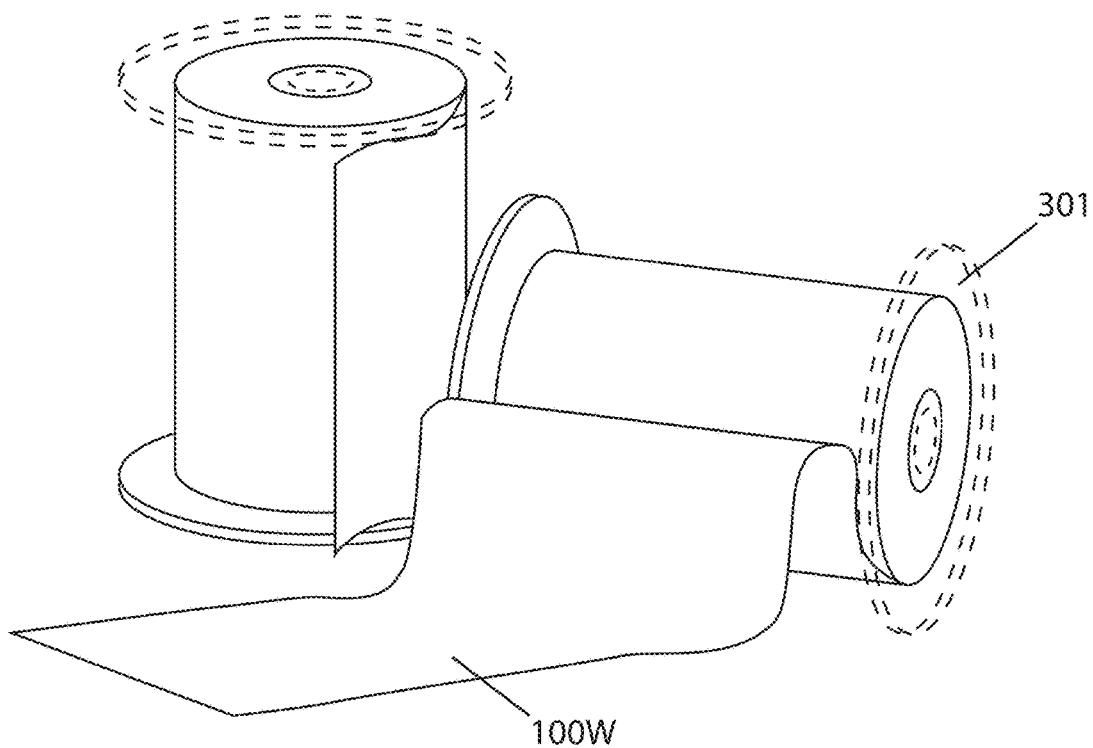
FIG. 3A illustrates a continuous roll of the instant solid electrolyte sheet wound on a spool.

With reference to FIG. 3A, in various embodiments the solid electrolyte sheet may be of sufficient flexibility, length and manufacturability to be fabricated as a continuous web of vitreous inorganic Li ion conducting sulfide glass 100W, having a length typically greater than 50 cm, and preferably greater than 100 cm, and even more preferably greater than 1000 cm long. In various embodiments, glass web 100W serves a solid electrolyte substrate-sheet for the formation of downstream battery cell components, including electrode subassemblies, electrode assemblies, and battery cells of this disclosure.

As illustrated in FIG. 3A, in various embodiments web 100W is sufficiently flexible that it may be formed into a continuous roll 100R without fracture, and typically wound on a support spool 301 for storage and/or transportation. Preferably continuous web 100W has bending-radius ≤100 cm, and preferably ≤50 cm, more preferably ≤10 cm, even more preferably ≤5 cm, and yet even more preferably ≤2.5 cm, and thus capable of being wound as such without fracture. In various embodiments the spool or drum has a diameter in the range of 100 cm-200 cm; or 50 cm to 100 cm; or 20 to 50 cm; or 10 cm to 20 cm; or 5 cm to 10 cm; or 2.5 cm to 5 cm. In various embodiments continuous roll 100R serves as a supply roll or a source roll for R$_2$R manufacture or roll-to-sheet processing of downstream battery cell components and battery cells.

As illustrated in FIG. 3B, in various embodiments, multiple discrete solid electrolyte sheets 100Z (e.g., a stack of solid electrolyte sheets) may be excised (i.e., cut to size) from Li ion conducting glass web 100W. The sheet may be cut into pieces of any suitable size for use, such as a separator in into a battery cell or component. In various embodiments, web 100W yields at least 5 discrete solid electrolyte sheets having length of at least 10 cm, preferably at least 10 such sheets, more preferably at least 50 such sheets, and even more preferably at least 100 such sheets.

In various embodiments, to facilitate winding, storage and/or use of a supporting spool, a protective material interleave (not shown) may be disposed between adjacent layers of the source roll in order to prevent the opposing web surfaces from contacting each other. Generally, the protective interleave is not a lithium ion conductor. In various embodiments the interleave may be a porous polymer layer (e.g., micro-porous) or a dry swellable polymer layer (i.e., a dry gel-able polymer layer), suitable to serve as both interleave in the source roll and as a porous or gel separator component in a battery cell.

In accordance with the disclosure, the continuous Li ion conducting amorphous material phase has room temperature intrinsic Li ion conductivity ≥10$^{-5}$ S/cm, preferably ≥10$^{-4}$ S/cm, and more preferably ≥10$^{-3}$ S/cm. To achieve this level of conductivity in an inorganic amorphous material phase, sulfide based Li ion conducting glasses are particularly suitable (i.e., sulfur-containing glasses). Without intending to be limited by theory, compared to oxygen, sulfur is found to be a highly desirable element of the material phase. Sulfur is generally more polarizable than oxygen, and this tends to weaken the interaction between glass forming skeletal ions and mobile lithium ions, which in turn enhances lithium ion mobility and increases associated ionic conductivity. Accordingly, in various embodiments the material phase has a glass skeleton composed in part of sulfur and through which Li ions move. Without intending to be limited by theory, sulfur may serve several roles, including cross-linking sulfur that forms the glass structure and non-cross-linking sulfur that combines terminally with mobile Li ions.

Accordingly, in various embodiments the continuous amorphous material phase of solid electrolyte sheet 100 is an inorganic sulfide based glass comprising S (sulfur) as a constituent element, Li (lithium) as a constituent element and further comprising one or more constituent elements selected from the group consisting of P (phosphorous), B (boron), Al (aluminum), Ge (germanium), Se (selenium), As (arsenic), O (oxygen) and Si (silicon).

In embodiments, the sulfide-based solid electrolyte glass comprises O (oxygen) as a constituent element (e.g., typically as a secondary constituent element). In other embodiments, the amorphous sulfide glass is a non-oxide, and thus substantially devoid of oxygen as a constituent element. Typically the mole % of Li in the glass is significant, and in particular embodiments the mole percent of Li in the glass is at least 10 mole %, and more typically at least 20 mole % or at least 30 mole %; in some embodiments it is contemplated that the mole percent of Li in the glass is greater than 40 mole % or greater than 50 mole % or even greater than 60 mole %. In various embodiments the concentration of lithium as a constituent element in the glass is between 20-60 mole %, or between 20%-50 mole % (e.g., about 20 mole %, about 25 mole %, about 30 mole %, about 35 mole %, about 40 mole %, about 45 mole %, about 50 mole %, or about 55 mole %). In various embodiments the glass is substantially devoid of alkali metal ions other than Li (e.g., devoid of sodium).

In various embodiments sulfur (S) is present in the glass to at least 10 mole %, and typically significantly higher; for instance, ≥20 mole % of S, or ≥30 mole % of S, or ≥40 mole % of S. In various embodiments the concentration of sulfur as a constituent element in the glass is between 20-60 mole %, or between 30%-50 mole % (e.g., about 25 mole %, about 30 mole %, about 35 mole %, about 40 mole %, about 45 mole %, or about 50 mole %). In various embodiments sulfur is the major elemental constituent of the glass, which is to mean the mole % of sulfur is greater than that of any other constituent element.

Various Li ion conducting sulfur based glass systems (i.e., sulfur-containing glasses) are contemplated for use herein. These include lithium phosphorous sulfide, lithium phosphorous oxysulfide, lithium boron sulfide, lithium boron oxysulfide, lithium boron phosphorous oxysulfide, lithium silicon sulfide, lithium silicon oxysulfide, lithium germanium sulfide, lithium germanium oxysulfide, lithium arsenic sulfide, lithium arsenic oxysulfide, lithium selenium sulfide, lithium selenium oxysulfide, lithium aluminum sulfide, lithium aluminum oxysulfide, and combinations thereof.

In various embodiments the sulfur-based glass may include certain additives and compounds to enhance conductivity, processing, or properties generally, such as halide salts (e.g., LiCl, LiBr, LiI), Ga$_2$S$_3$, Sb$_2$O$_3$, Sb$_2$S$_3$, Al$_2$S$_3$, PbS, BiI$_3$, CuS, ZnS, nitrogen (e.g., thio-nitrides and Li$_3$N), as well as phosphate (e.g., lithium phosphate (e.g., Li$_3$PO$_4$, LiPO$_3$), sulfate (e.g., Li$_2$SO$_4$), silicate (e.g., Li$_4$SiO$_4$), borate salts (e.g., LiBO$_3$), and others including germinates (e.g., GeS$_2$, Li$_4$GeO$_4$), aluminum compounds such as aluminates (e.g., Li$_3$AlO$_3$), Li$_3$CaO$_3$, and indium compounds (e.g., In$_2$S$_3$, Li$_3$InO$_3$), tin compounds (SnS, SnS$_2$), titanium, tantalum and tellurium compounds (Ti$_2$S, TiS$_2$, TaS$_2$, TeO$_2$). In embodiments, constituent elements Al, In, Ca, Ge, Pb, Bi, Ta, Ti, Sb, Te, As, Cu, Zn, Se, Sn, F, I and/or Cl, may be incorporated in the glass (e.g., as secondary constituent elements). In embodiments, various devitrifying agents may be added to the sulfide glass to enhance its stability against crystallization. In various embodiments the sulfur-based glass is made in the absence of Ga$_2$S$_3$ or Al$_2$S$_3$, for example the sulfur-based glass devoid of Al or Ga as a constituent element. In various embodiments the sulfur-based glass is devoid of halide elements, and in particular devoid of Cl, F, or I (e.g., devoid of I).

In various embodiments the sulfur-based glass is of the type: Li$_2$S—YS$_n$ wherein Y is a glass former constituent element and may be Ge, Si, As, B, or P; and wherein n=2, 3/2 or 5/2. For example, in various embodiments the glass system may be $Li_2S$—$PS_{5/2}$ or $Li_2S$—$BS_{3/2}$ or $Li_2S$—$SiS_2$.

In various embodiments the sulfur-based glass is of the type: $Li_2S$—$YS_n$—$YO_n$ wherein Y is a glass former constituent element, and may be Ge, Si, As, B, or P; and wherein n=2, 3/2 or 5/2. For example, in various embodiments the glass system may be $Li_2S$—$PS_{5/2}$—$PO_{5/2}$ or $Li_2S$—$BS_{3/2}BO_{3/2}$ or $Li_2S$—$SiS_2$—$SiO_2$.

In various embodiments the sulfur-based glass is of the type: $Li_2S$—$YS_n$; $Li_2S$—$YS_n$—$YO_n$ and combinations thereof; for which Y=Ge, Si, As, B, and P; and n=2, 3/2, 5/2.

In various embodiments the sulfur-based glass is of the type: $Li_2S$—$Y^1S_n$—$Y^2O_m$ wherein $Y^1$ and $Y^2$ are different glass former constituent elements, and may be Ge, Si, As, B, or P; and wherein n=2, 3/2 or 5/2 and m=2, 3/2 or 5/2, as appropriate based on the common standard valence of the constituent element. For example, in various embodiments the glass system may be $Li_2S$—$PS_{5/2}$—$BO_{3/2}$ or $Li_2S$—$BS_{3/2}$—$PO_{5/2}$ or $Li_2S$—$PS_{5/2}$—$SiO_2$.

In various embodiments, $Li_2S$ may be wholly, or partially, substituted with $Li_2O$.

In various embodiments the glass may be a combination of two or more such types; for instance, $Li_2S$—$PS_{5/2}$—$BS_{3/2}$ or $Li_2S$—$PS_{5/2}$—$SiS_2$ or $Li_2S$—$PS_{5/2}$—$BS_{3/2}$—$SiS_2$. Specific examples include, $Li_2S$—$PS_{5/2}$—$PO_{5/2}$; $Li_2S$—$BS_{3/2}$—$BO_{3/2}$; $Li_2S$—$SiS_2$—$SiO_2$; $Li_2S$—$P_2S_5$; $Li_2S$—$B_2S_3$; $Li_2S$—$SiS_2$; $Li_2S$—$P_2$—$P_2O_5$; $Li_2S$—$P_2S_5$—$P_2O_3$; $Li_2S$—$B_2S_3$—$B_2O_3$; $Li_2S$—$P_2S_5$—$B_2S_3$; $Li_2S$—$P_2S_5$—$B_2S_3$—$B_2O_3$; $Li_2S$—$B_2S_3$—$P_2O_5$; $Li_2S$—$B_2S_5$—$P_2O_3$; $Li_2S$—$SiS_2$—$P_2O_5$; $Li_2S$—$P_2S_5$—$SiO_2$; $Li_2S$—$P_2S_5$—$P_2O_5$—$B_2S_3$—$B_2O_3$.

The continuous Li ion conducting inorganic glass may be described as having a glass network former that brings about the skeletal lattice and a glass network modifier, such as a lithium compound, that introduces ionic bonds and thereby serves as a disrupter of the lattice and provides mobile lithium ions for conduction. In various embodiments additional network formers may be incorporated in the glass. For instance, in various embodiments the glass system may have the general formula:

$$x\text{NET(major former)}: y\text{NET(minor former)}: z\text{NET (modifier)}$$

wherein $z=1-(x+y)$

NET(major former) is the major glass network former and its mole fraction, x, is the largest of all the network formers used to make the glass. Net(minor former) represents one or more minor glass network formers that is present in the glass with mole fraction, y. In all instances the mole fraction of the major glass former is larger than that of any minor glass former. However, the combined mole fraction of the minor glass formers may be greater than that of the major glass former. NET(modifier) is generally $Li_2S$ or $Li_2O$ or some combination thereof.

The network former (major or minor) may be a compound of the type $A_aR_b$, or a combination of two or more different compounds of this type. For instance, A may be Silicon, Germanium, Phosphorous, Arsenic, Boron, Sulfur and R may be Oxygen, Sulfur, or Selenium; and the network modifier may be of the type $N_mR_c$, with N being Lithium and R being Oxygen, Sulfur, or Selenium; and a,b, m, and c represent the indices corresponding to the stoichiometry of the constituents.

In various embodiments the major network former is $B_2S_3$, $P_2S_5$ or $SiS_2$, and the minor network former is one or more of $B_2O_3$, $P_2O_5$, $P_2O_3$, $SiO_2$, $B_2S_3$, $P_2S_5$, $SiS_2$, $Al_2S_3$, $Li_3PO_4$, $LiPO_3Li_2SO_4$ $LiBO_3$. Specific examples include: i) $Li_2S$ as the network modifier, $B_2S_3$ as the major former, and one or more minor formers selected from the group consisting of $B_2O_3$, $P_2O_5$, $P_2O_3$, $SiO_2$, $P_2S_5$, $SiS_2$, $Al_2S_3$, $Li_3PO_4$, $LiPO_3Li_2SO_4LiBO_3$; ii) $Li_2S$ as the network modifier, $P_2S_5$ as the major former, and one or more minor formers selected from the group consisting of $B_2O_3$, $P_2O_5$, $P_2O_3$, $SiO_2$, $B_2S_3$, $SiS_2$, $Al_2S_3$, $Li_3PO_4$, $LiPO_3Li_2SO_4LiBO_3$; iii) $Li_2S$ as the network modifier, $SiS_2$ as the major former, and one or more minor formers selected from the group consisting of $B_2O_3$, $P_2O_5$, $P_2O_3$, $SiO_2$, $P_2S_5$, $B_2S_3$, $Al_2S_3$, $Li_3PO_4$, $LiPO_3Li_2SO_4LiBO_3$. In various embodiments, the network modifier is $Li_2S$ or $Li_2O$, or some combination thereof.

Selecting the appropriate sulfide glass composition depends on the end of use of the solid electrolyte sheet, and ultimately on the type and application of the battery cell in which it is intended to operate. Among the many potential considerations are form factor, cell construction, cost, power requirements, and service life. Accordingly, the glass composition may be adjusted to enhance one or more of i) chemical and electrochemical compatibility of the glass in direct contact with lithium metal and/or a liquid electrolyte; ii) flexibility, shape and size; iii) glass formability (especially as it relates to thermal properties); and iv) Li ion conductivity. Optimizing one or more of these parameters generally requires a tradeoff.

In various embodiments the sulfide glass system is selected for its chemical and electrochemical compatibility in direct contact with lithium metal.

Chemical compatibility to lithium metal is an attribute that relates to the kinetic stability of the interface between glass sheet 100 and a lithium metal layer, and electrochemical compatibility generally assesses the ability of that interface to function in a battery cell. Both properties require the formation of a solid electrolyte interphase (SEI) that stops reacting with the glass surface once formed (i.e., chemical compatibility) and is sufficiently dense and conductive that its interface resistance is acceptable for its use in a battery cell.

Incorporating certain constituent elements into glass sheet 100 is desirable for creating an SEI commensurate with both chemical and electrochemical compatibility. In various embodiments, phosphorous is incorporated as a main constituent element for producing an effective SEI, as phosphorous in direct contact with lithium metal reacts to form lithium phosphide (e.g., $Li_3P$), a compound highly conductive of Li ions and fully reduced. To form an acceptable SEI, phosphorous may be present in small amount (e.g., as a secondary constituent of the glass). Adding phosphorous as a secondary constituent element provides an effective method for reducing resistance at the interface, and may be used to effect compatibility in a glass system, which, as contemplated herein, may not form a stable SEI, such as silicon sulfide glasses, with $SiS_2$ as the exclusive network former. Accordingly, in some embodiments, Si may be intentionally excluded as a constituent element of the sulfide glass sheet 100.

Notably, it has been discovered that phosphorous sulfide glass systems are not the only glasses chemically and electrochemically compatible in direct contact with lithium metal. Surprisingly, boron sulfide glasses, even in the absence of phosphorous, have shown remarkable chemical and electrochemical compatibility against metallic lithium (Li metal). Accordingly, in various embodiments phosphorous may be excluded from the glass as a constituent element to mitigate potential issues associated with high vapor pressure and chemical reactivity; for example, the glass substantially devoid of phosphorous. However, in small amount, adding phosphorous as a secondary constituent element to the boron sulfide glasses may not impart processing issues, and, as described below, may be added as a method for reducing interface resistance in direct contact with Li metal.

In various embodiments adding oxygen and/or silicon provides a method for improving thermal properties, especially for enhancing glass formability, including glass stability (e.g., increasing the glass stability factor and/or Hruby parameter) and/or viscosity at the liquidus temperature ($T_{liq}$). For instance, adding silicon as a secondary constituent to a phosphorous sulfide or boron sulfide glass provides a method for increasing glass stability and/or viscosity at $T_{liq}$ (i.e., the liquidus viscosity), while retaining compatibility to Li metal. The addition of oxygen as a constituent element may also afford benefit in these regards. In various embodiments oxygen may be incorporated as a main or secondary constituent element in lithium phosphorous sulfide and lithium boron sulfide glass systems as a method for increasing the glass stability factor and/or Hruby parameter. For instance, $xLi_2S$-$yP_2S_5$-$zSiS_2$, $xLi_2S$-$yB_2S_3$-$zSiS_2$, $xLi_2S$-$yP_2S_5$-$zSiO_2$, $xLi_2S$-$yB_2S_3$-$zSiO_2$, $xLi_2S$-$yB_2S_3$-$zB_2O_3$, $xLi_2S$-$yP_2S_5$-$zP_2O_5$; wherein with x+y+z=1 and x=0.4-0.8, y=0.2-0.6, and z ranging from 0 to 0.2 (e.g., about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2).

Solid electrolyte sheets of silicon sulfide based glasses are particularly advantageous for use as a separator sheet in battery cells which employ a common liquid electrolyte, as described in more detail herein below, or wherein the separator sheet does not contact electroactive material. For instance, $xLi_2S$-$ySiS_2$; $xLi_2S$-$ySiS_2$-$zSiO_2$; $xLi_2S$-$ySiS_2$-$yB_2S_3$; $xLi_2S$-$ySiS_2$-$yB_2O_3$, $xLi_2S$-y $B_2S_3$-$zSiO_2$; wherein with x+y+z=1 and x=0.4-0.8, y=0.2-0.6, and z ranging from 0 to 0.2 (e.g., about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2).

With consideration of the above discussion, it is clear that in limited amount certain elements can have a beneficial role for enhancing performance of sheet 100 and/or improving glass stability for processing. The addition of phosphorous can reduce interfacial resistance with Li metal and the addition of oxygen can improve glass stability. In a boron sulfide glass, the addition of phosphorous, as a secondary constituent element, can be made via the incorporation of $P_2S_5$ and the addition of oxygen via $B_2O_3$; yielding the glass system: $Li_2S$—$B_2S_3$—$P_2S_5$—$B_2O_3$; wherein $B_2S_3$ is the primary network former, $P_2S_5$ and $B_2O_3$ are secondary network formers, and $Li_2S$ is the network modifier. As such, the oxygen to phosphorous mole ratio can be varied. In another embodiment the phosphorous and oxygen mole ratio may be constrained by incorporating $P_2O_5$ as a single ingredient, giving rise to the glass system $Li_2S$—$B_2S_3$—$P_2O_5$; wherein $B_2S_3$ is the primary network former, $P_2O_5$ is a secondary former, and $Li_2S$ is the network modifier.

In various embodiments the sulfur-based glass comprises $Li_2S$ and/or $Li_2O$ as a glass modifier and one or more of a glass former selected from the group consisting of $P_2S_5$, $P_2O_5$, $SiS_2$, $SiO_2$, $B_2S_3$ and $B_2O_3$.

In various embodiments the sulfur-based glass comprises at least 20-mole % lithium, or at least 30-mole % lithium, or at least 40-mole % lithium. In embodiments thereof the sulfur-based glass further comprises at least 20-mole % sulfur, or at least 30-mole % sulfur, or at least 40-mole % sulfur. Moreover, in embodiments thereof the sulfur-based glass further comprises at least 5-mole % of one or more of boron, phosphorous and silicon (e.g., between 5-30 mole %). For instance the sulfur-based glass comprising between 5-25 mole % of one or more of boron, phosphorous and silicon (e.g., between 5-20 mole %, and more typically 10-20 mole %). For example, the sulfur-based glass comprising about 10 mole %, 11 mole %, 12 mole %, 13 mole %, 14 mole %, 15 mole %, 16 mole %, 17 mole %, 18 mole %, 19 mole % or 20 mole % of one or a combination of boron, phosphorous and silicon. In particular embodiments the sulfur-based glass comprises about 10 mole %, 11 mole %, 12 mole %, 13 mole %, 14 mole %, 15 mole %, 16 mole %, 17 mole %, 18 mole %, 19 mole % or 20 mole % of boron. In particular embodiments the sulfur-based glass comprises about 10 mole %, 11 mole %, 12 mole %, 13 mole %, 14 mole %, 15 mole %, 16 mole %, 17 mole %, 18 mole %, 19 mole % or 20 mole % of phosphorous. In particular embodiments the sulfur-based glass comprises about 10 mole %, 11 mole %, 12 mole %, 13 mole %, 14 mole %, 15 mole %, 16 mole %, 17 mole %, 18 mole %, 19 mole % or 20 mole % of silicon. In particular embodiments the sulfur-based glass comprises about 10 mole %, 11 mole %, 12 mole %, 13 mole %, 14 mole %, 15 mole %, 16 mole %, 17 mole %, 18 mole %, 19 mole % or 20 mole % of a combination of boron and phosphorous but no silicon, or a combination of boron and silicon, but no phosphorous, or a combination of phosphorous and silicon but no boron.

In various embodiments the sulfur-based glass comprises at least 20 mole % sulfur and at least 20 mole % lithium and greater than 5 mole % of one, or a combination of, boron, phosphorous or silicon, and the glass further comprising oxygen. In particular embodiments oxygen is present in the glass in an amount that is at least 0.5% (e.g., between 1-20 mole %) such as between 1-10 mole % oxygen (e.g., at least 0.5 mole % but less than 5 mole % oxygen, or at least 5 mole % but no more than 10 mole % oxygen). In other embodiments the sulfur-based glass is substantially devoid of oxygen.

In various embodiments the sulfur based glass system is of the type having composition: $xLi_2S$-$yP_2S_5$-$zSiS_2$, $xLi_2S$-$yB_2S_3$-$zSiS_2$, $xLi_2S$-$yP_2S_5$-$zSiO_2$, $xLi_2S$-$yB_2S_3$-$zSiO_2$, $xLi_2S$-$yB_2S_3$-$zB_2O_3$, or $xLi_2S$-$yP_2S_5$-$zP_2O_5$; wherein x+y+z=1 and x=0.4-0.8, y=0.2-0.6, and z ranging from 0 to 0.2 (e.g., about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2), and particularly x+y+z=1 and x=0.6-0.7, y=0.2-0.4, and z ranging from 0 to 0.2 (e.g., z is between 0.01-0.2, Such as about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2); and more particularly x+y+z=1 and x=0.7, y=0.2-0.3, and z ranging from 0 to 0.2 (e.g., z is between 0.01-0.2, such as about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2).

In various embodiments the sulfur-based glass system is of the type having composition: $xLi_2S$-$ySiS_2$-$zP_2S_5$ or $xLi_2S$-$ySiS_2$-$zP_2O_5$; wherein x+y+z=1 and x=0.4-0.6, y=0.2-0.6, and z ranging from 0 to 0.2 (e.g., z is between 0.01-0.2 such as about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2), and particularly wherein x+y+z=1 and x=0.5-0.6, y=0.2-0.5, and z ranging from 0 to 0.2 (e.g., z is between 0.01-0.2 Such as about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2), Specific compositional examples include, $0.7Li_2S$-$0.29P_2S_5$-$0.01P_2O_5$; $0.7Li_2S$-$0.28P_2S_5$-$0.02P_2O_5$; $0.7Li_2S$-

$0.27P_2S_5$-$0.03P_2O_5$; $0.7Li_2S$-$0.26P_2S_5$-$0.04P_2O_5$; $0.7Li_2S$-$0.25P_2S_5$-$0.05P_2O_5$; $0.7Li_2S$-$0.24P_2S_5$-$0.06P_2O_5$; $0.7Li_2S$-$0.23P_2S_5$-$0.07P_2O_5$; $0.7Li_2S$-$0.22P_2S_5$-$0.08P_2O_5$; $0.7Li_2S$-$0.21P_2S_5$-$0.09P_2O_5$; $0.7Li_2S$-$0.2P_2S_5$-$0.1P_2O_5$; $0.7Li_2S$-$0.29B_2S_3$-$0.01B_2O_3$; $0.7Li_2S$-$0.28B_2S_3$-$0.02B_2O_3$; $0.7Li_2S$-$0.27B_2S_3$-$0.03B_2O_3$; $0.7Li_2S$-$0.26B_2S_3$-$0.04B_2O_3$; $0.7Li_2S$-$0.25B_2S_3$-$0.05B_2O_3$; $0.7Li_2S$-$0.24B_2S_3$-$0.06B_2O_3$; $0.7Li_2S$-$0.23B_2S_3$-$0.07B_2O_3$; $0.7Li_2S$-$0.22B_2S_3$-$0.08B_2O_3$; $0.7Li_2S$-$0.21B_2S_3$-$0.09B_2O_3$; $0.7Li_2S$-$0.20B_2S_3$-$0.1B_2O_3$; $0.7Li_2S$-$0.29B_2S_3$-$0.01P_2O_5$; $0.7Li_2S$-$0.28B_2S_3$-$0.02P_2O_5$; $0.7Li_2S$-$0.27B_2S_3$-$0.03P_2O_5$; $0.7Li_2S$-$0.26B_2S_3$-$0.04P_2O_5$; $0.7Li_2S$-$0.25B_2S_3$-$0.05P_2O_5$; $0.7Li_2S$-$0.24B_2S_3$-$0.06P_2O_5$; $0.7Li_2S$-$0.23B_2S_3$-$0.07P_2O_5$; $0.7Li_2S$-$0.22B_2S_3$-$0.08P_2O_5$; $0.7Li_2S$-$0.21B_2S_3$-$0.09P_2O_5$; $0.7Li_2S$-$0.20B_2S_3$-$0.1P_2O_5$; $0.7Li_2S$-$0.29B_2S_3$-$0.01SiS_2$; $0.7Li_2S$-$0.28B_2S_3$-$0.02SiS_2$; $0.7Li_2S$-$0.27B_2S_3$-$0.03SiS_2$; $0.7Li_2S$-$0.26B_2S_3$-$0.04SiS_2$; $0.7Li_2S$-$0.25B_2S_3$-$0.05SiS_2$; $0.7Li_2S$-$0.24B_2S_3$-$0.06SiS_2$; $0.7Li_2S$-$0.23B_2S_3$-$0.07SiS_2$; $0.7Li_2S$-$0.22B_2S_3$-$0.08SiS_2$; $0.7Li_2S$-$0.21B_2S_3$-$0.09SiS_2$; $0.7Li_2S$-$0.20B_2S_3$-$0.1SiS_2$; $0.6Li_2S$-$0.39SiS_2$-$0.01P_2S_5$; $0.6Li_2S$-$0.38SiS_2$-$0.02P_2S_5$; $0.6Li_2S$-$0.37SiS_2$-$0.03P_2S_5$; $0.6Li_2S$-$0.36SiS_2$-$0.04P_2S_5$; $0.6Li_2S$-$0.35SiS_2$-$0.05P_2S_5$; $0.6Li_2S$-$0.34SiS_2$-$0.06P_2S_5$; $0.6Li_2S$-$0.33SiS_2$-$0.07P_2S_5$; $0.6Li_2S$-$0.32SiS_2$-$0.08P_2S_5$; $0.6Li_2S$-$0.31SiS_2$-$0.09P_2S_5$; $0.6Li_2S$-$0.30SiS_2$-$0.1P_2S_5$; $0.6Li_2S$-$0.39SiS_2$-$0.01P_2O_5$; $0.6Li_2S$-$0.38SiS_2$-$0.02P_2O_5$; $0.6Li_2S$-$0.37SiS_2$-$0.03P_2O_5$; $0.6Li_2S$-$0.36SiS_2$-$0.04P_2O_5$; $0.6Li_2S$-$0.35SiS_2$-$0.05P_2O_5$; $0.6Li_2S$-$0.34SiS_2$-$0.06P_2O_5$; $0.6Li_2S$-$0.33SiS_2$-$0.07P_2O_5$; $0.6Li_2S$-$0.32SiS_2$-$0.08P_2O_5$; $0.6Li_2S$-$0.31SiS_2$-$0.09P_2O_5$; $0.6Li_2S$-$0.30SiS_2$-$0.1P_2O_5$.

In various embodiments these sulfide-based glass systems may further include $Li_xMO_y$ compounds, wherein M is boron, silicon, or phosphorous, and the x and y indicia are stoichiometric values (e.g., lithium borates such as $LiBO_2$, $Li_3BO_3$, or lithium silicates such as $Li_4SiO_4$, $Li_2SiO_4$, or lithium phosphate such as $Li_3PO_4$).

In various embodiments the sulfur-based glass is a silicon sulfide glass such as $(1-x)(0.5Li_2S$-$0.5SiS_2)$-$xLi_4SiO_4$; $(1-x)(0.6Li_2S$-$0.4SiS_2)$-$xLi_4SiO_4$; $(1-x)(0.5Li_2S$-$0.5SiS_2)$-$xLi_3BO_3$; $(1-x)(0.6Li_2S$-$0.4SiS_2)$-$xLi_3BO_3$; $(1-x)(0.5Li_2S$-$0.5SiS_2)$-$xLi_3PO_4$; $(1-x)(0.6Li_2S$-$0.4SiS_2)$-$xLi_3PO_4$; wherein x ranges from 0.01-0.2. Specific examples include: $0.63Li_2S$-$0.36SiS_2$-$0.01Li_3PO_4$; $0.59Li_2S$-$0.38SiS_2$-$0.03Li_3PO_4$; $0.57Li_2S$-$0.38SiS_2$-$0.05Li_3PO_4$; and $0.54Li_2S$-$0.36SiS_2$-$0.1Li_3PO_4$.

In various embodiments the mole % of lithium and that of sulfur in the glass is greater than 20%, or greater than 30% or greater than 40% (e.g., between about 20%-40%). In embodiments thereof, the sulfur-based glass further comprises a constituent element selected from the group consisting of Si, B, P or Al, and which is present in the glass with a mole % that is at least 5 mole %, or at least 10 mole %, or at least 15 mole %, or at least 20 mole % (e.g., between 5 mole % and 10 mole %, or between 10 mole % and 15 mole %, or between 15 mole % and 20 mole %). In various embodiments the sulfur based glass has a mole % of lithium and a mole % of sulfur that is at least 20%, a mole % of silicon or boron that is at least 5% but not greater than 20%, and a mole % of phosphorous that is at least 0.5% but not greater than 10%. In various embodiments the sulfur based glass has a mole % of lithium and a mole % of sulfur that is at least 25%, a mole % of silicon or boron that is at least 10% but not greater than 20%, and a mole % of phosphorous that is at least 0.5% but not greater than 5%. For instance, in various embodiments the sulfur-based glass has a mole % of sulfur and lithium that is at least 25% or at least 30%; a mole % of boron or silicon that is at least 10%, and a mole % of phosphorous that is at least 0.5% but less than 10% (e.g., between 5-10% or between 0.5%-5%).

In various embodiments a certain amount of oxygen is substituted for some of the sulfur in the sulfide-based glass, despite the fact that the substituting oxygen leads to a decrease in conductivity relative to the same glass without any oxygen substitution, and this due to oxygen serving as sites for trapping mobile Li ions but improving manufacturability of the vitreous sheet. For instance, the substituting oxygen is present in an amount typically in the range of 0.1-10 mole % (e.g., between 0.1-1 mole %, or between 1-5 mole %, or between 5 to 10 mole %). In various embodiments, the oxygen substitution decreases the conductivity by at least a factor of 2, a factor of 5, or a factor of 10.

In a particular embodiment, the sulfur-based glass comprises $Li_2S$ and/or $Li_2O$ as a glass modifier, $B_2S_3$ as the major glass former and $SiS_2$ as a minor glass former, wherein the amount of $SiS_2$ is sufficient to yield a glass stability factor greater than 50° C., without decreasing the Li ion conductivity below $10^{-5}$ S/cm, and preferably does not decrease below $10^{-4}$ S/cm, and more preferably does not decrease below $10^{-3}$ S/cm. Preferably the glass stability factor is greater than 60° C., and more preferably greater than 60° C., and even more preferably greater than 100° C. For example, wherein the amount of silicon in the glass is between 0.5-10 mole %.

In another particular embodiment, the sulfur-based glass comprises $Li_2S$ and/or $Li_2O$ as a glass modifier, $B_2S_3$ as the major glass former and $P_2O_5$ as a minor glass former, wherein the amount of $P_2O_5$ in the glass is sufficient to yield an ASR as measured against Li metal that is less than 200 $\Omega$-cm$^2$, without decreasing the Li ion conductivity below $10^{-5}$ S/cm, and preferably does not decrease below $10^{-4}$ S/cm, and more preferably does not decrease below $10^{-3}$ S/cm. Preferably, the ASR is less than 100 $\Omega$-cm$^2$, and more preferably less than 50 $\Omega$-cm$^2$. For example, wherein the amount of phosphorous in the glass is between 0.5-10 mole %.

In yet another particular embodiment, the sulfur-based glass comprises $Li_2S$ and/or $Li_2O$ as a glass modifier, $B_2S_3$ as the major glass former, and $P_2O_5$ and $SiS_2$ as minor glass formers, wherein the amount of $SiS_2$ and $P_2O_5$ is sufficient to yield a glass stability factor of no less than 50° C.; an ASR as measured against Li metal that is less than 200 $\Omega$-cm$^2$, and without decreasing the Li ion conductivity below $10^{-5}$ S/cm, and preferably does not decrease below $10^{-4}$ S/cm, and more preferably does not decrease below $10^{-3}$ S/cm. Preferably, the ASR is less than 100 $\Omega$-cm$^2$, and more preferably less than 50 $\Omega$-cm$^2$. For example, wherein the amount of phosphorous in the glass is between 0.5-10 mole %, and the amount of silicon and/or oxygen in the glass is between 0.5-10 mole %.

In a particular embodiment the vitreous sheet is composed of a sulfur-based glass having more than 20 mole % of S as a first constituent element; more than 20 mole % of Li as a second constituent element; more than 10 mole % of a third constituent element selected from the group consisting of B or P; and at least 1 mole % but not greater than 10 mole % of a fourth constituent element selected from the group consisting of O, Si, and a combination of O and Si as the fourth constituent element(s); wherein the mole % of the fourth constituent element is sufficient to yield a glass stability factor greater than 50° C., preferably greater than 60° C., more preferably greater than 80° C., and even more preferably greater than 100° C., without decreasing the conductivity below $10^{-5}$ S/cm, and preferably without decreasing the conductivity below $10^{-4}$ S/cm, and more preferably without decreasing the conductivity below $10^{-3}$ S/cm.

In another particular embodiment, the vitreous sheet is composed of a sulfur-based glass having more than 20 mole % of S as a first constituent element; more than 20 mole % of Li as a second constituent element; more than 10 mole % of a third constituent element selected from the group consisting of B or P; and at least 1 mole % but not greater than 10 mole % of a fourth constituent element selected from the group consisting of O, Si, and a combination of O and Si as the fourth constituent element(s); wherein the mole % of the fourth constituent element(s) is sufficient to effect a viscosity at $T_{liq}$ that is greater than 200 poise, preferably greater than 500 poise, more preferably greater than 1,000 poise, and even more preferably greater than 3000 poise, without decreasing the conductivity below $10^{-5}$ S/cm, preferably without decreasing the conductivity below $10^{-4}$ S/cm, and more preferably without decreasing the conductivity below $10^{-3}$ S/cm.

In yet another particular embodiment, the vitreous sheet is composed of a sulfur-based glass having more than 20 mole % of S as a first constituent element; more than 20 mole % of Li as a second constituent element; more than 10 mole % of a third constituent element selected from the group consisting of Si or B; and at least 1 mole % but not greater than 10 mole % of P as a fourth constituent element; wherein the mole % of P is sufficient to effect an ASR for the vitreous sheet, as measured between opposing principal sides in direct contact with Li metal, that is less than 200 Ω-cm², preferably less than 100 Ω-cm², and more preferably less than 50 Ω-cm², without decreasing the conductivity of the sheet below $10^{-5}$ S/cm, preferably without decreasing the conductivity below $10^{-4}$ S/cm, and more preferably without decreasing the conductivity below $10^{-3}$ S/cm. For instance, the amount of phosphorous in the sulfide glass is between 1-10 mole %, such as about 1 mole %, about 2 mole %, about 3 mole %, about 4 mole %, about 5 mole %, about 6 mole %, about 7 mole %, about 8 mole %, about 9 mole %, or about 10 mole %).

The Li ion conductive glass phases having conductivity $\geq 10^{-5}$ S/cm, preferably $\geq 10^{-4}$ S/cm and more preferably $\geq 10^{-3}$ S/cm are embodied herein above by sulfide glasses, however the disclosure contemplates alternatives, including those which are based on selenium and/or oxygen, and may be devoid of sulfur. Accordingly, it is contemplated that the instant disclosure may be embodied by Li ion conducting oxide, phosphate and silicate glasses. Other amorphous phases are also contemplated, such as glassy lithium halides (e.g., $Li_{3-2x}M_xHalo$; wherein M is typically a cation of valence $\geq 2$, Such as Mg, Ca or Ba, and Hal is a halide such as Cl, I or a mixture thereof).

A battery serviceable solid electrolyte sheet devoid of continuous interconnected pathways into which lithium metal dendrites could grow and ultimately short circuit through the sheet is described. The sheet is generally embodied by high Li ion conductivity sulfide-based glass (i.e., sulfur-containing glass).

While this disclosure is not limited by any particular theory of operation, it is believed that the ability of the instant solid electrolyte sheet to resist and preferably prevent dendritic through penetration in a lithium battery cell is based on it having a bulk microstructure that is absent of continuous chain-like voids extending between the first and second principal side surfaces, and, in particular, continuous void-like discontinuities in the form of crystalline grain boundaries and/or particle-to-particle boundaries, as defined above. Preferably, the surface of the solid electrolyte sheet is liquid-like, by which it is meant a smooth amorphous surface, as resulting from the action of surface tension on a quiescent liquid.

To create such a bulk microstructure and liquid-like surface, the instant solid electrolyte sheet is composed in whole or in part of a continuous vitreous glass phase (i.e., a vitreous material expanse) configured to intersect potential dendritic pathways while providing conduction for Li ions.

With reference to FIGS. 4A-H there is illustrated cross sectional views of Li ion conductive solid electrolyte sheets 400A-H in accordance with various embodiments of the disclosure. While each of the sheets has a somewhat distinct microstructure, or microstructural feature(s), when considered in totality of their respective bulk and surface microstructures, they all result in the common aspect of being resistant to facile through penetration of lithium metal dendrites. Accordingly, sheet 400A-H is devoid of chain-like voids in the form of discrete and/or pressed powder interparticle boundaries, especially amorphous powder interparticle boundaries, and interconnected continuous crystalline grain boundaries extending across the thickness of the sheet.

With reference to FIGS. 4A-E, solid electrolyte sheet 100 is embodied as a vitreous monolith of a Li ion conducting sulfide based glass 400A-E.

Vitreous monoliths 400A-E are each composed of a vitreous sulfide glass phase 401 that is continuous throughout its respective sheet and has room temperature intrinsic Li ion conductivity $\geq 10^{-5}$ S/cm, preferably $\geq 10^{-4}$ S/cm, and more preferably $\geq 10^{-3}$ S/cm. The vitreous sulfide glass phase constitutes a majority volume fraction of the monolithic sheet, and thus is considered the primary material phase. In various embodiments, the vitreous sulfide glass phase is not only the primary material phase of the sheet, and pervasive throughout, it also represents a significant volume fraction of the monolith, as well as a majority of the area fraction of its first and second principal side surfaces.

When the volume fraction of the primary sulfide glass phase is less than 100%, the remaining solid volume is generally accounted for by secondary phase(s), which may be crystalline 403 or amorphous 405. In such embodiments, the continuous Li ion conducting primary glass phase 401 effectively serves as a glass matrix with the secondary phases 403/405 embedded and typically isolated therein. In various embodiments, the continuous Li ion conducting sulfur-based glass phase 401 is not only the primary material phase of the sheet, as defined above, it also constitutes a majority area fraction of the first and/or second principal side surfaces (e.g., at least 50%, at least 60%, at least 70%, at least 80%, at least 90%, or at least 95%, and preferably 100% of the first and/or second principal side surface(s) is defined by the continuous Li ion conducting glass phase).

Preferably, the first and second principal side surfaces of the vitreous monolithic solid electrolyte sheets are essentially free of crystalline phases, and more preferably the surfaces are essentially free of secondary phases, including both crystalline phases and secondary amorphous phases. In particular, the vitreous monolithic solid electrolyte sheet of the present disclosure is preferably absent/devoid of all secondary metal phases (i.e., phases that are actually the metal material itself), including nano-sized secondary metal phases (e.g., metal boron or metal silicon), which, if present, can lead to mechanical failure on cooling the sheet due to differential thermal expansion between the secondary metal phase and the glass. Moreover, care should be taken to ensure that the instant continuous vitreous sheet is preferably devoid of secondary phases derived from incomplete reaction of raw material crystalline precursor particles, especially $Li_2S$, and for specific embodiments, when the vitreous sheet is a lithium boron sulfide or oxysulfide glass comprising boron sulfide as a network former and/or boron oxide in some amount, the sheet is preferably devoid of secondary phases, especially unreacted crystalline or amorphous boron sulfide or boron oxide phases, and elemental boron metal; and in other embodiments, when the vitreous sheet includes silicon sulfide as a network former, or some amount of silicon oxide, the vitreous sheet is preferably devoid of elemental silicon. For instance, the presence of $Li_2S$ phase on the surface of the sheet may ultimately lead to dissolution when disposed adjacent to a liquid electrolyte in a battery cell. And unreacted boron metal, or elemental silicon, especially if on the surface of the glass sheet, may adversely react in direct contact with lithium metal, leading to issues including potential fracture. Preferably, the vitreous monolithic sheet of Li ion-conducting glass is amorphous as determined by X-ray diffraction and preferably essentially free of crystalline phases, and more preferably completely devoid of any detectable crystalline phases or inclusions. Preferably the vitreous monolithic sheet of Li ion conducting glass is homogeneous and thus devoid of secondary phases that derive from the glass composition itself. During processing the solid electrolyte glass may come into contact with external contaminates that can lead to impurity phases, the origin of which is not solely the glass composition itself, but rather derived from contact with a foreign material during processing or from an impurity present in a precursor material. Any such contamination should be minimized, if not fully eliminated. Preferably, the vitreous monolith is essentially free of any such impurity or point type defects, such as stones of refractory material or crystalline refractory phases (e.g., α-alumina, zirconia, and α-quartz) and gaseous inclusions (i.e., bubbles), which may form as a result of impurities reacting with the glass composition, including impurities present in the environment about which the sheet is processed. For example, in various embodiments the vitreous monolith is essentially free of alumina or zirconia phases.

The vitreous monolithic sheets of this disclosure are further advantaged by the quality of their bulk and surface, and, in particular, a lack of flaws normally associated with sulfide glass particle compaction, including an undue density of internal pores and irregularly shaped surface voids, both of which are commonplace for die pressed and hot-pressed sulfide glass powder compacts. Preferably, the vitreous solid electrolyte sheets of this disclosure have a very low concentration of internal pores and surface voids; for instance, a concentration of internal micropores less than 100 micropores/1000 $um^3$, and preferably less than 50 micropores/1000 $um^3$, and more preferably less than 10 micropores/1000 $um^3$; ii) a concentration of internal nanopores less than 100 nanopores/1000 $um^3$, more preferably less than 50 nanopores/1000 $um^3$, and even more preferably less than 10 nanopores/1000 $um^3$; iii) a concentration of surface microvoids less than 10 micropores/$cm^2$ and preferably less than 10 micropores/$cm^2$; and iv) a concentration of surface nanovoids less than 50 nanovoids/$cm^2$; more preferably less than 25 Surface nanovoids/$cm^2$, and even more preferably less than 10 Surface nanovoids/$cm^2$.

In preferred embodiments, the vitreous monolithic solid electrolyte sheet is essentially free of internal micropores and surface microvoids (i.e., none are observable), and even more preferably the vitreous solid electrolyte sheet is substantially free of internal nanopores (≤2 nanopores/1000 $um^3$) and substantially free of surface nanovoids (≤2 nanovoids/$cm^2$), and yet even more preferably essentially free of internal nanopores and surface nanovoids. Since surface voids and internal pores may be irregularly shaped; the equivalent diameter of a pore is taken to be the maximum diameter of a circle inscribed about the pore. By use of the term "microvoid" or "micropore" it is meant a void/pore having a minimum diameter ≥1 um and up to about 100 μm (microvoid), and by "nanovoid" or "nanopore" it is meant a void/pore having a minimum diameter ≥10 nm but <1 um.

Figure 4A:
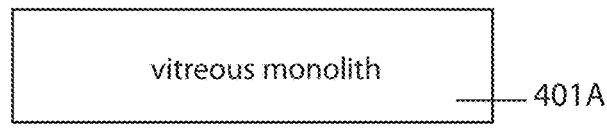
FIGS. 4A-H illustrate cross sectional views of Li ion conductive solid electrolyte sheets in accordance with various embodiments of the disclosure.

With reference to FIG. 4A, substantially amorphous vitreous monolith 400A essentially consists of the primary sulfide glass phase 401A, which constitutes more than 95%, and preferably 100% of the total sheet volume, with the remaining volume fraction (i.e., less than 5%), if any, accounted for by incidental secondary phases embedded within the primary glass phase. Preferably the primary sulfide glass phase 401A constitutes at least 96% of the total sheet volume, and more preferably at least 97%, or at least 98%, or at least 99%. Preferably substantially amorphous sheet 400A is essentially free of crystalline phases and completely amorphous as determined by X-ray diffraction, and more preferably it is completely devoid of crystalline phases (i.e., none detectable). In a preferred embodiment, sheet 400A is a homogeneous vitreous sulfide-based glass sheet, essentially free of secondary phases, including crystalline phases and secondary amorphous phases, and preferably entirely devoid of secondary phases (i.e., none are detectable). Preferably the first principal side surface is liquid-like, with an exceptionally smooth topography having an average surface roughness $R_a$<0.1 um, preferably <0.05 um, more preferably $R_a$<0.01 um, and even more preferably $R_a$<0.005 um, and yet even more preferably $R_a$<0.001 um.

Figure 4B:
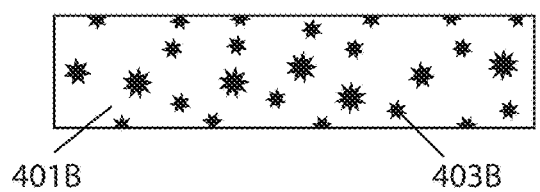

With reference to the cross sectional bulk microstructure depicted in FIG. 4B, in other embodiments, the vitreous monolithic sulfide-based solid electrolyte sheet 400B is substantially amorphous, but contains at least a discernable amount of crystalline phases/regions 403B, typically isolated and appearing as inclusions embedded in the continuous vitreous glass matrix phase 401B, with the proviso that the crystalline phases/regions do not, in combination, create a continuous grain boundary pathway across the thickness of the sheet. In various embodiments, substantially amorphous sheet 400B contains a volume fraction of crystalline phases that is between 5-20 vol %. In alternative embodiments, the fraction of crystalline phases is greater than 20 vol % but typically less than 70 vol %. The acceptable volume fraction depends on several factors, including the desired flexibility of the sheet as well as the spatial distribution and Li ion conductivity of the crystalline phases themselves. In various embodiments, the crystalline phases are highly conductive of Li ions (preferably, $\sigma$>$10^{-4}$ S/cm) and may have a volume fraction greater than 20% (e.g., in the range of 50-70 vol %), provided that the Li ion conductive primary glass matrix remains continuous and extensive throughout the sheet, and that the crystalline phases are sufficiently spaced apart to not percolate in contiguity across the sheet (along the thickness direction). In various embodiments the volume fraction of crystalline phases embedded in the continuous vitreous sulfur-based glass matrix phase is in the range of 5-10 vol %; 10-20 vol %; 20-30 vol %; 40-50 vol %; 50-60 vol %; and 60-70 vol %.

Figure 4C:
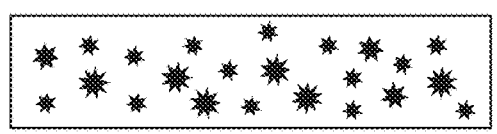

As illustrated in FIG. 4C, with respect to monolith 400C, the first and second principal side surfaces are essentially free of crystalline phases, despite the fact that the monolith itself contains some amount in its bulk. And more preferably the surface(s) are entirely devoid of detectable crystalline phases. For instance, it is contemplated that the monolith may be surface treated with heat to dissolve the crystalline phases.

Figure 4D:
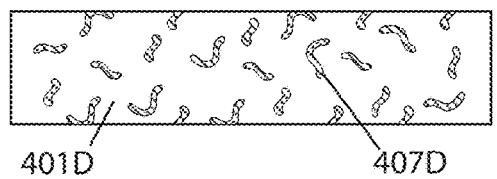
Figure 4E:
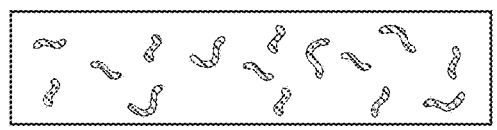
Figure 4F:
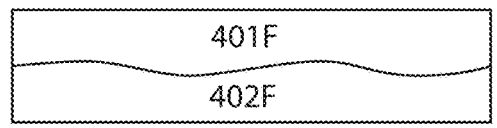

With reference to FIGS. 4D-E, there are illustrated cross sectional depictions of a substantially amorphous vitreous monolithic sulfur based solid electrolyte glass sheet that is preferably essentially free of crystalline phases but contains some amount of secondary amorphous phases 407D embedded in the continuous primary sulfur-based Li ion conducting glass phase 401D. Preferably, the secondary phase(s) is conductive of Li ions ($\geq 10^{-7}$ S/cm), and more preferably highly conductive ($\geq 10^{-5}$ S/cm). In accordance with this embodiment, the volume fraction of the secondary amorphous/glass phase(s) may be significant, and greater than 5 vol %. In various embodiments, the volume fraction of secondary phases is in the range of 5-10 vol %; 10-20 vol %; 20-30 vol %; 40-50 vol %; 50-60 vol %; 60-70 vol %; 70-80 vol %, provided that the primary sulfur based glass matrix phase retains its continuity throughout the sheet, and that the interfaces between the secondary amorphous phases and the primary phase do not create a contiguous phase boundary continuous between the first and second principal side surfaces. As illustrated in FIG. 4E, preferably the majority of the secondary phases are present in the bulk of the sheet, and the first and second principal side surfaces are essentially free of secondary phases (i.e., an area fraction less than 2%), and more preferably there are no detectable secondary phases on either principal side surface.

In an alternative embodiment, solid electrolyte sheet 100 may be embodied by two or more substantially amorphous and continuous vitreous glass matrices (layer-like), each a continuous layer-like matrix composed of a different Li ion conducting sulfide-based glass having room temperature intrinsic Li ion conductivity $\geq 10^{-5}$ S/cm. As illustrated in the cross sectional depiction shown in FIG. 4F, solid electrolyte sheet 400F is composed of two vitreous matrix layers: a first substantially amorphous vitreous matrix 401F and a second substantially amorphous vitreous matrix 402F, each defining the first and second principal side surfaces of the sheet respectively. In various embodiments, first vitreous glass matrix 401F is chemically compatible in direct contact with lithium metal and second vitreous glass matrix 402F is not chemically compatible with lithium metal. In other embodiments, both first and second vitreous matrix layers are chemically compatible with lithium metal. While the illustrated embodiment is composed of two vitreous matrix layers, the disclosure contemplates multiple vitreous sulfide glass matrix layers (e.g., three or more). In various embodiments one or both vitreous matrix layers 401F/402F are essentially free of crystalline phases, and in preferred embodiments each vitreous matrix layer is a homogeneous vitreous glass layer essentially free of secondary phases (crystalline or amorphous). Preferably, each vitreous matrix layer is entirely devoid of detectable secondary phases. For example, solid electrolyte sheet 400F may be fabricated using a fusion draw process wherein two different glass streams are fusion bonded to each during the drawing step, as described in more detail herein below.

Figure 4G:
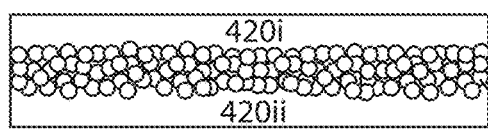
Figure 4H:
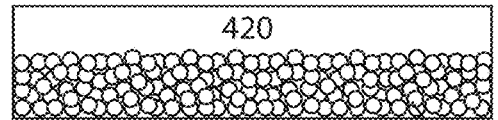

With reference to FIGS. 4G-H, there is illustrated cross sectional depictions of freestanding sulfide based solid electrolyte sheets in accordance with other alternative embodiments of this disclosure. In accordance with these embodiments, the bulk microstructure of the solid electrolyte sheet 400G/400H is not fully vitreous, but rather the sheet has a composite microstructure composed of a region 410 which forms the interior and is made by compaction of Li ion conducting sulfide glass particles, sulfide glass-ceramic particles, sulfide polycrystalline particles, or some combination thereof (typically sulfide glass particles), and a substantially amorphous vitreous stratum 420 of Li ion conducting sulfide glass, which defines at least the first principal side surface of sheet 400G/400H. With reference to FIG. 4G, solid electrolyte sheet 400G has first and second vitreous strata 420$i$/420$ii$ (e.g., composed of first and second glass matrix phases in the form of a stratum) defining the first and second principal side surfaces respectively. With reference to FIG. 4H, solid electrolyte sheet 400H has a single vitreous stratum 420 defining the first principal side surface. The vitreous stratum may be formed by a rapid surface melting operation (e.g., using a laser or hot gas), followed by a cooling quench. Preferably the vitreous stratum is essentially free of crystalline phases, and even more preferably the stratum, homogeneous, is essentially free of secondary phases. Typically the sulfide glass composition of the stratum and that of the particle compact region is substantially the same.

In addition to enabling flexibility, and substantial dendrite impenetrability, physical aspects of the surface can also be important for effecting and maintaining a tight interface with a lithium metal layer, and this is important for achieving uniform plating and striping of lithium metal, high lithium metal cycling efficiency (>99%), and ultimately a long cycle life lithium battery cell. Accordingly, in various embodiments, the principal side of sheet 100 in contact with lithium metal (i.e., first principal side 101A) should have a liquid-like surface that is also flat. Deviations from flatness can result in impedance variability as waviness can cause local positional variance of the ionic sheet resistance, leading to uneven Li metal plating and striping reactions resulting from non-uniform current density across the solid electrolyte sheet. As opposed to surface roughness, surface waviness $W_a$ is defined by a larger sampling length (typically >0.5 cm), and thus is an important factor for achieving a desirably uniform and homogeneous lithium plating morphology. In various embodiments, the waviness of first principal side surface 101A is low enough to maintain a gap free interface with the lithium metal layer upon repeated plating and striping of lithium metal; and, in particular, the level of waviness is sufficiently low to maintain a gap free interface after 50 charge cycles at an area ampere-hour charging capacity of >1 mAh/cm$^2$. Preferably the waviness of the sheet is less than 5 μm, and even more preferably less than 1 μm, and yet even more preferably less than 0.5 μm. For instance, in various embodiments, the acceptable level of waviness will depend on the thickness of the sheet itself. And thus, for a sheet having thickness in the range of about 5 um to 10 μm, $W_a$ is preferably less 1 um; for a sheet having a thickness in the range of about 10 μm to 20 μm, $W_a$ is preferably less than 1 um, and even more preferably less than 0.5 μm; for a sheet having a thickness in the range of about 20 μm to 50 μm, Wa is preferably less than 5 μm, and even more preferably less than 2 um, and yet even more preferably less than 1 μm; for a sheet having a thickness >50 μm (e.g., about 100 μm, 150 μm or 200 μm), Wa is preferably less than 10 μm, and even more preferably less than 5 um, and yet even more preferably less than 2 μm.

The ability to achieve long cycle life in a lithium metal battery cell of high energy density (preferably >250 Wh/l, and more preferably >500 Wh/l) depends not only on preventing dendritic shorting, which is certainly a requisite feature, but also requires high efficiency (>99%) and cycling at significant electrode area ampere-hour capacities (typically >1 mAh/cm$^2$). The chemical and physical interface between the sheet and the lithium metal layer are important considerations for cycling efficiency. As described in more detail below, the sheet surface composition is a key factor in determining the chemical interface, whereas the structure of the interface (i.e., the physical interface), is a function of both the surface composition and the surface topography, and, in particular, surface roughness is an important consideration, especially as it pertains to the morphology of lithium metal plated during charging of a battery cell in which sheet 100 is utilized. A sheet surface (e.g., principal side surface 101A) that is too rough can lead to a porous plating morphology, and thereby a porous interface of high surface area, and ultimately low cycling efficiency. A smooth surface is therefore desirable for achieving lithium metal cycling efficiency >99.0%, and preferably >99.2%, and more preferably >99.5%, and even more preferably >99.8%. Accordingly, in various embodiments the major area portion of the first principal side surface of the instant sheet has an average surface roughness $R_a$ that is sufficient to yield a dense interface between the lithium metal layer and the sheet, and in particular the lithium metal layer-like region immediately adjacent to the sheet is preferably >90% dense after 50 cycles under a charge corresponding to at least 1 mAh/cm$^2$, and more preferably >90% dense after 100 cycles under said charging condition, and more preferably >90% dense after 200 cycles. Accordingly, in various embodiments the average surface roughness of the major area portion of the first principal side surface is $R_a$<0.2 µm, preferably $R_a$<0.1 µm, or $R_a$≤0.05 µm, and even more preferably $R_a$≤0.05 µm, and yet even more preferably $R_a$≤0.01 µm. In other embodiments, as detailed herein below, having a surface topography with a controlled uniform surface roughness can be of benefit for bonding material layers, such as a lithium metal layer to the solid electrolyte during fabrication. For instance, in various embodiments, smooth first principal side surface 101A may be intentionally roughened, in a controlled manner, to effect a uniform surface roughness >0.2 µm (e.g., between 0.5 to 1 µm).

Preferably the afore described smoothness ($R_a$) and flatness ($W_a$) values are obtained in the virgin state, and by this expedient circumvents the costly and potentially prohibitive steps of grinding and polishing, and furthermore enables production of solid electrolyte sheets with pristine first and second principal side surfaces, which are untouched by an abrasive foreign solid surface, and therefore preferably of very high cleanliness values.

In addition to roughness and flatness, surface cleanliness is also a consideration for achieving a tight consistent interface between sheet 100 and a lithium metal layer or plated lithium metal, and thus in embodiments the glass inspection (GI) value of first principal side surface 101A is preferably less 1000 pcs/m$^2$ and more preferably less than 500 pcs/m$^2$, wherein the GI value is defined as the number of impurity particles having a major diameter of 1 nm or more and existing in a region of 1 m$^2$.

Preferably, sheet 100 is of optical quality, by which it is meant that the sheet has a surface roughness Ra≤0.02 µm and is essentially free of: i) crystalline phases ii) surface microvoids; and iii) internal nanopores. Preferably, the optical quality of the vitreous sheet is obtained in its virgin state as a solid.

Mechanical failure of any glass (e.g., window glass) will occur when the stress and defect size reach a threshold combination. The reliability is therefore statistical, but nonetheless related to the largest sized flaws on the surface. In contrast, small shallow flaws are perceived as less important, since the underlying mechanical strength of the sheet is largely unaffected by their existence. When shallow flaws are small in number density, or even singular, their very existence is generally considered insignificant from a practical perspective.

Figure 4I:
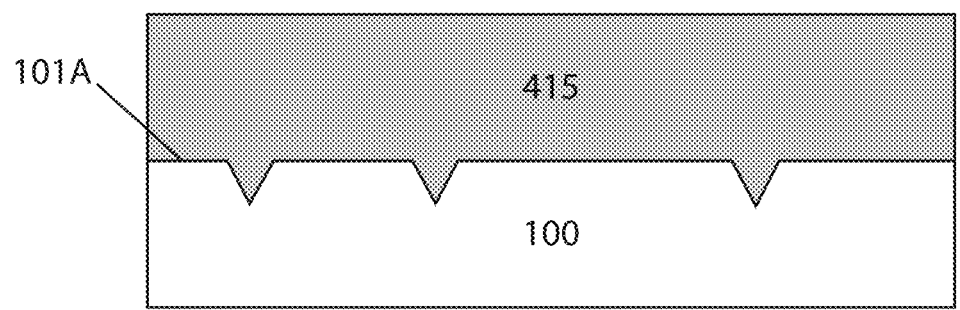
FIG. 4I illustrates a cross sectional view of a lithium metal layer and solid electrolyte sheet having a surface flaw.

At practical current densities however, as described further herein, a shallow flaw at an otherwise liquid-like surface can be prohibitive for realizing a dendrite resistant solid electrolyte glass sheet, if the flaw depth is beyond a threshold size for dendrite initiation. With reference to FIG. 4i, in a lithium metal battery cell, wherein first principal side surface 101A of vitreous solid electrolyte sheet 100 is in contact with a solid Li metal layer 415, a flaw extending beyond a threshold depth can create a highly localized hot spot for current focusing, which can lead to very high local current densities and dendritic penetration of Li metal into the sheet during cell charging, even for electrolytes with elastic moduli well above 20 GPa.

The threshold flaw depth is determined by several factors, including the detailed flaw geometry, the effective fracture toughness of the electrolyte, $K_{1c}^{eff}$ which is typically less than the fracture toughness determined from a mechanical fracture test, $K_{1c}$, the sheet thickness (t), and the local current density, $I_{local}$, which in turn is proportional to the nominal lithium anode current density, $I_{nominal}$. The general functional relationship for the nominal lithium anode current density, $I_{thr}$, may be expressed as $$I_{thr}=f(K_{1c}^{eff},t/(\Gamma,\nu,J_{local}))$$

where $K_{1c}^{eff}$ is the effective fracture toughness at the flaw tip where flaw extension most readily occurs $\Gamma$ is the deepest flaw extension into the solid electrolyte t is the sheet thickness $\nu$ is the viscosity or the equivalent flow stress (both temperature dependent) of the solid lithium, and $I_{local}$ is the solid electrolyte/lithium metal anode interface current density in the immediate vicinity of the surface flaw. Typically $I_{local}$>$I_{nominal}$.

To mitigate dendrite propagation through a solid electrolyte sheet having a liquid-like surface in direct contact with a solid lithium metal layer, the deepest flaw extension $\Gamma$ into the sheet should be less than 1% of the sheet thickness, and preferably less than 0.1%, and certainly no more than 5 µm. For example, the deepest flaw extension in a 100 µm thick sheet should be less than 1 µm, and preferably less than 0.1 µm; and for a 50 µm thick sheet it should be less than 0.5 µm, and preferably less than 0.05 µm.

Moreover, threshold current densities associated with dendrite initiation can be determined experimentally, or can be estimated from analytical approximations to the associated fracture mechanics-electrochemical problem. Typical experiments on polycrystalline solid electrolytes in direct contact with solid lithium metal anodes have typically shown threshold charging current densities for dendrite initiation below 0.5 mA/cm$^2$. In contrast, vitreous sulfide solid electrolytes with smooth interfaces, such as prepared by the methods contemplated herein, have surprisingly sustained current densities in excess of 2 mA/cm$^2$ without dendrite penetration, when cycling 2 mAh/cm$^2$ of lithium metal for over 50 cycles. Subject to these principles, the inventors are now able to characterize the surface quality of the sheet based on experimentally determined values for $I_{thr}$, by cycling a solid lithium metal layer in direct contact with first principal side surface 101A of solid electrolyte sheet 100 at 1 mAh/cm$^2$ for at least 50 charge cycles without propagating a dendrite across the sheet. In various embodiments the solid electrolyte sheet is characterized as having a surface quality commensurate with an $I_{thr}$ no less than 1 mA/cm$^2$, preferably no less than 2 mA/cm$^2$, more preferably I$_{thr}$ is no less than 3 mA/cm$^2$, even more preferably I$_{thr}$ is no less than 4 mA/cm$^2$, and yet even more preferably I$_{thr}$ is no less than 5 mA/cm$^2$.

Considering the sensitivity of dendrite initiation to the presence of shallow flaws, in order for the vitreous solid electrolyte sheet to retain its I$_{thr}$ value during handling and downstream processing of cell components and cells, special care should be given to minimize contact damage.

Figure 5A:
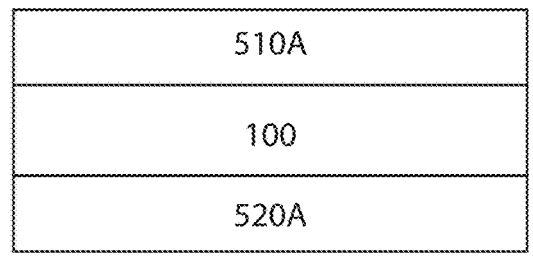
FIGS. 5A-C illustrate various electrode and battery assemblies in accordance with the instant disclosure.

With reference to FIG. 5A, in various embodiments, sheet 100 may be used as a solid electrolyte separator in a lithium battery cell 500A disposed between positive electrode 520A and negative electrode 510A. Typically battery cell 500A is a secondary cell (i.e., rechargeable).

In various embodiments battery cell 500A may be fully solid state or include a liquid/gel phase electrolyte. In various embodiments the liquid phase electrolyte contacts the electroactive material of the positive electrode but does not contact the electroactive material of the negative electrode, and in such embodiments the cell is referred to herein as a hybrid or a hybrid cell. In some embodiments the liquid electrolyte is continuous and contacts both the positive and negative electrodes, and such cells are referred to herein as having a common electrolyte (i.e., the electrolyte is common to both electrodes). In other embodiments the cell has two discrete liquid phase electrolytes that do not contact each other: i) a first liquid phase electrolyte that contacts the electroactive material of the positive electrode but does not contact the negative electroactive material, and may be referred to herein as catholyte; and ii) a second liquid phase electrolyte that contacts the electroactive material of the negative electrode but does not contact the positive electroactive material, and may be referred to herein as anolyte.

In various embodiments the negative electroactive material is lithium metal. In various embodiments the positive electroactive material is a lithium ion intercalating material. In particular embodiments the negative electroactive material is lithium metal and the positive electroactive material is a Li intercalation compound. In various embodiments the battery cells of the present disclosure are of a Li ion type, and make use Li ion intercalating material as the electroactive material in the negative and positive electrode respectively. For instance, Li ion intercalating carbon(s) and/or silicon for the negative electrode and Li ion intercalating transition metal oxides, sulfates/sulfides, phosphates/phosphides for the positive electrode.

Continuing with reference to FIG. 5A, in a particular embodiment cell 500A is rechargeable, and negative electrode 510A comprises a lithium metal layer (e.g., a lithium metal foil and/or an evaporated lithium metal layer) as the negative electroactive layer in direct contact with the first principal side surface of solid electrolyte sheet 100 (e.g., a vitreous sulfide glass sheet of thickness no greater than 100 µm). In various embodiments, the rechargeable lithium metal battery cell has: i) a rated ampere-hour capacity in the range of 0.5 mAh-10 Ah (e.g., about 1 Ah, about 2 Ah, about 3 Ah, about 4 Ah, or about 5 Ah); ii) a rated lithium metal electrode area capacity of about 1.0 mAh/cm$^2$, or about 2 mAh/cm$^2$, or about 3 mAh/cm$^2$; and is cycled for more than 50 cycles without propagating a dendrite at a discharge/charge current that corresponds to C/3-rate cycling (e.g., 1 mA/cm$^2$ at 3 mAh/cm$^2$), C/2-rate cycling (e.g., 0.5 mA/cm$^2$ at 1 mAh/cm$^2$), and preferably C-rate cycling (e.g., 1 mA/cm$^2$ at 1 mAh/cm$^2$), the sheet substantially impenetrable to dendrites, and preferably dendrite impenetrable, as defined above. Preferably, the cell cycles under the same conditions for greater than 100 cycles without propagating a dendrite, and even more preferably for greater than 500 cycles. And even more preferably, under the same cycling conditions, the solid electrolyte sheet remains impervious to any ingrowth of lithium metal (e.g., in the form of small lithium filaments) for more than 100 cycles, and preferably for more than 500 cycles. By use of the term rated area capacity it is meant the capacity at which the cell is cycled.

Figure 5B:
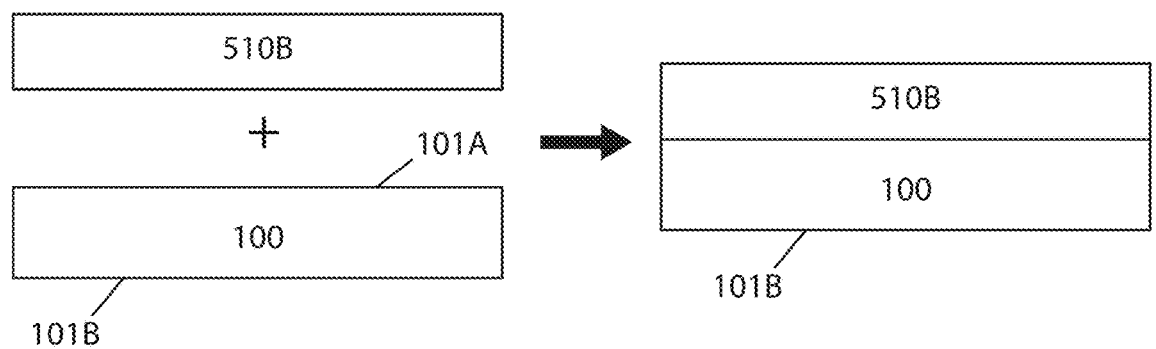

With reference to FIG. 5B, in various embodiments, sheet 100 Serves as a separator layer (or substrate-sheet) in a lithium metal electrode assembly 500B; the assembly composed of solid electrolyte sheet 100 Serving as a substrate for a lithium metal electroactive layer 510B disposed adjacent first principal side 101A. In various embodiments lithium metal electroactive layer 510B of assembly 500B is a foil of extruded lithium metal adhered directly to surface 101A or via a transient tie-layer, such as a metal coating that reacts (e.g., alloys) with the extruded lithium film on contact to form an electrochemically operable interface. In various embodiments, lithium metal layer 510B may be a coating deposited by physical vapor deposition directly onto surface 101A (e.g., evaporation or sputtering) or via a tie-layer coating as described above. As discussed in more detail below, when applying an extruded lithium metal layer, the lithium metal surface is preferably fresh; for example, freshly extruded or freshly treated to expose a fresh Li surface.

Figure 5C:
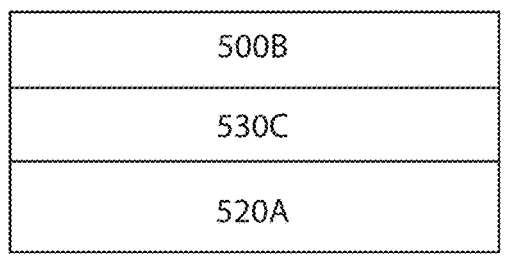

With reference to FIG. 5C, in various embodiments, lithium electrode assembly 500B is incorporated in hybrid battery cell 500C. The cell includes positive electrode 520C, lithium electrode assembly 500B, serving as a fully solid-state negative electrode, and optional liquid/gel electrolyte layer 530C between sheet 100 and positive electrode 520A. In embodiments, battery cell 500C makes use of a liquid electrolyte in contact with the positive electrode (e.g., a catholyte). Optional electrolyte layer 530C may be composed, in whole or in part, of the liquid phase catholyte. In various embodiments electrolyte layer 530C comprises a porous separator layer or gel layer impregnated with the liquid phase catholyte. In embodiments, wherein a liquid phase catholyte is used, it should be selected to ensure that it is chemically compatible in direct contact with the second principal side surface 101B of solid electrolyte sheet 100, and solid electrolyte sheet 100 should also be chemically compatible with and substantially impervious to the liquid catholyte. To prevent contact between the liquid phase electrolyte (i.e., catholyte) and lithium metal layer 510B, in various embodiments the lithium electrode assembly includes a backplane component seal and an edge seal that isolates the lithium metal layer 510B from the catholyte. For instance, the lithium layer effectively housed in a liquid impermeable compartment wherein solid electrolyte sheet 100 provides at least one major wall portion. In another embodiment of a hybrid cell, it is contemplated that the electrode assembly may be a positive electrode assembly, wherein the electroactive material of the positive electrode (e.g., a Li ion intercalation material) and a liquid phase catholyte are combined and encapsulated inside a liquid impermeable compartment composed of first and second solid electrolyte sheets edge sealed to each other.

Methods for making Li ion conducting solid electrolyte sheet 100 in accordance with the instant disclosure are provided, and, in various embodiments, for making a dense substantially amorphous vitreous sheet of sulfide based Li ion conducting glass.

In various embodiments, the method involves solidifying an inorganic fluid sheet of unbroken continuity having a composition corresponding to that of a Li ion conducting glass with a room temperature intrinsic Li ion conductivity $\geq 10^{-5}$ S/cm, preferably $\geq 10^{-4}$ S/cm, and more preferably $\geq 10^{-3}$ S/CM (e.g., a sulfide-based glass). In particular embodiments, the fluid sheet of sulfide glass is caused to flow along its lengthwise dimension as a continuous fluid stream having substantially parallel lengthwise edges, and then solidified to form the vitreous solid electrolyte sheet, mother-sheet or web.

Preferably the fluid stream is, itself, thin and of uniform thickness, as described above. In various embodiments the sulfide glass is air sensitive, and the processes used in making the instant vitreous sheet is performed in an atmosphere substantially devoid of moisture and oxygen (e.g., dry air or dry nitrogen or dry argon).

In various embodiments, the solidified fluid stream is a long solid electrolyte sheet of vitreous sulfide glass with area aspect ratio >2, and typically >5, and more typically >10. In various embodiments, the methods are suitable for making a very long vitreous Li ion conducting glass sheet; for instance, >10 cm, >50 cm, and in embodiments >100 cm long and typically at least 1 cm wide, and more typically between 2-10 cm wide (e.g., about 2 cm, 3 cm, 4 cm, or about 5 cm wide).

In embodiments the fluid stream, as it flows, is unconstrained along its lengthwise edges and does not expand in a widthwise direction. In various embodiments the thin fluid stream of uniform thickness is substantially untouched by a foreign solid surface upon solidification. In various embodiments, the fluid stream is a vitreous sulfide based glass, preferably essentially free of crystalline phases, and more preferably homogeneous (i.e., essentially free of secondary phases, crystalline or amorphous).

To facilitate flow, the fluid stream may have a viscosity low enough to allow it to flow under its own weight. In various embodiments, the fluid stream is caused to flow under the force of gravity while retaining its sheet-like shape, or by pulling/drawing (e.g., via motorized rollers), and in an alternative embodiment, the vitreous solid electrolyte sheet is made by a novel capillary draw method wherein the fluid stream is driven to flow by capillary forces.

In some embodiments the fluid stream is formed directly from a liquid melt of Li ion conducting sulfide glass composition, and the liquid stream of molten glass, so formed, is cooled from $T_{liq}$, or about $T_m$ (e.g., a temperature slightly above the liquidus temperature), to a temperature below the glass transition temperature ($T_g$). The cooling process may be natural or facilitated to cause solidification within a time frame sufficient to yield the instant freestanding sulfide based solid electrolyte sheet substantially amorphous and preferably essentially free of crystalline phases. Preferably, the sulfide based solid electrolyte glass composition is selected such that it can be repeatedly heated and cooled between the solid glass phase and the liquid melt phase without crystallizing, phase segregating, or undergoing any other adverse thermal event.

In other embodiments sheet 100 is formed by: i) heating a section of a Li ion conducting sulfide glass preform above its $T_g$, ii) pulling on the preform; and iii) cooling the fluid stream so formed to a temperature below $T_g$. The heated section of the preform reaches a temperature above $T_g$ but below $T_m$, and preferably below $T_x$ (i.e., the crystallization temperature upon heating). In various embodiments, the Li ion conducting sulfide glass preform is itself a vitreous, and made by melting and quenching the glass to a desired shape and size, or by melting and quenching the glass to a large construct, and then sizing down the construct (e.g., by cutting, grinding and/or drawing) to the shape and dimension desired of the preform.

Similar to a mother-sheet, the fluid stream from which it is derived may also be characterized as having a high quality center portion (i.e., major area portion) and peripheral edge portions, which, when compared to the center portion, may be of a different thickness, lower surface quality, and/or having poor thickness uniformity. Preferably, the high quality center portion of the fluid glass stream defines >30% of the total area (or total volume) of the fluid stream, and more preferably >50%, >70%, and even more preferably >90%. In various embodiments the high quality center portion of the fluid stream is thin ($\leq 500$ μm) with a uniform thickness (e.g., about 20 μm, about 30 μm, about 40 μm, about 50 μm, about 60 μm about 70 μm, about 80 μm, about 90 μm or about 100 μm). In various embodiments the length and width of the high quality center portion of the thin fluid stream is greater than 10 cm long (e.g., greater than 50 cm or greater than 100 cm) and greater than 1 cm wide; for instance between 2-10 cm wide (e.g., about 2 cm, about 3 cm about 4 cm, about 5 cm, about 6 cm, about 7 cm, about 8 cm, about 9 cm or about 10 cm). In some embodiments the fluid stream is of sufficient surface quality and thickness uniformity across its entire length and width, that whence solidified, the solid electrolyte sheet or web formed there from does not require removal of edge portions, except optionally for the purpose of sizing. In various embodiments, the major opposing surfaces of the high quality center portion of the fluid stream are pristine, and thus untouched by a foreign solid surface immediately prior to solidification. For instance, the fluid stream is caused to flow and traversed by edge rollers and/or edge guide rolls in direct contact with the solidified peripheral edge portions but not the center portion from which the separator sheets are ultimately cut-to-size.

In various embodiments, drawing techniques such as melt draw and preform draw are used to make the fluid stream of unbroken continuity, and ultimately the solid electrolyte sheet. Draw processing yields the advantage of naturally developed shapes and surfaces, and thus the geometric shape (e.g., substantially parallel lengthwise edges), thickness and/or surface topography of the solid electrolyte sheet may manifest directly from the as-solidified fluid stream (i.e., from the sheet in its virgin state as a solid).

In various embodiments, the sulfide glass compositions are selected based on the separation between $T_x$ and $T_g$ (i.e., the glass stability factor). Preferably the glass composition has a glass stability factor >100° C. However, sulfide-based glasses in accordance with this disclosure may be drawn, and in some embodiments will be drawn, to a substantially amorphous sheet, and preferably essentially free of crystalline phases, in spite of having a glass stability factor <100° C. For instance, in various embodiments the sulfide based glass has a glass stability factor <100° C., <90° C., <80° C., <70° C., <60° C., <50° C., <40° C. and even less then <30° C. (e.g., no more than 50° C.). To prevent crystal nucleation, the time span over which the glass material is heated is preferably kept to a minimum.

Draw processing of sheet 100 is suitable for yielding, in its as-solidified state, a substantially amorphous vitreous sheet of battery serviceable size, uniform thickness and substantially parallel lengthwise edges. Consequently, it is contemplated that the vitreous sheet, as drawn (i.e., as solidified), requires little to no post formation processing (i.e., post solidification processing), other than annealing and slicing off low quality edge portions. For instance, the drawn solid electrolyte sheet, once formed, is annealed to remove stresses, but does not require any grinding and/or polishing to bring about the desired surface topography (e.g., a smooth liquid-like surface). To retain the amorphous nature of the vitreous solid electrolyte sheet once it has been drawn (e.g., essentially free of crystalline phases), care should be taken to avoid processes that might expose the sheet to temperatures which would effect crystallization, and thus the solid electrolyte sheet should not be subjected to a post-solidification heat treatment near (or above) its crystallization temperature ($T_x$).

Draw processing is generally used in the large-scale manufacture of ion-exchangeable flat glass, and glass strips for semiconductor and display technologies. Herein, draw processing is being utilized to make highly Li ion conductive vitreous solid electrolyte glass, and in particular Li ion conducting sulfur-based glass sheets, including those with a glass stability factor less than 100° C., as are described herein throughout the specification.

The chemical composition of the sulfur-based solid electrolyte glass will determine its thermal properties. Accordingly, as described above, in various embodiments the glass composition is selected to optimize its thermal properties for formability, while retaining acceptable Li ion conductivity ($>10^{-5}$ S/cm). In various embodiments the glass composition is selected for its ability to achieve a viscosity of $10^3$ to $10^8$ poise, and preferably $10^4$ to $10^7$ poise, at a temperature below that at which it starts to crystallize, while having a room temperature Li ion conductivity of no less than $10^{-5}$ S/cm, preferably no less than $10^{-4}$ S/cm, and more preferably no less than $10^{-3}$ S/cm.

In various embodiments sulfide based glass sheet 100 is fabricated using an overflow technique such as fusion draw, which uses a drawing tank and takes advantage of gravity to allow molten glass to flow down the outside surfaces of the tank, and by this expedient yields two flowing glass surfaces (i.e., two liquid streams) which are joined (by fusion) to form a single flowing sheet (i.e., a single liquid glass stream of unbroken continuity).

Figure 6A:
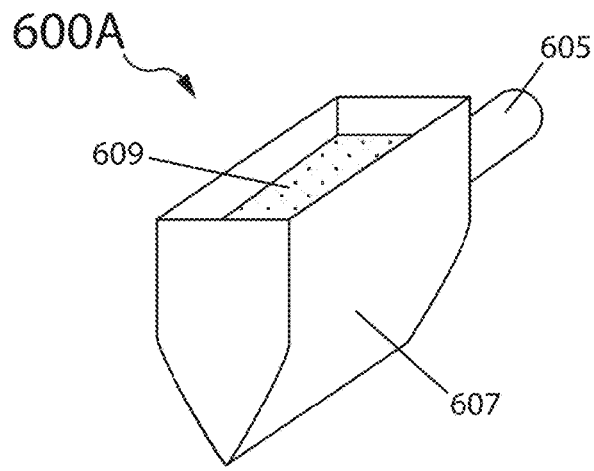
FIGS. 6A-E illustrate apparatus' for making a freestanding Li ion conducting solid electrolyte sheet in accordance with various embodiments of the disclosure.
Figure 6B:
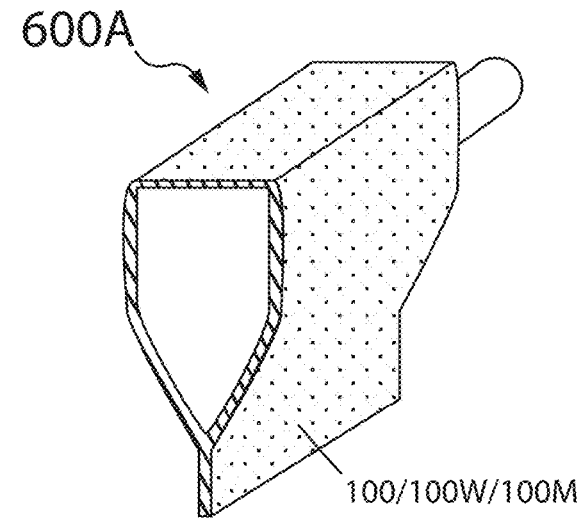

In one embodiment the disclosure provides a method for making vitreous sulfide based solid electrolyte sheet 100 by fusion draw. With reference to the fusion draw apparatus in FIGS. 6A-B, a material batch of Li ion conducting sulfide glass powder, which may be formed by mechanical milling, is heated in a melting vessel (e.g., above $T_{liq}$) wherefrom it is caused to flow (via flow pipes 605) into a trough-like container 607 in an amount sufficient to cause overflow of the fluid glass 609 from both sides of the trough. The opposing flows are then combined by fusion to form a single liquid stream of unbroken continuity 100, which may be fed to drawing equipment (e.g., via edge rollers or glass pulling rods), for controlling the thickness of the sheet depending upon the rate at which the solidified portion of the sheet is pulled away. Preferably, the major surfaces of the as-solidified glass sheet, or at least its high quality center portion, are pristine, as they have not contacted any part of the apparatus (e.g., the trough walls or flow pipes), and therefore may have superior surface quality. In various embodiments, the fusion draw process may be modified to allow for the drawing of two dissimilar glasses; for example, one optimized for contact with lithium metal and the other optimized for a different purpose(s) or utility, such as contact with a positive electrode battery cell component (e.g., a lithium positive electroactive material) or a liquid phase electrolyte, or ease of processing or high conductivity. For instance, a first sulfide glass stream of unbroken continuity (e.g., having as constituent elements: lithium, sulfur, and silicon, but devoid of phosphorous) fused to a second sulfide glass stream (e.g., having as constituent elements: lithium, sulfur, and one or more of boron or phosphorous, but devoid of silicon).

Figure 6C:
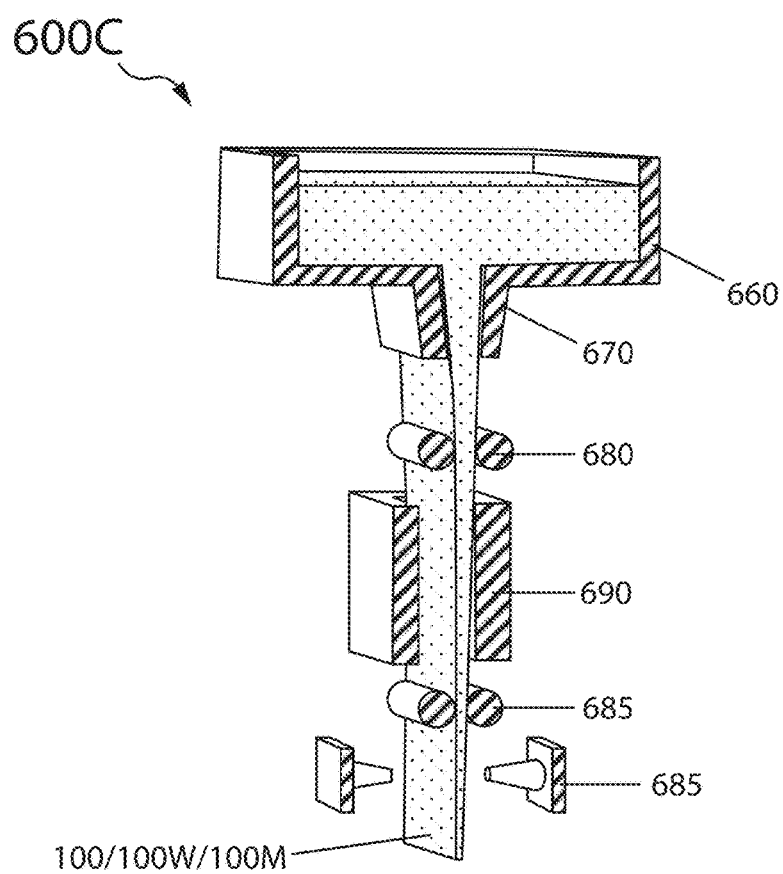

In various embodiments, freestanding solid electrolyte sheet 100 may be formed by slot draw to yield a substantially amorphous vitreous monolithic solid electrolyte sheet of Li ion conducting sulfur-containing glass. With reference to FIG. 6C, an apparatus 600 for making the freestanding sheet using a slot drawing process is illustrated. The apparatus includes i) melting vessel 660, for heating and holding a material batch above the melting temperature; and ii) open slot 670 near the bottom of the tank and through which the batch of glass flows by drawing to form a continuous glass sheet 100 which may be optionally pulled through rollers 680 for shaping, and optionally traversed into furnace 690 for an annealing heat treatment, and thereafter optionally placed through a second set of rollers 685 and/or subjected to an edge removal process (as described above) to yield the vitreous sheet as a solid electrolyte separator or web in its final or near final form.

Additional processing steps may be used to enhance the cooling rate, such as flowing a non-reactive fluid (e.g., dry nitrogen) over one or both surfaces; including a warm inert fluid (i.e., above room temperature, 25° C.), a cold inert fluid (i.e., below room temperature, 25° C.), a cryogenic fluid of nitrogen, or other inert gas over the surface(s) of the fluid glass stream (e.g., helium or argon). The cooling gas will generally have a very low moisture content (e.g., dry air or dry nitrogen), preferably less than 0.5%, and more preferably ultra dry nitrogen or gas devoid of oxygen, and with a dew point less than −50° C., and preferably less than −70° C.

In various embodiments the material batch is composed of raw precursor powders in proper stoichiometry for making the glass (e.g., $Li_2S$, $B_2S_3$, $P_2S_5$, $P_2O_5$ and the like), and the precursor ingredients should be thoroughly blended during melting to avoid stria-like inhomogeneities, such as ream, and may be fined as necessary to mitigate bubbles.

In various embodiments the material batch is already a glass (i.e., it is a glass or amorphous batch), typically in powder form. In embodiments the glass/amorphous powder batch may be made by mechanically milling precursor powders (typically via ball milling), the process sometimes referred to herein and elsewhere as mechanochemistry, wherein the process is generally understood to be based on a mechanically induced self-propagating reaction (sometimes referred to herein as a MSR process). For instance, material batches of sulfide glass may be prepared via mechanical milling of precursor ingredients. The milling may be performed at room temperature for several hours (e.g., about 10 hours) using a planetary ball mill, zirconia milling media, and rotating speeds of several hundred revolutions per minute (e.g., about 500 RPM). Methods for processing batches of Li ion conducting sulfide glass powders using mechanical milling are generally described in U.S. Pat. No. 8,556,197 to Hama and Hayaahi, and US Patent Publication No.: 2005/0107239 to Akiba and Tatsumisago, both of which are hereby incorporated by reference for their disclosure of these methods. Alternatively, the batch glass may be processed by melt quenching precursor ingredients, followed by optional pulverizing of the quenched blob or boule to a powder; in such instances the material batch is itself an already melt-processed glass.

The sulfide glasses, and their precursor powder ingredients, are generally sensitive to constituents of air (e.g., water and oxygen), and so handling of the glass and its ingredients is performed in an inert environment (typically a dry noble gas such as argon), and operations such as heating (e.g., heating above the melt or above $T_{liq}$) and quenching (e.g., cooling the melt below $T_g$), and/or mechanical milling (e.g., high energy ball milling) may be performed in a vacuum evacuated chamber (e.g., in a vacuum sealed quartz tube in the case of melt/quench processing) or under an inert environment of a dry noble gas.

In various embodiments an MSR produced powder is used as a glass batch in the making of the vitreous sheet or as a precursor ingredient for making a glass batch or glass melt. In various embodiments the MSR produced powder is a Li ion conductive glass (e.g., sulfide glass). In various embodiments the MSR produced powder may be a precursor ingredient for making a batch glass, such as a boron sulfide or silicon sulfide powder, typically amorphous. The precursor ingredients for making the glass batch powder (e.g., Li ion conductive) or for making the MSR precursor powder (e.g., amorphous boron sulfide) include compounds (e.g., sulfides and oxides), elemental ingredients such as phosphorous, boron, silicon and sulfur, and combinations thereof. For instance $SiS_2$ or $B_2S_3$ precursor ingredients may be made by high-energy ball milling of elemental silicon with elemental sulfur, or elemental boron with elemental sulfur. Likewise, an MSR produced lithium boron sulfide or lithium silicon sulfide glass batch (e.g., Li ion conducting), may be processed by high energy ball milling lithium sulfide and elemental sulfur with elemental boron or elemental silicon, respectively.

Starting with a material batch that is already a Li ion conducting glass, as described above, has distinct advantages for drawing, and generally for shaping the glass. For instance, as opposed to starting with precursor powder materials (e.g., $Li_2S$ and $P_2S_5$), the batch powder glass can be melted at lower temperature and will generally have a lower vapor pressure when compared to a melt derived from raw precursor ingredients. Typically, as outlined above, the process includes a first step of making a batch sulfide glass powder using mechanical milling (or conventional melt/quench/grind); a second step of heating the glass powder batch to a temperature sufficient to allow drawing (e.g., about $T_{liq}$); and a third step, which is to process the molten glass to a vitreous glass sheet by drawing as outlined above.

Accordingly, in various embodiments the Li ion conducting vitreous sheet is formed by a first step of i) providing or making a material batch of Li ion conducting glass (e.g., sulfide glass particles or powder, or as a bulk sulfide glass element/preform); a second step of ii) heating the material glass batch or preform to a temperature sufficient to effect a workable viscosity (e.g., to form a viscous fluid of unbroken continuity, e.g., a melt at or above $T_{liq}$, or the preform at or above its softening temperature); and a third step of forming and cooling the viscous fluid into a solid vitreous sheet of Li ion conducting sulfide glass.

In contrast to melting a multi-component precursor mixture of ingredients (e.g., $Li_2S$, $B_2S_3$, $SiS_2$, and the like) and then processing the melt to form a solid vitreous sheet, the method of using an already formed Li ion conducting glass as the material batch (e.g., in particle or powder form) is somewhat counterintuitive as it adds a potentially costly additional glass making step to the process, and, in particular, it effectively leads to making the Li ion conducting glass twice—initially as a glass material batch made from precursor ingredients, then, secondly, processing the batch glass back to the molten state at a temperature at or above $T_{liq}$ (sometimes referred to herein as a re-melt), and thereafter forming the vitreous sheet from the re-melted glass. In various embodiments, the re-melt is formed by heating a batch glass, made by MSR, above $T_{liq}$.

In various embodiments the method of making the Li ion conducting glass material batch is, itself, a multi-step process; for example: i) forming a glass powder by MSR of raw precursor ingredients (e.g., $Li_2S$, $B_2S_3$ powders, B, S, P and the like), and, preferably, the MSR processed glass, highly Li ion conductive; and ii) heating the MSR glass batch to a temperature sufficient to ensure that it (the MSR glass) is fully reacted as a molten glass (sometimes referred to herein as a re-melt), typically at or above $T_{liq}$; iii) cooling the re-melt to form bulk glass (e.g., quenching the molten glass in a gaseous or liquid medium which is at a temperature below $T_g$); and iv) optionally pulverizing the bulk glass to yield a material batch of Li ion conducting glass powder for downstream processing of a vitreous sheet (e.g., by re-melting the glass powder back to the molten state).

In various embodiments vitreous solid electrolyte sheet 100 is formed by preform drawing, wherein a preform of the sulfide based solid electrolyte glass is drawn (e.g., pulled) in length at a temperature above the glass transition temperature of the prefrom, to the desired shape and size. Typically, to be drawn from a preform, it (the preform) is heated to a temperature at which it has low enough viscosity that it can deform under its own weight. This generally occurs at around the "softening point"—typically defined as having a viscosity of about $10^{7.65}$ poise. Upon drawing the preform, the heated section (i.e., that part of the preform in the deformation zone) becomes a highly viscous fluid of unbroken continuity, as it reaches a viscosity typically in the range of $10^4$-$10^6$ poise.

Figure 6D:
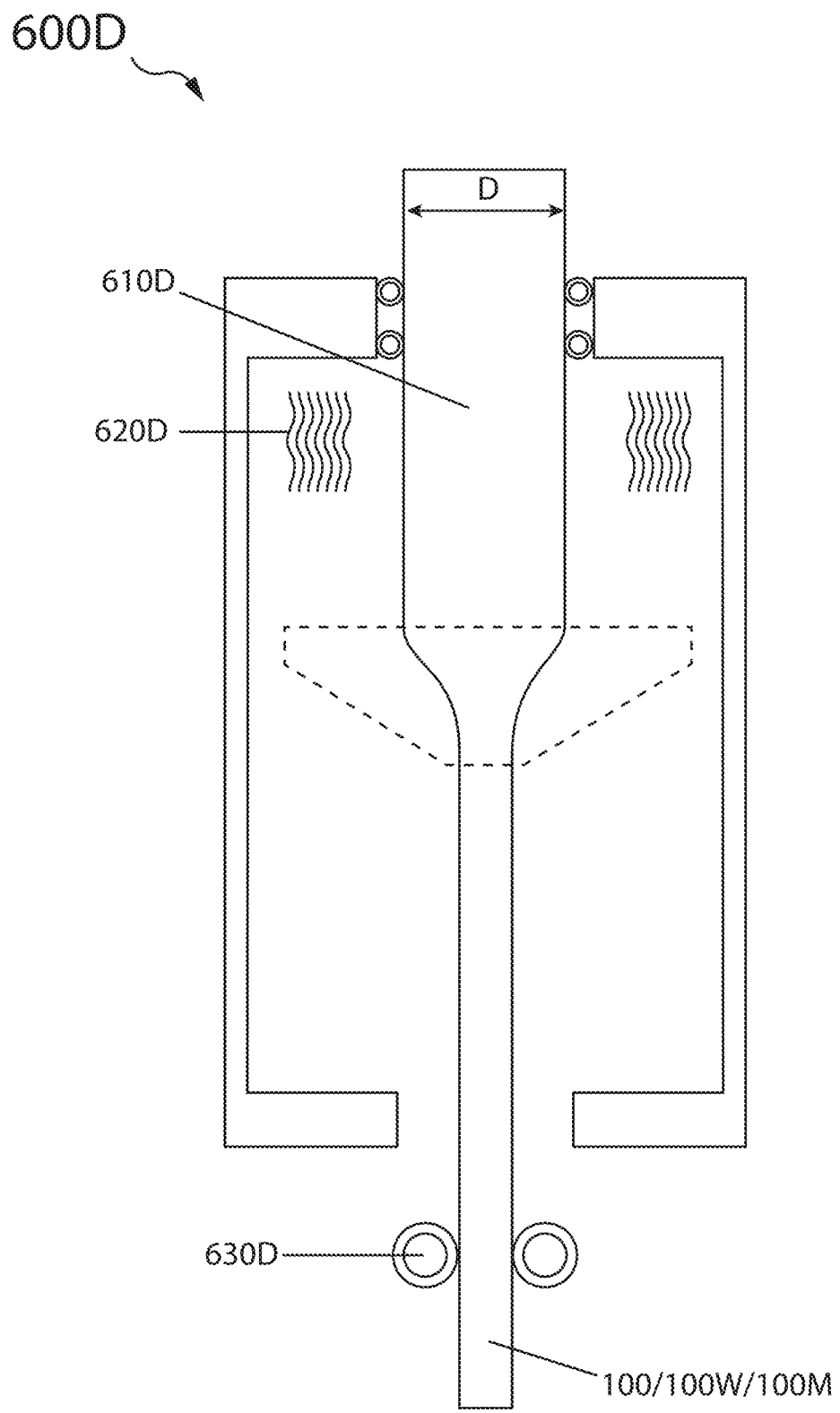

With reference to FIG. 6D there is shown an apparatus 600D suitable for preform drawing sulfide based solid electrolyte sheet 100. In operation, the vitreous preform 610D is heated in a deformation zone 620D and then drawn using mechanized rollers 630D. Within the deformation zone the preform is exposed to heat sufficient to raise its temperature above $T_g$ but below $T_m$ and preferably below $T_x$, wherefrom it forms a viscous fluid stream of unbroken continuity that is drawn to yield a wall structure of desired battery serviceable shape and size (e.g., a sheet), the fluid stream thinning as it flows. In some embodiments it is contemplated that the drawing apparatus includes a flow system for flowing an inert gas nearby the drawn sheet in order to speed up cooling of the pulled sheet section, the gas preferably having a very low moisture and oxygen content, as described above.

The resulting cross sectional shape of the formed sheet is usually similar to that of the preform from which it was drawn. Preferably, the preform has a smooth flat surface with minimal surface roughness and waviness. In various embodiments the preform is, itself, a vitreous monolithic construct. For instance, the preform may be made by molding molten glass into a rectangular bar-like shape of significant thickness and width, and typically 10 times thicker than that desired for sheet 100. For instance, to a draw a thin vitreous solid electrolyte sheet in the range of 10 to 500 μm thick, in various embodiments the preform is a rectangular bar having a thickness in the range of 200 μm to 1000 μm, a width of 5 to 20 cm, and a length of about 30 cm to 100 cm (e.g., about 5 cm wide, about 30 cm long and about 400 um thick). Methods and apparatus' for drawing a glass preform to form a substrate for semiconductor devices and flat panel displays are described in US Pat. Pub. No.: US20070271957, US20090100874; 20150068251; all of which are incorporated by reference herein.

In various embodiments the preform may be made by dispensing a molten sulfide glass of the desired composition into a hot mold of vitreous/glassy carbon, preferably at a temperature above $T_g$ (of the glass), and, in some instances, the mold may be held at a temperature above $T_x$, and then, given sufficient time to minimize turbulence, cooling the mold to the solidify the glass preform. By this expedient, the preform is more readily processed without voids or cracks that might otherwise arise if cooled too rapidly. In various embodiments, the preform may be processed via precision glass molding, or ultra precision glass processing. Depending on the chemical composition of the sulfide glass, the material from which the mold is made can be an important aspect of processing. The mold should be chemically compatible with the glass at high temperature, and it should also have a surface quality commensurate with that required of the preform itself, and thus preferably of a smooth liquid-like surface (e.g., vitreous carbon, also referred to herein and elsewhere as glassy carbon).

In various embodiments, the preform is fabricated from the melt in a glassy carbon mold (e.g., the mold is made of glassy carbon or at least the mold surfaces which contact the sulfide glass are made of glassy carbon). In other embodiments, the preform may be processed by melting a material batch of an already processed glass or its raw precursor materials in an evacuated and sealed quartz ampoule. The furnace employed may be horizontal but is preferably vertical and even more preferably a rocking furnace, which allows for mixing during heating. Once the glass has fully melted, the ampoule is held vertical for a sufficient time to minimize turbulent flow, and then immersed in a quenching medium (e.g., a water bath, or a gaseous environment (such as air) at room temperature (25 C), or at about $T_g$ of the glass, or just below $T_g$). For instance, the furnace may be a vertical furnace with automation control for manipulating the ampoule. In various embodiments, rather than fast quench the melt, the melt may be slow cooled (e.g., by less than 10° C. per minute) to enable thermal equilibrium throughout the entirety of the melt, and by this expedient reducing the tendency for cracking via thermal shock. The cooling rate and temperature time cycle on cooling depends on a number of factors, including the glass stability factor and crystal growth rate. In various embodiments, especially when the glass stability factor is <100° C., the melted sulfur based glass (e.g., in the ampoule) is slow cooled to a temperature above $T_x$ (e.g., >20° C., >50° C. above $T_x$) but below $T_{liq}$, and then quenched below $T_g$ to prevent crystallization. For glasses having thermal stability >100° C., it is contemplated to slow cool to a temperature above $T_g$ (e.g., >20° C., >50° C. above $T_g$) and then quench below $T_g$. Immediately following quenching, the vitreous glass preform may be annealed to remove internal stresses that may develop as a result of the process.

Cylindrical ampoules are commonly employed, however, the disclosure contemplates using an elliptical or rectangular shaped ampoule, to produce, directly from the melt/quench, a rectangular shaped vitreous bar of Li ion conducting sulfur based glass, preferably of thickness <5 mm, and more preferably <1 mm thick. For instance, the preform, as-formed, is ≤1 mm thick and >1 cm wide, and preferably >10 cm long. By this expedient the preform is of the desired shape for drawing a glass sheet or ribbon. The use of a rectangular shaped ampoule improves the cooling profile across the thickness of the preform, as opposed to cylindrical ampoules, which typically have diameter 1 cm or greater. The various methods described herein to produce the preform may also be suitable for batch fabrication of flat specimens by cutting the preform (e.g., via a wire saw) to a desired shape and thickness, followed by polishing and/or controlled roughening to achieve the desired surface quality. Typically, the sample produced in this manner will be cut along the width of the preform. For example, if the preform so formed is cylindrical, the flat specimens are generally circular shaped pieces with diameter matching, or near that of, the preform itself. In this way, a disc or rectangular flat specimen of about 1-3 cm diameter or side, may be provided for testing or use in a stacked or single layer battery cell. Small solid electrolyte specimens may be batch produced in this manner. In another embodiment, flat specimens may be batch processed by stamping molten sulfur based glass between pressing plates (e.g., vitreous carbon plates) to a desired thickness, or vitreous glass blanks (e.g., blobs or boules) of the Li ion conducting sulfur-based glass may be precision molded as described above by heating the blanks above $T_g$ (e.g., to about or above the softening point), and molding the blanks to the desired shape and thickness, followed by cooling to below $T_g$. It is also contemplated to use glass powder in place of the vitreous blanks, followed by precision molding.

In accordance with the disclosure, drawing apparatus 600A-D are generally enclosed in a controlled atmosphere housing or the drawing is performed in a dry room or in a large dry box to minimize or eliminate exposure of the vitreous sulfide preform or molten sulfide glass to moisture and/or oxygen in the air. For instance, the controlled atmosphere has less than 100 parts per million (ppm) $H_2O/O_2$ (e.g., no more than 10 ppm). In various embodiments the atmosphere nearby, or inside, the melting vessel contains an inert gas partial pressure (e.g., argon) effective to reduce volatilization and condensation of elemental constituents, especially sulfur and phosphorous (when present), which are prone to evaporate from the melt. To minimize the loss of volatiles, in various embodiments the inert gas pressure inside the housing or vessel is greater than 1 atm (e.g., about 2 atm or greater). In certain embodiments the melting vessel is capped with a cover plate to achieve an overpressure of sulfur above the melt, for reducing volatilization. In various embodiments the inert gas is maintained at a higher pressure over the melt than the vapor pressure of sulfur at the temperature of the melt, or that of phosphorous when present. In various embodiments, it is contemplated that a certain amount of nitrogen gas may be combined with the inert gas for the purpose of incorporating nitrogen as a component of the sulfide glass skeleton.

The as drawn solidified sheet may be placed on a backing layer to facilitate conveyance of the solid electrolyte sheet. For example, a polymeric web may serve as a conveying backing layer or as a conveyer belt. In various embodiments the backing layer also serves as interleave for protecting surfaces when the sheet is formed continuously into a web and rolled. The backing layer may be a non-lithium ion conducting glass sheet (e.g., a silica glass or borosilicate glass) or a polymer film (e.g., a polyester layer). Generally the backing layer does not strongly adhere to the solid electrolyte sheet, and so readily removed. In some embodiments the backing layer may be coated with a liquid layer (e.g., an organic solvent or organic substance) that enhances adhesion but still allows for easy removal. It is also contemplated that the backing layer may also serve as interleave and as a polymeric separator layer (e.g., a porous or gel-able polymer layer). In such embodiments the instant separator is a combination of the polymeric separator layer and free-standing glass sheet in a hybrid battery cell, as described in more detail herein below, or in a solid state cell, if the polymeric separator layer is a solid polymer electrolyte in the absence of a liquid electrolyte.

In some embodiments the continuously drawn solid electrolyte sheet is cut-to-size inline with the drawing process. The cut-to-size solid electrolyte sheets may then be stacked for storage and transport. In various embodiments a material interleave may be incorporated between adjacently stacked sheets to prevent their direct contact, or the solid electrolyte glass sheets may by fitted with an edge-protector elements that serve to protect the edges of the sheet from physical damage, and may also serve as a spacer for creating a gap between stacked or rolled sheets, as described in more detail below.

With reference to FIGS. 7A-C there is illustrated flowcharts representative of various methods 700A-C of making solid electrolyte sheet 100 using draw processes as described above. Methods 700A-C include a first step of selecting a glass composition 705. For example, the composition may be selected for suitability to the particular draw process of making sheet 100 (e.g., preform draw and/or melt draw).

In various embodiments the elemental constituents are selected and adjusted to enhance thermal properties, including one or more of the glass stability factor, hruby parameter and thermal expansion. In some embodiments that adjustment leads to a significant reduction in conductivity (e.g., by a factor of 2, 3, 4 or 5, or an order of magnitude reduction).

In various embodiments, the mole ratios of elemental constituents are adjusted to increase the glass stability factor of the sulfide-based glass. In various embodiments the adjustment results in a glass stability factor $\{T_x-T_g\} \geq 30°$ C., preferably $\geq 50°$ C., and even more preferably $\geq 100°$ C. In various embodiments the adjustment results in an increase of the glass stability factor by at least 10° C., but with a subsequent loss in conductivity of between a factor of 2-100 (e.g., by a factor of between 2-5, 5-10, 10-20, 20-50 and 50-100), while still retaining a conductivity $\geq 10^{-5}$ S/cm, and preferably $\geq 10^{-4}$ S/cm. In various embodiments, the glass stability factor increases by more than 20° C., or more than 30° C., or more than 50° C.

In various methods, the step of selecting the sulfur containing glass composition is based on glass stability factor and conductivity; e.g., selecting a glass composition having a glass stability factor >20° C., or >30° C., or >40° C., or >50° C., or >60° C., or >70° C., or >80° C. or >90° C. or >100° C. and a Li ion conductivity $\geq 10^{-5}$ S/cm, and preferably $\geq 10^{-4}$ S/cm, and more preferably $\geq 10^{-3}$ S/cm. In embodiments, the glass composition having the above glass stability factor comprises one or more of oxygen and/or silicon. In particular embodiments the amount of oxygen in the glass is between 0.5% to 10 mole % (e.g., between 0.5% to 1% or about 1%, about 2%, about 3%, about 4%, about 5%, about 6%, about 7%, about 8%, about 9%, or about 10 mole %). In embodiments the amount of boron in the glass is between 10 to 20 mole % (e.g., about 10%, about 11%, about 12%, about 13%, about 14%, about 15%, about 16%, about 17%, about 18%, about 19%, or about 20%).

In various methods, the step of selecting the sulfur containing glass composition is based on Hruby parameter and conductivity; e.g., selecting a glass composition having Hruby parameter >0.4, or >0.5, or >0.6, or >0.7, or >0.8, or >0.9, or >1, and a Li ion conductivity $\geq 10^{-5}$ S/cm, and preferably $\geq 10^{-4}$ S/cm, and more preferably $\geq 10^{-3}$ S/cm. In embodiments, the glass having the above composition comprises one or more of oxygen and/or silicon. In particular embodiments the amount of oxygen in the glass is between 0.5% to 10 mole % (e.g., between 0.5% to 1% or about 1%, about 2%, about 3%, about 4%, about 5%, about 6%, about 7%, about 8%, about 9%, or about 10 mole %). In embodiments the amount of boron in the glass is between 10 to 20 mole % (e.g., about 10%, about 11%, about 12%, about 13%, about 14%, about 15%, about 16%, about 17%, about 18%, about 19%, or about 20%).

In various methods the step of selecting the sulfur containing glass composition involves adjusting the mole percent of Li and/or S (sulfur) and/or O (oxygen) in the glass to achieve a Hruby parameter of >0.5, or >0.6, or >0.7, or >0.8, or >0.9, or >1 and a Li ion conductivity $\geq 10^{-5}$ S/cm, and preferably $\geq 10^{-4}$ S/cm, and more preferably $\geq 10^{-3}$ S/cm.

In various methods the step of selecting the sulfur containing glass composition involves adjusting the mole ratio of Li and/or S (sulfur) and/or 0 (oxygen) in the glass to achieve a glass stability factor of >50° C., or >60° C., or >70° C., or >100° C. and a Li ion conductivity $\geq 10^{-5}$ S/cm, and preferably $\geq 10^{-4}$ S/cm, and more preferably $\geq 10^{-3}$ S/cm.

In various methods, the step of selecting the glass composition includes replacing a certain amount of S (sulfur) in the glass with O (oxygen), the amount sufficient to increase the glass stability factor by at least 10° C. or the Hruby parameter by at least 0.1, while maintaining a Li ion conductivity $\geq 10^{-5}$ S/cm, and preferably $\geq 10^{-4}$ S/cm, and more preferably $\geq 10^{-3}$ S/cm. In various embodiments the glass stability factor is increased by at least 20° C., 30° C., 40° C., 50° C., 60° C., or 70° C. by the oxygen replacement for sulfur, while maintaining the requisite Li ion conductivity $\geq 10^{-5}$ S/cm. In various embodiments the Hruby parameter is increased by at least 0.2, 0.3, 0.4, 0.5, 0.6, or 0.7 by the oxygen replacement for sulfur, while maintaining the requisite Li ion conductivity.

In various methods, the step of selecting the glass composition includes incorporating additives and/or constituent elements in an amount sufficient to alter the coefficient of thermal expansion (CTE) of the glass to a value close to that of lithium metal (e.g., substantially matching that of lithium metal, or for achieving a CTE ratio between 0.5 to 3, and preferably between 0.7 to 2, and even more preferably between 1 to 1.5 wherein the CTE ratio is measured as the CTE of lithium metal divided by the CTE of the vitreous glass sheet). In various embodiments the composition of the solid electrolyte sheet is selected, or additives (as described above) are incorporated, to effect a CTE in the range of 10 to 50 1/° C. (e.g., about 10 1/° C., about 15 1/° C., about 20 1/° C., about 25 1/° C., about 30 1/° C., about 35 1/° C., about 40 1/° C., about 45 1/° C., or about 50 1/° C.).

In various methods, the step of selecting the glass composition includes: i) selecting constituent elements of the sulfur-based glass, the constituent elements comprising S (sulfur), Li (lithium), and one or more of P (phosphorous), B (boron), Si (silicon), and O (oxygen); and ii) adjusting the mole ratio of the constituent elements to maximize viscosity at $T_{liq}$ (i.e., the liquidus viscosity), without decreasing the room temperature Li ion conductivity of the sheet below $10^{-5}$ S/cm, and preferably not decreasing the conductivity below $10^{-4}$ S/cm. For example, the maximized liquidus viscosity greater than 200 poise, preferably greater than 500 poise, more preferably greater than 1,000 poise, and even more preferably greater than 3,000 poise. In preferred embodiments, the maximizing step does not increase the ASR, as measured against Li metal, to a value greater than 200 Ω-cm², and preferably not greater than 100 Ω-cm², or greater than 50 Ω-cm², or greater than 20 Ω-cm².

In various methods, the step of selecting the glass composition includes: i) selecting constituent elements of the sulfur-based glass, the constituent elements comprising S (sulfur), Li (lithium), and one or more of P (phosphorous), B (boron), Si (silicon), and O (oxygen); and ii) adjusting the mole ratio of the constituent elements to maximize the glass stability factor $\{T_x-T_g\}$, without decreasing the room temperature Li ion conductivity of the sheet below $10^{-5}$ S/cm, and preferably not decreasing the conductivity below $10^{-4}$ S/cm. For example, maximizing the glass stability factor to a value greater than 50° C., and preferably greater than 100° C. In preferred embodiments, the maximizing step does not increase the ASR against lithium metal to a value greater than 200 Ω-cm², and preferably not greater than 100 Ω-cm², or greater than 50 Ω-cm², or greater than 20 Ω-cm².

Continuing with reference to FIGS. 7A-C, once the Li ion conducting sulfur containing glass composition is selected 705, the raw precursor materials (e.g., $Li_2S$, $SiS_2$, and $P_2S_5$ powders) 710 are processed. With reference to methods 700A-B, as illustrated in FIGS. 7A-B, the processing steps involve forming a vitreous preform 730A from the raw precursor materials, or melting the raw precursor materials 730B for making the vitreous solid electrolyte sheet by melt drawing. In method 700C the process involves the extra step of making a glass batch 720C from the raw precursor materials, and then processing the glass preform or drawing a sheet from the twice-melted glass. In various embodiments, the batch glass formed in step 720C may be processed by melt/quenching the raw material precursors or by mechanical milling. The re-melting or formation of a vitreous preform from a batch glass, regardless of how it (the batch glass) is formed, allows better control of processing variables, including minimizing loss of volatile constituents. Melt quenching to form the batch glass is particularly advantageous, and care should be taken to ensure that the precursor mixture is fully reacted in the melt. Accordingly, the glass batch, when fully reacted, is absent of precursor components such as $Li_2S$, $B_2S_3$, $P_2S_5$, $SiS_2$ or the like. Having a fully reacted glass is particularly important when the vitreous sheet is to be used as a glass separator layer in a hybrid battery cell, wherein the vitreous glass separator sheet comes into direct contact with a liquid electrolyte that might otherwise dissolve the precursor components on contact (e.g., $Li_2S$ phases). Accordingly, in various embodiments the vitreous glass separator sheet is melt-processed to ensure that it is completely reacted and devoid of $Li_2S$ particles, and in particular devoid of lithium sulfide crystalline phases. For instance, when placing such a vitreous sheet in a non-aqueous organic solvent such as an ether (DME) or glyme (which has at least some limited solubility for $Li_2S$), there is no detectable presence of polysulfide species in the solvent.

To enhance homogenization of the resulting glass melt and/or reduce dwell time of the melt and/or effect full reaction of an MSR prepared glass material batch, the average powder particle size and particle size distribution of the various precursor powder ingredients should be considered, and, in particular, that of the major network former and major network modifier precursor powder components (e.g., $Li_2S$ and $B_2S_3$ or $SiS_2$ respectively), as described in more detail herein below. For instance, engineering the particle size and particle size distribution can lead to enhanced stability of the glass by allowing reduction of the dwell time employed at the melt temperature, or at the sheet processing temperature (e.g., the softening temperature of the glass).

When making a homogeneous vitreous solid electrolyte sheet, and especially of optical grade homogeneity, processes beyond that of ensuring high purity of the raw materials is necessary. To ensure full reaction of the melt, and minimize/eliminate the presence of solid phase inhomogenieties and unwanted second phases embedded in the vitreous matrix, it is advantageous to reduce particle size and control/engineer the particle size distribution of some or all of the precursor powder components (e.g., $Li_2S$, $B_2S_3$, $SiS_2$, $B_2O_3$, B, Si and the like), and this is especially germane for glass compositions based on hard network formers (e.g., $B_2S_3$ and/or $SiS_2$) which are difficult to dissolve, especially $B_2S_3$. For instance, in various embodiments the precursor component of the major network former (e.g., $B_2S_3$ or $SiS_2$), or elemental boron, or elemental silicon, and/or that of the major network modifier (e.g., Li2 S) is particle engineered to reduce particle size, control particle size distribution, and engineer the relative size of the particles.

In various embodiments the average particle size of the major network forming precursor powder ingredient (e.g., $B_2S_3$ or $SiS_2$) is no greater than 600 μm, and preferably no greater than 300 μm, and more preferably no greater than 150 μm, and even more preferably no greater than 75 μm (e.g., about 50 μm, or about 40 μm, or about 30 μm, or about 20 μm, or about 10 μm, or less than 10 μm. In embodiments thereof the particle size distribution of the major network forming precursor powder ingredients is: for an average particle size of 500 μm, at least 70 w % of the powder is in the range of 400 to 600 μm; for an average particle size of 250 μm, at least 70 wt % of the powder is in the range of 200 to 300 um; for an average particle size of 100 μm, at least 7 wt % of the powder is in the range of 50 to 150 μm; and for an average particle size of 50 μm, at least 70 wt % of the powder is in the range of 25 to 75 μm; and for an average particle size of 20 um, at least 70 wt % of the powder is in the range of 10 to 30 μm; and for an average particle size of 10 μm, at least 70 wt % of the powder is in the range of 5 to 15 μm. Preferably the particles defined within the above mentioned size distributions is defined by at least 80 wt %, and even more preferably at least 90 wt %.

In various embodiments the combination of precursor powder ingredients is particle engineered to enhance homogenization. In some embodiments, especially for an MSR processed batch glass, the major network modifying precursor powder ingredient (e.g., $Li_2S$) is engineered to have a substantially matching particle size and preferably particle size distribution as that of the major network forming precursor powder; for instance, $B_2S_3$ and/or $SiS_2$ combined with $Li_2S$ (as modifier). In other embodiments, especially for melt processing the batch glass, the particle size and distributions of the precursor ingredients (e.g., the major forming and modifying ingredient components) are engineered to take into account the various melting and reaction kinetics of each particle composition, and the particles are engineered not to match. For instance, the precursor ingredient with the higher melting temperature (e.g., the major network modifying precursor ingredient) having a substantially smaller average particle size than that of the lower melting precursor (e.g., the major network forming precursor ingredient). By substantially different it is meant that the average particle size should differ by at least a factor of two.

In various embodiments the interior surface of the vessel in which the batch glass or precursor ingredients are heated and/or melted and/or reacted is vitreous carbon. In some embodiments, the vessel has dense graphite walls with vitreous carbon defining the interior surface. The vessel is generally sealable, and/or may be incorporated in a sealable secondary container (e.g., when the vessel has an open structure, the secondary container is used sealed to seal off the external environment).

In various embodiments continuous solid electrolyte sheet 100 (e.g., a sheet of vitreous Li ion conducting sulfur-containing glass) is sufficiently long and robust when flexed to be configurable as a vitreous web of Li ion conducting glass. In various embodiments the web is sufficiently flexible to be wound (e.g., on a spool) and thus suitable as a source/supply roll for downstream ($R_2R$) or roll-to-sheet processing of discrete cut-to-size sheets and or battery cell components. Preferably, the vitreous solid electrolyte web has sufficient surface quality and thickness uniformity that it requires no post solidification grinding and/or polishing, and even more preferably does not require removal of low quality peripheral edge portions.

In various embodiments the continuous web has bending-radius ≤100 cm, and preferably ≤50 cm, more preferably ≤30 cm, even more preferably ≤20 cm, and yet even more preferably ≤10 cm, or ≤5 cm, or ≤2 cm, and thus can be wound as such without fracture. In various embodiments the spool or drum on which the web is wound has diameter between 100-200 cm; or 50-100 cm; or 20-50 cm; or 10-20 cm; or 5-10 cm; or 1-5 cm; or 0.5-1 cm; for example, a spool having a diameter no greater than 20 cm, or no greater than 10 cm, or no greater than 5 cm.

The vitreous web is typically of sufficient length to serve as a source for multiple discrete solid electrolyte separator sheets (i.e., cut-to-size), or the web may serve as a long substrate sheet for making multiple cell components (e.g., multiple electrode assemblies or multiple sub-electrode assemblies). Typically, the length of the web is sufficient for making many multiples of such said components (e.g., at least 5, at least 10, or at least 20). In various embodiments the length of the solid electrolyte web of vitreous Li ion conducting sulfide glass is more than 20 cm, or more than 50 cm, or more than 100 cm, or more than 500 cm, or more than 1000 cm. Discrete solid electrolyte separator sheets, of predetermined length and width, are usually cut-to-size from the web by a laser (i.e., by laser cutting). The discrete vitreous solid electrolyte separator sheets are typically of thickness between 10 to 100 mm, and width between 1 and 10 cm. In various embodiments the instant vitreous solid electrolyte separator sheet is particularly suitable for winding in a battery cell; for example, 10 to 50 mm thick, 2 to 10 cm wide, and between 20 and 200 cm long. In various embodiments the instant vitreous solid electrolyte separator sheet is particularly suitable for incorporation into a prismatic battery cell of folded or stacked construction; for example having an area aspect ratio less than 2 or less than 1.5 (e.g., about 1); for example, 2 to 20 cm wide and 2 to 20 cm long; for instance, between 5-20 cm wide and 5-20 cm long and an area aspect ratio of about 1 (e.g., about 5-20 cm wide and an area aspect ratio of 1).

In various embodiments, the as-fabricated web may be referred to herein as a mother-web when having a high quality center portion and lower quality edge portions, which are sliced off (e.g., by laser or mechanical cutting), typically inline, and then followed by rolling to form a supply roll.

When making a lithium metal electrode assembly or subassembly, the vitreous web may serve as a substrate for depositing the lithium metal or tie-layer in an intermittent fashion, to form periodic sections of coated and uncoated regions (e.g., by using a mask or masking techniques). Alternatively, discrete separator sheets or discrete tie-layer coated substrate laminates may be cut-to-size from the web, followed by lithium metal deposition.

Figure 8:
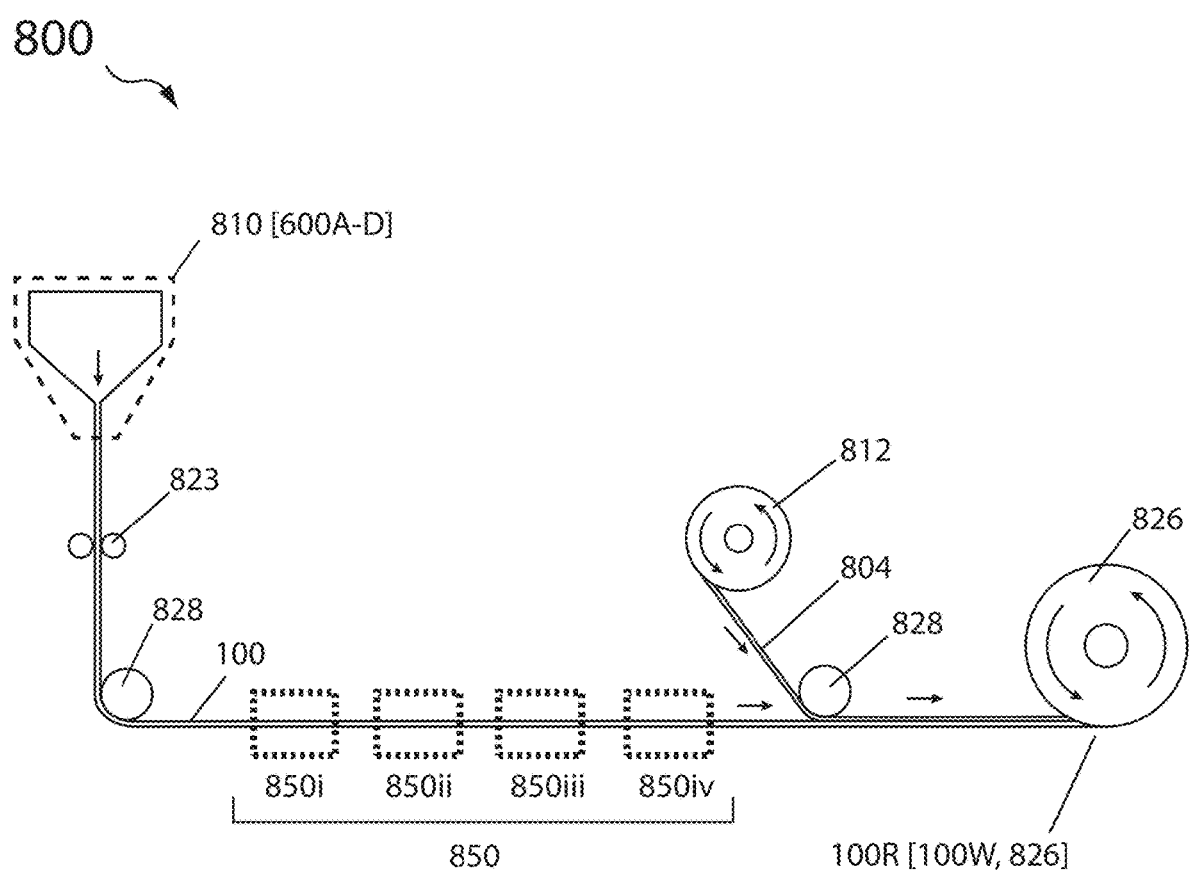
FIG. 8 illustrates a fabrication system and method for making a continuous web of the instant freestanding Li ion conducting solid electrolyte sheet in the form of a continuous roll; the web configured using an inline sheet to roll process.

In various embodiments roll processing of the web is inline with solid electrolyte sheet fabrication (e.g., the drawing process). With reference to FIG. 8, there is illustrated a sheet to roll fabrication system 800 for processing a vitreous web of solid electrolyte glass 100W in the form of a continuous roll. Sheet to roll fabrication system 800 includes solid electrolyte sheet drawing apparatus 810 (e.g., melt draw or preform draw apparatus 600 or 700 respectively, such as a fusion draw apparatus, a slot draw apparatus, or a redraw/preform draw apparatus) configured inline with roll processing apparatus that includes one or more drive mechanisms 823 (e.g., a pair of opposing counter rotating rollers), guide rollers 828, and take-up spool 826 for winding the inorganic vitreous solid electrolyte glass web into a continuous roll 100R. Preferably, the counter rollers, which are generally motor-driven, are positioned to contact a peripheral edge region of the as-drawn solid electrolyte sheet or edge-protectors, and by this expedient the major area portion of the solid electrolyte sheet (e.g., the high quality center portion) is maintained in a pristine surface state condition (i.e., untouched). Driven by the rotating rollers, solid electrolyte ribbon (long sheet) 100W is typically conveyed along one or more guide rollers (e.g., roller 828) before engaging with take-up roll 826. The web of solid electrolyte glass 100W may be conveyed in an unsupported fashion, or the apparatus may include a support mechanism for supporting the moving sheet as it is conveyed toward the take-up roll, and/or into one or more processing stages 850 (850i, 850ii, 850iii, 850iv). Typically, solid electrolyte web 100W is caused to traverse through a furnace or hot zone stage 850i for annealing the glass sheet prior to engaging with the take-up roll for winding. The processing stages may include a slitting stage 850ii with a cutting device (e.g., a laser cutter or wire saw/scribe) configured to remove low quality edge portions. Other stages are contemplated, including a stage for configuring a protector element along the lengthwise edges of the solid electrolyte sheet 850iii and/or material layer deposition stages 850iv for coating the surface of solid electrolyte glass web 100W with a tie-layer and/or a current collector layer and/or a lithium metal layer, as described in more detail herein below with respect to making a web of electrode sub-assemblies and/or a web of lithium electrode assemblies.

To keep the surfaces of the vitreous web from directly contacting each other, interleave 804 (i.e., a self-supporting material layer for protecting the web surfaces) may be wound together with the web via interleave supply roll/take off-roll 812, interleaf 804 interposed between layers of the glass web. Care should be taken in the proper selection of the interleaf, and in particular embodiments the major opposing surfaces of interleave material layer 804 are exceptionally smooth (e.g., the interleave may be an organic polymer layer such as polyolefin or polyester layer). Also contemplated is the use of edge-protector elements, which, as described above, protect the edges of the solid electrolyte sheet against physical damage, and may also serve as a spacer between sheet layers when the web is wound on a spool, and by this expedient, the high quality center portion of the solid electrolyte sheet is kept in a pristine surface state (i.e., untouched by a foreign solid surface). The use of edge-protectors may circumvent the need for an interleaf, and in various embodiments the edge-protector element is multi-functional in that it can be used downstream as a sealing component in an electrode assembly or as a spacer in a battery cell.

When the web is a continuous sulfide based solid electrolyte sheet, sheet to roll system 800 is typically contained inside an enclosure (not shown) substantially devoid of moisture, and in certain embodiments substantially devoid of oxygen, as described above for the drawing apparatus housings. In various embodiments, the roll apparatus is housed in a dry room of exceptionally low moisture content or in a dry box with very low moisture and oxygen content (e.g., <10 ppm, and preferably <5 ppm).

In an alternative embodiment sheet 100 may be fabricated as a nearly flawless monolithic vitreous sheet of a sulfide based solid electrolyte glass by making use of capillary forces. The method is based on the fabrication of the sheet as a thin film, a sheet or a ribbon from a sulfide glass melt that infiltrates or is injected into a narrow gap between two smooth plate surfaces provided by polished glassy carbon, polished metal, polished and coated (in particular, anodized) metal, polished glass with a higher melting point than that of the sulfide glass, pyrolytic graphite or other materials. The obtained vitreous sheet can be used "as is" or as a pre-form for a subsequent drawing operation.

The plate materials of choice are chemically stable to the sulfide glass melt and do not exhibit reactive wetting. Another requirement to the plate material and surface quality is dictated by necessity to separate a formed sulfide glass film from the plate surface without damaging the film. Thus, the sulfide glass of choice does not stick to the polished plate surface. In a preferred embodiment, two glassy-carbon plates with a mirror-like surface finish form the gap.

Glass is melted in a crucible and poured onto a smooth horizontal or tilted plate (i.e., smooth plates), or melted directly on the limited area of the plate surface next to its edge. Another smooth plate is placed on top of the first one, adjacent to the molten glass. Alternatively, molten glass is poured into a gap between two vertical plates. The width of the narrow gap between the plates is in the range of 5 µm-1 mm and is fixed with spacers. In some embodiments, glass is melted under vacuum to avoid formation of gas bubbles due to gases being trapped within the bulk of molten glass.

The glass fabrication procedure consists of four stages: i) glass melting—temperature of glass is increased above Tm (glass melting point); ii) gap infiltration—temperature of glass melt and plates is maintained above Tm; iii) cooling—temperature of glass melt and plates is brought below Tg (glass transition temp); iv) glass separation.

Figure 9:
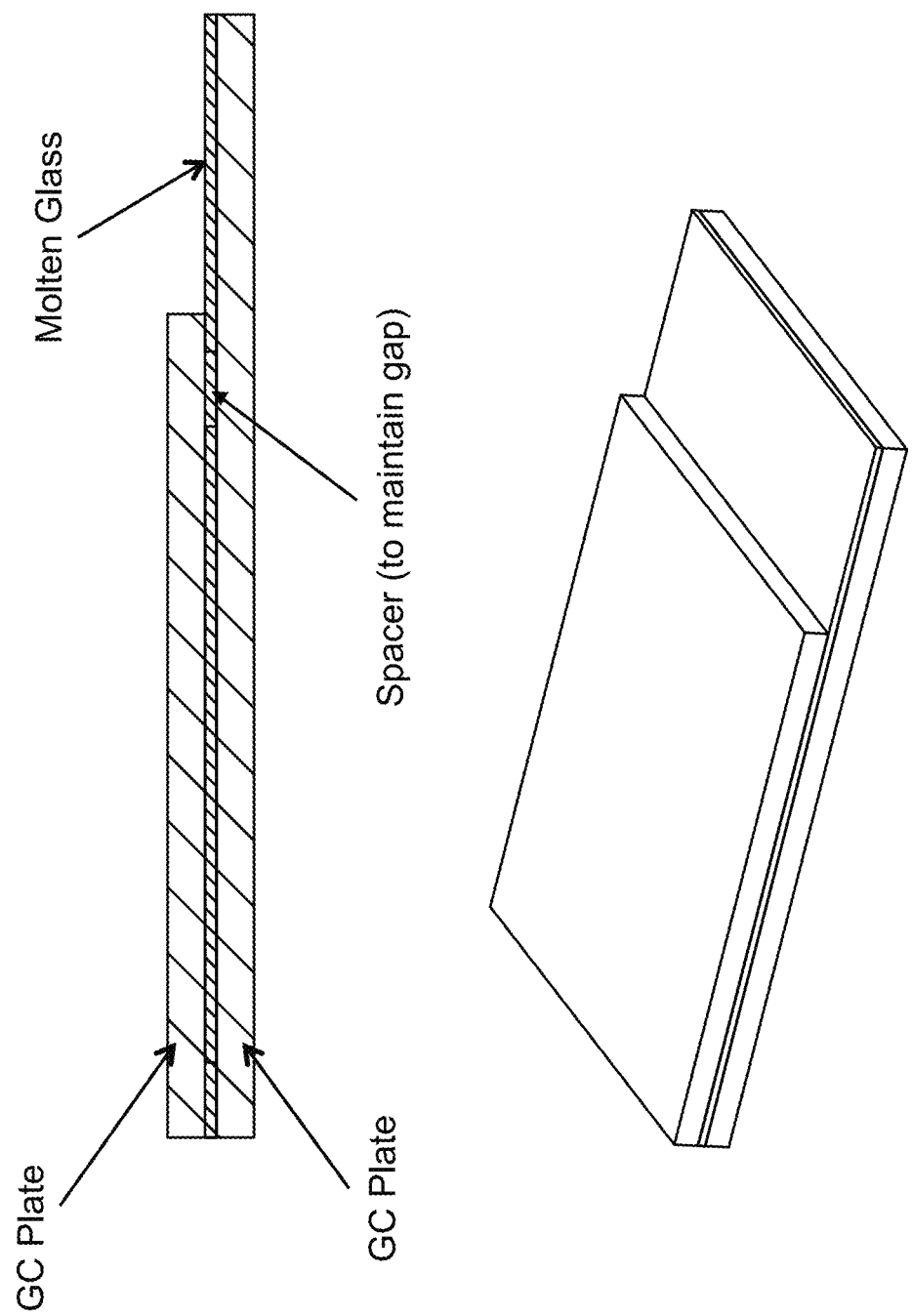
FIG. 9 illustrates a method of making a vitreous solid electrolyte sheet in accordance with an embodiment of the disclosure, the method involving the use of capillary force to infiltrate a molten glass of the solid electrolyte between adjacent smooth plates.

All the operations are performed in the atmosphere of inert gas or in the dry air. In one embodiment (illustrated in FIG. 9), the intrinsic contact angle of molten glass on the plate material is less than 90° and the molten glass is drawn into the narrow gap between two horizontal or tilted plates due to capillary forces. In this embodiment, the distance that the molten glass infiltrates in the narrow gap between the two smooth horizontal plates is governed by Washburn's equation. The distance is directly proportional to the square roots of the gap width and the surface tension of molten glass in processing atmosphere and is inversely proportional to the square root of molten glass dynamic viscosity. In an alternative embodiment, the plates are tilted at an angle less than 90° (less than vertical) instead of being placed horizontally, and the component of the force of gravity parallel to the plate surface aids the capillary force in driving the molten glass into the gap.

Figure 10A:
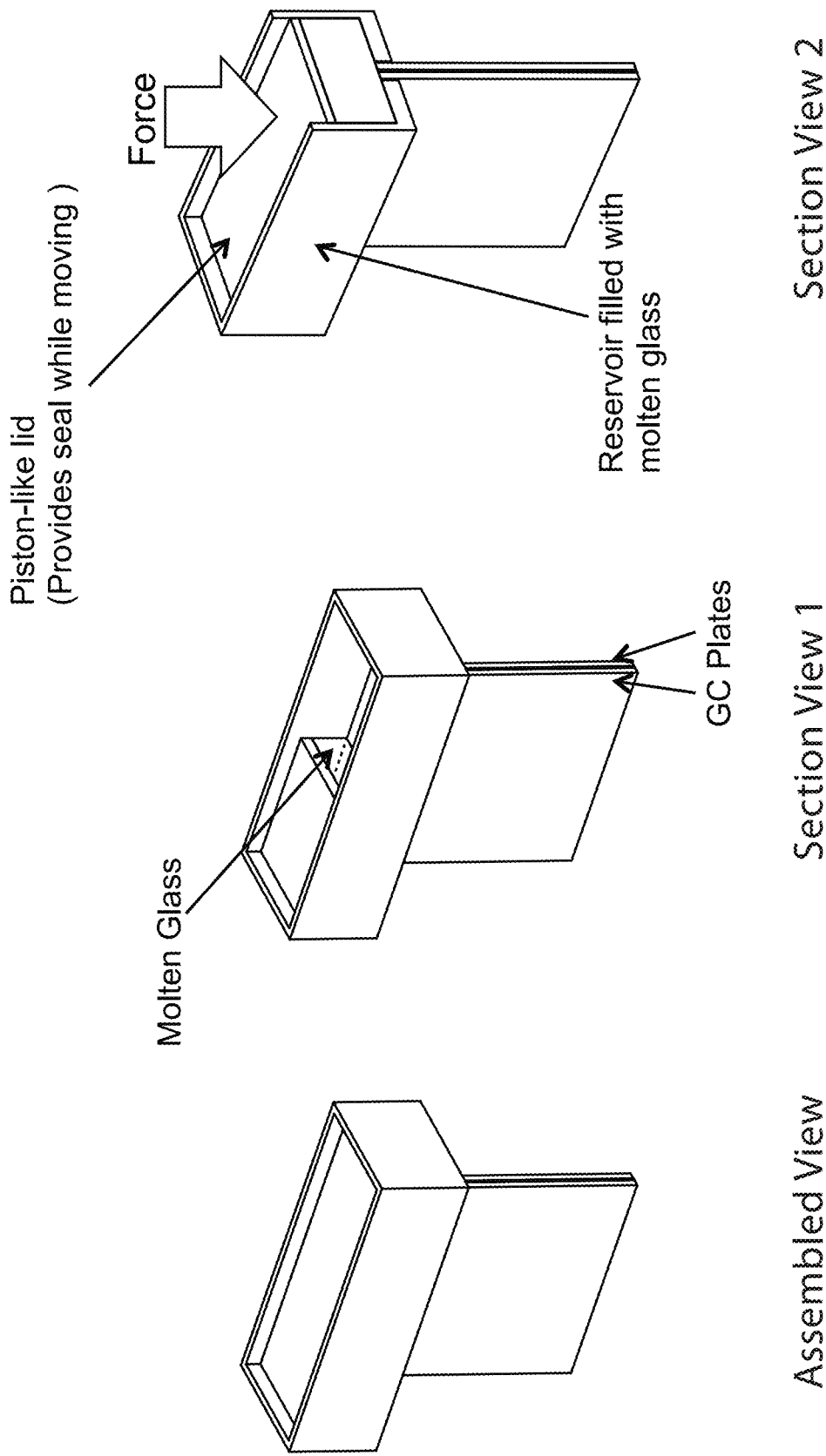
FIGS. 10A-C illustrates methods of making a vitreous solid electrolyte sheet in accordance with an embodiment of the disclosure.

In a different embodiment (illustrated in FIG. 10A), the intrinsic contact angle is less than 90°, the plates are placed vertically and the molten glass is poured into the gap from above. In a modification of this embodiment, additional pressure is applied to the molten glass in the downward direction with a piston or with compressed inert gas. Here, the force of gravity, the capillary force and the external force applied to the melt are all acting in the downward direction and are aiding the infiltration of the gap by the molten glass.

Figure 10B:
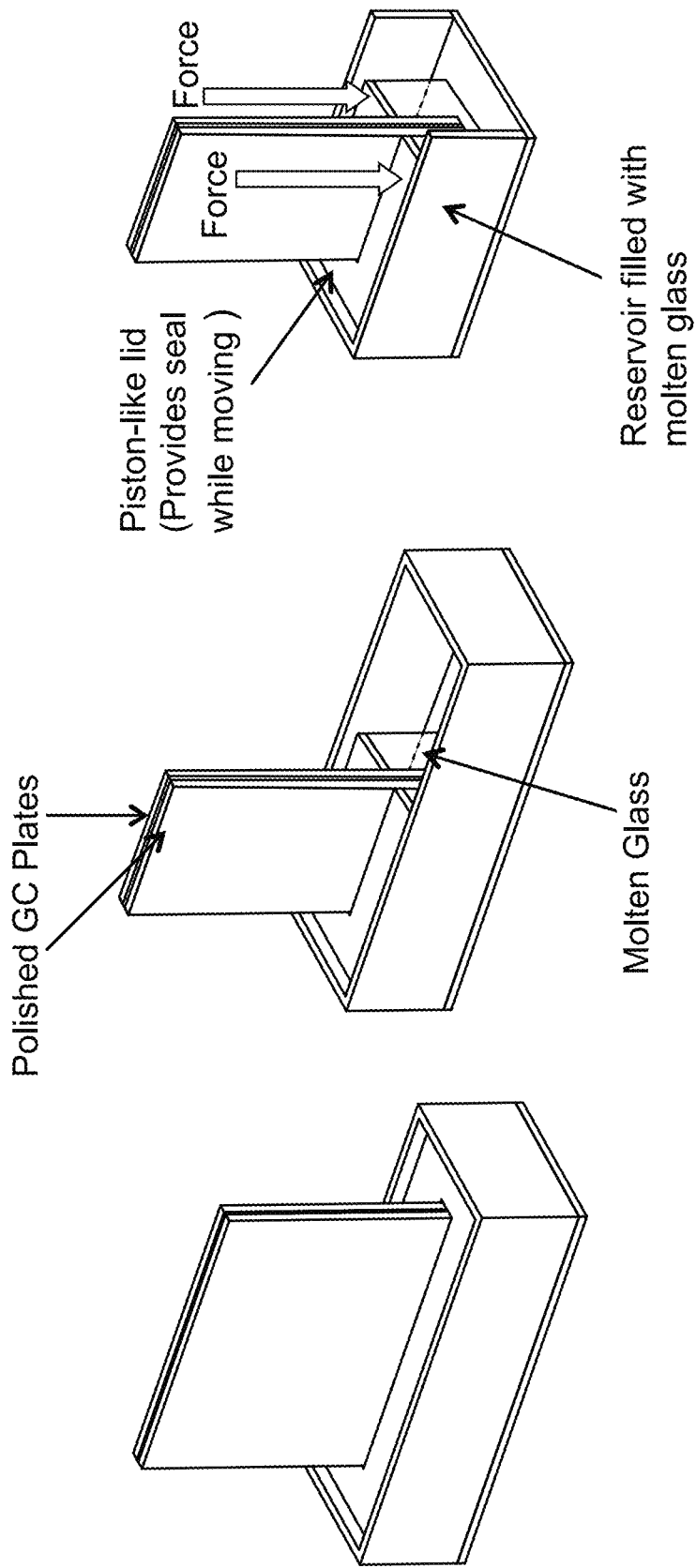
Figure 10C:
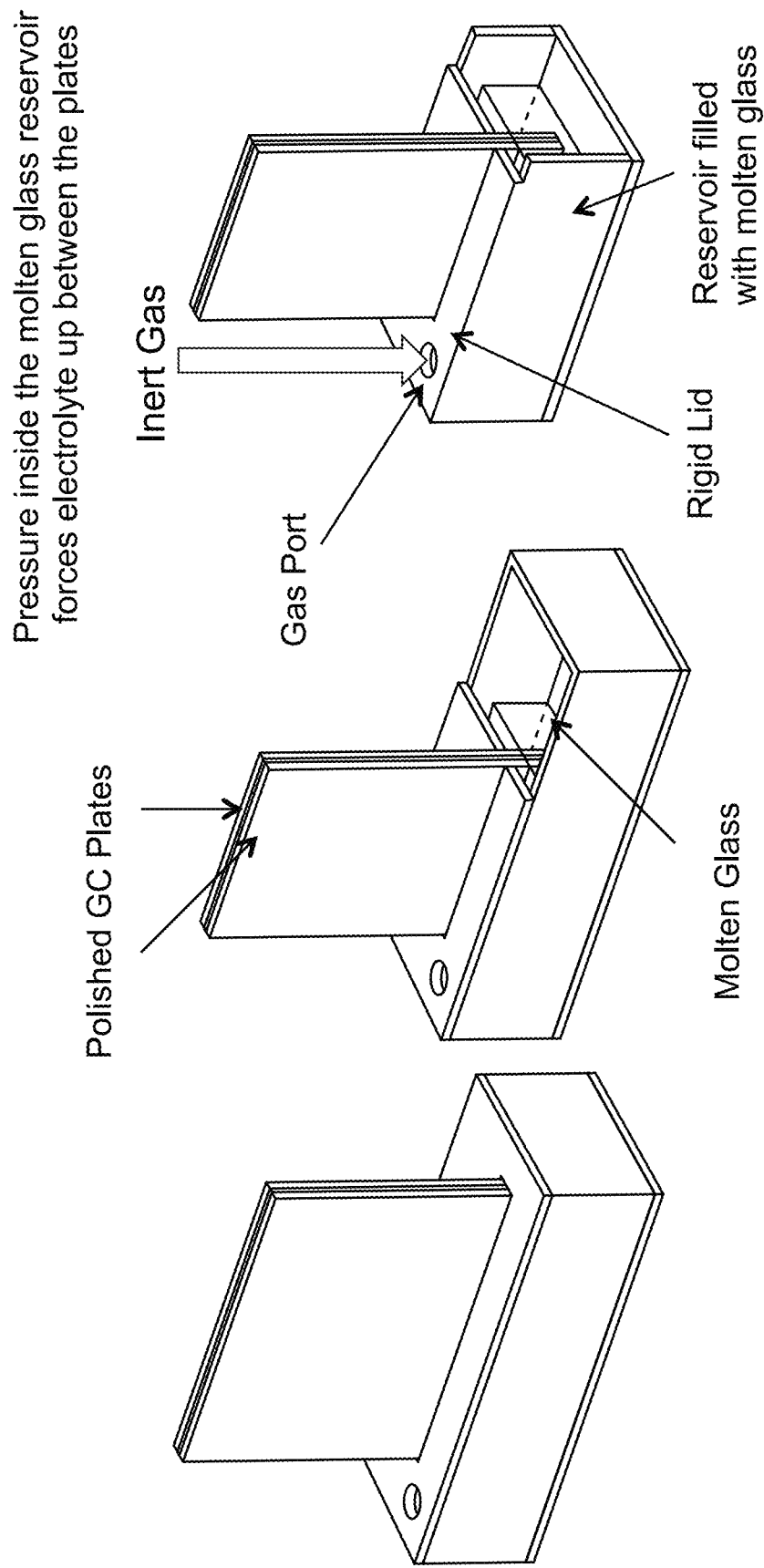

Alternatively, the intrinsic contact angle is less than 90°, the bottom edges of the vertical plates are submerged into the molten glass and the molten glass infiltrates the gap due to the capillary force acting in the upward direction. In a modification of this embodiment, additional pressure is applied to the free surface of the molten glass in the downward direction with a piston (illustrated in FIG. 10B) or with compressed inert gas (illustrated in FIG. 10C). In an alternative embodiment, the process is scaled up by using a long crucible with multiple pairs of plates being submerged into molten glass.

In another embodiment (illustrated in FIG. 9), the intrinsic contact angle is greater than 90° and an external pressure greater than the capillary force is applied to the molten glass with a fluid-dispensing device with a piston or with compressed inert gas in order to force molten glass into the narrow gap between two horizontal (or tilted) plates.

In a different embodiment (illustrated in FIG. 10A), the intrinsic contact angle is greater than 90°, the plates are placed vertically and the molten glass is poured into the gap from above. The molten glass infiltrates the gap in the downward direction due to the force of gravity counteracting the capillary force acting in the upward direction. In a modification of this embodiment, a piston or compressed inert gas applies additional pressure to the molten glass in the downward direction.

If the intrinsic contact angle is much greater than 90° and exceeds a certain threshold value determined by the plate surface roughness, the melt contacts the plate surfaces only in a limited number of points (composite wetting), making the glass separation operation easier, but possibly affecting the smoothness of the formed glass surface. Even at lower contact angle values above 90°, spontaneous dewetting can occur due to various surface defects.

In another embodiment, after forming the glass electrolyte film and separating it from both plates, either one or both film surfaces are additionally melted to eliminate surface flaws and defects.

According to the Hagen-Poiseuille equation, the pressure required for infiltration of a narrow gap is directly proportional to dynamic viscosity of the glass melt and to the infiltration distance and is inversely proportional to the fourth power of the gap width. In some embodiments, in order to reduce the force required to achieve reasonable infiltration times, the glass melt viscosity is reduced by heating the glass to temperatures 10-50, 50-100, 100-300° C. above the glass melting point, $T_m$.

In an alternative embodiment sheet 100 may be fabricated by particle compaction followed by surface melting. For instance, with reference to FIG. 4G-H, the particles (i.e., powder particles), typically prepared by mechanical milling, are pressed together (e.g., at a temperature above $T_g$) to form a tape, and this is followed by heating at least one or both major surfaces of the tape to bring about a surface melting condition which is sufficient to dissolve the powder inter-particle boundaries within the confines of the treated (i.e., melted) surface layer, effectively forming a vitreous stratum that defines the first principal side surface. The vitreous stratum is typically formed by flash heating the tape surface (e.g., via a laser or hot inert gas) to cause melting, and then quickly cooling the surface, e.g., by flowing an inert gas. Preferably, the vitreous stratum is formed on the surface without touching a foreign solid body. When incorporated in a battery cell or a lithium electrode assembly, the vitreous stratum disrupts powder inter-particle pathways residing within the interior of the sheet, preventing them from reaching the first principal side surface, and preferably the stratum is of sufficient mass to turn down dendrites. Preferably, the vitreous stratum has a liquid-like surface (as described above), whereas the interior bulk of the sheet, composed of pressed powder particles, may be rife with particle boundaries and internal voids, and thus highly undesirable, but unavoidable from a powder compact. With reference to FIG. 4G, in embodiments it is contemplated that both first and second principal sides are surface melted and quenched to form a sandwich structure of a powder particle compact between two vitreous strata. However, it is also contemplated that only a single side of the tape is surface melted and thus the sheet a particle compact having a first principal side surface (e.g., 101A) defined by a vitreous stratum with a liquid-like surface, and the other principal side surface composed of a powder compact. In various embodiments the pressed powder compact (or tape) is made by hot pressing under vacuum or helium to enhance the dissolution of voids and lessen the concentration of micropores and/or nanopores in the bulk of the sheet.

In alternative embodiments, discrete wall structure 100 or a glass preform for drawing sheet 100 may be processed using a melt quench method that forms, as an initial step, a vitreous glass block or bar (e.g., rectangular or cylindrical), such as by pouring the melt from a crucible into a mold or melting a raw material batch of the glass in an evacuated and sealed quartz ampoule. Once solidified upon cooling, the bar is typically annealed and cut to a desired wall thickness, and/or sliced widthwise/lengthwise to yield the desired shape and area dimension (e.g., using a diamond blade, or wire saw, or laser cutter). Once cut, the surface of the as-cut wall structure may be subjected to polishing steps (e.g., fire polishing) to achieve a desired surface finish (e.g., liquid-like with $R_a$ as defined above), preferably of optical quality. Other methods contemplated for making and/or processing sheet 100 include variations of the float glass method (e.g., melting the glass on a vitreous carbon surface or a hard metal sulfide surface such as nickel sulfide and molybdenum sulfide), updrawing the sheet, and rolling methods, such as hot rolling a vitreous glass sheet as it cools from the molten state or shaping a vitreous preform into a glass sheet by rolling the preform at a temperature above $T_g$ but below $T_m$ (e.g., at a temperature less than 100° C. above $T_g$, or less than 50° C. above $T_g$, or less than 20° C. above $T_g$), or more generally at or above the softening point temperature. For instance, it is contemplated that precision glass molding (e.g., ultra-precision glass pressing) may be used to form a discrete wall structure or a preform for downstream drawing of a continuous sheet or web. The molding process includes loading a vitreous/glass blank of desired composition into a molding tool, heating up the mold (e.g., using infrared lamps), and upon reaching the working temperature (e.g., above $T_m$, or between $T_g$ and the softening point of the glass), closing the mold to form a vitreous glass construct. With reference to preform drawing of sheet 100, the aforesaid melt/quench crucible method or precision glass molding techniques may be useful processes for making the vitreous preform, especially precision glass molding. The precision glass molding process may also be suitable for batch fabrication of flat sheets no more than 100 um thick, with circular, square or rectangular form factor.

Figure 6E:
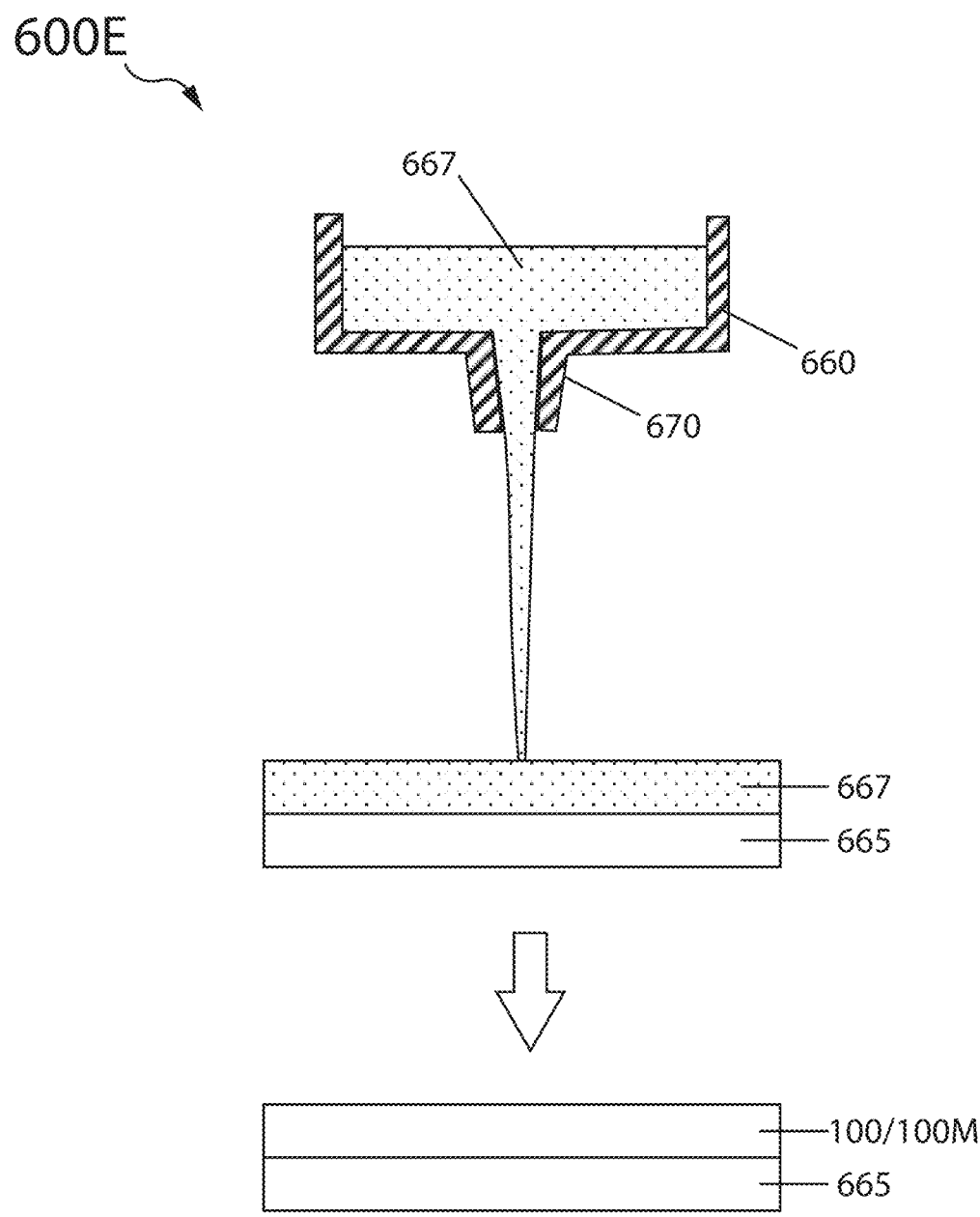

With reference to FIG. 6E in alternative embodiments it is contemplated that Li ion conducting solid electrolyte sheet 100 or a mother sheet thereof is made by applying a melt of the Li ion conducting glass onto a fluid bed to form a vitreous sheet of Li ion conducting glass; the molten glass sheet 667 solidifying on the surface of the fluid bed 665, and thereafter removed from the bed to yield freestanding vitreous sheet 100. In various embodiments the as-solidified vitreous sheet, formed as such, may serve as a mother sheet that is sliced and cut to yield discrete solid electrolyte ribbons of battery serviceable size. In various embodiments, the composition of the fluid bed is selected to be substantially non-reactive with the molten glass sheet. However, the disclosure is not limited as such, and in other embodiments it is contemplated that the molten glass sheet reacts in contact with the fluid bed to effect a solid crust layer which does not adhere strongly to the solidified vitreous glass sheet, or may be removed in a downstream process, including sand blasting or chemically reacted away, and/or removed by mechanical grinding/polishing. In various embodiments the fluid bed is itself a molten material layer (e.g., a molten metal such as tin, or a metal/semi-metal alloy, or a molten salt). In yet other embodiments the bed on which the molten glass is applied and solidified onto, is itself a solid. In various embodiments the solid bed is an amorphous metal or amorphous graphite (e.g., vitreous carbon) or a polished metal, or a non-reactive glass having $T_g$ greater than the melt temperature of the sulfide glass.

In various embodiments the aforesaid solid electrolyte glass sheets, including those processed by melt draw, preform draw, or melt quench/cut, may be subjected to a post fabrication treatment, e.g., flattening and/or polishing steps (e.g., fire polishing), to perfect the surface topography (e.g., to minimize waviness and/or surface roughness). Preferably the glass sheet, after post fabrication processing, has flatness <5 µm, and more preferably ≤1 µm; waviness <5.0 µm, and preferably ≤1.0 µm; thickness variation ±5 µm, and preferably ±0.2 µm; and an average surface roughness of $R_a$≤1.0 um, preferably <0.5 um, more preferably $R_a$<0.2 µm (e.g., $R_a$≤0.05 µm or $R_a$≤0.05 µm), and yet even more preferably $R_a$≤0.01 µm. In various embodiments, solid electrolyte sheet 100 achieves one or more of the aforesaid properties (i.e., flatness, smoothness, uniform thickness) in its virgin state as a solid.

In various embodiments freestanding solid electrolyte sheet 100 serves as a substrate for the formation of a lithium metal electrode assembly. As described in more detail herein below, the assembly is composed of solid electrolyte sheet 100 having an intimate solid-state interface with a lithium metal layer. In various embodiments, prior to forming the solid-state interface, it is useful to fabricate what is termed herein an electrode subassembly, which is effectively a substrate laminate composed of solid electrolyte sheet 100 coated with a material layer that serves to enhance interface function.

Figure 11A:
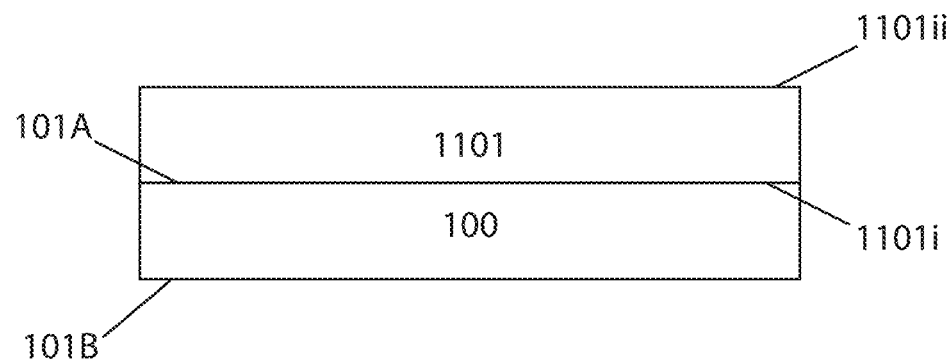
FIGS. 11A-B illustrate electrode subassemblies in accordance with various embodiments of this disclosure.
Figure 11B:
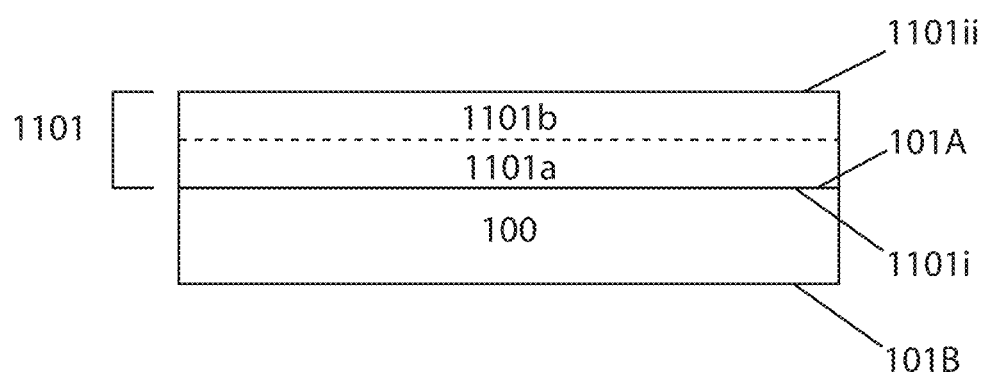

With reference to FIGS. 11A-B, there is illustrated electrode subassembly 1100A-B, which, in accordance with the present disclosure, generally serves as a component for making a standalone lithium metal electrode assembly, and in some embodiments may be incorporated directly into a battery cell, also of the present disclosure. As illustrated, subassembly 1100A-B is a freestanding substrate laminate of solid electrolyte sheet 100 covered in direct contact by material layer 1101, which provides a surface for creating an electrochemically efficient interface with a lithium metal layer during the making of a standalone lithium metal electrode assembly or during the course of charging in a battery cell.

Material layer 1101 may be characterized as having interior surface 1101i adjacent to and in direct contact with surface 101A of solid electrolyte sheet 100, and exterior/exposed surface 1101ii opposing the exterior environment about the subassembly. Typically, material layer 1101 is significantly thinner than solid electrolyte sheet 100 on which it is coated, formed on or adhered to. In various embodiments material layer 1101 or a layer portion thereof is a transient layer that effectively disappears (e.g., by alloying) once a lithium metal layer is applied or deposited onto it.

As mentioned above electrode subassembly 1100A-B is a standalone component for making a lithium metal electrode assembly or battery cell of the present disclosure. However, the electrode subassembly by itself is not a capacity-bearing electrode, and thus does not contain electroactive material (e.g., lithium metal) for providing ampere-hour capacity to a battery cell. Accordingly, electrode subassembly 1100A-B has exceptional component shelf life and handle-ability for manufacturing.

With reference to FIG. 11A, in various embodiments electrode subassembly 1100A is a bi-layer laminate of material layer 1101 (a single layer, typically of uniform composition) coated onto solid electrolyte sheet 100. With reference to FIG. 11B, in various embodiments, subassembly 1100B is composed of more than two layers; for instance, material layer 1101 may itself be a multilayer of two or more material layers disposed on first principal side surface 101A of sheet 100 (e.g., 1101a a tie-layer in direct contact with solid electrolyte sheet 100, and second layer 1110b a current collector layer in direct contact with the tie-layer).

In various embodiments material layer 1101 is a chemically functional tie-layer coating for creating an electrochemically efficient interface between sheet 100 and a lithium metal layer, and may also provide some protection against damage during storage and handling. Accordingly, the tie layer is of suitable composition and thickness to enhance bonding. In particular embodiments the tie-layer reactively alloys with Li metal on contact to form an electrochemically operable interface. The tie-layer is preferably a transient layer, which transforms and essentially disappears upon the formation or deposition of lithium metal on its surface. In various embodiments the tie-layer is thin enough and/or the lithium layer is of sufficient mass (i.e., thickness) to completely dissolve the tie layer (e.g., via an alloying reaction), and preferably the elements of the tie-layer are in such small amount and fully dispersed throughout the lithium metal layer to be insignificant.

In various embodiments protective tie-layer 701 is a coating of a metal or semi-metal suitable for forming an electrochemically operable interface between a lithium metal layer and solid electrolyte sheet 100, and, in particular, an electrochemically efficient interface for plating and stripping lithium metal in a battery cell. In various embodiments, the tie-layer is a metal or semi-metal such as Al, Ag, In, Au, Sn, Si, or the like, or an alloy or inter-metallic combination of metals or semi-metals capable of alloying or being alloyed by lithium metal on contact.

In various embodiments tie-layer 1101 is a metal or semi-metal coating deposited by physical vapor deposition (e.g., by evaporation) onto first principal side surface 101A of sheet 100. Tie-layer 1101 is a transient film sufficiently thin to be effectively completely dissolved by lithium metal on contact, and preferably atomically dispersed throughout, the lithium metal layer. In various embodiments tie-layer 1101 is of a composition and thickness to fully alloy with lithium metal on contact at room temperature, and in some embodiments heat may be applied to facilitate alloying and atomic diffusion. In various embodiments the tie-layer thickness is in the range of 0.05 to 5 μm and more typically between 0.05 to 1 μm (e.g., about 0.05 μm, or 0.1 μm, 0.2 μm, 0.3 μm, 0.4 μm, 0.5 μm, 0.6 μm, 0.7 μm, 0.8 μm, 0.9 μm, or about 1.0 μm, or 2.0 μm, 3.0 μm, 4.0 μm or about 5.0 μm).

The tie-layer provides a subassembly surface for mating the solid electrolyte sheet to a lithium metal layer (e.g., extruded lithium film), when forming a lithium electrode assembly or battery cell of the present disclosure. In particular, by reactively alloying with Li metal, the tie layer facilitates formation of an electrochemically operable interface. Moreover, the tie-layer is a transient material layer in that once the lithium metal layer is applied or formed, the tie-layer effectively disappears as it alloys with Li.

With reference to FIG. 11A, various embodiments the lithium metal layer is applied onto exterior tie-layer surface 1101ii during fabrication of a lithium metal electrode assembly (e.g., a lithium foil hot rolled onto the tie-layer). In other embodiments the lithium metal layer is formed by electrochemically plating lithium metal adjacent to interior tie-layer surface 1101ii during initial charging of a battery cell in which the electrode subassembly is incorporated. Whether formed electrochemically in a battery cell or applied or coated to form a lithium metal electrode assembly, lithium metal interacts with the tie-layer to form an intimate electrochemically operable interface between the as-formed or applied lithium metal layer and first principal side surface 101A of solid electrolyte sheet 100.

With reference to subassembly 1100B in FIG. 11B, in various embodiments material layer 1101 is a multilayer (e.g., a bi-layer) devoid of Li metal. In various embodiments bi-layer 1101 is composed of tie-layer 1101a in direct contact with first principal side surface 101A of sheet 100, and current collecting layer 1101b in direct contact with the tie-layer. The tie-layer sandwiched between sheet 100 and current collecting layer 1101b. In various embodiments the tie-layer may be evaporated onto the solid electrolyte sheet 100 followed by applying a current collecting layer 1101b directly onto the tie-layer 1101a. In other embodiments it is contemplated that the tie-layer may be evaporated onto the current collector layer, and the multi-layer, so formed, applied onto the sheet. Multiple tie-layer coatings are also contemplated herein, such as one or more additional tie-layer coatings disposed between tie-layer 1101a and current collecting layer 1101b. For instance, an additional tie-layer may be utilized to enhance and improve the Li metal interface in direct contact with current collecting layer 1101b.

In alternative embodiments it is contemplated that the current collecting layer may be applied directly onto sheet surface 101A, in the absence of a tie-layer.

The current collector layer may be a thin metal foil, or a thin metal film on a polymer substrate, or a coating applied directly onto sheet surface 101A, or indirectly via a tie-layer. For example a thin Cu or Ni foil, or a laminate of a Cu film on a polyethylene terephthalate (PET) substrate. The current collector should be a material layer that is substantially unreactive in contact with Li metal and of sufficient electronic conductivity to provide effective current collection, typically a metal (e.g., Cu or Ni).

In various embodiments, the current collecting layer is preferably significantly thinner than solid electrolyte sheet 100 (e.g., $\leq 1/5$ or $\leq 1/10$ the thickness of sheet 100), and preferably no thicker than 10 μm. In various embodiments the current collecting material layer is <20 μm thick, and typically <15 μm, and more preferably ≤10 um, and even more preferably ≤5 μm thick (e.g., between 10 to 5 μm thick; for example about 5 μm, or 4 μm, or 3 μm, or 2 μm, or 1 μm thick).

In various embodiments, electrode subassembly 1100A serve as a substrate component for making a standalone lithium metal electrode assembly of the present disclosure.

In other embodiments electrode subassembly 1100A may be directly incorporated into a lithium battery cell as a lithium free negative electrode, completely devoid of Li metal, as described in more detail below.

In various embodiments, the electrode subassembly is fabricated by processing material layer 1101 (e.g., tie-layer and/or current collector layer) directly onto glass web 100W (as described above), the glass web serving as substrate for the laminate. In various embodiments, material layer 1101 may be coated or adhered to the glass web in a continuous or intermittent fashion, and the web laminate referred to herein as an electrode subassembly web.

Figure 12A:
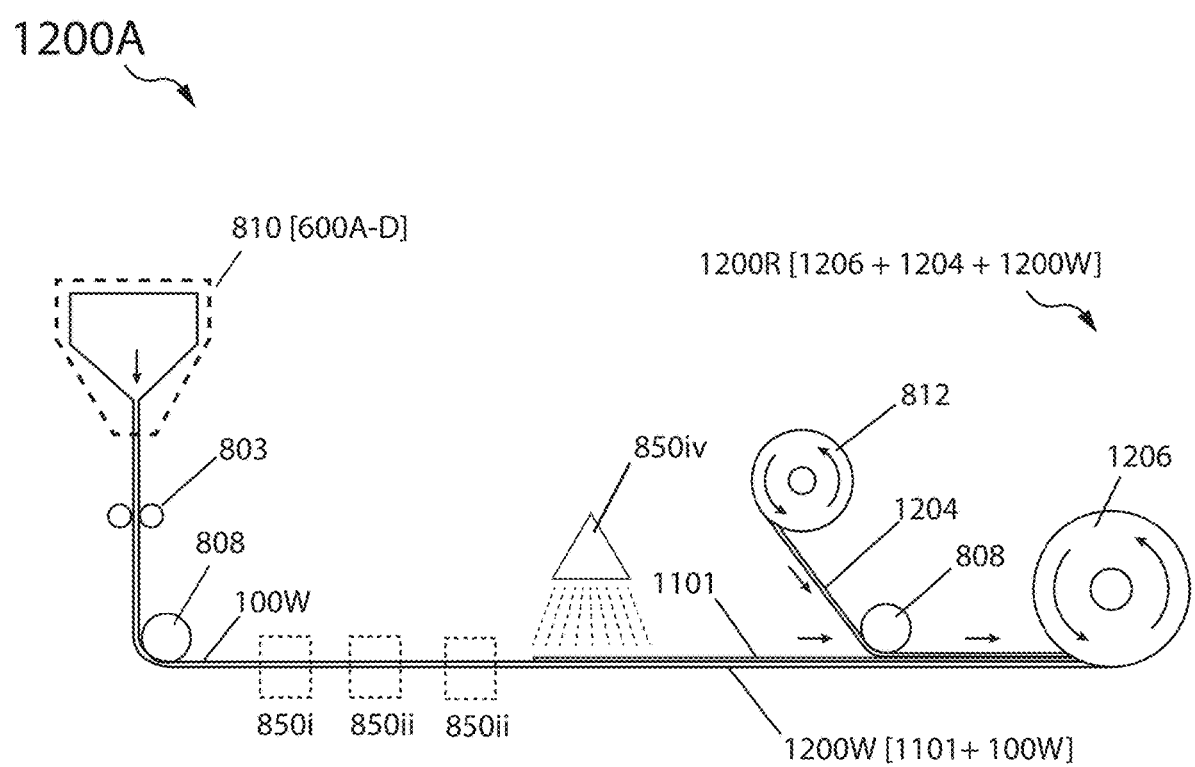
FIGS. 12A-C illustrates a fabrication system and methods for making an electrode subassembly and a continuous web of multiple electrode subassemblies in accordance with an embodiment of the disclosure.

With reference to FIG. 12A, there is illustrated a sheet to roll fabrication system 1200A for processing an electrode sub-assembly web 1200W in the form of a continuous source roll 1200R. In various embodiments sub-assembly web 1200W is formed by coating a web of Li ion conducting glass 100W with a tie-layer and/or current collector layer 1101 downstream of, and inline with, drawing solid electrolyte sheet 100 as a continuous web of glass 100W, as described above with reference to FIG. 8. The tie-layer and/or current collector layer is coated onto the web via processing stage 850iv (as shown in FIG. 8) or coating stage 850iv as shown in FIG. 12A. In various embodiments, coating 1101 is a multi-layer of a tie-layer 1101a and a current collector layer 1101b, and in such embodiments, coating stage 850iv is understood to incorporate more than one coating unit for each of the layers.

In various embodiments, fabrication of an electrode subassembly involves: i) forming a continuous web of the instant solid electrolyte sheet 100W via drawing apparatus 810 (as described above); ii) traversing the as-formed/as-drawn continuous solid electrolyte web 100W (e.g., in the form of a self-supporting layer) through a series of optional stages (annealing 850i, slicing 850ii, and edge protecting 850iii), and there from into coating stage 850iv, wherein the first principal side surface of web 100W, preferably pristine, is coated with a tie layer and/or current collector layer as described above (e.g., via vacuum evaporation); and iii) winding the coated solid electrolyte web via take-up spool 1206, to form an electrode subassembly source roll 1200R suitable for storage, transportation and downstream $R_2R$ manufacturing or roll-to-sheet processing of lithium electrode assemblies and/or battery cells.

To achieve inline processing, coating unit(s) of stage 850iv should be disposed in a differentially pumped chamber (not shown), wherein the tie layer (e.g., a thin aluminum or silver layer) and/or current collector layer (e.g., copper layer) is deposited. Similar to winding a continuous web of solid electrolyte sheet, winding of sub-assembly web 1200W to form continuous roll 1200R optionally involves interposing an interleave 1204 to prevent contact between adjacent surfaces. Alternatively, the edge-protector elements on web 100W, when present, can serve as a spacer.

Figure 12B:
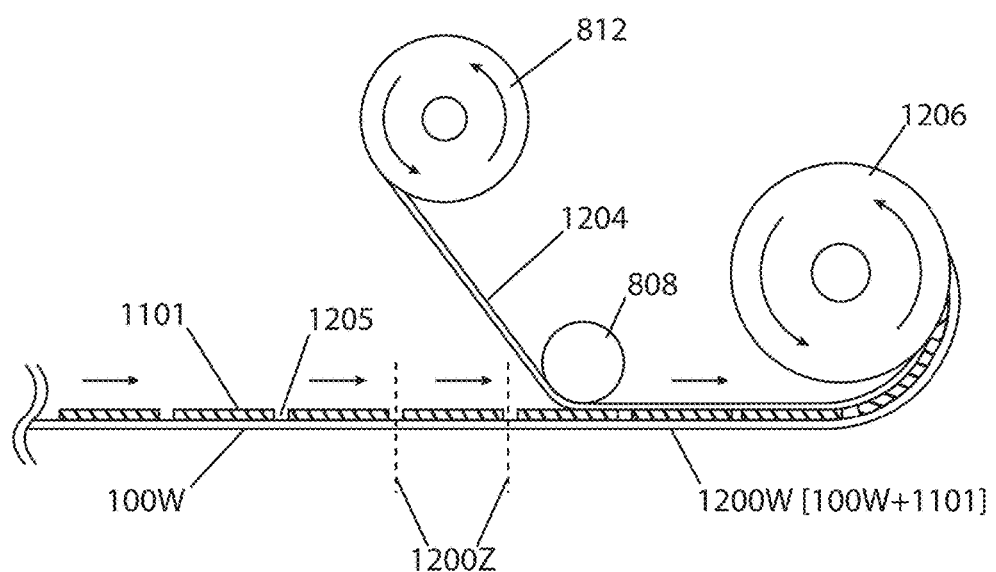

As described above, material layer 1101 (e.g., tie-layer and/or current collector) may be formed as a continuous coating onto solid electrolyte web 100W (thus forming a continuous laminate of coated web 100W, or, with reference to FIG. 12B, layer 1101 may be coated intermittently to yield periodic well-defined sections of coated and uncoated regions (as illustrated). Discrete electrode subassemblies are formed from the coated regions, and may be excised from sub-assembly web 1200W by cutting along the widthwise and/or lengthwise dimension of the web, preferably laser cut. With the cutting operation performed within the confines of uncoated region 1205, discrete/individual electrode subassemblies 1200Z are excised without having to cut or score through a tie-layer and/or current collector layer.

Figure 12C:
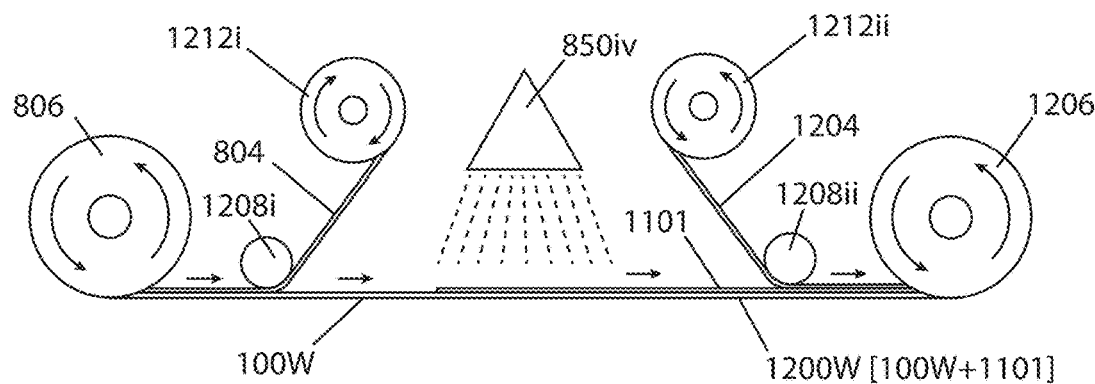

With reference to FIG. 12C, in other embodiments, fabrication of subassembly source roll 1200R involves $R_2R$ processing of a continuous web of solid electrolyte sheet 100W, which has already been configured as supply roll 806, and is used herein as a source roll for making subassembly web 1200W and ultimately roll 1200R. The process involves the steps of unwinding source roll 800R to expose the first principal side surface of vitreous web 100W, conveying/traversing the continuous solid electrolyte sheet (i.e., web 100W) into coating stage 850iv, as described above. Electrode subassembly web 1200W, thus formed, is then wound on spool 1206 to yield supply roll 1200R for downstream $R_2R$ manufacture of a lithium electrode assembly, or battery cell. Similar to that described above, in various embodiments material interleave 1204 may be incorporated into the roll to prevent direct contact between adjacent layers of the web. Guide rollers 1208i-ii, and interleave supply roll/take off-rolls 1212i-ii provide mechanisms for removing and introducing interleaves 804 and 1204 respectively.

In accordance with the present disclosure, electrode subassembly 1100A-B (see FIG. 11), as described above, or sheet 100 (absent of a tie-layer coating) may be utilized as a Li ion conducting solid electrolyte separator layer in a lithium metal electrode assembly of the present disclosure.

Figure 13A:
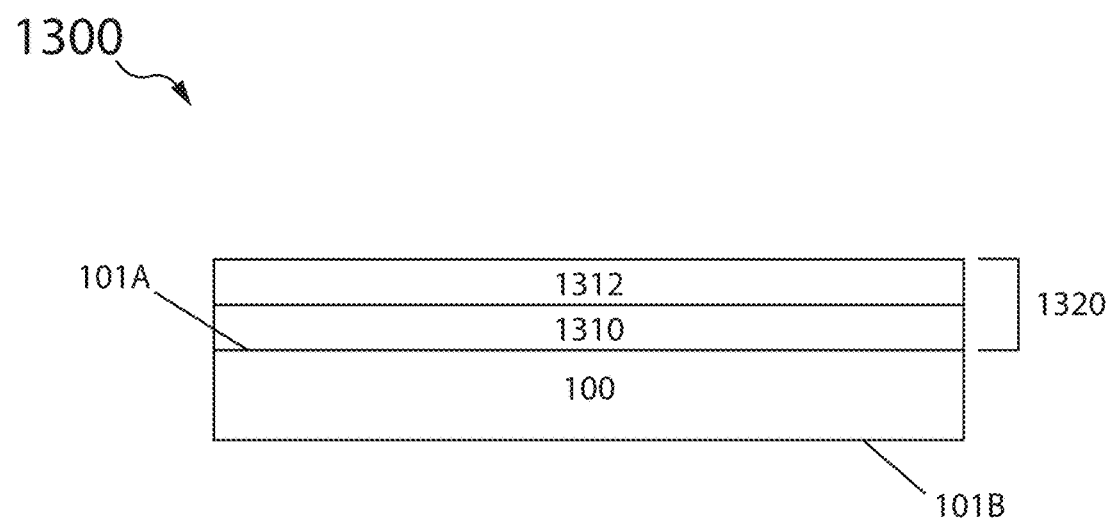
FIG. 13A illustrates a cross sectional depiction of a lithium metal electrode assembly in accordance with this disclosure.

With reference to FIG. 13A, standalone electrode assembly 1300 is a lithium metal electrode assembly composed of solid electrolyte sheet 100 serving as a substrate for lithium metal component layer 1320, which is composed of lithium metal layer 1310 and optional current collecting layer 1312. By use of the term standalone with respect to lithium metal electrode assembly 1300 it is meant that the electrode assembly is a discrete cell component devoid of positive electroactive material, and that it exists as a freestanding component outside of a battery cell.

The electrode assembly generally takes the shape and size of the solid electrolyte sheet from which it is made. In various embodiments, the lithium metal electrode assembly is rectangular shaped having lengthwise and widthwise dimensions and associated edges. In particular embodiments, when the solid electrolyte sheet is ribbon-like, the lengthwise dimension is significantly longer than the widthwise dimension; for instance, the rectangular shaped lithium metal electrode assembly (itself ribbon-like) has a length to width area aspect ratio substantially matching that of the solid sheet(s) from it is formed. For example, the Li metal electrode assembly having an area aspect ratio greater than 2, greater 3 or greater than 5 (e.g., an area aspect ratio of about 2, 3, 4, 5, 6, 7, 8, 9 or about 10). In various embodiments the area aspect ratio is at least 2 and the length of the Li metal electrode assembly is ≥5 cm, ≥10 cm, ≥15 cm, or ≥20 cm. In various embodiments the electrode assembly is at least 1 cm wide, and typically greater than 1 cm in width, such as between 2 to 20 cm wide (e.g., >2 cm and ≤5 cm; or >5 cm and ≤10 cm; or >10 cm and ≤20 cm). In such said embodiments the aspect ratio is generally at least 2, and more typically at least 5 or at least 10. For instance, the electrode assembly having a width between 2 to 5 cm and a length of at least 10 cm (e.g., 5 cm wide and a length of at least 10 cm (e.g., between 10-50 cm long); or the electrode assembly having a width between 5 to 10 cm and a length of at least 10 cm (e.g., 10 cm wide and a length of at least 20 cm long). In other embodiments the electrode assembly, having substantially parallel lengthwise edges, is large substantially square shaped, having an area of at least 25 cm$^2$, or at least 50 cm$^2$ or at least 100 cm$^2$.

In various embodiments, standalone lithium metal electrode assembly 1300 contains at least a sufficient amount of lithium metal to support the rated capacity of the cell in which it is disposed, and, in particular, is sufficient to match or exceed the rated area ampere-hour capacity of the positive electrode. For instance, in various embodiments the positive electrode may have an area capacity of about 1 mAh/cm$^2$, about 1.5 mAh/cm$^2$, about 2 mAh/cm$^2$, about 2.5 mAh/cm$^2$, about 3 mAh/cm$^2$, about 3.5 mAh/cm$^2$, about 4 mAh/cm$^2$, about 4.5 mAh/cm$^2$ or about 5 mAh/cm$^2$; and Li metal layer 1310 has a respective thickness of at least 5 μm, 7.5 μm, 10 μm, 12.5 μm, 15 μm, 17.5 μm, 20 μm, 22.5 μm, or at least 25 μm.

In other embodiments, the amount of lithium metal in standalone electrode assembly 1300, prior to incorporation into a battery cell, is insufficient to support the rated capacity of the cell. For instance, the rated capacity of the cell is about 50% greater than the Li metal capacity in the standalone electrode assembly, or about 100% greater, or about 150% greater, or about 200% greater, or about 250% greater, or about 300% greater, or about 350% greater, or about 400% greater, or about 450% greater, or about 500% greater.

In various embodiments, the amount of lithium metal in the standalone electrode assembly prior to incorporation into the battery cell is insufficient to support the discharge capacity. In various embodiments, lithium metal layer 1310 is less than 15 μm thick (e.g., between 5 to 10 μm) and the rated area capacity of the battery cell into which the lithium metal electrode assembly is ultimately intended is >3 mAh/cm$^2$, or >4 mAh/cm$^2$, or >5 mAh/cm$^2$, or >6 mAh/cm$^2$, or >7 mAh/cm$^2$; or the lithium metal layer 1310 is less than 20 μm (e.g., between 5 to 20 μm; e.g., about 10 μm) and the rated area capacity of the battery cell into which the lithium metal electrode assembly is ultimately intended is >4 mAh/cm$^2$, or >5 mAh/cm$^2$, or >6 mAh/cm$^2$, or >7 mAh/cm$^2$. In various embodiments the positive electrode of the cell into which the electrode assembly is to be employed has an area capacity between 1 mAh/cm$^2$ to 2 mAh/cm$^2$ and the lithium metal thickness in the standalone assembly is less than 5 μm; or the positive electrode has an area capacity ≥3 mAh/cm$^2$ (e.g., about 3 mAh/cm$^2$, about 3.5 mAh/cm$^2$, about 4 mAh/cm$^2$, about 4.5 mAh/cm$^2$, or about 5 mAh/cm$^2$) and the lithium metal thickness is ≤10 μm; or the positive electrode has an area capacity ≥5 mAh/cm$^2$ (e.g., about 5 mAh/cm$^2$, about 6 mAh/cm$^2$, or about 7 mAh/cm$^2$) and the lithium metal thickness is ≤20 μm.

In particular embodiments the amount of Li metal on the surface of solid electrolyte sheet 100, in assembly 1300, is scant relative to the rated capacity of the positive electrode or cell into which it is to be employed. For example, the Li metal layer in the electrode assembly is no greater than 5 um thick, for instance less than about 1 um, less than about 2 um, less than about 3 um, less than about 4 um, or less than about 5 um thick, and the rated capacity of the cell is greater than 1 mAh/cm$^2$.

In various embodiments lithium metal layer 1310 is deposited by physical vapor deposition (PVD), such as evaporation or sputter deposition. For instance, when Li metal layer 1310 is an evaporated layer, it typically has thickness in the range of 5 to 30 μm (e.g., about 5 μm, about 10 μm, about 15 μm, about 20 μm, about 25 μm, or about 30 μm. In certain embodiments Li metal layer, evaporated, has a thickness of less than 1 μm, and is used primarily as a bonding layer for attaching a current collector to surface 101A of sheet 100. The evaporated lithium metal may be deposited directly onto sheet 100, or via a transient tie-layer on surface 101A.

Li metal layer 1310 may be attached to solid electrolyte sheet 100 (or a subassembly of a tie-layer coated sheet) by adhering a lithium foil or lithium film to first principal side surface 101A of sheet 100 (e.g., via lamination, such as by hot rolling). In various embodiments, Li metal layer 1310 may be an extruded Li foil, or Li film on a current collecting substrate, with the thickness of the lithium metal layer between 5 to 50 μm thick (e.g., about 5 μm thick, 10 μm, 15 μm, 20 μm, 25 μm, 30 μm, 35 μm, 40 μm, 45 μm, or 50 μm thick). Preferably Li metal layer 1310 has a fresh surface. For example, a Li foil that is freshly extruded just prior to placing it onto solid electrolyte sheet surface 101A. Exposure of the freshly extruded foil to the ambient environment should be minimized prior to contacting the solid electrolyte sheet or tie layer coating (when present). If not freshly extruded, the lithium foil may be treated (e.g., bristle scrubbed) to create freshly exposed surfaces which are then immediately mated to first principal side surface 101A of sheet 100 (e.g., directly onto the sulfide glass surface or the tie layer surface if a subassembly is employed).

By use of the term "fresh" when referring to an extruded lithium foil or a freshly scrubbed lithium metal surface, it is meant that the post-extrusion/post-scrubbing exposure time to the ambient environment is sufficiently limited to prevent forming a prohibitively thick resistive film on the lithium metal surface (typically the resistive film some combination of oxide, hydroxide and carbonate). Generally, the ambient environment in which the foil is extruded or scrubbed has a moisture content <100 ppm, preferably <50 ppm, and more preferably <10 ppm; and preferably the oxygen content is also low (e.g., <100 ppm, preferably <50 ppm, and more preferably <10 ppm).

Regardless of the extremely low moisture and oxygen content of the ambient environment in which the Li metal layer may be formed or treated, in order to be considered herein as fresh (e.g., freshly extruded or freshly treated), the exposure time between extrusion (or surface treatment) and placing/positioning the extruded lithium foil onto solid electrolyte sheet 100 should be limited to minutes, typically <10 minutes, and preferably <1 minute and more preferably <30 Seconds. In embodiments, it is contemplated that the time period between extruding (or surface scrubbing) and placing the Li foil onto the solid electrolyte sheet surface is about 1 minute-3 minutes, or less than 60 Seconds, or less than 30 Seconds, or less than 20 Seconds, or less than 10 Seconds (e.g., within about 10 or 5 Seconds of extrusion/scrubbing).

In various embodiments Li metal layer 1310 (e.g., Li foil) is disposed onto the surface of sheet 101 to induce a compressive stress, thereby forming a laminate wherein the solid electrolyte layer, and in particular surface 101A, is in compression (i.e., it experiences a compressive force, and thus the sheet is not under tension), and preferably the compressive force is sufficient to assist in resisting crack formation and growth on the surface or in the bulk of sheet 101 (e.g., at least 10 MPa). To achieve a useful compressive stress, lithium metal layer 1310 is generally at least as thick as the solid electrolyte sheet 101, and preferably thicker. For instance, sheet 100 may be between 5 to 50 μm thick and the lithium metal layer of substantially the same thickness, and in embodiments the lithium metal layer may be at least 5 μm thicker than the solid electrolyte sheet, or at least 10 μm, or at least 20 μm thicker. For instance, in various embodiments the compressive stress is in the range of 10 MPa-100 MPa; sheet 100 has a thickness of 10-50 um; the lithium metal layer has a thickness between that of sheet 100 and 50 μm thick; and the CTE of sheet 100 is preferably in the range of 10-40 1/° C., and more preferably in the range of 10-30 1/° C., and even more preferably in the range of 20-30 1/° C.

The compressive force may be induced during fabrication of the electrode assembly, and in particular by controlling the temperature difference between the temperature of the lithium metal layer ($T_{lithium}$) and that of the vitreous solid electrolyte sheet ($T_{vitreous}$) during processing of the electrode assembly at the time the lithium metal layer is disposed in direct contact with the sheet (e.g., during lamination). In various embodiments that temperature difference ΔT ($T_{lithium}-T_{vitreous}$) is between 10° C.-200° C., and typically 20-180° C., and even more typically 40-160° C. In embodiments thereof, the temperature of the lithium metal layer is below its melting point (e.g., 180° C. for lithium metal), and the temperature of the vitreous sheet may be room temperature (about 25° C.), or below room temperature.

In various embodiments, surface 101A may be intentionally transformed (via a roughening step) from having a smooth surface to a rougher surface for the purpose of enhancing interfacial contact with a Li metal film or foil; for example, by abrasive scrubbing or bristle blasting (e.g., spraying grit onto the surface). For instance, in various embodiments the first principal side surface is transformed to increase its roughness by a factor of 10 or more; for example, from having an initial smooth surface with $R_a$<0.05 μm to a rougher surface with $R_a$>0.1 μm, or from $R_a$<0.1 μm to $R_a$>1 μm.

In a particular embodiment a self-supporting current collector layer is adhered to the first principal side surface of the freestanding vitreous solid electrolyte sheet by roller laminating the layer to the sheet while forming a thin lithium metal bonding layer on the surface of the current collector immediately prior to, or simultaneous with, the laminating step (e.g., the bonding layer no more than 1 μm thick). In various embodiments, the lithium metal bonding layer is of sufficient thickness to also serve as a seed layer for enhancing uniformity of electrochemically deposited Li metal in a battery cell (e.g., the bonding layer about 0.1, 0.2, 0.3, 0.4, 0.5, 0.6, 0.7 0.8, 0.9 or 1.0 μm thick).

Figure 13B:
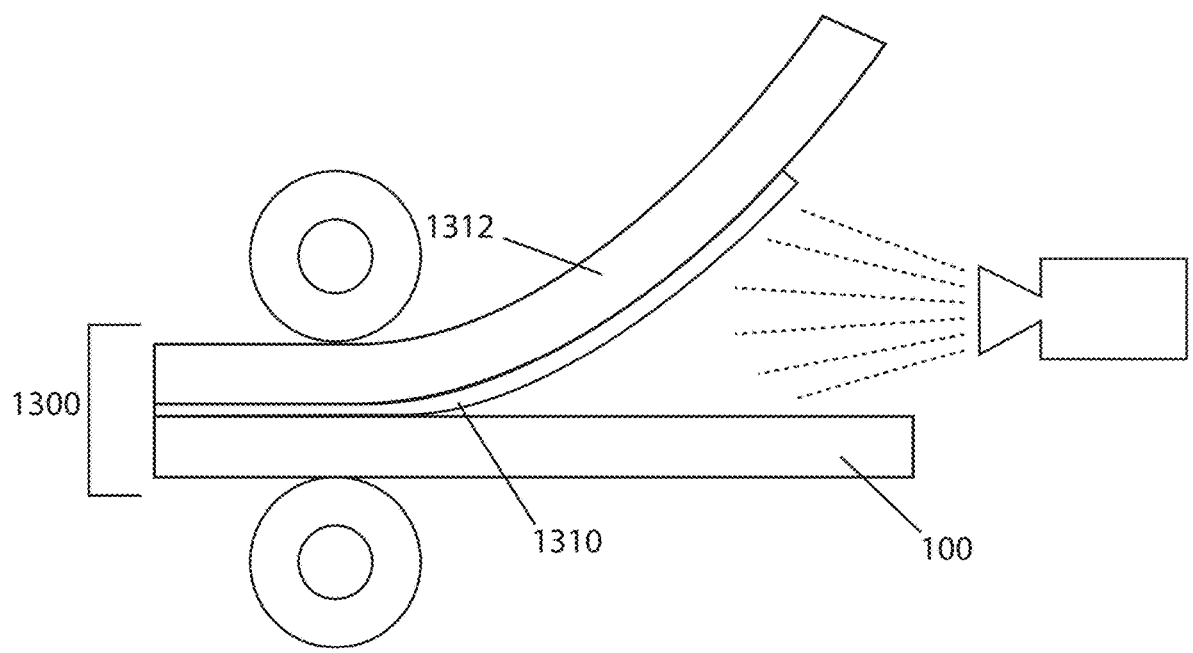

For example, with reference to FIG. 13B, standalone lithium metal electrode assembly 1300 may be formed by rolling or placing current collecting layer 1312 directly onto solid electrolyte sheet 100 in combination with evaporating lithium metal or spraying Li metal vapor between it (1312) and sheet 100. This technique provides a mechanism for bonding a discrete self-supporting current collecting layer to the solid electrolyte sheet. For example, the discrete current collecting layer 1312 a thin Cu foil or a laminate of a Cu metal coated on a polymeric substrate. In an alternative embodiment, not shown, it is contemplated that current collector layer 1312 may have a pre-existing lithium metal layer already present on its surface prior to laminating to the solid electrolyte in the presence of Li metal vapor.

Figure 13C:
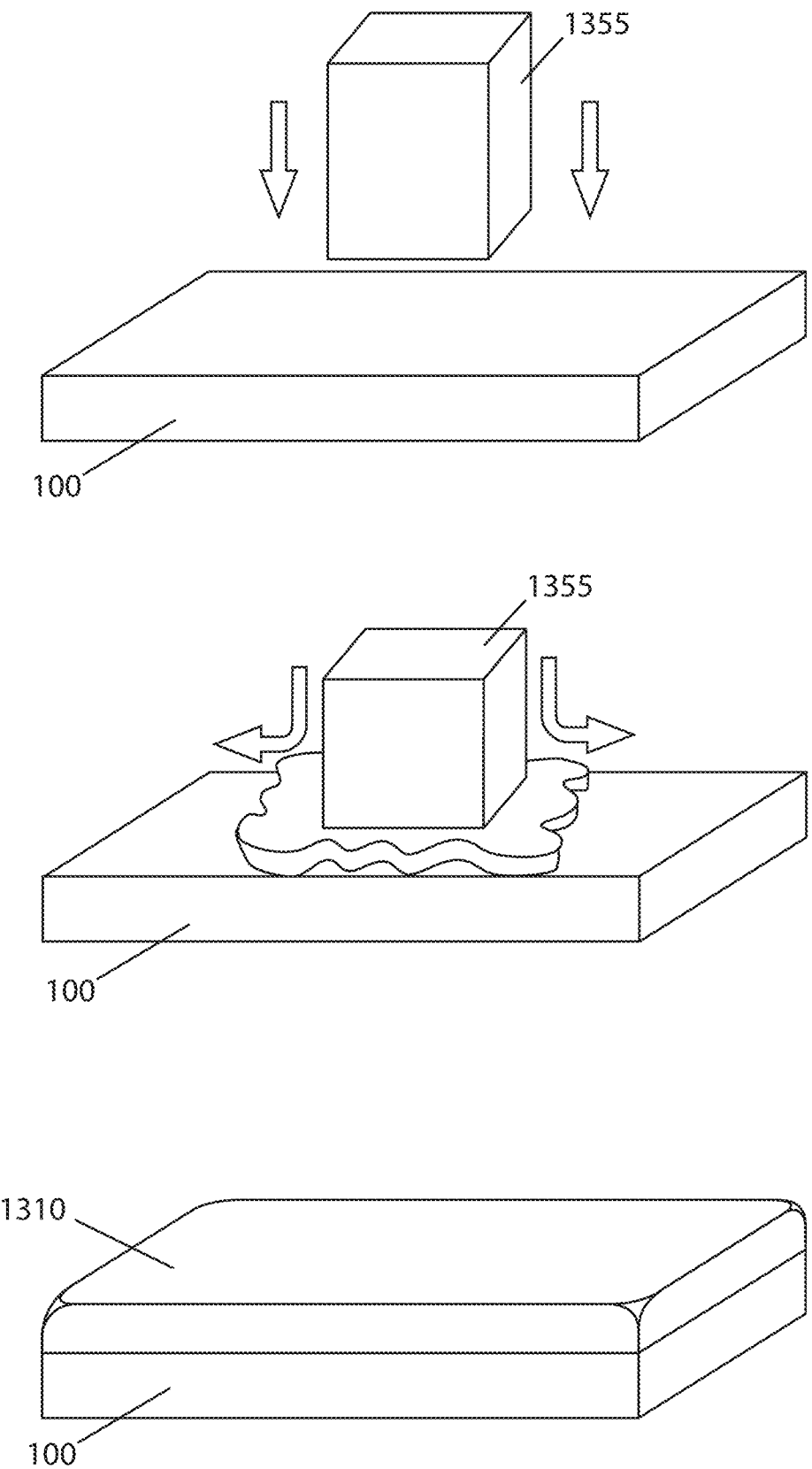

With reference to FIG. 13C there is illustrated another process for making lithium metal electrode assembly 1300, by pressure spreading a Li metal block 1355 onto first principal side surface 101A of sulfide glass sheet 100. The spreading operation, which may be performed with heat, breaks apart the resistive film to effect immediate contact of fresh lithium surfaces to the solid electrolyte sheet. Lithium metal block 1355 is sized relative to the total area of solid electrolyte sheet 100 and the desired thickness of the lithium metal layer to be formed, preferably the as-spread lithium metal layer is of a substantially uniform thickness (e.g., about 5um, or about 10 um, or about 15 um or about 20 um, or about 25 um, or about 30 um, or about 35 um, or about 40 um, or about 45 um or about 50 um). In some embodiments, as-spread lithium metal layer 1310 is a thin layer of about 5 to 20 um, and a thicker Li foil is then subsequently adhered to its surface to impart a higher Li metal capacity to the electrode assembly.

While standalone Li metal electrode assembly 1300 comprises a lithium metal layer, the disclosure also contemplates a lithium-free electrode in the form of an electrode subassembly, as described above and illustrated in FIG. 13D. In such embodiments, lithium metal layer 1310 is formed inside a battery cell by electrochemically plating lithium metal onto a tie-layer and/or current collector layer adjacent to first principal side surface 101A. In various embodiments the assembly is considered substantially lithium-free when the amount of Li metal in the standalone electrode assembly is scant (e.g., a seed layer less than 1 um thick).

Figure 13E:
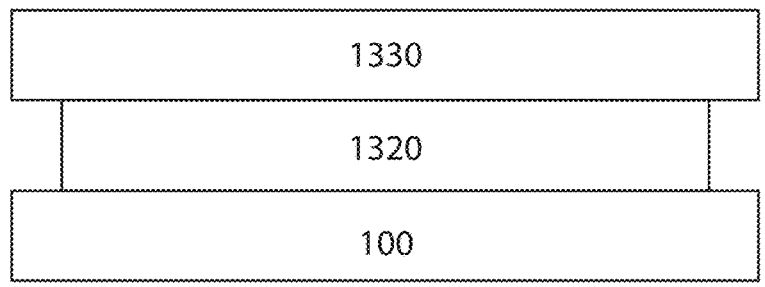
FIGS. 13E-G illustrate cross sectional depictions of backplane encapsulated lithium metal electrode assemblies, in accordance with various embodiments of this disclosure.

With reference to FIG. 13E there is illustrated what is termed herein an encapsulated standalone lithium metal electrode assembly 1300E. In various embodiments encapsulated assembly 1300E is composed of lithium metal component layer 1320 encapsulated between a first solid electrolyte sheet 100 and an opposing backplane component 1330, both of which are substantially impervious to liquids they may come into contact with during manufacture, storage and operation, and preferably non-reactive with said liquids. Lithium metal component layer 1320 comprises a Li metal layer in direct contact with sheet 100, and one or more optional layers, as described in more detail below, which are adjacent to backplane 1330. Solid electrolyte sheet 100 and backplane component 1330 respectively define the major exterior opposing surfaces of the Li metal electrode assembly. By use of the term encapsulate when referring to the lithium metal component layer of the assembly it is meant that the solid electrolyte sheet and backplane component are in contiguous mechanical force contact with the lithium metal component layer. Accordingly, as a result of the encapsulation, lithium metal component layer 1320, and in particular the lithium metal layer, may be subjected to stacking pressure when incorporated in a battery cell.

In some embodiments encapsulated lithium metal electrode assembly 1300E is double-sided and the backplane component is a second vitreous solid electrolyte sheet (e.g., substantially identical to the first solid electrolyte sheet). In other embodiments, backplane component is not a Li ion conductor, and the encapsulated lithium metal electrode assembly is referred to herein as single-sided; for instance, the backplane may be a substantially inert material layer or an electronically conductive material layer with current collector functionality. By use of the term single-sided or double-sided it is meant with respect to whether one or both sides of the electrode assembly supports Li ion through transport (via electrical migration).

Figure 13F:
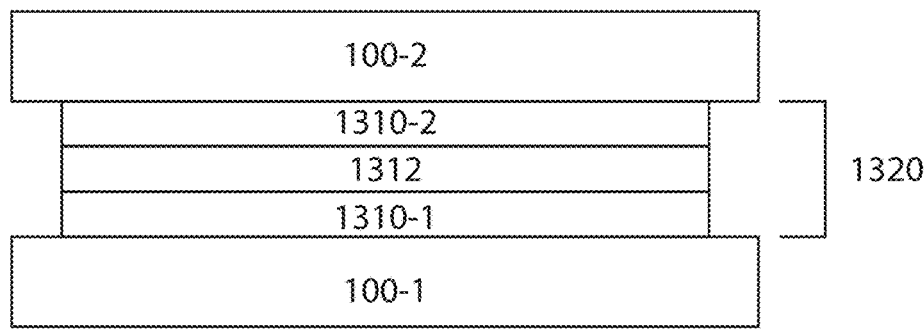

With reference to FIG. 13F, in some embodiments encapsulated electrode assembly 1300F is double-sided, and the backplane component is a second solid electrolyte sheet (designated as 100-2), and the first solid electrolyte sheet, likewise designated as 100-1. When double-sided, lithium metal component layer 1320 is typically a tri-layer composed of current collecting layer 1312 disposed between first and second lithium metal layers, 1310-1 and 1310-2 respectively.

In various embodiments, the encapsulated double-sided lithium metal electrode assembly is fabricated by providing a first and a second Li metal electrode assembly as described above with reference to FIG. 13A, and combining the two assemblies between a single current collecting layer 1312, or when the two assemblies are provided each with their own current collecting layer, they may be combined by placing one on the other (i.e., current collector to current collector).

Figure 13G:
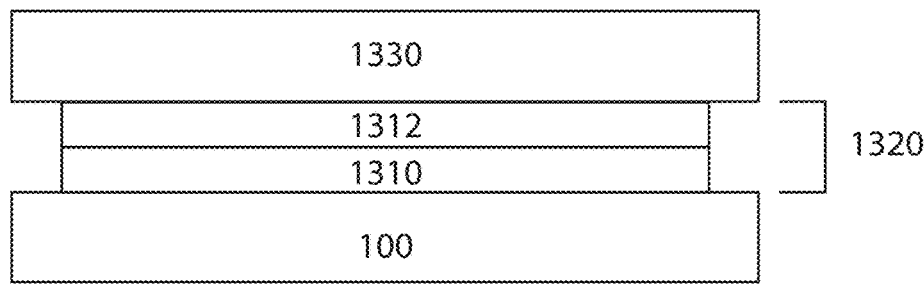

With reference to FIG. 13G, in other embodiments, the backplane component is not a Li ion conductor, and assembly 1300G, encapsulated, is single-sided. In various embodiments, when single-sided, backplane component 1330 may be an inert material component layer, or electronically conductive with current collector functionality. For instance, inert backplane component 1330 may be a polymeric/plastic layer (rigid or flexible) or when electronically conductive, the backplane may be a multi-layer of at least one polymer layer providing an exterior surface of the assembly and an electronically conductive metal layer in electronic communication with the lithium metal layer (e.g., in direct contact with the lithium metal layer or in direct contact with a Cu current collecting layer).

In various embodiments the encapsulated assembly may be edge sealed along the lengthwise and/or widthwise dimensions. When entirely sealed along its edges, the assembly is considered sealed and preferably hermetic, and the lithium metal layer(s) are isolated from the external environment.

With reference to FIG. 13H, in various embodiments the edge seals (e.g., lengthwise edges as shown) may be effected by fusion or pinch sealing the peripheral edges of solid electrolyte sheet 100-1 to that of solid electrolyte sheet 100-2. The direct bonding between sheets 100-1 and 100-2 may be performed with heat and/or pressure. For instance by heating the periphery of one or both sheets above $T_g$ (e.g., using a laser to heat the edges), and more typically above the softening temperature, and pressing/compressing (i.e., pinching) to effect the seal, or heating above $T_m$ and allowing the sheets to fusion seal to each other.

In other embodiments, as shown in FIG. 13I, the edge seal(s) may include a discrete sidewall component 1335 interfacing with solid electrolyte sheet 100-1 and backplane component 1330. The discrete sidewall component may be an inert polymer or a glass wire placed along the lengthwise edge and then heat/fusion sealed to sheet 100 and the backplane component 1330 (e.g., a second solid electrolyte sheet). When the edge is sealed made with a fusion sealable glass, it is generally not a Li ion conductor (e.g., a non-conducting sulfide glass). In other embodiments the discrete sidewall component 1335 may be an epoxy seal; e.g., the epoxy applied as a viscous fluid along the lengthwise edge(s), and then cured (e.g., with heat). Sulfur containing epoxy resins, for example, are contemplated for this purpose.

In various embodiments the lengthwise edges of the assembly may be sealed as described above, and the widthwise edges sealed likewise (e.g., all the edges fusion sealed). In other embodiments, the widthwise edges, which are generally of significantly shorter length, may be sealed in a different manner. For instance, in a double sided encapsulated electrode assembly, the lengthwise edges of the solid electrolyte sheets may be pinch or fusion sealed to each other (as described above), and the widthwise edges sealed via a discrete sidewall component, such as an epoxy seal or a non-conductive glass seal (e.g., a sulfide glass wire seal) or a polymeric wire seal.

Figure 13J:
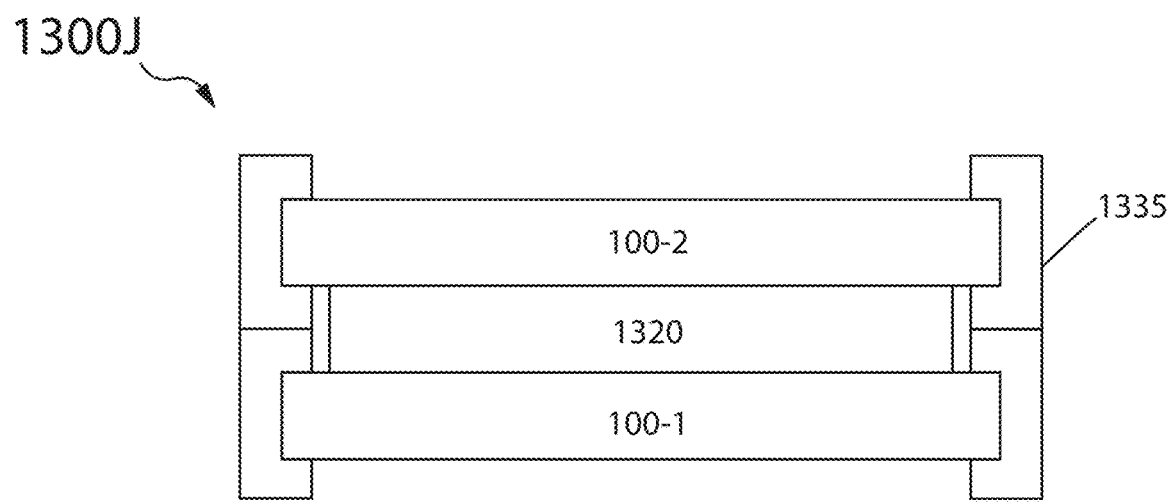

With reference to FIG. 13J, in various embodiments discrete sidewall component 1335 is edge-protecting element 105 as illustrated in FIG. 1G, which as described above may be a polymeric bracket that protects the sheet against edge cracking. When the assembly is double-sided, the edge-protecting elements may be adhered to each other, directly or indirectly. For example, directly heat/fusion bonded to each other (when element 105 is heat/fusion sealable) or otherwise adhered to each other using a discrete bonding material, such as an epoxy. The edge protecting elements may be polymeric (e.g., a polyolefin seal or bracket). Epoxy, metal, ceramic, glass ceramic or glass edge protecting elements are also contemplated (e.g., glass edge protecting elements).

With reference to FIGS. 13H-J, in an alternative solid-state negative electrode assembly embodiment, lithium metal component layer 1320, and in particular lithium metal layer 1310, is replaced with an alternative electroactive layer comprising an electroactive material having a potential within about 1V of Li metal (e.g., intercalatable carbon). In various embodiments, the alternative negative electroactive component layer is formed as a powder particle composite comprising: i) particles of intercalatable carbon, silicon or some combination thereof as the electroactive material of the component layer; ii) ionically conductive component particles of sulfide glass/glass-ceramic powder for ionic conductivity within the layer; and iii) optionally an amount of a carbon black particles as a diluent for enhancing electronic conductivity. When a solid-state particle composite compact, layer 1320 may be laminated directly to solid electrolyte sheets 100-1 and 100-2 (as shown in FIG. 13H/13I) and edge sealed, as described above, to yield a sealed double-sided solid-state negative electrode assembly. As described in more detail below, this alternative sealed solid-state negative electrode assembly is particularly beneficial for use in a hybrid battery cell when combined with a high voltage Li ion intercalating positive electrode (e.g., having a potential vs. Li metal that is greater than 3.5V, and preferably greater than 4V or 4.5V). For instance, phosphates and oxides including $LiNiPO_4$, $LiCoPO_4$, $LiMn_{1.5}Ni0.5O_4$, and $Li_3V_2(PO_4)_3$.

In other embodiments the lithium metal electrode assembly has what is termed herein an unconstrained backplane architecture, wherein the assembly is configured to allow the lithium metal layer(s) of the assembly to undergo electrochemical plating and striping reactions in an unconstrained fashion, wherein the backplane of the Li metal layer (i.e., its second major surface) is not encapsulated by the backplane component, and thus the lithium metal layer is unconstrained along the normal direction and free to expand and contract without pressure along its thickness direction during lithium metal plating/stripping (when the cell is being charged/discharged). By this expedient the lithium metal layer is not subjected to stacking pressure in a battery cell.

Figure 13K:
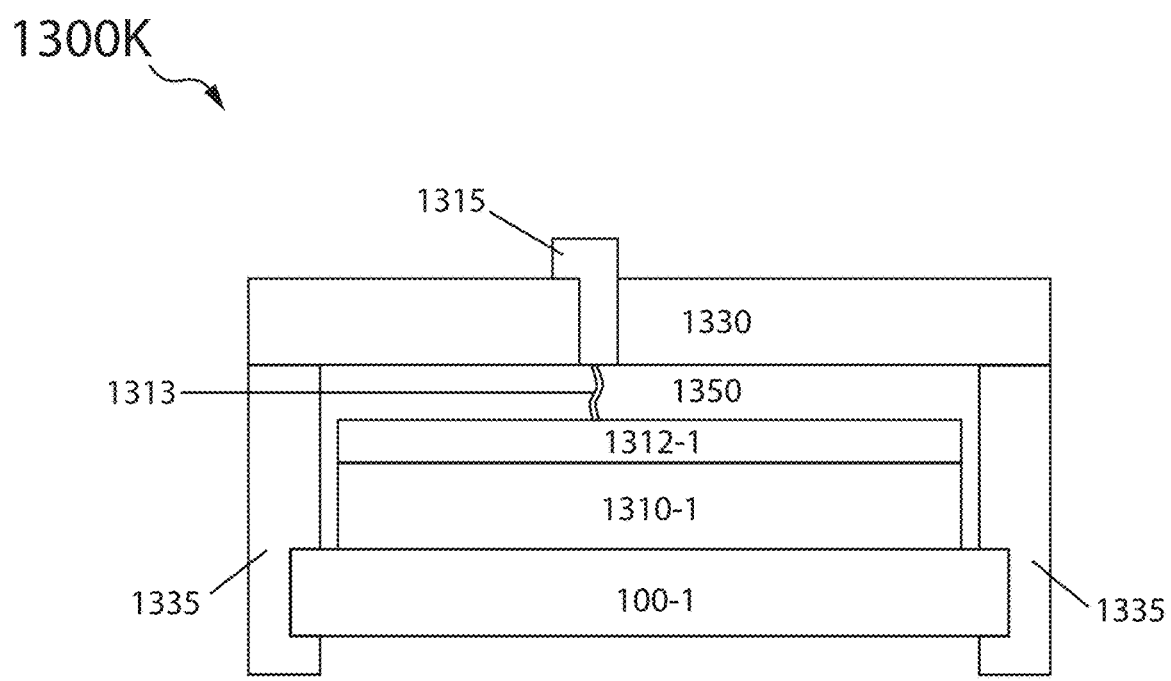
FIGS. 13K-L illustrate cross sectional depictions of lithium metal electrode assemblies having an unconstrained backplane architecture, in accordance with various embodiments of this disclosure.

With reference to FIG. 13K there is illustrated single-sided lithium metal electrode assembly 1300K having unconstrained backplane architecture. In various embodiments, the assembly is sealed along its lengthwise edges or it may be entirely sealed about all edges, and preferably hermetic, as described above. Assembly 1300K includes solid electrolyte sheet 100 encapsulating first major surface of lithium metal layer 1310 in direct contact, and discrete side wall component 1335 interfacing with solid electrolyte sheet 100 and backplane component 1330—effectively sealing the lengthwise edges of the assembly. Notably, the assembly is configured to effect gap 1350 between backplane 1330 and lithium metal layer 1310, and to maintain a gap over the course of operation of a battery cell in which the assembly is employed; the size of the gap will generally increase during discharge (as lithium metal is stripped) and decrease during charge (as Li metal is plated). In accordance with this embodiment, lithium metal layer 1310 is not subjected to stacking pressure in the battery cell, and, in particular, external pressure (mechanical force) is not exerted on layer 1310 by backplane component 1330, and thus configured to freely expand and contract (in thickness) during charge and discharge. In various embodiments lithium metal layer 1310 has current collector 1312 on its second major surface, and flexible conductive element 1313 (e.g., a metal wire or strip) tethered to the current collector or lithium metal layer for providing electronic communication to electrode assembly terminal 1315 (e.g., a metal connector), the terminal for providing electrical power to/from an external device.

Figure 13L:
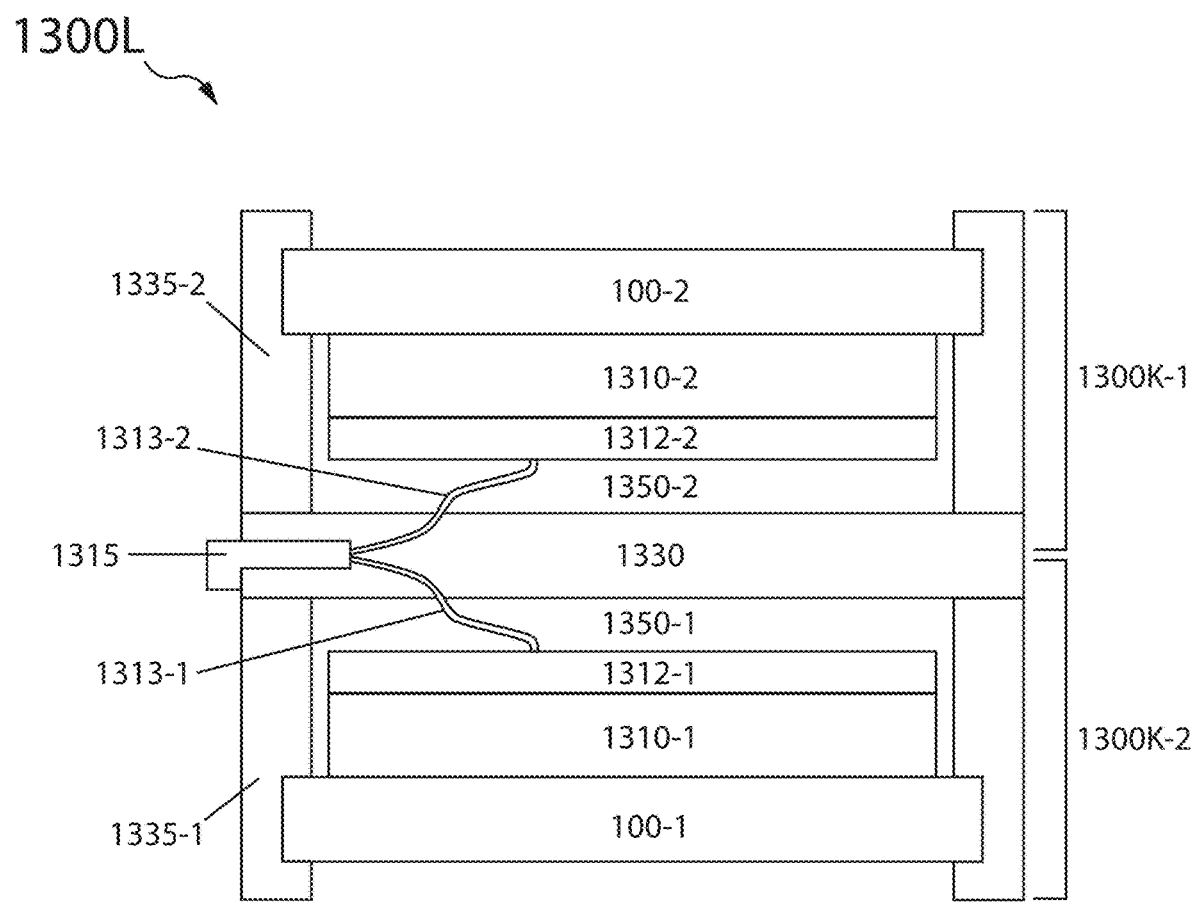

With reference to FIG. 13L there is illustrated double-sided assembly 1300L having an unconstrained backplane architecture in accordance with the present disclosure. In various embodiments assembly 1300L may be fabricated by combining a first single sided assembly (designated 1300K-1) and a second single sided assembly (designated 1300K-2), with optional sharing of a single backplane component 1330, as illustrated in FIG. 13K.

The electrode assemblies described above are freestanding battery cell components, which, entirely self-supporting, may be manufactured, stored and/or handled (by machine manipulation or otherwise) as a standalone component absent, for example, an opposing electrode (e.g., a positive electrode) or a battery cell housing. The assemblies have also been embodied in the absence of liquid electrolyte, and are therefore completely solid-state (i.e., fully solid-state Li metal electrode assemblies). Preferably, the electrode assemblies are sufficiently thin and flexible to be suitable for use in wound or folded battery cell constructions. In various embodiments, the electrode assembly is sealed (i.e., entirely edge sealed), and thus hermetic, and therewith when incorporated in a battery cell having a liquid electrolyte, the assembly protects the lithium metal layer(s) (or more generally electroactive layers) from contact with catholyte (i.e., the liquid electrolyte in contact with the positive electrode). In alternative embodiments, it is contemplated that the sealed electrode assembly (e.g., double-sided) is not a solid-state negative electrode assembly, and includes a porous/gel-able separator layer disposed between sheet 100 and electroactive component layer 1320, the gel layer impregnated with liquid electrolyte (i.e., anolyte).

In accordance with another aspect of the disclosure, there is provided a continuous web of lithium electrode assemblies.

Figure 14A:
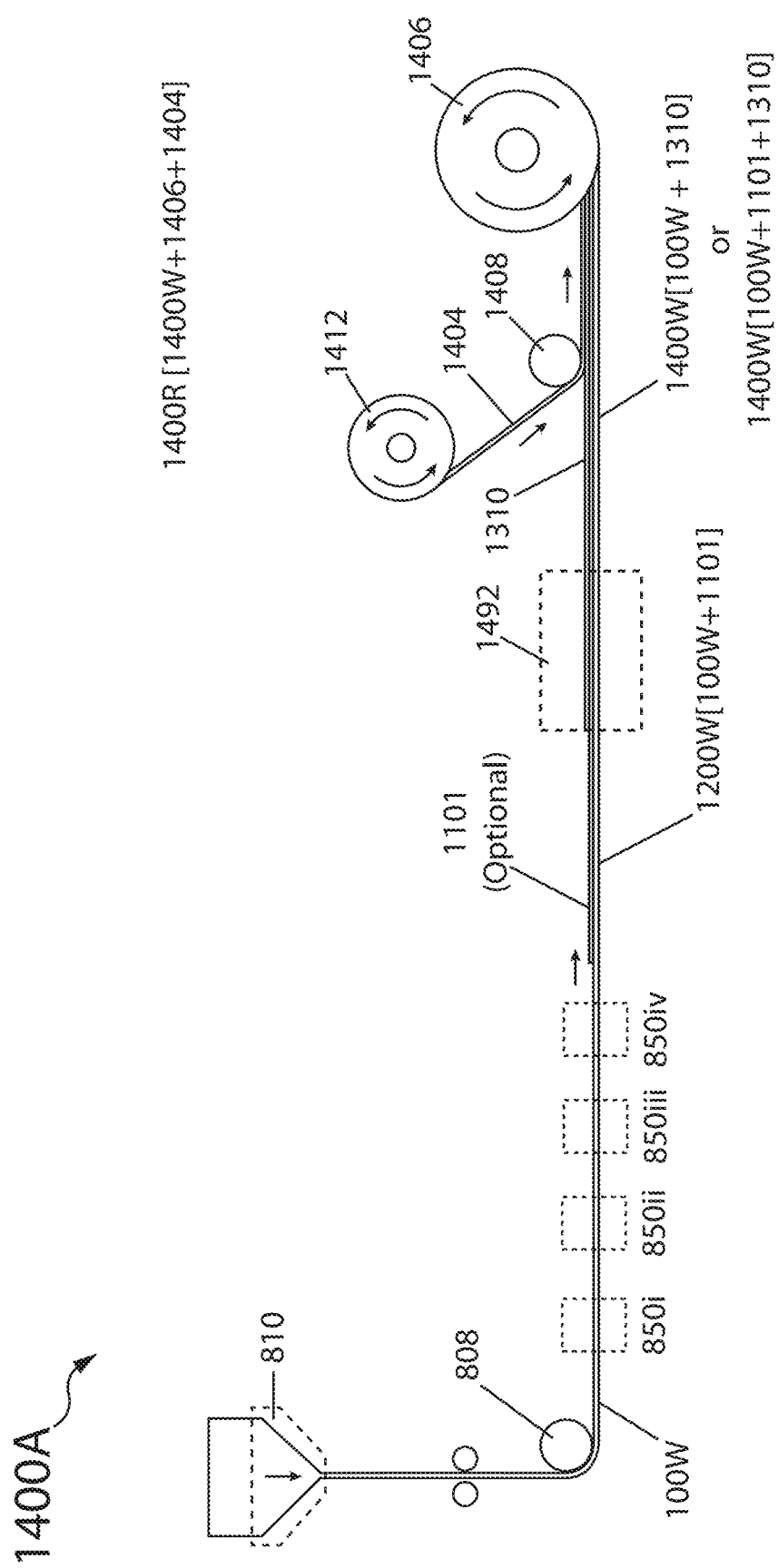
FIGS. 14A-C illustrate fabrication systems and methods for making a lithium metal electrode assembly and a continuous web and source roll thereof, the web configured using inline sheet to roll or $R_2R$ processing methods in accordance with embodiments of this disclosure.

With reference to Li metal electrode assembly manufacturing process 1400A illustrated in FIG. 14A, in various embodiments lithium electrode assemblies are fabricated inline with drawing of the continuous web of solid electrolyte sheet 100W, the overall process including one or more of the following post-solidification processing stages of: i) annealing 850i; ii) edge removal 850ii; iii) edge protecting 850iii; iv) coating stage 850iv for creating tie-layer 1101; v) lithium deposition stage 1492 for depositing (e.g., evaporating or hot rolling/laminating) lithium metal layer 1310 directly onto web 100W or onto tie-layer coating 1101 when present; and vi) winding the as-formed lithium electrode assembly web 1400W onto take-up roll 1406, to form lithium electrode assembly source roll 1400R, with optional interleave 1404; and slitting the web, lengthwise and/or widthwise, to form individual/discrete lithium electrode assemblies (e.g., lithium electrode assembly 1300 as illustrated in FIG. 13A).

In various embodiments lithium metal layer 1310 is deposited via stage 1492 using physical or chemical vapor deposition (e.g., via evaporation of lithium metal in a differentially pumped chamber). In other embodiments, stage 1492 is a laminating stage wherein lithium metal layer 1310 (e.g., a lithium metal foil) is laminated directly onto web 100W (e.g., via hot rolling). In other embodiments, stage 1492 includes apparatus for applying a current collecting layer directly to the surface of web 100W, as illustrated in FIG. 13B.

Figure 14B:
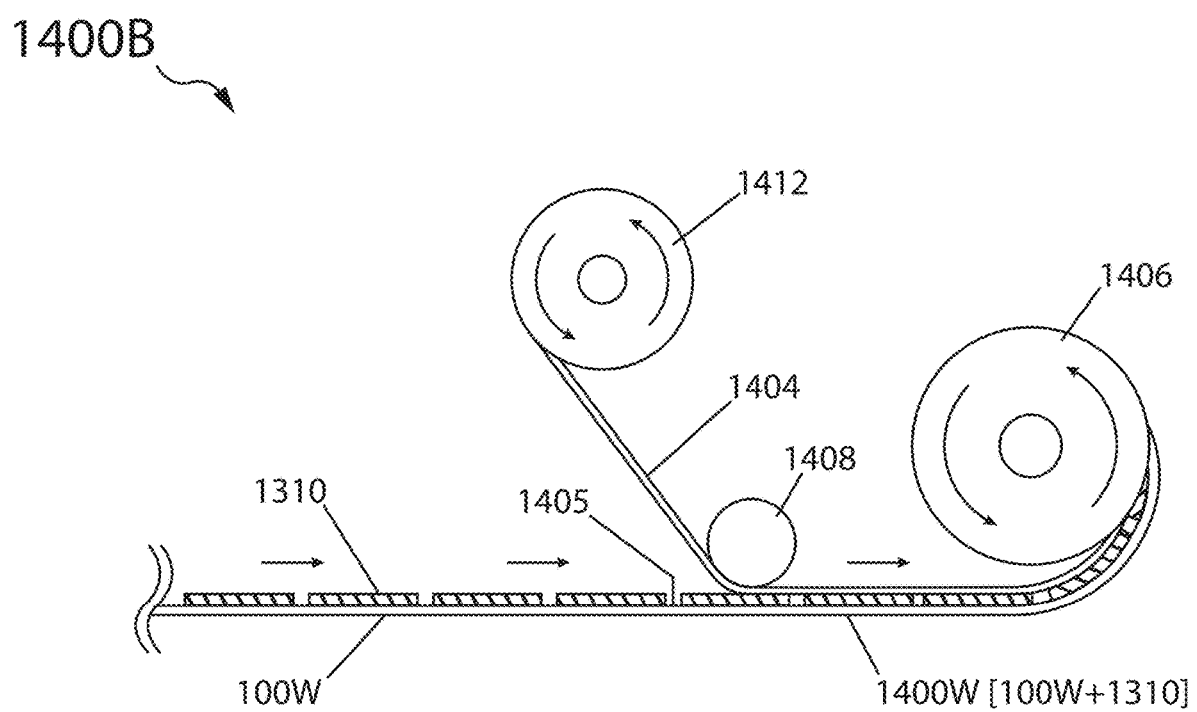

As illustrated in FIG. 14B, in various embodiments lithium metal layer 1310 is deposited or laminated intermittently to form well defined lithium coated regions 1310 and uncoated regions 1405, and by this expedient, lithium electrode assembly web 1400W comprises a multitude of discrete electrode assemblies, which may be excised by slicing (e.g., by laser cutting) within the confines of the uncoated regions. In various embodiments, the discrete electrode assemblies are excised from web 1400W inline with fabrication process 1400A but prior to any downstream rolling.

Figure 14C:
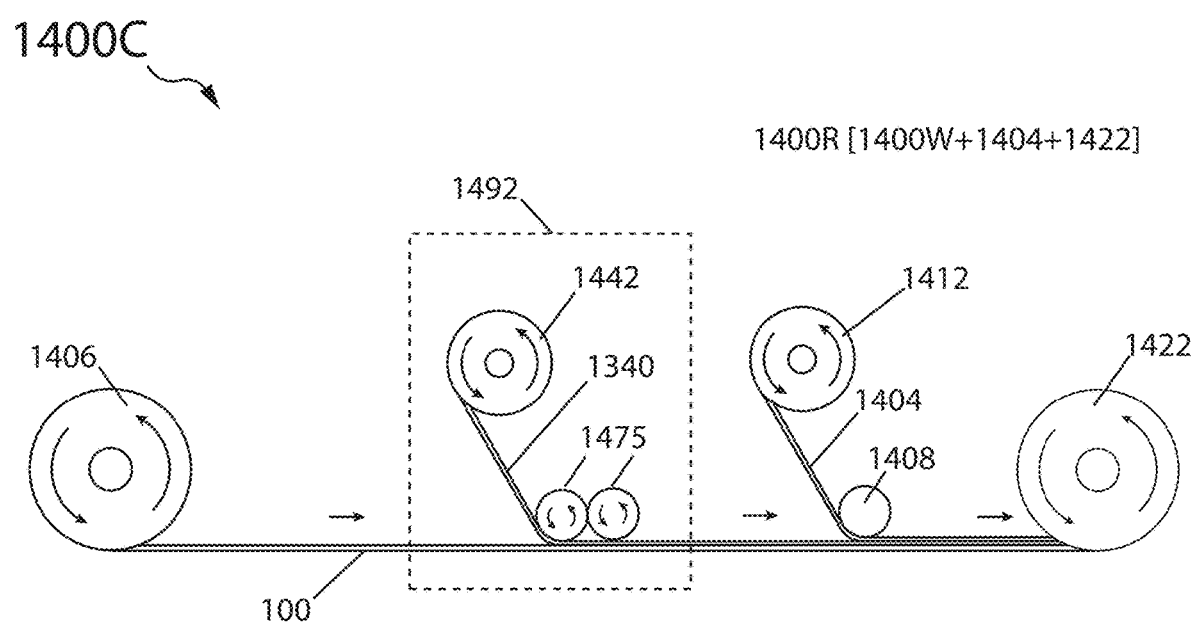

As illustrated in FIG. 14C, in other embodiments, lithium electrode assembly web 1400W may be R$_2$R processed from a continuous source roll of solid electrolyte web 100R (as shown in FIGS. 3A-B and FIG. 8) or from source roll 1200R of subassembly web 1200W (as shown in FIGS. 3A-B and FIGS. 12A-C), whereby web 100W/1200W is unwound from its source roll 100R/1200R, traversed into lithium stage 1492, coated or laminated therein with lithium metal layer 1310. Typically the lithium is coated in an intermittent fashion to yield discrete lithium coated and uncoated regions. Thereafter, discrete lithium electrode assembly components may be excised from web 1400W by cutting across uncoated region 1405 (e.g., with a laser cutter), or wound onto spool 1422 to form source roll 1400R.

In various embodiments, lithium deposition stage 1492 involves laminating a fresh lithium metal foil (e.g., freshly extruded) onto web 100W/1200W. In various embodiments Li metal layer 1310 is unwound from a source roll 1442 and surface scrubbed to expose fresh lithium metal surfaces, and then bond laminated via hot rollers 1475 to web 100W/1200W. In other embodiments, the lithium metal deposition stage involves evaporating Li metal onto web 100W or 1200W. In an alternative embodiment stage 1492 involves unwinding a roll of a current collecting layer (e.g., Cu foil) and bonding the Cu foil directly to web 100W or 1200W using lithium vapor as described above with reference to FIG. 13B.

Figure 15:
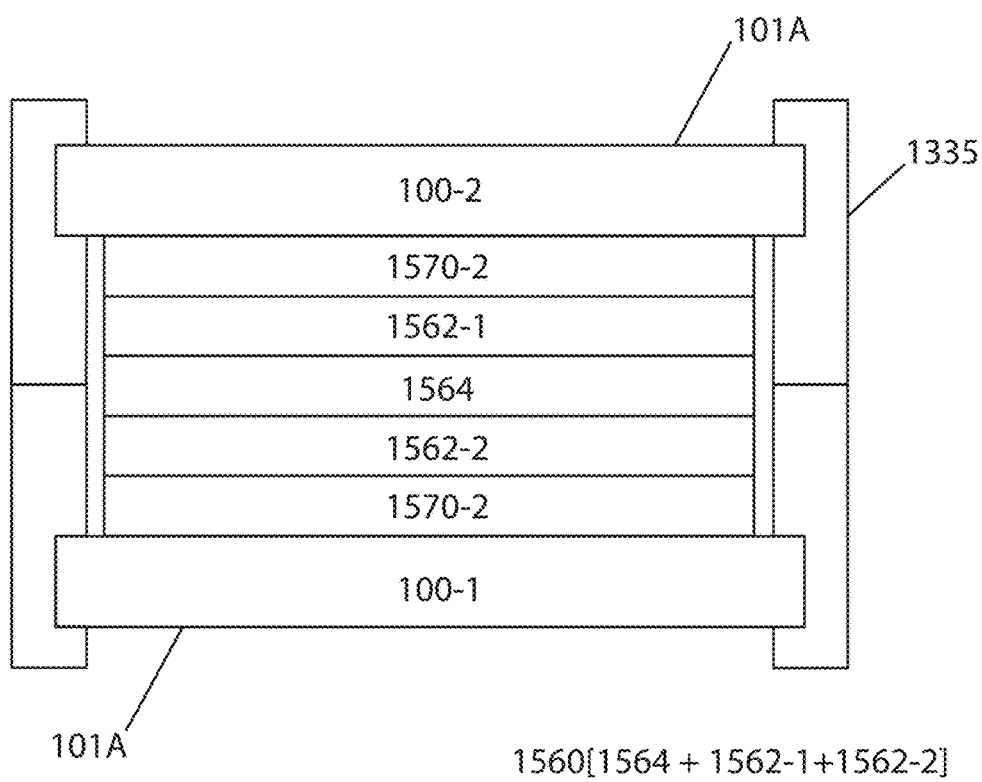
FIG. 15 illustrates a positive lithium electrode assembly in accordance with this disclosure.

With reference to FIG. 15, in various embodiments the electrode assembly is a standalone positive electrode assembly, wherein a positive electroactive component layer is encapsulated on both major surfaces by first and second solid electrolyte sheets of the present disclosure. Specifically, positive electrode assembly 1500 is double-sided and composed of first and second solid electrolyte sheets 100-1 and 100-2 edge sealed via discrete sidewall component 1335 (e.g., as described above in various embodiments for the lithium metal electrode assemblies). Positive electroactive material component layer 1560 is typically a tri-layer of current collecting layer 1564 (e.g., aluminum or stainless foil) coated on both sides by an electroactive material layer 1562-1 and 1562-2, which, in various embodiments has a lithium ion intercalation compound as its electroactive material (e.g., an oxide (e.g., a transition metal oxide) such as e.g., $LiCoO_2$, $LiMn_2O_4$, $LiNiO$, $LiNi_{0.33}Mn_{0.33}Co_{0.33}O_2$, $LiNi_{0.8}Co_{0.15}Al_{0.05}O_2$). In various embodiments, positive electrode assembly 1500 includes liquid electrolyte in contact with electroactive layer 1562, and present in its pores. In various embodiments, as shown, the assembly includes a first and second porous separator layer or gel electrolyte layer (designated as 1570-1 and 1570-2, respectively), which, impregnated with liquid electrolyte, provide positive separation between the electroactive layers and their opposing solid electrolyte sheets. Preferably the assembly is well sealed around its edges, and the liquid electrolyte is prevented from seeping out (e.g., hermetically sealed). In alternative embodiments the positive electrode assembly may be single-sided and the second solid electrolyte sheet replaced with an inert or current collecting backplane component impermeable to the liquid electrolyte and preferably non-reactive (e.g., a polymer and/or metal layer). When double-sided, it is contemplated that positive electrode assembly 1500 may be edge sealed with a fusion or pinch seal as described above, rather than using a discrete sidewall component. In some embodiments, a solid polymer electrolyte layer (e.g., a polyethylene oxide (PEO) based solid electrolyte film) may be used to effect positive separation between the electroactive layers and the opposing solid electrolyte sheets. In this way, the positive electrode assembly may be devoid of a liquid electrolyte. In embodiments, it is contemplated that the positive electroactive material component layer 1562-1/1562-2 is of a homogenous composition (e.g., a homogenous layer of $LiCoO_2$) may be fabricated by physical vapor deposition onto current collecting layer 1564, and that layer 1570-1/1570-2, disposed on the surface of the $LiCoO_2$ layer, may be a thin coating of an inorganic solid electrolyte layer that provides positive separation between the LiCoO2 layer and the solid electrolyte sheet. For instance, the inorganic film, preferably less than several microns thick (e.g., less than 1 mm thick) may be a lithium ion conductive glass, such as a lithium phosphorous oxynitride glass (e.g., LiPON) or a Li ion conducting sulfide-based glass layer, the thin glass layer typically deposited onto the $LiCoO_2$ layer by physical vapor deposition (PVD), such as sputtering or evaporation. In other embodiments it is contemplated that an inorganic powder compact layer, preferably thin, may be disposed between the electroactive layer and the solid electrolyte sheet, or the electrode itself may be a particle compact with a graded composition, as described herein below with reference to FIG. 16F.

Figure 16A:
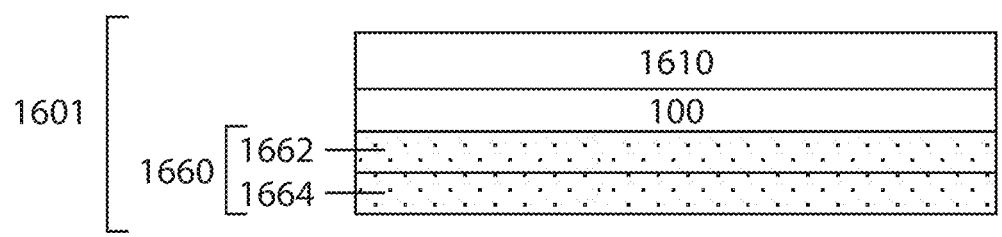

With reference to FIG. 16A there is illustrated a lithium battery cell 1600A in accordance with the present disclosure, the battery cell comprising a cell laminate 1601 including solid electrolyte sheet 100 disposed between positive electrode 1660 and negative lithium electroactive layer 1610, for example a Li metal layer such as those described above with reference to layer 1310.

In various embodiments the combination of lithium electroactive layer 1610 (e.g., an evaporated or extruded lithium metal layer) and solid electrolyte sheet 100 (e.g., a vitreous sulfide glass) is incorporated in the battery cell as standalone Li metal electrode assembly 1300, as described with reference to FIGS. 13A-L, or more generally as a standalone negative electrode assembly (e.g., having intercalatable carbon as the electroactive material of layer 1610).

In various embodiments the standalone negative electrode assembly is fully solid-state (i.e., no liquid comes into direct contact with the electroactive material of layer 1610). As described in more detail herein below: i) in some embodiments the fully solid-state standalone negative electrode assembly is combined with a fully solid-state positive electrode in forming a fully solid-state battery cell; ii) in some embodiments, the fully solid-state negative electrode assembly is combined with a positive electrode impregnated with a liquid electrolyte, in forming a hybrid battery cell construct, wherein the cell, or solid-state negative electrode assembly, includes seals, as described above, that prevent the liquid electrolyte from directly contacting the electroactive material of the negative electrode assembly; and iii) in some embodiments the cell includes a common liquid electrolyte in contact with both.

Cell laminate 1601 is generally disposed in a cell housing (not shown). In various embodiments the cell laminate is sufficiently flexible to be foldable and more preferably windable, and thereby cell 1600A may be of a wound prismatic or wound cylindrical construction, or a foldable construct disposed in a pouch-like housing (e.g., a multi-layer laminate material). Battery cell 1600A may be made by: i) combining layers: 1610, 100, and 1660, to form laminate 1601; ii) winding or folding the laminate into a shaped construct (e.g., cylindrical or prismatic); iii) placing the shaped construct into a rigid or flexible housing such as a multilayer laminate pouch or rigid container; and then iv) sealing the pouch or container. When a liquid electrolyte is employed in the cell, it is typically dispensed after the laminate is disposed in the cell housing. In some cell embodiments, particularly those that make use of an hermetically sealed standalone positive electrode assembly, the liquid electrolyte may be incorporated in the electrode assembly prior to its incorporation in the cell housing.

In various embodiments, laminate 1601 is wound or folded with radius of curvature ≤3 cm, ≤2 cm, ≤1 cm, ≤0.5 cm, or ≤0.25 mm without fracturing solid electrolyte sheet 100. In various embodiments cell 1600A includes a spindle about which laminate 1601 is wound, the spindle typically having diameter ≤6 cm, ≤4 cm, ≤2 cm, ≤1 cm, or ≤6 mm.

In various embodiments, positive electrode 1660 includes positive electroactive layer 1662 disposed on current collecting layer 1664 (e.g., a metal foil, such as aluminum, nickel, stainless steel or the like). In various embodiments positive electrode 1660 may be solid-state (i.e., devoid of a liquid electrolyte) or it may contain a liquid electrolyte, typically impregnated in the pores of electroactive layer 1662. In various embodiments positive electroactive layer 1662 is a lithium ion intercalation layer composed of a lithium ion intercalation compound as the electroactive material. When combined with a liquid electrolyte, positive electroactive layer 1662 is typically porous, and when solid-state the layer is preferably dense (e.g., a highly compacted particle composite). Particularly suitable lithium ion intercalation compounds include, for example, intercalating transition metal oxides such as lithium cobalt oxides, lithium manganese oxides, lithium nickel oxides, lithium nickel manganese cobalt oxides, lithium nickel cobalt aluminum oxides (e.g., $LiCoO_2$, $LiMn_2O_4$, $LiNiO$, $LiNi_{0.33}Mn_{0.33}Co_{0.33}O_2$, $LiNi_{0.8}Co_{0.15}Al_{0.05}O_2$ and the like) or intercalating transition metal phosphates and sulfates (e.g., $LiFePO_4$, $Li_3V_2(PO_4)_3$, $LiCoPO_4$, $LiMnPO_4$, and $LiFeSO_4$) or others (e.g., $LiFeSO_4F$ and $LiVPO_4F$), as well as high voltage intercalating materials capable of achieving operating cell voltages versus lithium metal in excess of 4.5 Volts, including $LiNiPO_4$, $LiCoPO_4$, $LiMn_{1.5}Ni_{0.5}O_4$, and $Li_3V_2(PO_4)_3$. In some embodiments the intercalating material (e.g., an oxide), is unlithiated prior to incorporation in a battery cell, such as vanadium oxides and manganese oxides, including $V_2O_5$ and $V_6O_{13}$.

In various embodiments the electroactive material of layer 1662 is of the conversion reaction type including transition metal oxides, transition metal fluorides, transition metal sulfides, transition metal nitrides and combinations thereof (e.g., $MnO_2$, $Mn_2O_3$, $MnO$, $Fe_2O_3$, $Fe_3O_4$, $FeO$, $Co_3O_4$, $CoO$, $NiO$, $CuO$, $Cu_2O$, $MoO_3$, $MoO_2$, and $RuO_2$).

In various embodiments the electroactive material of layer 1662 is elemental sulfur and/or lithium polysulfide species, typically dissolved in a non-aqueous liquid electrolyte. In such said embodiments, the battery cell may be considered a lithium sulfur battery. Generally, when making use of dissolved electroactive speices (polysulfides or otherwise), electroactive layer 1662 is an electron transfer medium that facilitates electrochemical redox during discharge and charge, and, as such, is typically a porous metal or porous carbonaceous layer.

Continuing with reference to FIG. 16A, in some battery cell embodiments (especially those of the solid-state type described in more detail herein below), positive electroactive layer 1662 is disposed adjacent to and in direct contact with second principle side surface 101B of solid electrolyte sheet 100, and, in some embodiments, the positive electroactive material directly contacts surface 101B. However, in other embodiments, an additional Li ion conductive material layer (not shown), such as a solid organic or inorganic Li conducting layer, may be incorporated between solid electrolyte sheet 100 and positive electroactive layer 1662. For instance, the additional material layer may be a solid polymer electrolyte layer, such as a polyethylene oxide (PEO) or a PEO like layer, or block copolymer electrolyte infused with a lithium salt (e.g., as described in U.S. Pat. No. 8,691,928 incorporated by reference herein), or it may be an inorganic Li conducting layer (e.g., PVD coated onto the second side surface of solid electrolyte sheet 100). The solid polymer electrolyte layer (not shown) can provide benefit as it pertains to chemical compatibility at the interface with the positive electroactive layer. Solid-state positive electroactive layer 1662 may be a particle composite of electroactive particles and sulfide glass/glass ceramic particles, and in some embodiments, may be engineered to effect a surface that is absent electroactive material, as described in more detail herein below.

In various embodiments battery cell 1600A is of the hybrid cell type, having a fully solid-state negative electrode (e.g., a fully solid-state and sealed lithium metal electrode assembly) and a positive electrode impregnated with a liquid electrolyte, and thus the positive electrode not solid-state. In other embodiments cell 1600A is fully solid-state, and thus entirely devoid of liquid phase electrolyte. In various fully solid-state cell embodiments, solid electrolyte sheet 100 serves as the sole continuous solid electrolyte separator layer between negative lithium electroactive layer 1610 (e.g., a lithium metal layer) and positive electrode 1660.

In various embodiments cell 1600A is not fully solid state, and thus includes a liquid phase electrolyte. In some embodiments the liquid phase electrolyte is a common electrolyte present throughout the cell and contacts both the positive electrode (e.g., positive electroactive layer 1662) and negative lithium electroactive layer 1610 (e.g., lithium metal layer). By use of the term "common electrolyte" it is meant that the liquid electrolyte in contact with the negative electroactive layer also contacts the positive electroactive layer, and thus the "common liquid electrolyte" is continuous throughout cell laminate 1601. A common liquid electrolyte yields a rather unusual and counterintuitive cell construction, in that it employs both a solid-state separator composed of solid electrolyte sheet 100 (preferably devoid of through porosity) and a continuous liquid phase electrolyte that contacts both positive electroactive layer 1662 and negative electroactive layer 1610. In fact, solid electrolyte sheet 100 may be used as a Li ion conducting solid electrolyte separator layer in an otherwise conventional lithium ion cell, with the solid electrolyte sheet providing through conduction for Li ions while preventing short circuiting by lithium dendrites and providing protection against thermal runaway. In some embodiments, sheet 100 serves as a direct replacement for the micro-porous polymeric separator layer or gel electrolyte layer commonly employed in conventional lithium ion cells (e.g., Celgard® or the like), and in such embodiments battery cell 1600A includes a common liquid electrolyte but is explicitly devoid of a porous separator layer or gel layer. For example, battery cell 1600A may be embodied by positive electrode 1660 having porous positive electroactive layer 1662 comprising a lithium ion intercalation compound (e.g., $LiCoO_2$) and porous negative electroactive layer 1610 having as its electroactive material a lithium ion intercalation material or alloying material (e.g., intercalatable carbon or silicon or some combination thereof). Moreover, while this disclosure contemplates that the common liquid electrolyte may exist primarily in the pores of the positive and negative electroactive layers, it is not limited as such, and in some embodiments the cell may include one or more porous separator layers (e.g., a microporous polymer layer such as a porous polyolefin or the like) or gel electrolyte layer positioned between solid electrolyte sheet 100 and electroactive layer(s) 1610 and/or 1662. When incorporated in a cell having a common liquid electrolyte, solid electrolyte sheet 100 is preferably dense and substantially impervious to the common liquid electrolyte, but the disclosure is not necessarily so limited.

In various embodiments the battery cell of the present disclosure is of a hybrid cell construction: composed of a solid-state and sealed negative electrode assembly, as described above, and a positive electrode impregnated with a liquid electrolyte. When referring to an electrode assembly as solid-state, it is meant that the assembly does not contain liquid, and in particular that the electroactive material of the assembly does not contact liquid phase electrolyte. In various embodiments the hybrid cell construction is composed of a sealed positive electrode assembly, having a liquid electrolyte sealed within the assembly, and a solid-state negative electrode (e.g., a lithium metal layer).

Figure 16B:
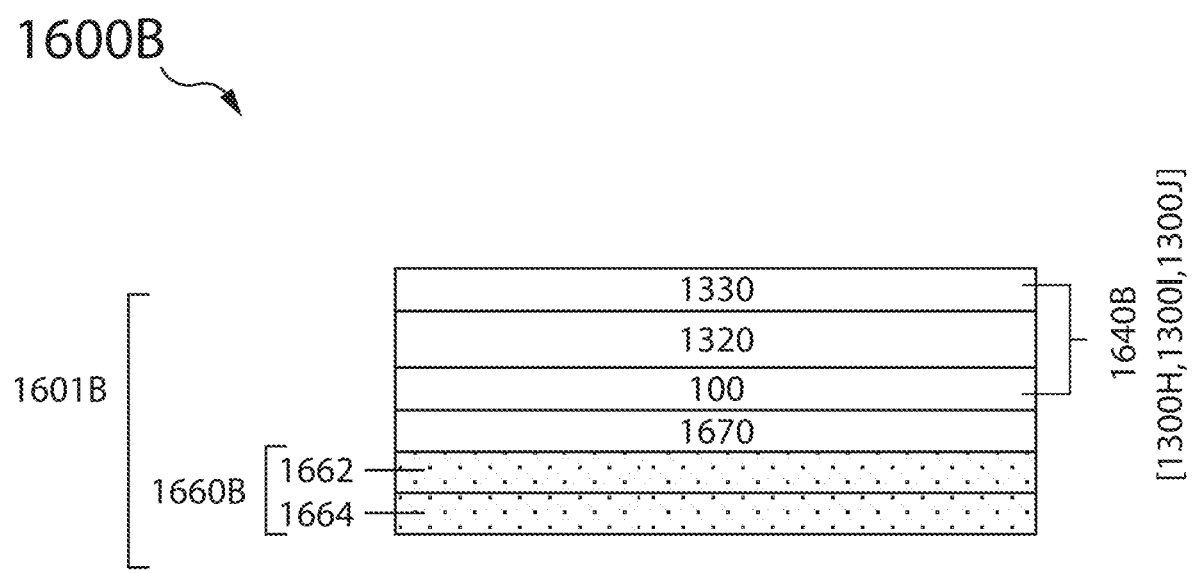

With reference to FIG. 16B, in various embodiments battery cell 1600B is of a hybrid cell construction, and solid-state negative electrode assembly 1640B is a sealed solid-state negative electrode assembly, such as those illustrated in FIGS. 13H-J. In particular embodiments the liquid electrolyte is present in the pores of positive electroactive material layer 1662, and is chemically compatible in direct contact with second side surface 101B of sheet 100. To prevent the liquid electrolyte from contacting the lithium metal layer 1310 of lithium metal component layer 1320, Solid electrolyte sheet 100 should be free of through porosity and impermeable to the liquid electrolyte, and therefore substantially impervious.

In various embodiments, and in particular when the solid electrolyte sheet is a sulfide based glass, the liquid phase electrolyte is non-aqueous, and exceptionally dry, meaning that it is has very low moisture content, preferably less than 20 ppm, more preferably less than 10 ppm, and even more preferably less than 5 ppm. Non-aqueous liquid electrolytes suitable for use herein include solutions of organic solvent(s), such as carbonates (e.g., cyclic carbonates such as propylene carbonate (PC), ethylene carbonate (EC), acyclic carbonates such as dimethyl carbonate (DMC), ethylmethyl carbonate (EMC) and diethyl carbonate (DEC), and a lithium salt dissolved therein (e.g., $LiBF_4$, $LiClO_4$, $LiPF_6$, LiTf and LiTFSI; where Tf=trifluormethansulfonate; TFSI=bis(trifluoromethanesulfonyl)imide), as well as liquid electrolytes based on ionic liquids, as are known in the battery field arts. Other solvents contemplated include ethers (e.g., 2-Methyltetrahydrofuran (2-MeTHF), Tetrahydrofuran (THF), 4-Methyldioxolane (4-MeDIOX), Tetrahydropyran (THP) and 1,3-Dioxolane (DIOX)) glymes (e.g., 1,2-dimethoxyethane (DME/mono-glyme), di-glyme, tri-glyme, tetra-glyme and higher glymes). Moreover, by ensuring that the raw material components that form the vitreous glass sheet 100 are fully reacted, and that the sheet itself is homogeneous, sulfur dissolution from the glass into the liquid electrolyte is reduced or minimized. As measured during the course of storage (e.g., cell storage) and operation, the amount of sulfur present in the liquid electrolyte as a result of dissolution from the vitreous glass sheet preferably does not exceed 1000 ppm, and preferably is less than 500 ppm, and more preferably less than 100 ppm, even more preferably less than 50 ppm, or less than 20 ppm, or less than 10 ppm. For instance, in various embodiments, the concentration of sulfur in the liquid electrolyte is in the range of 10 ppm to 1000 ppm. In various embodiments the fully reacted and homogenous vitreous glass sheet is substantially or completely insoluble in the liquid electrolyte of the cell in which it is employed and comes into direct contact with. For instance, in various embodiments the vitreous sulfur based glass sheet is insoluble in contact with liquid carbonate electrolytes.

In various embodiments, cell laminate 1601B includes separator layer 1670 disposed between sealed negative electrode assembly 1640B and positive electrode 1660B; the separator layer typically a porous material layer or gel electrolyte layer that is impregnated with the non-aqueous liquid electrolyte. For instance, separator layer 1670 a porous organic polymer, such as a porous polyolefin layer (e.g., microporous). Separator layer 1670 provides positive separation between second principal side surface 101B of solid electrolyte sheet 100 and positive electroactive material layer 1662. The separator layer may provide various benefits. In particular embodiments, layer 1670 enables the combination of a solid electrolyte sheet and a positive electroactive material layer that are chemically incompatible in direct contact with each other. In other hybrid cell embodiments, the composition of solid electrolyte sheet 100 is chemically compatible in direct contact with the positive electroactive material of layer 1662, and laminate 1601B may be absent layer 1670, and sheet 100 and layer 1662 disposed in direct contact. Cell laminate 1601B may be wound or folded and incorporated into a cell housing. Thereafter, the liquid phase electrolyte dispensed into the cell, wherein it contacts positive electrode 1660B, and in particular layer 1662, but does not contact lithium metal of layer 1320, as it (lithium metal layer 1310) is isolated inside the sealed electrode assembly.

In particular embodiments cell 1600B is composed of: i) electroactive layer 1310—a lithium metal layer; ii) solid electrolyte sheet 100—a substantially impervious sheet of vitreous Li ion conducting sulfur-based glass sheet; iii) positive electroactive material layer 1662—composed of a lithium intercalation material, such as an oxide (e.g., $LiCoO_2$, $LiMn_2O_4$, $LiNiO$, $LiNiMnCoO_2$ or the like) or phosphate (e.g., $LiFePO_4$); iv) optional separator layer 1670—a porous polymer or gel, impregnated with a liquid phase electrolyte; v) a non-aqueous liquid phase electrolyte present in the pores of layers 1662 and 1670, and chemically compatible with second principal side surface 101B of sulfide based solid electrolyte glass sheet 100. For instance, lithium metal layer 1310 and solid electrolyte sheet 100 incorporated into cell 1600B as a sealed solid-state lithium metal electrode assembly.

In various embodiments hybrid cell 1600B may include a thin porous ceramic layer, typically <10 μm thick, disposed between solid electrolyte sheet 100 and electroactive layer 1662. The thin porous ceramic layer may be formed as a coating on the surface of first principal side 101B, or on the surface of electroactive layer 1662. In some embodiments the thin porous ceramic layer may be coated on the surface of separator layer 1670. In various embodiments the porous ceramic layer may be a composite of ceramic particles held together with an organic binder. In various embodiments the ceramic particles may be a ceramic powder not conductive of Li ions (e.g., alumina powder particles), or conductive of Li ions (e.g., a Li ion conductive garnet-like or LATP ceramic powder particles), or some combination thereof. In embodiments the porous ceramic layer has thickness of about 5um, or about 4 um or about 3 um or about 2 um. In some embodiments the porous ceramic layer may provide positive separation between solid electrolyte sheet 100 and positive electroactive layer 1662, in the absence of a porous polymeric or gel separator layer 1670.

Figure 16C:
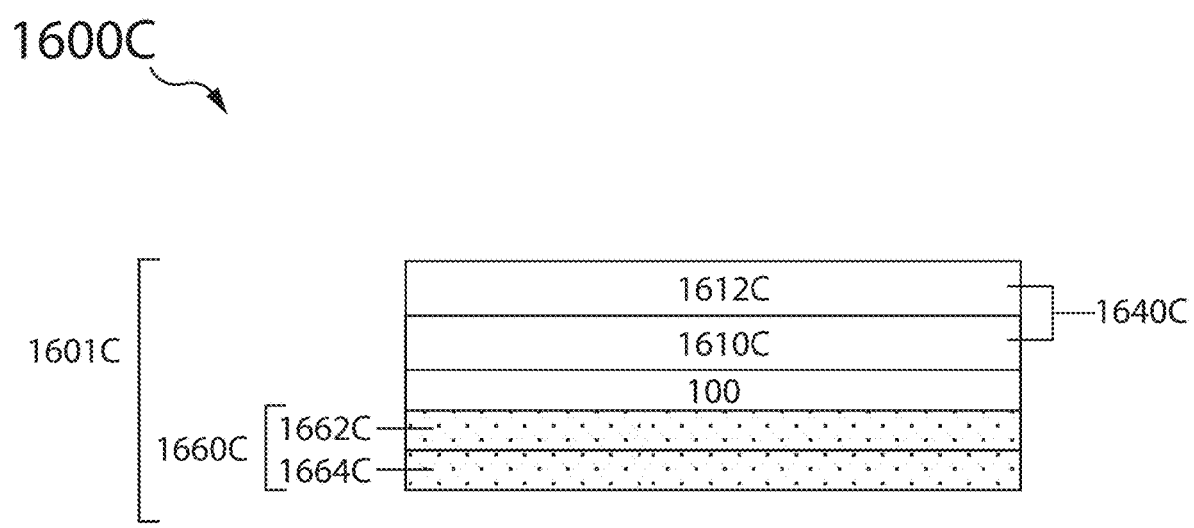

With reference to FIG. 16C there is illustrated a fully solid-state battery cell 1600C in accordance with various embodiments of this disclosure. The cell includes solid-state positive electrode 1660C; solid-state negative electrode 1640C; and Li ion-conducting solid electrolyte sheet 100 serving as separator. In some embodiments components 1660C/1640C/100 are incorporated into the cell as discrete material layers. In other embodiments, separator sheet 100 and negative/positive electrodes 1640C/1660C are incorporated in the cell as standalone components (e.g., standalone solid-state negative electrode assembly or as a standalone solid-state positive electrode assembly.

Solid-state positive electrode 1660C includes positive electroactive layer 1662C and current collector layer 1664C. In various embodiments electroactive layer 1662C is a composite of positive electroactive material combined with solid electrolyte material of composition similar to, or the same as, that of vitreous sulfide glass sheet 100. Without limitation, particle composite layer 1662C may be fabricated by compaction or tape casting of positive electroactive particles, Li ion conducting sulfide glass or sulfide glass-ceramic particles, and optionally electronically conductive particles for enhancing electronic conductivity, such as a carbonaceous material, (e.g., carbon black particles). In particular embodiments the positive electroactive particles are Li ion intercalating compounds, as described above (e.g., metal oxides). In various embodiments, the component particles of composite layer 1662C are uniformly distributed throughout the electroactive layer. In some embodiments, composite layer 1662C is engineered to have a surface that is defined by compacted Li ion conducting sulfide particles, and substantially devoid of electroactive particles and electronically conductive additives.

In particular embodiments positive electroactive material layer 1662C is of the lithium ion intercalation type, and preferably has potential vs. Li metal that is >2 Volts, such as, but not limited to those described above with reference to positive electroactive layer 1662 in FIG. 16A (e.g., transition metal oxides such as $LiCoO_2$, $LiMn_2O_4$, $LiNiO$, $LiNiMnCoO_2$ or the like, or phosphates such as $LiFePO_4$). In some embodiments the positive electroactive intercalation material has an amorphous atomic structure, which can be advantageous for enhancing uniform plating and striping of lithium metal due to the diffuse nature of the ionic current emanating from an amorphous layer, and in some embodiments layer 1662C is a dense layer, solely composed of amorphous Li ion intercalation material (e.g., an amorphous vanadate deposited directly onto surface 101B of solid electrolyte sheet 100).

Solid-state negative electrode 1640C is composed of negative electroactive material layer 1610C, which may be a lithium metal layer as described above, with optional current collecting layer 1612C. In various embodiments lithium metal layer 1610C and solid electrolyte sheet 100 are incorporated into cell 1600C as a standalone solid-state lithium metal electrode assembly in accordance with various embodiments of the present disclosure. In alternative embodiments, negative electroactive layer 1610C is not a lithium metal layer, but rather a layer comprising electroactive material having a potential near that of lithium metal, such as, but not limited to, intercalatable carbon, silicon or a combination thereof. In such said embodiments, electroactive layer 1610C may be a particle compact or tape cast layer of negative electroactive material particles (e.g., intercalatable carbon) combined with solid electrolyte particles of composition similar to, or the same as, that which constitutes sheet 100. Negative electroactive layer 1610C may further contain electronically conductive diluents (such as high surface area carbons) as well as binder materials for enhancing mechanical integrity of the layer.

In various embodiments fully solid-state battery cell 1600C is composed of positive and negative electrodes that are each composite powder compacts or tape cast layers, separated by a solid electrolyte sheet of the present disclosure (e.g., a vitreous sheet of a Li ion conducting sulfide based glass).

In another aspect, the solid electrolyte sheet of the present disclosure may be used as an interlayer in a protective membrane architecture as a Li ion conducting layer disposed between a substantially impervious lithium ion conducting membrane and a Li metal anode layer. The incorporation of a vitreous sulfide based solid electrolyte sheet in accordance with various embodiments of the present disclosure as an interlayer provides improved performance as the vitreous solid electrolyte sheet is devoid of pathways for through penetration of lithium metal dendrites. Protective membrane architectures and protected lithium electrode architectures are fully described in Applicant's co-pending patent applications and issued patents, including U.S. Pat. Nos. 7,282, 296; 7,390,591; 7,282,295; 8,129,052; 7,824,806; and U.S. Pat. Pub. No. 20140170465, all of which hereby incorporated by reference.

With reference to FIG. 16D there is illustrated a process for making a lithium metal battery cell 1600D that, in its as-fabricated state, is devoid or substantially devoid of lithium metal. The cell is composed of cell laminate 1601D comprising: i) electrode subassembly 1100B having current collecting layer 1101b and optional tie layer 1101a, as described above with reference to FIG. 11B; and ii) positive electrode 1660 comprising electroactive layer 1662 and current collecting layer 1664. In some embodiments cell 1600D has a hybrid cell construction, with a liquid electrolyte impregnated as described with reference to FIG. 16B In other embodiments cell 1600D may be a solid-state battery cell, and therefore absent liquid electrolyte and associated porous or gel separator layer 1670. Continuing with reference to FIG. 16D, electroactive layer 1662 is a fully lithiated lithium intercalation material layer, and is the sole source of Li capacity in the as-fabricated cell. Lithium metal layer 1310 is formed as a result of the initial cell charge, as Li from layer 1662 is plated onto electrode subassembly 1100B, thereby producing lithium metal component layer 1620. In another embodiment laminate 1100B may be provided by lithium metal electrode assembly 1300 having a scant amount of lithium metal (e.g., <5 μm thick, or <4 μm, or <3 μm, or <2 μm (e.g., about 1 μm), or <1 μm thick (e.g., between 0.1 and 0.9 μm), which as described above with reference to FIG. 13B is used therein as a bonding layer, and herein also provides a seed layer, for enhancing uniform plating onto the current collector layer during initial charging.

Figure 16E:
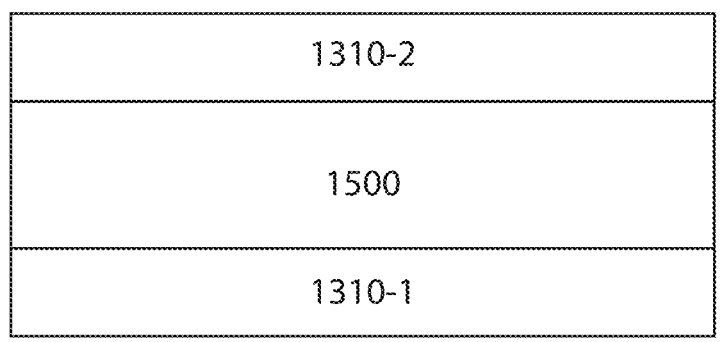

With reference to FIG. 16E there is illustrated a lithium metal battery cell 1600E in accordance with an embodiment of the present disclosure; cell 1600E is composed of positive electrode assembly 1500 (shown in detail in FIG. 15) and lithium metal layer 1310-1 and 1310-2 disposed in direct contact with first surface 101A of respective solid electrolyte sheets 100-1 and 100-2. In various embodiments the positive electrode assembly is a solid-state assembly, or it may contain a liquid electrolyte in direct contact with the positive electroactive material as described above with reference to battery cells having a hybrid cell construction. Accordingly, in various embodiments cell 1600 is fully solid state, and in other embodiments it has a hybrid cell construction.

Figure 16F:
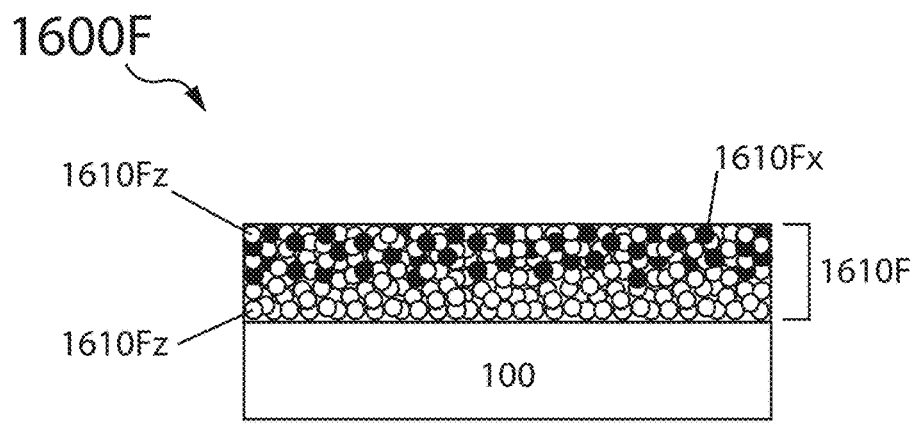
FIGS. 16F-I illustrate positive and negative electrode assemblies and battery cell laminates in accordance with various alternative embodiments of this disclosure.

With reference to FIG. 16F there is illustrated a negative lithium electrode assembly composed of solid electrolyte sheet 100 that is a vitreous glass monolith of sulfur based glass and electroactive material layer 1610F is a particle compact of at least two different material particles/powders in intimate contact with each other, a first particle 1610Fx that is a negative electroactive particle (e.g., an intercalating carbon, a lithium alloying metal, or silicon or the like having a potential within about 1V of lithium metal when in a lithiated state) and a second particle 1610Fz that is a Li ion conductive solid electrolyte particle. In various embodiments second particle 1610Fz is a sulfide glass that is chemically and electrochemically compatible in direct contact with the electroactive material/particle of the layer (e.g., lithiated carbon). In certain embodiments thereof, the sulfide glass particles are of a composition that is the same, or nearly the same (i.e., having similar elemental constituents; e.g., the main elemental constituents are the same) as the composition of vitreous sulfur based solid electrolyte sheet 100. In other embodiments sulfide glass particles 1610Fz are of a different composition than that of the vitreous solid electrolyte sheet, and in particular at least one element constituent of sheet 100 is not present in particle 1610Fz), or vice versa. For instance, in various embodiments vitreous solid electrolyte sheet 100 comprises silicon (e.g., in an amount between 2 to 20 mole %) and particle 1610Fz is devoid of silicon, or sheet 100 comprises boron (e.g., in an amount between 2 to 20 mole %) and particle 1610Fz is devoid of boron, or sheet 100 is devoid of phosphorous and particle 1610Fz contains phosphorous (e.g., in an amount between 2 to 20 mole %). In accordance with assembly 1600F illustrated in FIG. 16F, the electroactive layer has a graded compositional architecture wherein the surface of the electroactive layer in contact with sheet 100 is composed entirely of compressed particles 1610Fz. For instance, the electroactive layer may be formed by tape casting and pressing (e.g., by calendaring) an aggregate mixture of particles 1610Fx and 1610Fz, followed by a second tape cast and calendar of a compressed compact composed entirely of particles 1610Fz, and by this expedient effectively creating a surface layer compositionally distinguishable from that of the interior bulk of electroactive layer 1610F. For instance, it is contemplated herein that the composition of continuous vitreous sheet 100 may be chemically and/or electrochemically incompatible in direct contact with lithiated carbon, and such contact is prevented by the graded compositional architecture of electroactive layer 1610F, as shown in assembly 1600F. For example, vitreous sheet 100 may be a silicon sulfide glass (i.e., a glass comprising significant amounts of silicon, sulfur and lithium (e.g., as main elemental constituents), and in some instances devoid of phosphorous and/or boron) and particle 1610Fz may be a phosphorous sulfide glass (i.e., a glass comprising significant amounts of phosphorous, sulfur and lithium (e.g., as main constituent elements), and devoid of silicon and in some instances also devoid of boron).

Figure 16G:
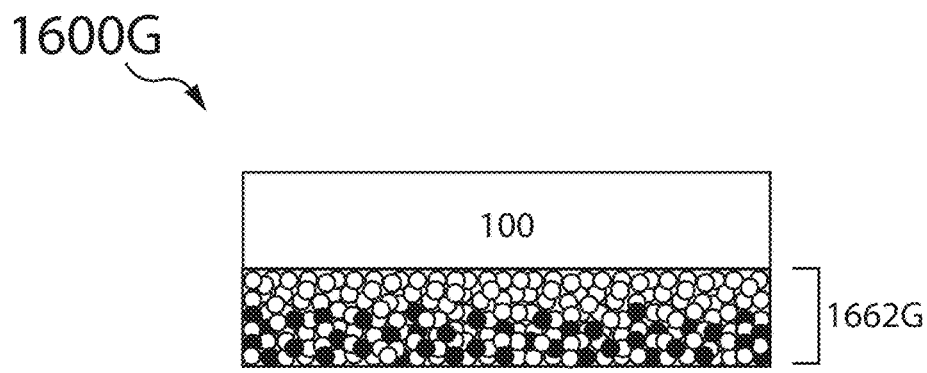

Similarly, with reference to FIG. 16G, there is illustrated positive electrode assembly 1600G composed of vitreous solid electrolyte sheet 100 and positive electroactive layer 1662G that is a compact of at least two different material particles compressed to form layer 1662G (e.g., a tape cast layer that is subsequently pressed/calendared). Layer 1662G comprises at least a first particle 1662Gx that is a positive electroactive material, and a second particle that is a Li ion conductive particle 1662Gz typically embodied herein by a Li ion conducting sulfide glass. Other material particles may be incorporated in the compact, such as optional electronically conductive particles (e.g., carbon black or the like). In similar manner to that described above for particle compact layer 1610F in FIG. 16F, layer 1662G has a similarly graded compositional architecture, wherein the surface of the compact, adjacent to sheet 100, is composed entirely of particles 1662Gz. Particularly suitable electroactive particles are lithium intercalatable compounds such as transition metal oxides including, but not limited to, $LiCoO_2$, and the like, as described above. Particularly suitable sulfide glasses for use as particle 1662Gz are the phosphorous sulfides. It is also contemplated that particle 1662Gz may be a thio-Lisicon or the highly conductive lithium thiophosphate materials, including $Li_{10}GeP_2S_{12}$, $LiPS_4$ and the like.

Figure 16H:
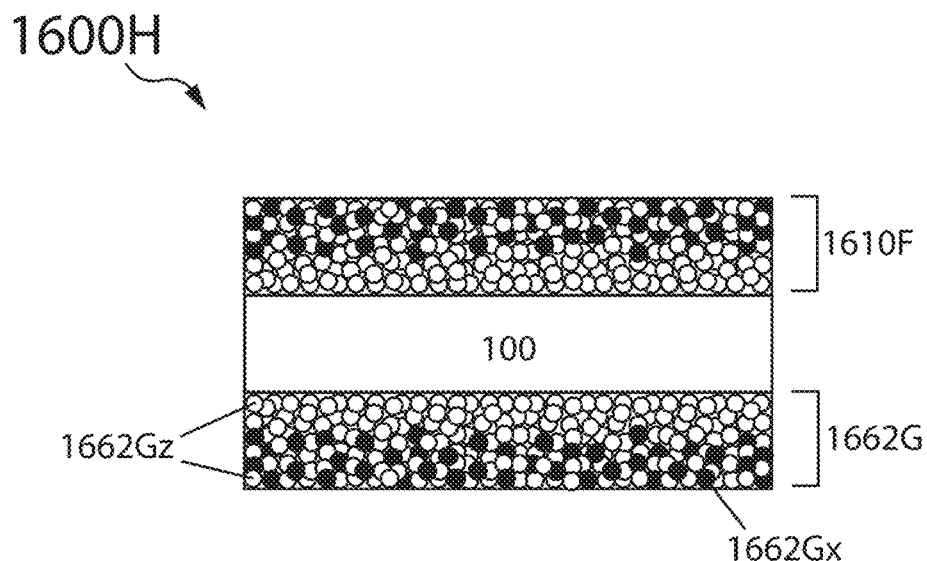
Figure 16I:
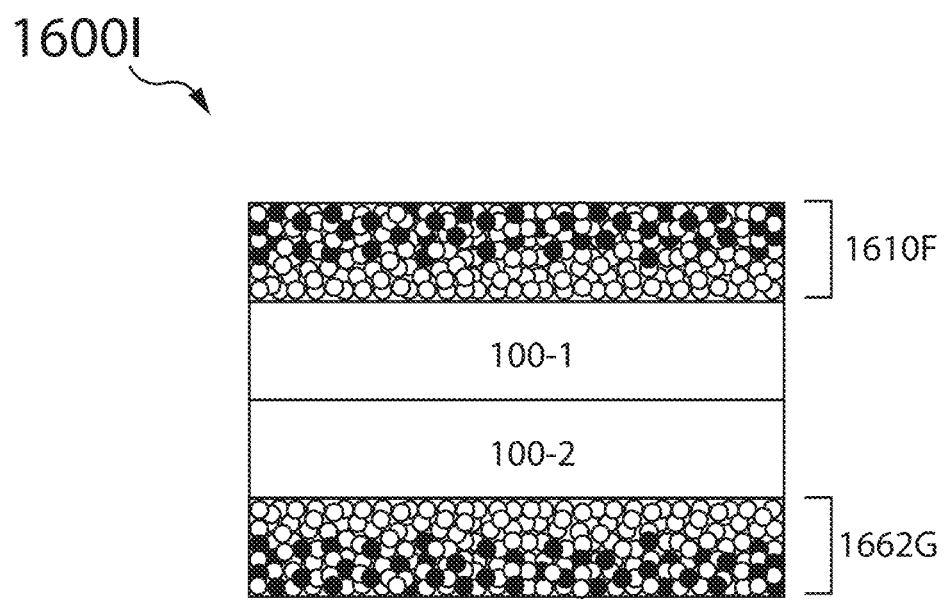

With reference to FIG. 16H there is illustrated a battery cell laminate 1600H composed of vitreous solid electrolyte sheet 100 sandwiched between electroactive layer 1610F and 1662G. In other embodiments, a first solid electrolyte sheet 100-1 is disposed adjacent to layer 1610F and a second solid electrolyte sheet 100-2, of composition different than that of sheet 100-1 is disposed adjacent to layer 1662G. With reference to FIG. 16I, in various embodiments the composition of sheet 100-1 is similar, or identical, to that of particle 1610Fz (e.g., having the same main elemental constituents), and the composition of sheet 100-2 is similar, or identical, to that of particle 1662Gz (e.g., having the same main elemental constituents).

In various embodiments, an electroactive layer may be coated onto the solid electrolyte web 100W using a mask to form a web containing a discrete array of coated and uncoated regions (e.g., a discrete array of lithium electrode assemblies). In some embodiments the electroactive layer of the discrete array is lithium metal. In other embodiments, the electroactive layer is a positive electroactive material layer (as described above), such as a lithium intercalation material layer (e.g., lithiated or unlithiated). Accordingly, in some embodiments the web array is composed of a large number of positive and/or negative lithium electrode assemblies (e.g., more than 10, more than 100, more than 500, or more than 1000 of such assemblies). In various embodiments, the opposing side of the assembly may be coated with an electroactive layer of opposite polarity to form a discrete array of solid-state batteries. The web of discrete arrays of the lithium electrode assemblies and/or solid-state battery cells may be subsequently excised from the web to form discrete components and cells (e.g., by laser cutting across the uncoated regions). The discrete electrode assemblies or battery cells may be of varying dimensions and shapes, including circular, square and rectangular. In various embodiments the web may contain more than 10, or more than 100, or more than 500, or more than 1000 discrete assemblies or solid-state cells.

In various embodiments the solid electrolyte sheet of the present disclosure and components thereof are inspected for quality control, and in particular spectrophotometry methods are used to characterize the surfaces and interfaces. In various embodiments the inspection is an automated machine based process (i.e., not a purely human inspection) that includes a quality control defect detection system comprising one or more light sources and one or more sensors for detecting reflected/transmitted light. The light source may include fluorescent; strobe; LED; incandescent and laser light, and the light may be directed at various angles to the glass. The light sensor is generally a passive device that converts this light energy from such a source into an electrical signal output. Examples of suitable light sensors are photoelectric devices that convert light energy (photons) into electricity (electrons), such as photo-voltaic, photoemissive, photo-resistive, photo junction or photo-conductive cells.

In particular embodiments the automated inspection is performed inline with the fabrication of the solid electrolyte glass separator sheet, and/or inline with the fabrication of an electrode subassembly composed of the glass separator sheet and a material layer on a surface of the glass sheet (e.g., a metal layer other than lithium metal), and/or inline with the fabrication of a lithium electrode assembly composed of the solid electrolyte glass separator sheet combined with a lithium metal or lithium alloy layer, as described above. For instance, in various embodiments the automated inspection system is inline with the making of a vitreous web of solid electrolyte glass, as described above (e.g., the automated inspection taking place after solidification of the web but prior to winding of the web into coil form or prior to slicing the web into discrete sheets. In other embodiments, the automated inspection is performed on discrete sheets of the vitreous solid electrolyte glass sheet. Accordingly, in such said embodiments the detection system may further comprise a conveyance system (e.g., a convey belt) for conveying the glass sheet, sub-electrode assembly, and/or electrode assembly through the quality control glass sheet defect detection system, as well as a computer for system control and in-line analysis of data collected from the sensors and image processing.

The computer may include one or more memory devices, one or more mass storage devices, and one or more processors. One or more processors may include a CPU, analog and/or digital input/output connections, etc. In some embodiments, the computer may include a system controller to control the activities of the automated inspection/manufacturing apparatus. The system controller may execute system control software stored in a mass storage device, loaded into a memory device, and executed on a processor. Alternatively, the control logic may be hard coded in the controller. Applications Specific Integrated Circuits, Programmable Logic Devices (e.g., field-programmable gate arrays, or FPGAs) and the like may be used for these purposes. System control software may be configured in any suitable way. For example, various system component subroutines or control objects may be written to control operation of the system or apparatus components necessary to carry out various described processes. System control software may be coded in any suitable computer readable programming language. In some embodiments, the system control software may include input/output control (IOC) sequencing instructions for controlling the various parameters described above. Other computer software and/or programs stored on the mass storage device and/or the memory device associated with system controller may be employed in some embodiments.

Figure 17:
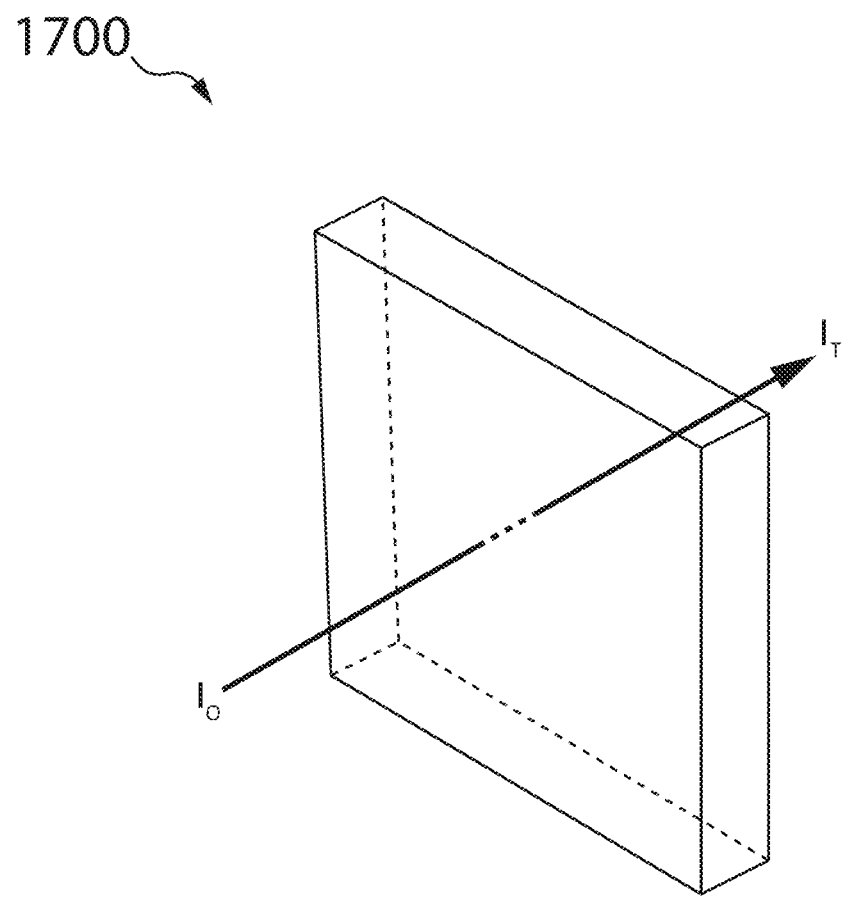
FIG. 17 illustrates the use of light attenuation for inspecting a standalone $Li^+$ ion conducting vitreous sheet disclosure, in accordance with a method disclosure.

In various embodiments, light attenuation (e.g., visible spectrum, ultraviolet (UV) spectrum, and near infrared spectrum) is used to characterize a standalone vitreous sheet of the instant disclosure. Measurements are made based on comparison of incident light and transmitted light intensities at various wavelengths (see the schematic in FIG. 17). Light attenuation is determined by light absorption in the vitreous sheet, which is not affected by the presence of glass flaws, and light scattering due to presence of flaws in the bulk of the vitreous sheet and on its surfaces. Certain types of flaws can lead to light scattering, including: glass inter-particle boundaries (i.e., particle to particle boundaries), inclusions of crystalline phase due to partial crystallization, bubbles, cracks, digs, surface scratches. The overall concentration of scattering centers is approximated from the spectral dependence of light attenuation using Mie theory of independent light scattering on spherical particles. Since light-scattering flaws generally have a more complex shape, accurate quantitative determination of scattering center concentration is quite difficult. However, approximation based on spherical particles can be used for semi-quantitative characterization of light-scattering flaws in glass layers. In a particular embodiment of a quality control method contemplated herein, incident light intensity is kept constant and transmitted light intensities for glass layers of the same thickness are compared with a reference sample of acceptable quality, as determined from electrochemical cycling data (improved protection of Li metal or Li alloy electrode that manifests itself as an increase in lithium cycling efficiency and number of charge/discharge cycles).

Figure 18:
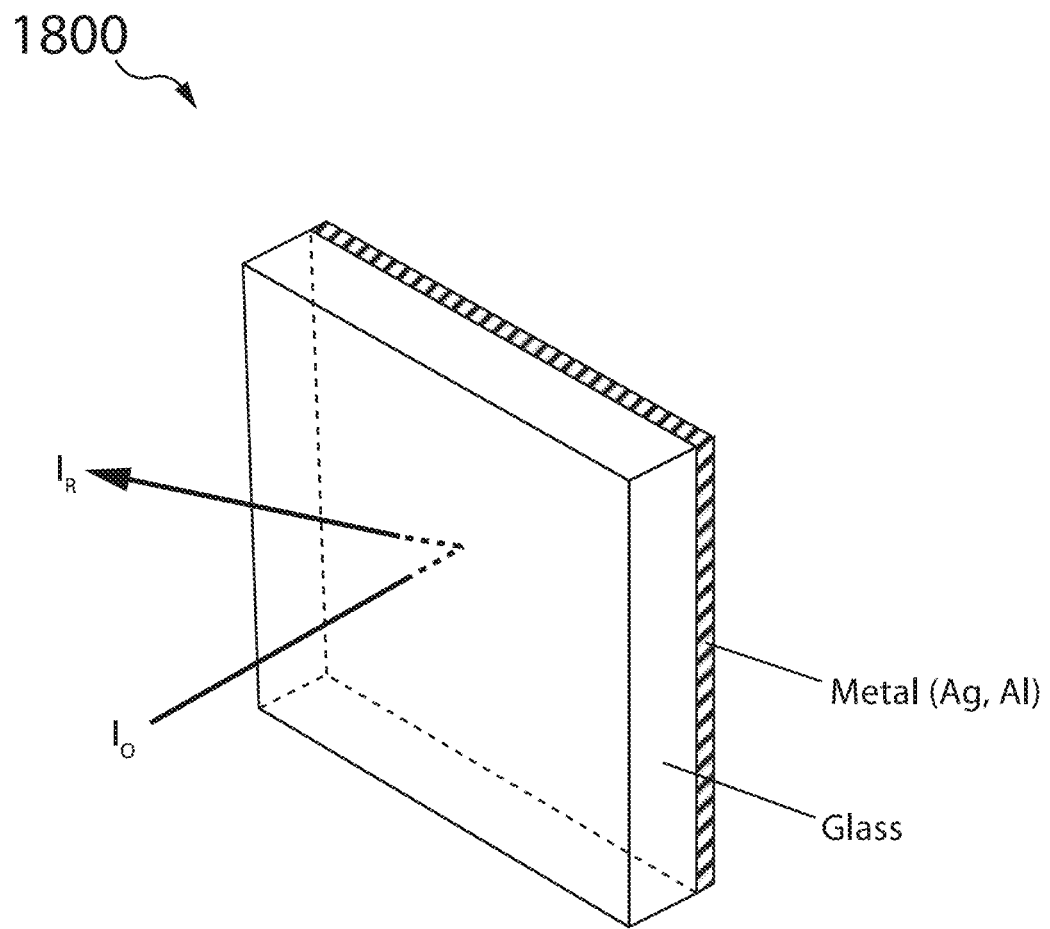
FIG. 18 illustrates the use of light reflection for inspecting an electrode subassembly disclosure, in accordance with a method disclosure.

In various embodiments the light reflection from a metal surface in contact with the vitreous sheet is used for characterization of such a substrate laminate such as for an electrode subassembly or electrode assembly of the instant disclosure. If vitreous sheet is coated with a metal film (e.g., Ag, Sn or Al, in particular with vacuum deposition), light reflection from the metal film interface with the vitreous layer (internal interface) is used to evaluate concentrations of scattering centers in the bulk of the vitreous sheet and on the vitreous sheet-metal interface (see the schematic in FIG. 18). For example, the reflected light intensities with a reference sample consisting of a completely transparent silicate glass slide coated with the same metal film can be compared. The measured reflected light intensity is reduced because both incident and reflected light intensities are attenuated by the scattering flaws in the bulk of the sheet. For this purpose, metals with reflection coefficients close to 100% (Al, Ag) are used (e.g., about 100%).

Figure 19A:
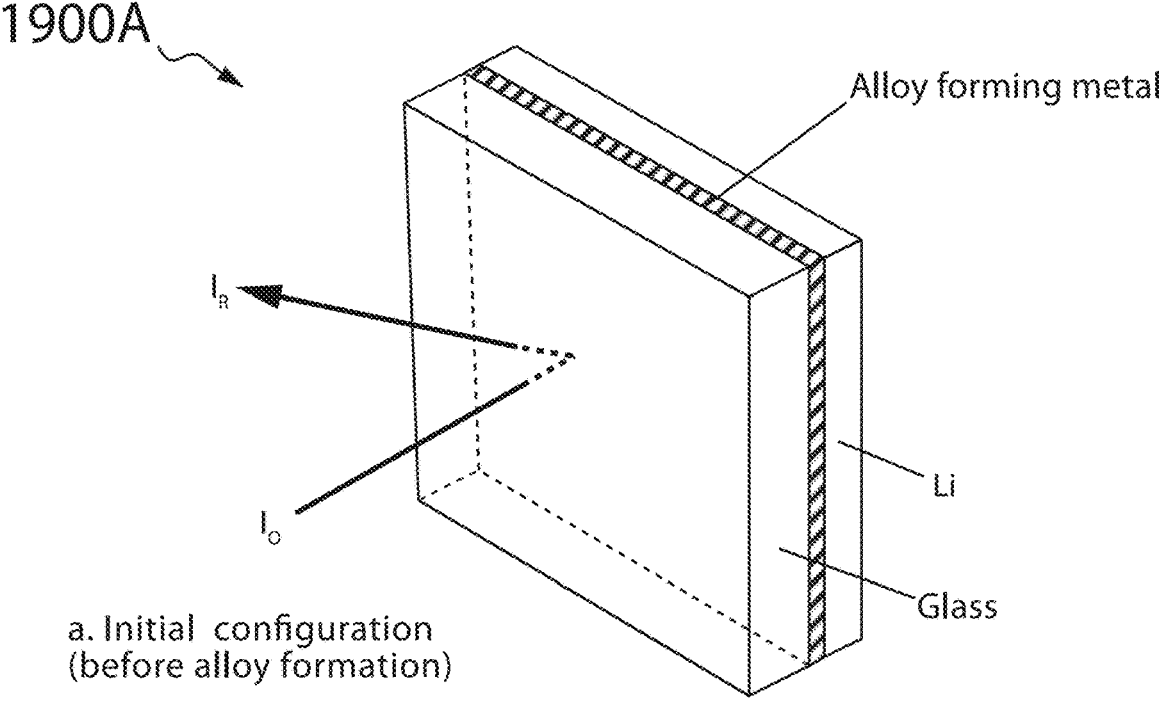
FIGS. 19A-B illustrate the use of light reflection for inspecting a lithium electrode assembly disclosure, in accordance with a method disclosure.
Figure 19B:
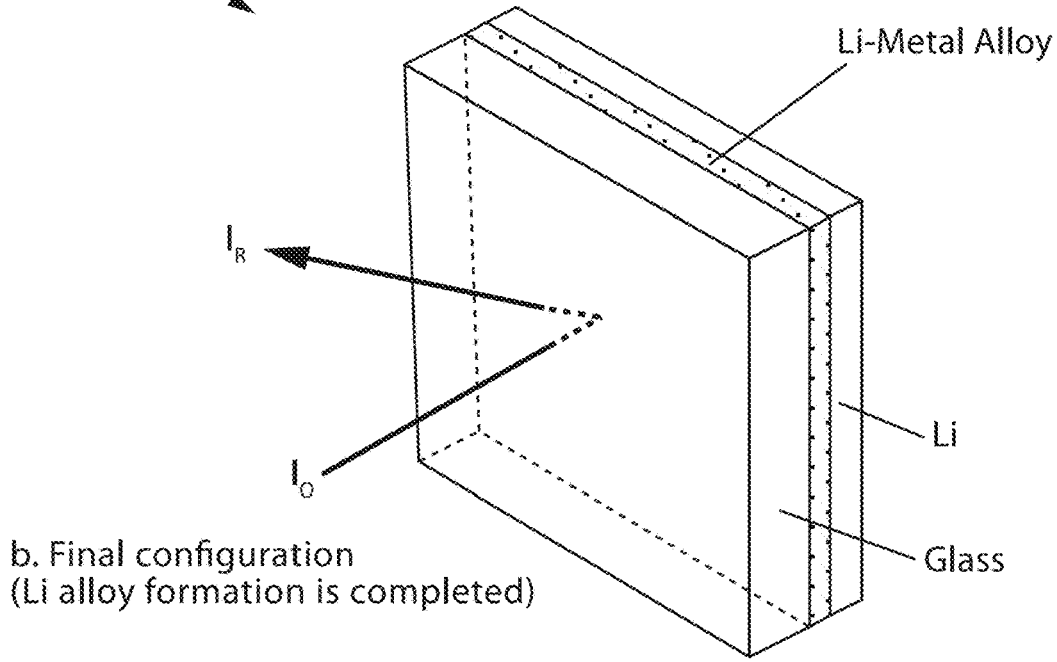

In one important embodiment, the metals in contact with the vitreous sheet are Li alloy-forming metals, such as Ag, Sn, Al, In, that form a reactive bond between Li metal and the sheet (see the schematic in FIGS. 19A-B). After Li reacts with the alloy-forming metal, the reflection coefficient of the solid electrolyte sheet—metal interface drops significantly (e.g., by 20%, 30%, 40%, 50% or greater), since instead of being reflected from a metal with close to 100% reflection coefficient (such as Ag), the light is now reflected from a Li-alloy surface. Under conditions when there is an excess of lithium metal compared to an alloy forming metal, the alloy forming metal will be lithiated and converted into a Li-Metal intermetallic or alloy compound with the highest possible lithium content. The reflection from the Li-Metal intermetallic compound can be diffuse rather than mirror-like, and the reflected light intensity is measured using a spectrophotometer equipped with integrated spheres that are coated with highly reflective materials, such as MgO or $BaSO_4$. This method allows for visualization of surface flaws at the vitreous sheet—Li alloy interface. In particular, if Li foil or layer is partially delaminated from the vitreous sheet surface or has areas with lower reactivity, for example due to inclusions of Li nitride or surface films that are thicker than in other areas of contact, the formation of Li intermetallic compound in these areas will be delayed or, in some cases, will not occur at all. In one embodiment, changes in reflectivity of the interface are monitored, in particular recorded on video, in order to identify areas of low Li reactivity.

Figure 20:
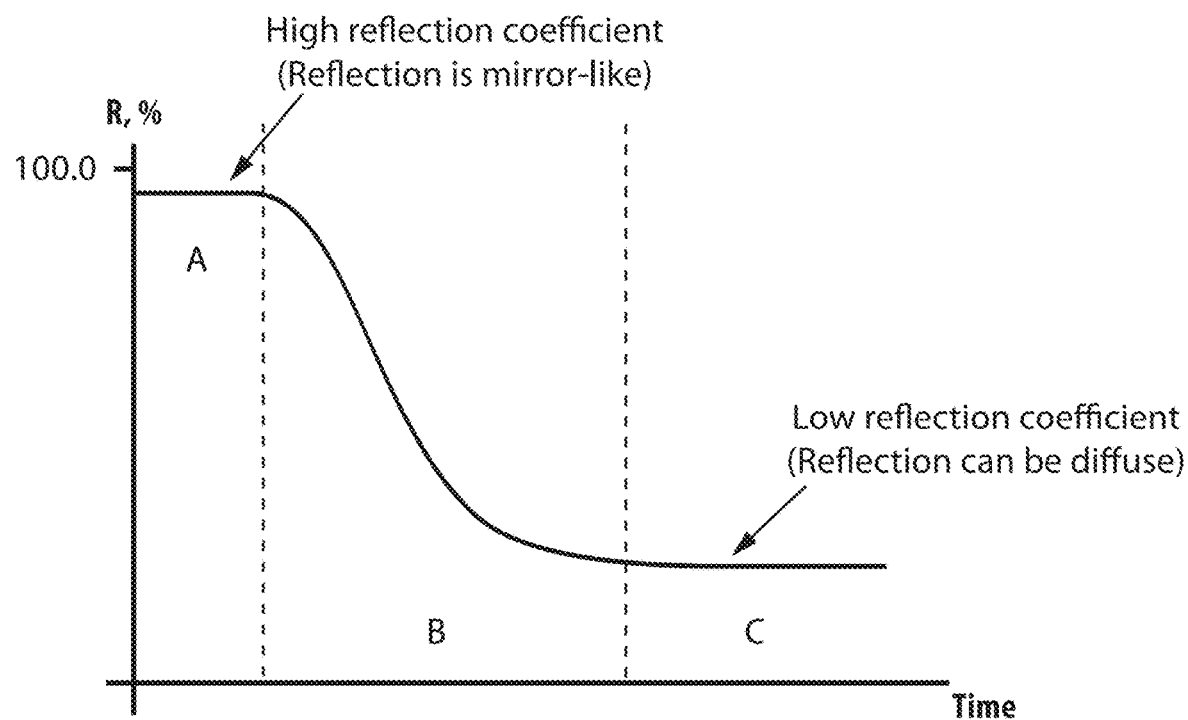
FIG. 20 illustrates a schematic plot illustrating changes in reflection from an inner metal surface in contact with an instant vitreous sheet after bringing lithium metal into contact with an outer metal surface.

FIG. 20 illustrates changes in reflection coefficient measured over time in the structure from FIG. 19. Region A corresponds to reflection from metal surface in contact with the vitreous sheet (glass) (before Li metal is brought into contact and Li alloy is formed on reflective surface). Region B illustrates a gradual drop in reflection coefficient value during the transition period. The intermediate values of reflection coefficient can be attributed to either non-uniform conversion of metal surface to Li alloy over the measured surface area or to incomplete conversion of metal surface to Li alloy with the highest Li metal content or to the combination of both processes. Region C corresponds to reflection from surface of Li rich intermetallic compound after its formation is complete and the system is in a steady state.

In another important embodiment, the metal in contact with the vitreous sheet is Li metal, in particular extruded Li foil or vacuum deposited or electrodeposited Li film. In this case, the light is reflected from the Li surface bonded to the glass layer. Depending on the Li surface morphology, the reflection can be either mirror-like or diffuse. Incomplete Li coating, areas of low Li reactivity or areas lacking intimate contact between Li and the vitreous sheet surface are visualized as areas with low reflection coefficient. In one embodiment, Li surface condition in a fabricated Li—sheet laminate is characterized by measurements of reflection coefficient and its changes over time. In another embodiment, the reflection coefficient is measured in situ, in an assembled cell equipped with an optical window, allowing for characterization of Li surface morphology at various stages of electrochemical cycling and during cell storage.

In various embodiments, characterization and quality control of the instant vitreous sheet and the interfaces it makes with Li and Li alloys in lithium electrode assemblies of the instant disclosure are made using measurements of local resistance (i.e., electrical resistance).

Figure 21A:
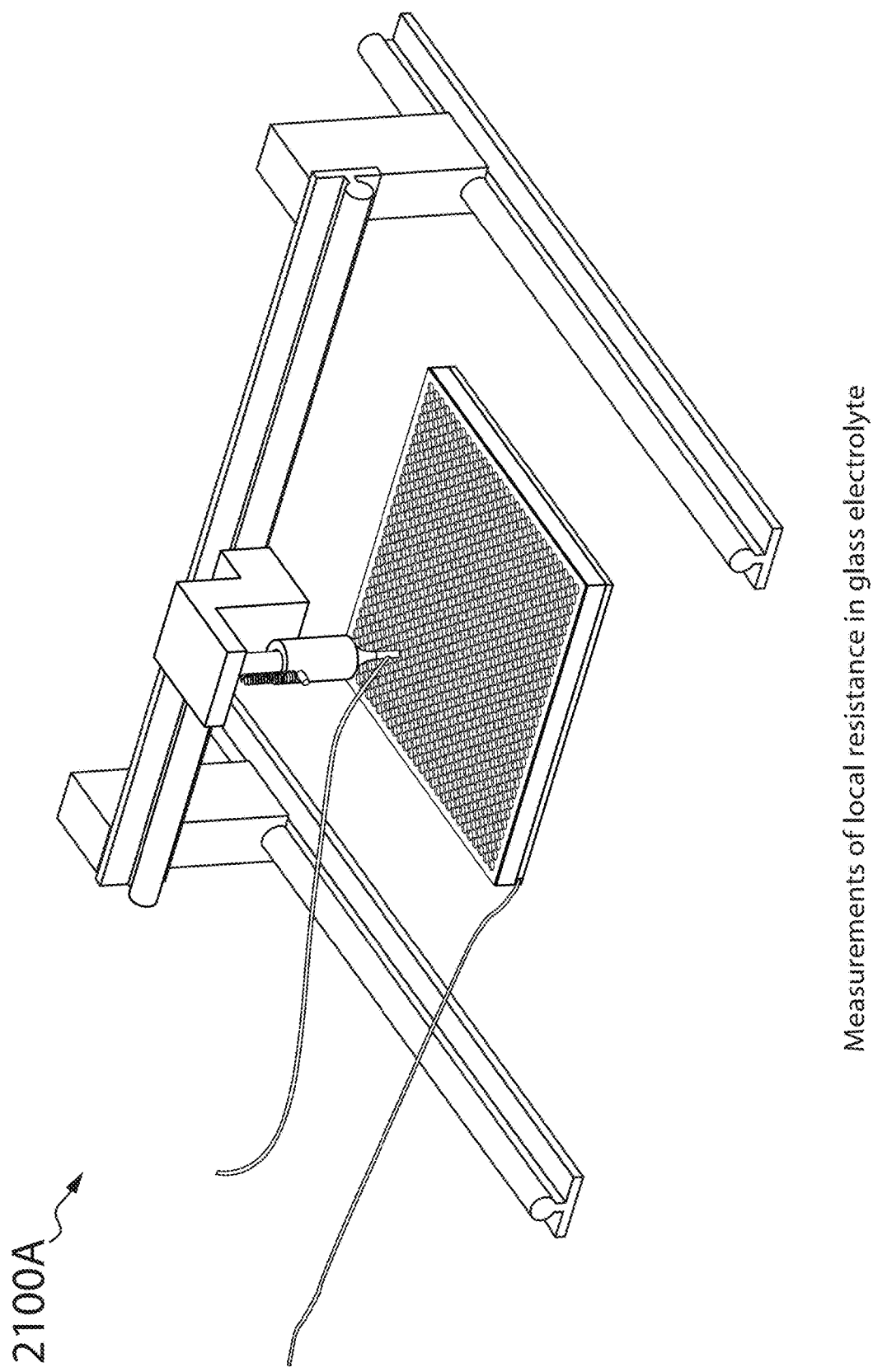
FIGS. 21A-B illustrate apparatus' for measuring positional resistance of a vitreous solid electrolyte sheet in a solid-state battery cell disclosure, in accordance with a method disclosure.
Figure 21B:
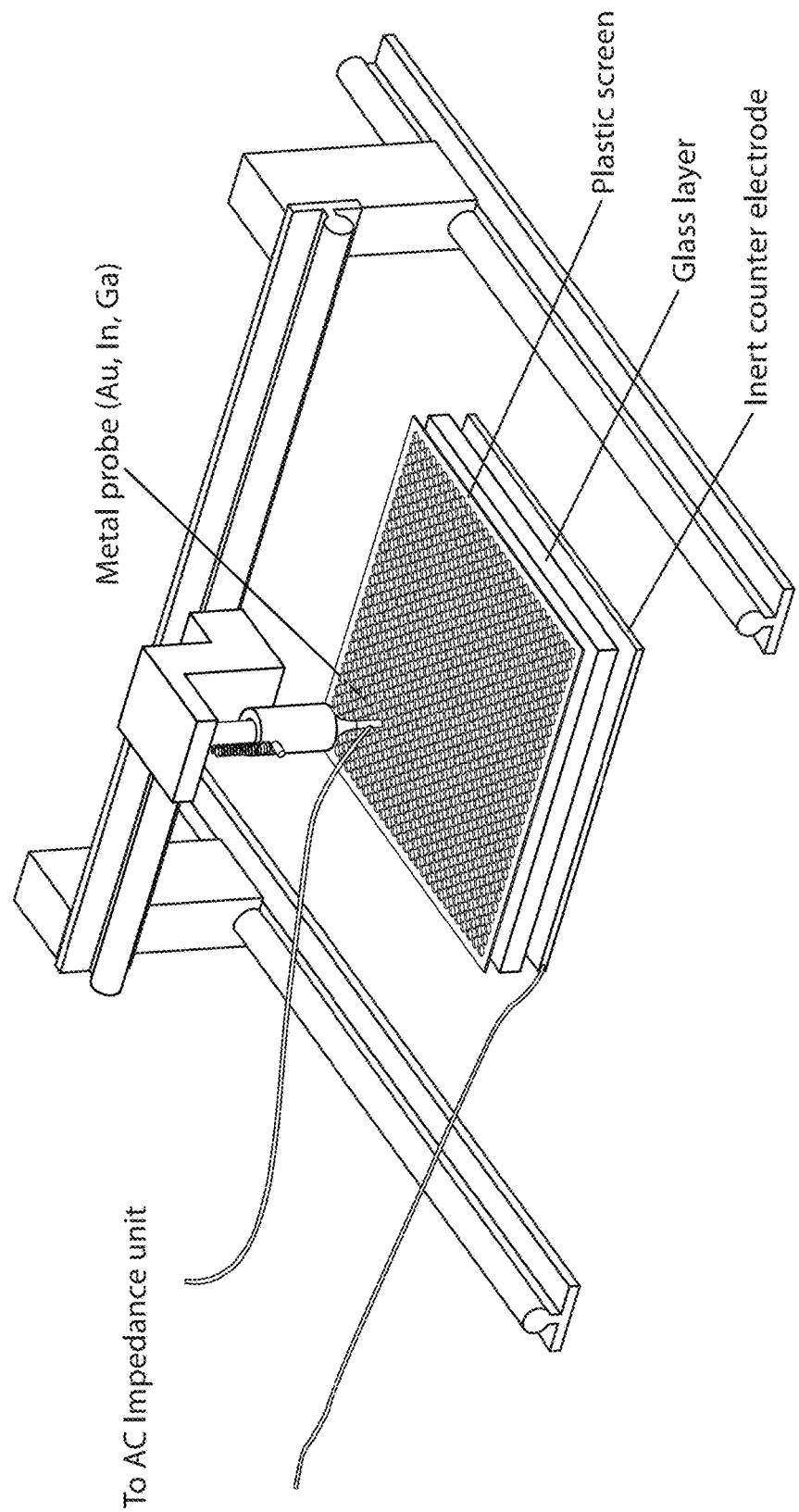

In one embodiment, measurements are performed in a solid-state cell (FIG. 21A-B). Resistance across the instant sheet is measured in various locations on the sheet surface. In this case, one electrode with a small tip, or a "probe", moves along the sheet surface. The probe diameter is in the range of 10 um-1 mm. In order to minimize the "current line spread" that decreases the accuracy of local resistance measurements, the sheet thickness is chosen from the range of 5 um-100 um. The second (counter) electrode with a significantly larger surface area (up to the full area of the glass layer) is located on the opposite side of the sheet (i.e., second principal side) and is stationary. The probe is made of a soft inert metal (not Li), such as Au, In, Ga, etc., that does not scratch or in any other way damage the sheet surface while maintaining reliable contact with the sheet. In this embodiment, the second electrode is not Li and could be the same metal as in the probe. Local resistance of the sheet is determined from AC impedance spectra. For quality control of sheet uniformity, a maximum acceptable deviation value of local resistance is set (e.g., 1%, 2%, 5%, 10% of average local resistance).

In one embodiment, the second electrode with a large area is a Li alloy forming metal, such as Ag, Sn, Al, In. In this case, after the solid electrolyte sheet is characterized by its local resistance, it can be used for fabrication of a Li alloy—solid electrolyte sheet laminate, since the quality control method is non-destructive. In another embodiment, measurements of local resistance along the sheet surface are performed with a larger probe to obtain a large scale map of surface flaws, and then the resistance is measured with a smaller probe to obtain a more detailed distribution of local surface flaws.

Figure 22A:
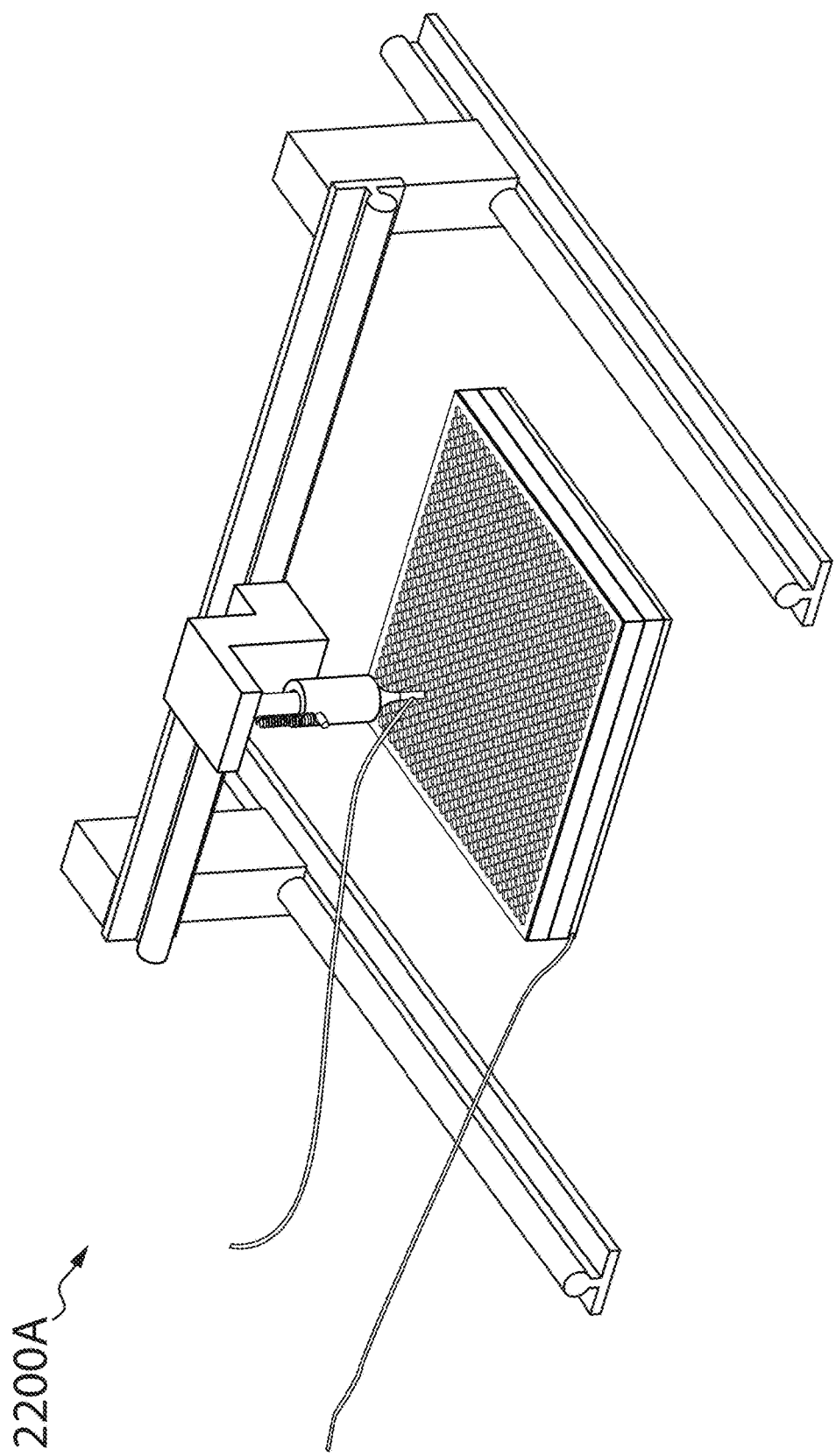
FIGS. 22A-B illustrate apparatus' for measuring positional resistance of a vitreous solid electrolyte in a battery cell disclosure having a liquid phase electrolyte, in accordance with a method disclosure.
Figure 22B:
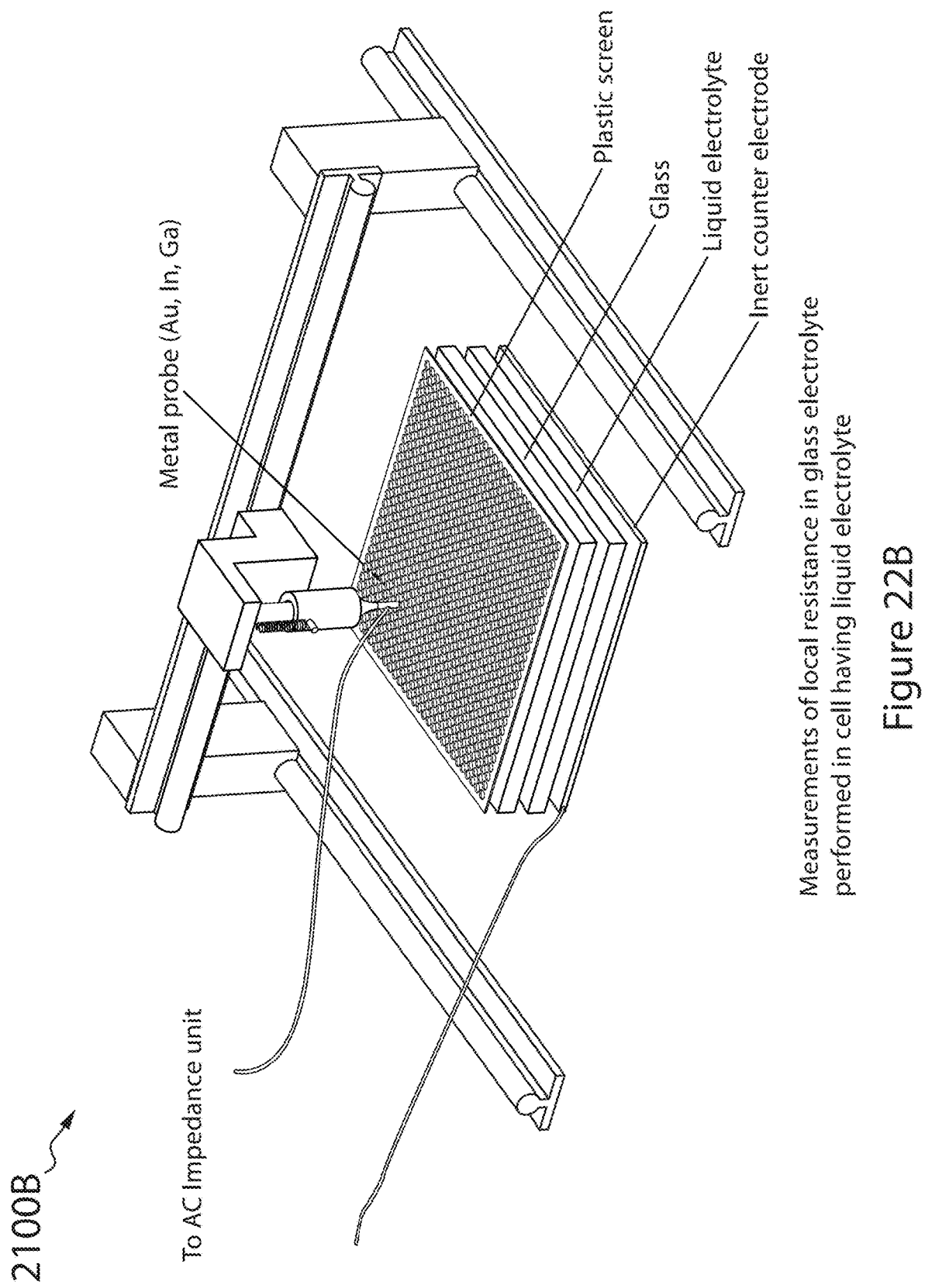

In one embodiment, impedance measurements are performed in a cell similar to the one described above, but having a liquid non-aqueous electrolyte located between the vitreous sheet and the counter electrode (FIG. 22A-B). The liquid non-aqueous electrolyte can be contained within the pores of a Celgard-type separator. The nonaqueous electrolyte contains a Li salt (LiTFSI, LiFSI, LiPF6) and an aprotic solvent or solvent mixtures, in particular such solvents as ethers (DME, dioxolane) or organic carbonates (DMC, EEC, PC, EC). The advantage of this method is that once the resistance measurements are performed on one side of the sheet (e.g., first principal side), the test cell can be disassembled, the non-aqueous electrolyte can be rinsed off with a nonaqueous solvent, and the resistance measurements can be repeated on the second principal side, since the method is non-destructive.

Figure 23:
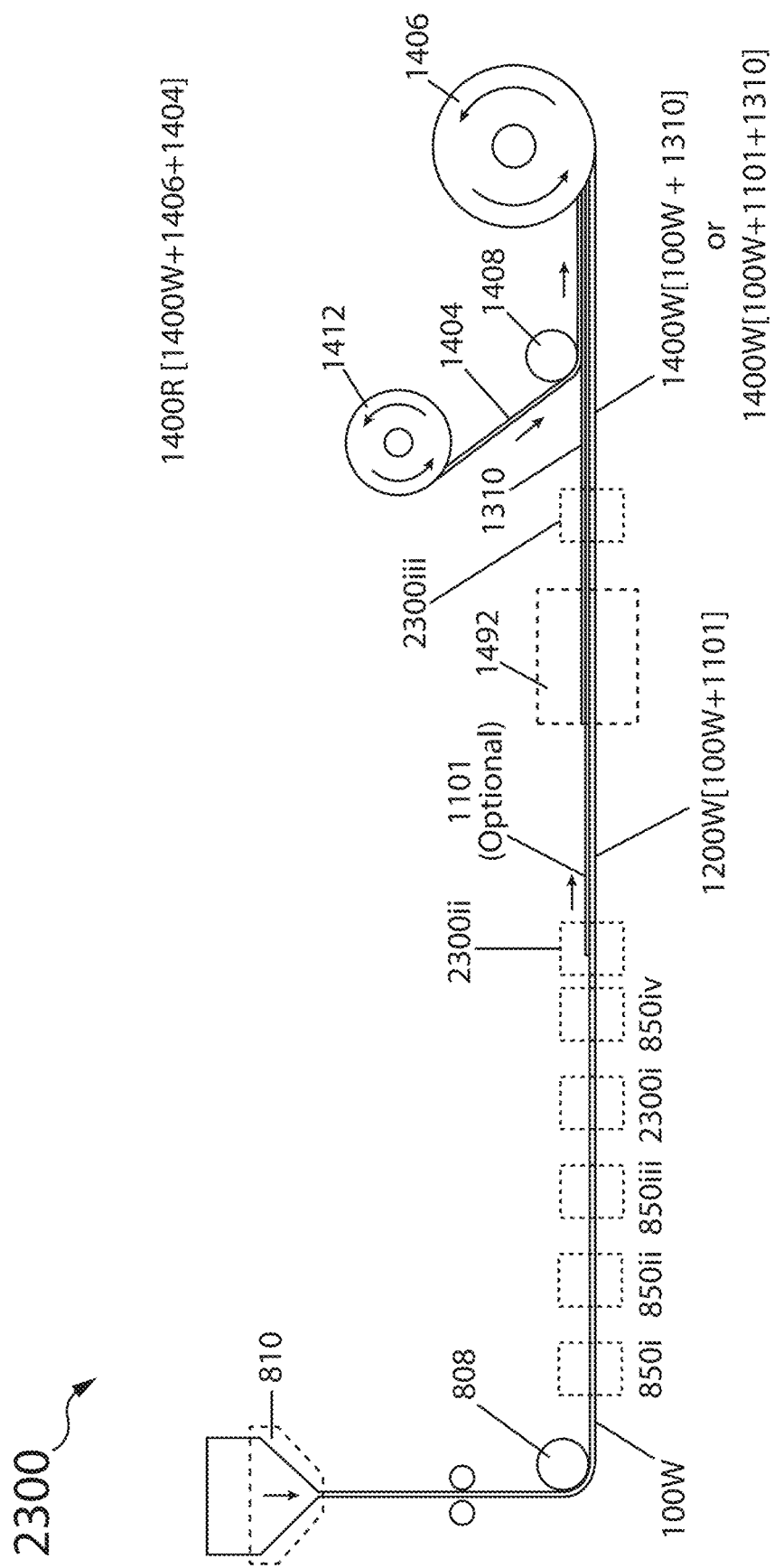
FIG. 23 illustrates an apparatus for making and inspecting a solid electrolyte sheet and web thereof, a sub-electrode assembly and web thereof, and a lithium metal electrode assembly and web thereof.

With reference to FIG. 23 there is illustrated an embodiment of an apparatus for fabrication and automated inspection of vitreous sheet/web 100/100w, electrode sub-assembly and web thereof, and a lithium metal electrode assembly and web thereof. The automated spectrophotometric inspection apparatus/system includes one or more stations for inspecting the surface of the vitreous solid electrolyte sheet and interfaces between the vitreous solid electrolyte sheet and a material layer (e.g., a lithium alloy layer or lithium metal layer). In embodiments, the automated inspection apparatus/system includes a source of light (for example, light at a specific wavelength in the visible, UV or near infrared region), sensors for detecting reflected/transmitted light, and a computer for collecting and storing data.

The spectrophotometric inspections, as described above, can be performed on the glass at station 2300i, on the electrode sub-assembly at station 2300ii, and on the lithium metal electrode assembly at station 2300iii. In various embodiments, the first inspection station can be configured to inspect the surfaces and/or interior of the vitreous solid electrolyte sheet for defects and flaws, and for that purpose the automated spectrophotometric inspection occurring at station 2300i can involve measuring the attenuation of transmitted light. The second inspection station can be configured to inspect the interface between the solid electrolyte sheet and a reflective coating layer (e.g., a metal layer) that is devoid of lithium metal and a third inspection station can be configured to inspect the interface between the solid electrolyte sheet and a material layer comprising lithium metal (e.g., a lithium metal layer or a lithium alloy layer), and for those purposes the automated spectrophotometric inspection occurring at sections 2300ii and 2300iii can involve measuring attenuation of reflected light.

CONCLUSION

Although this disclosure provides some detail for purposes of clarity of understanding, it will be apparent that certain changes and modifications may be practiced within the scope of this disclosure. It should be noted that there are many alternative ways of implementing both the process and compositions of this disclosure. Accordingly, the present embodiments are to be considered as illustrative and not restrictive, and this disclosure is not to be limited to the details given herein. For instance, the intrinsically Li ion conductive glasses described above are embodied by sulfide glasses, however it is to be appreciated that the description in many aspects is broadly applicable to other, as yet undiscovered, highly conductive inorganic glasses such as Li ion conducting oxides, phosphates, oxynitrides, and silicate glasses, which may be devoid of sulfur. Moreover, while the solid electrolyte wall structures (e.g., vitreous sheets) of this disclosure are generally intended for use in an electrochemical device such as a battery cell, they are, nonetheless, standalone material components that are fabricated apart from the device or electrode assembly into which they are ultimately incorporated, and may also be stored and/or transported independently as discrete battery cell components. The utility of the Li ion conducting solid electrolyte wall structures and sheets disclosed herein are therefore more generally applicable to a variety of electrochemical devices that require Li ion conduction.

What is claimed is:

1. A method of inspecting a battery cell, the method comprising:
    i) providing an electrode assembly comprising:
        a dense solid inorganic electrolyte sheet as an ionically conductive separator layer having first and second opposing principal side surfaces; and
        a material layer comprising electroactive lithium disposed on the first principal side surface; and
    ii) spectrophotometrically inspecting the electrode assembly for defects or flaws at an interface between the material layer comprising electroactive lithium and the inorganic electrolyte sheet;
    wherein the spectrophotometric inspection is an automated inspection comprising:
        providing a source of light of a specified wavelength, or the wavelength selectable from a range of wavelengths;
        providing sensors for measuring intensity of the light;
        providing a computer that interfaces with the sensors for collecting light intensity data;
        shining the light at the solid electrolyte sheet for transmission or reflection measurements;
        measuring the transmitted or reflected light intensity using said sensors; and
        storing data from said sensors using said computer.

2. The method of claim 1, wherein the material layer is lithium metal.

3. The method of claim 1, wherein changes in reflectivity of the interface are monitored in order to identify areas of low Li reactivity at the interface.

4. The method of claim 1, wherein the method involves monitoring reactions at the interface in real time.

5. The method of claim 1, wherein the spectrophotometric inspection is performed inline with the fabrication of the electrode assembly.

6. The method of claim 1, wherein the spectrophotometric inspection further comprises inspecting the first and second opposing principal side surfaces and/or interior of the inorganic electrolyte sheet for defects and flaws.

7. The method of claim 6, wherein the spectrophotometric inspection comprises measuring attenuation of reflected light for inspection of the interface between the inorganic electrolyte sheet and the material layer, and measuring attenuation of transmitted light for inspection of the first and second opposing principal side surfaces and/or interior of the inorganic electrolyte sheet.

8. The method of claim 6, wherein the spectrophotometric inspection further comprises inspecting an interface between the inorganic electrolyte sheet and a reflective coating layer that is devoid of lithium metal for defects and flaws.

* * * * *